(12) United States Patent
Oestergaard et al.

(10) Patent No.: US 10,221,416 B2
(45) Date of Patent: Mar. 5, 2019

(54) OLIGOMERIC COMPOUNDS COMPRISING ALPHA-BETA-CONSTRAINED NUCLEIC ACID

(71) Applicant: Ionis Pharmaceuticals, Inc., Carlsbad, CA (US)

(72) Inventors: Michael Oestergaard, Carlsbad, CA (US); Eric E. Swayze, Encinitas, CA (US); Punit P. Seth, Carlsbad, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 284 days.

(21) Appl. No.: 15/305,451

(22) PCT Filed: Apr. 24, 2015

(86) PCT No.: PCT/US2015/027439
§ 371 (c)(1),
(2) Date: Oct. 20, 2016

(87) PCT Pub. No.: WO2015/164693
PCT Pub. Date: Oct. 29, 2015

(65) Prior Publication Data
US 2017/0044539 A1 Feb. 16, 2017

Related U.S. Application Data

(60) Provisional application No. 61/983,546, filed on Apr. 24, 2014.

(51) Int. Cl.
*A61K 48/00* (2006.01)
*C12N 15/113* (2010.01)
*C12N 15/11* (2006.01)

(52) U.S. Cl.
CPC .......... *C12N 15/113* (2013.01); *C12N 15/111* (2013.01); *C12N 2310/11* (2013.01); *C12N 2310/31* (2013.01); *C12N 2310/314* (2013.01); *C12N 2310/315* (2013.01); *C12N 2310/322* (2013.01); *C12N 2310/3231* (2013.01); *C12N 2310/341* (2013.01); *C12N 2310/345* (2013.01); *C12N 2320/30* (2013.01); *C12N 2320/34* (2013.01); *C12N 2330/30* (2013.01)

(58) Field of Classification Search
None
See application file for complete search history.

(56) References Cited

U.S. PATENT DOCUMENTS

| | | |
|---|---|---|
| 3,687,808 A | 8/1972 | Merlgan et al. |
| 4,415,732 A | 11/1983 | Caruthers et al. |
| 4,458,066 A | 7/1984 | Caruthers et al. |
| 4,469,863 A | 9/1984 | Ts'o et al. |
| 4,476,301 A | 10/1984 | Imbach et al. |
| 4,500,707 A | 2/1985 | Caruthers et al. |
| 4,668,777 A | 5/1987 | Caruthers et al. |
| 4,725,677 A | 2/1988 | Koster et al. |
| 4,845,205 A | 7/1989 | Huynh Dinh et al. |
| 4,973,679 A | 11/1990 | Caruthers et al. |
| 4,981,957 A | 1/1991 | Lebleu et al. |
| 5,013,830 A | 5/1991 | Ohtsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| RE34,069 E | 9/1992 | Koster et al. |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer et al. |
| 5,177,198 A | 1/1993 | Spielvogel et al. |
| 5,185,444 A | 2/1993 | Summerton et al. |
| 5,188,897 A | 2/1993 | Suhadolnik et al. |
| 5,194,599 A | 3/1993 | Froehler et al. |
| 5,214,134 A | 5/1993 | Weis et al. |
| 5,216,141 A | 6/1993 | Benner |
| 5,220,007 A | 6/1993 | Pederson et al. |
| 5,223,618 A | 6/1993 | Cook et al. |
| 5,235,033 A | 8/1993 | Summerton et al. |
| 5,256,775 A | 10/1993 | Froehler |
| 5,264,423 A | 11/1993 | Cohen et al. |
| 5,264,562 A | 11/1993 | Matteucci |
| 5,264,564 A | 11/1993 | Matteucci |
| 5,276,019 A | 1/1994 | Cohen et al. |

(Continued)

FOREIGN PATENT DOCUMENTS

| | | |
|---|---|---|
| WO | WO 1994/002499 | 2/1994 |
| WO | WO 1994/014226 | 6/1994 |

(Continued)

OTHER PUBLICATIONS

Agrawal et al., "Protecting Groups in Oligonucleotide Synthesis" Protocols for Oligonucleotide Conjugates, Humana Press; New Jersey, 1994, 26, 1-71.

(Continued)

*Primary Examiner* — Patrick T Lewis
(74) *Attorney, Agent, or Firm* — McNeill Baur PLCC

(57) ABSTRACT

The present disclosure provides oligomeric compounds comprising at least one α-β-constrained nucleic acid as provided herein. More particularly, the α-β-constrained nucleic acid provided herein comprise an optionally modified nucleoside with a phosphorus containing constrained internucleoside linkage such as for example a cyclic phosphate internucleoside linkage. The α-β-constrained nucleic acid provided herein are expected to be useful for enhancing one or more properties of oligomeric compounds they are incorporated into such as for example nuclease resistance. In certain embodiments, the oligomeric compounds provided herein hybridize to a portion of a target RNA resulting in loss of normal function of the target RNA.

24 Claims, No Drawings
Specification includes a Sequence Listing.

(56) References Cited

U.S. PATENT DOCUMENTS

| | | |
|---|---|---|
| 5,278,302 A | 1/1994 | Caruthers et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,378,825 A | 1/1995 | Cook et al. |
| 5,386,023 A | 1/1995 | Sanghvi et al. |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Summerton et al. |
| 5,405,939 A | 4/1995 | Suhadolnik et al. |
| 5,432,272 A | 7/1995 | Benner |
| 5,434,257 A | 7/1995 | Matteucci et al. |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,491,133 A | 2/1996 | Walder et al. |
| 5,502,177 A | 3/1996 | Matteucci et al. |
| 5,508,270 A | 4/1996 | Baxter et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,555 A | 10/1996 | Froehler et al. |
| 5,567,811 A | 10/1996 | Misiura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci et al. |
| 5,596,091 A | 1/1997 | Switzer |
| 5,597,909 A | 1/1997 | Urdea et al. |
| 5,602,240 A | 2/1997 | Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bischofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci et al. |
| 5,652,355 A | 7/1997 | Metelev et al. |
| 5,652,356 A | 7/1997 | Agrawal et al. |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,700,920 A | 12/1997 | Altmann et al. |
| 5,700,922 A | 12/1997 | Cook |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,847 A | 8/1998 | Buhr et al. |
| 5,830,653 A | 11/1998 | Froehler et al. |
| 6,005,096 A | 12/1999 | Matteucci et al. |
| 6,147,200 A | 11/2000 | Manoharan et al. |
| 6,268,490 B1 | 7/2001 | Imanishi et al. |
| 6,426,220 B1 | 7/2002 | Bennett et al. |
| 6,525,191 B1 | 2/2003 | Ramasamy |
| 6,600,032 B1 | 7/2003 | Manoharan et al. |
| 6,670,461 B1 | 12/2003 | Wengel et al. |
| 6,770,748 B2 | 8/2004 | Imanishi et al. |
| 6,794,499 B2 | 9/2004 | Wengel et al. |
| 6,867,294 B1 | 3/2005 | Sanghvi et al. |
| 7,034,133 B2 | 4/2006 | Wengel et al. |
| 7,053,207 B2 | 5/2006 | Wengel |
| 7,399,845 B2 | 7/2008 | Swayze et al. |
| 7,427,672 B2 | 9/2008 | Imanishi et al. |
| 7,569,686 B1 | 8/2009 | Bhat et al. |
| 7,741,457 B2 | 6/2010 | Seth et al. |
| 8,501,805 B2 | 8/2013 | Seth et al. |
| 8,530,640 B2 | 9/2013 | Seth et al. |
| 8,546,556 B2 | 10/2013 | Seth et al. |
| 9,012,421 B2 | 4/2015 | Migawa et al. |
| 2003/0158403 A1 | 8/2003 | Manoharan et al. |
| 2004/0171570 A1 | 9/2004 | Allerson et al. |
| 2005/0130923 A1 | 6/2005 | Bhat et al. |
| 2007/0287831 A1 | 12/2007 | Seth et al. |
| 2008/0039618 A1 | 2/2008 | Allerson et al. |

FOREIGN PATENT DOCUMENTS

| | | |
|---|---|---|
| WO | WO 1994/017093 | 8/1994 |
| WO | WO 1994/022890 | 10/1994 |
| WO | WO 1998/039352 | 9/1998 |
| WO | WO 1999/014226 | 3/1999 |
| WO | WO 2001/049687 | 7/2001 |
| WO | WO 2002/036743 | 5/2002 |
| WO | WO 2004/106356 | 12/2004 |
| WO | WO 2005/021570 | 3/2005 |
| WO | WO 2005/121371 | 12/2005 |
| WO | WO 2005/121372 | 12/2005 |
| WO | WO 2006/047842 | 5/2006 |
| WO | WO 2007/090071 | 8/2007 |
| WO | WO 2007/134181 | 11/2007 |
| WO | WO 2008/101157 | 8/2008 |
| WO | WO 2008/150729 | 12/2008 |
| WO | WO 2008/154401 | 12/2008 |
| WO | WO 2009/006478 | 1/2009 |
| WO | WO 2009/023855 | 2/2009 |
| WO | WO 2009/135322 | 11/2009 |
| WO | WO 2009/143369 | 11/2009 |
| WO | WO 2010/036696 | 4/2010 |
| WO | WO 2010/036698 | 4/2010 |
| WO | WO 2010/048549 | 4/2010 |
| WO | WO 2010/048585 | 4/2010 |
| WO | WO 2010/077578 | 7/2010 |
| WO | WO 2010/091308 | 8/2010 |
| WO | WO 2010/101951 | 9/2010 |
| WO | WO 2011/115818 | 9/2011 |
| WO | WO 2011/123621 | 10/2011 |

OTHER PUBLICATIONS

Albaek et al., "Analogues of a locked nucleic acid with three-carbon 2',4'-linkages: synthesis by ring-closing metathesis and influence on nucleic acid duplex stability and structure" Journal of Organic Chemistry (2006) 71: 7731-7740.

Altmann et al., "Second-generation antisense oligonucleotides: structure-activity relationships and the design of improved signal-transduction inhibitors" Biochem. Soc. Trans. (1996) 24: 630-637.

(56) References Cited

OTHER PUBLICATIONS

Altmann et al., "Second Generation of Antisense Oligonucleotides: From Nuclease Resistance to Biological Efficacy in Animals" Chimia (1996) 50: 168-176.

Altmann et al., "Second Generation Antisense Oligonucleotides—Inhibition of PKC-a and c-RAF Kinase Expression by Chimeric Oligonucleotides Incorporating 6'-Substituted Carbocyclic Nucleosides and 2'-O-Ethylene Glycol Substituted Ribonucleosides" Nucleosides Nucleotides (1997) 16: 917-926.

Altschul et al., "Basic Local Alignment Search Tool" J. Mol. Biol. (1990) 215: 403-410.

Baker et al., "2'-O-(2-Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells" J. Biol. Chem. (1997) 272: 11944-12000.

Barany et al., "A New Amino Protecting Group Removable by Reduction. Chemistry of the Dithiasuccinoyl (Dts) Function" J. Am. Chem. Soc. (1977) 99: 7363-7365.

Barany et al., "Kinetics and Mechanism of the Thiolytic Removal of the Dithiasuccinoyl (Dts) Amino Protecting Group" J. Am. Chem. Soc. (1980) 102: 3084-3095.

Bass et al., "Double-Stranded RNA as a Template for Gene Silencing" Cell (2000) 101: 235-238.

Beaucage et al., "Advances in the Synthesis of Oligonucleotides by the Phosphoramidite Approach" Tetrahedron, 1992, 48(12): 2223-2311.

Beaucage et al., "The Functionalization of Oligonucleotides Via Phosphoramidite Derivatives" Tetrahedron, 1993, 49(10): 1925-1963.

Beaucage et al., "The Synthesis of Specific Ribomucleotides and Unrelated Phospholylated Biomolecules by the Phosphoramidite Method" Tetrahedron, 1993, 49(46): 10441-10488.

Braasch et al., "Locked nucleic acid (LNA): fine-tuning the recognition of DNA and RNA" Chem. Biol. (2001) 8: 1-7.

Brazma et al., "Gene expression data analysis" FEBS Lett. (2000) 480: 17-24.

Carulli, et al., "High Throughput Analysis of Differential Gene Expression" J. Cell Biochem. Suppl. (1998) 30: 286-96.

Catana et al., "Dioxaphosphorinane-Constrained Nucleic Acid Dinucleotides as Tools for Structural Tuning of Nucleic Acids" Journal of Nucleic Acids, (2012) 93(24): 6657-17.

Catana et al., "Synthesis of Phostone-Constrained Nucleic Acid (P-CAN) Dinucleotides Through Intramolecular Arbuzov's Reaction" Eur. J. Org. Chem., (2011) 34: 6857-6863.

Celis, et al., "Gene expression profiling: monitoring transcription and translation products using DNA microarrays and proteomics" FEBS Lett. (2000) 480: 2-16.

Chattopadhyaya, et al., "Fine tuning of electrostatics around the internucleotidic phosphate through incorporation of modified 2',4'-carbocyclic-LNAs and -ENAs leads to significant modulation of antisense properties." J. Org. Chem. (2009) 74: 118-134.

Chiang et al., "Antisense Oligonucleotides Inhibit Intercellular Adhesion Molecule 1 Expression by Two Distinct Mechanisms" J. Biol. Chem. (1991) 266: 18162-18171.

Clezio et al., "Diastereoselective and Regioselective Synthesis of Conformationally Restricted Thio-dioxa- and Oxo-oxathiaphosphorinane Dinucleotides Featuring Noncanonical α/β Torsion Angle Combinations (α,β-CNAs)" Eur. J. Org. Chem. (2007): 1935-1941.

Clezio et al., "Synthesis and Structure of an α,β-D-CNA Featuring a Noncanonical α/β Torsion Angle Combination within a Tetranucleotide" Eur. J. Org. Chem. (2007): 3894-3900.

Clezio et al., "Diastereoselective synthesis of a conformationally restricted dinucleotide with predefined alpha and beta torsional angles for the construction of alpha,beta-constrained nucleic acids (alpha,beta-CNA)." Organic Letters (2003) 5(2): 161-164.

Conte et al., "Conformational properties and thermodynamics of the RNA duplex r(CGCAAAUUUGCG)2: comparison with the DNA analogue d(CGCAAATTTGCG)2" Nucleic Acids Res. (1997) 25: 2627-2634.

Dupouy et al., "Watson-Crick Base-Pairing Properties of Nucleic Acid Analogues with Stereocontrolled α and β Torsion Angles (α,β-D-CNAs)" Angew. Chem. Int. Ed. (2006) 45: 3623-3627.

Dupouy et al., "Diastereoselective Synthesis of Conformationally Restricted Dinucleotides Featuring Canonical and Noncanonical α/β Torsion Angle Combinations(α,β-D-CNA)" Eur. J. Org. Chem. (2006): 5515-5525.

Dupouy et al. "[alpha], [beta]-D-CAN preorganization of unpaired loop moiety stabilizes DNA hairpin" Chemical Communications (2010) 46(28): 5142.

Egli et al., "RNA Hydration: A Detailed Look" Biochemistry (1996) 35: 8489-8494.

Elayadi et al., "Application of PNA and LNA oligomers to chemotherapy" Curr. Opinion Invens. Drugs (2001) 2: 558-561.

Elbashir et al., "RNA interference is mediated by 21- and 22-nucleotide RNAs" Genes Dev. (2001) 15: 188-200.

Elbashir et al., "Duplexes of 21-nucleotide RNAs mediate RNA interference in cultured mammalian cells" Nature (2001) 411: 494-498.

Englisch et al., "Chemically Modified Oligonucleotides as Probes and Inhibitors" Angewandte Chemie, International Edition (1991) 30: 613-722.

Fire et al., "Potent and specific genetic interference by double-stranded RNA in Caenorhabditis elegans" Nature (1998) 391: 806-811.

Frieden et al., "Expanding the design horizon of antisense oligonucleotides with alpha-L-LNA" Nucleic Acids Research (2003) 21: 6365-6372.

Freier et al., "The ups and downs of nucleic acid duplex stability: structure-stability studies on chemically-modified DNA:RNA duplexes" Nucleic Acids Research (1997) 25(22): 4429-4443.

Fuchs, et al., "Identification of Differentially Expressed Genes by Mutually Subtracted RNA Fingerprinting" Anal. Biochem. (2000) 286: 91-98.

Gait et al., Applications of Chemically synthesized RNA in RNA:Protein Interactions, Smith, Ed., 1998, 1-36.

Gallo et al., "2'-C-Methyluridine phosphoramidite: a new building block for the preparation of RNA analogues canying the 2'-hydroxyl group" Tetrahedron (2001) 57: 5707-5713.

Going et al., "Molecular Pathology and Future Developments" Eur. J. Cancer (1999) 35: 1895-1904.

Gu et al., "Enzymatic Resolution and Base Pairing Properties of D- and L-Cyclohexenyl Nucleic Acids (CeNA)" Nucleosides, Nucleotides & Nucleic Acids (2005) 24(5-7): 993-998.

Gu et al., "Base Pairing Properties of D- and L-Cyclohexene Nucleic Acids (CeNA)" Oligonucleotides (2003) 13(6): 479-489.

Gu et al., "Synthesis of enantiomeric-pure cyclohexenyl nucleoside building blocks for oligonucleotide synthesis" Tetrahedron (2004) 60(9): 2111-2123.

Horváth et al., "Stereoselective synthesis of (–)-ara-cyclohexenyl-adenine" Tetrahedron Letters (2007) 48: 3621-3623.

Jin et al., "Stereoselective Synthesis of Dithymidine Phosphorothioates Using Xylose Derivatives as Chiral Auxiliaries" J. Org. Chem, (1998) 63: 3647-3654.

Jones et al, "RNA Quantitation by Fluorescence-Based Solution Assay: RiboGreen Reagent Characterization" Analytical Biochemistry, (1998) 265: 368-374.

Jungblut, et al., "Proteomics in human disease: Cancer, heart and infectious diseases" Electrophoresis (1999) 20: 2100-10.

Jurecic et al., "Long-distance DD-PCR and cDNA microarrays" Curr. Opin. Microbiol. (2000) 3: 316-21.

Koshkin et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition" Tetrahedron (1998) 54: 3607-3630.

Kumar et al., "The First Analogues of LNA (Locked Nucleic Acids): Phosphorothioate-LNA and 2'-THIO-LNA" Bioorg. Med. Chem. Lett. (1998) 8: 2219-2222.

Larson, et al., "Rapid DNA Fingerprinting of Pathogens by Flow Cytometry" Cytometry (2000) 41: 203-208.

(56) References Cited

OTHER PUBLICATIONS

Larsson, et al., "High-throughput protein expression of cDNA products as a tool in functional genomics" J. Biotechnol. (2000) 80: 143-57.
Lesnik et al., "Relative Thermodynamic Stability of DNA, RNA, and DNA:RNA Hybrid Duplexes: Relationship with Base Composition and Structure" Biochemistry (1995) 34: 10807-10815.
Leumann, C. J., "DNA Analogues: From Supramolecular Principles to Biological Properties" Bioorg. & Med. Chem. (2002) 10: 841-854.
Madden, et al., "Serial analysis of gene expression: from gene discovery to target identification" Drug Discov. Today (2000) 5: 415-425.
Martin et al., "Synthesis, improved antisense activity and structural rationale for the divergent RNA affinities of 3'-fluoro hexitol nucleic acid (FHNA and Ara-FHNA) modified oligonucleotides." J. Am. Chem. Soc (2011) 133(41): 16642-16649.
Martin, P., "Ein neuer Zugang zu 2'-O-Alkylribonucleosiden and Eigenschaften deren Oligonucleotide" Helvetica Chimica Acta (1995) 78(2): 486-504.
Martinez et al., "alpha, beta-D-Constrained Nucleic Acids Are Strong Terminators of Thermostable DNA Polymerases in Polymerase Chaine Reaction." PLoS ONE, 2011, 6(10), published online, 1-8.
Maturano et al., "Synthesis and Structural Study of ribo-Dioxaphorphorinane-Constrained Nucleic Acid Dinucleotides (ribo-]alpha],[beta]-D-CAN)" Eur. J. Org. Chem., 2012, 4, 721-730.
Miura et al., "Fluorometric determination of total mRNA with oligo(dT) immobilized on microtiter plates" Clin. Chem. (1996) 42: 1758-1764.
Montgomery et al., "RNA as a target of double-stranded RNA-mediated genetic interference in Caenorhabditis elegans" Proc. Natl. Acad. Sci. USA (1998) 95: 15502-15507.
Nauwelaerts et al., "Structural Characterization and Biological Evaluation of Small Interfering RNAs Containing Cyclohexenyl Nucleosides" J. Am. Chem. Soc. (2007) 129(30): 9340-9348.
Nauwelaerts et al., "Cyclohexenyl nucleic acids: conformationally flexible oligonucleotides" Nucleic Acids Research (2005) 33(8): 2452-2463.
Nishikura et al., "A Short Primer on RNAi: RNA-Directed RNA Polymerase Acts as a Key Catalyst" Cell (2001) 107: 415-418.
Orum et al., "Locked nucleic acids: A promising molecular family for gene-function analysis and antisense drug development" Curr. Opinion Mol. Ther. (2001) 3: 239-243.
Prakash et al., "2'-O-[2-(amino)-2-oxoethyl] oligonucleotides." Org. Lett. (2003) 5(4): 403-406.
Prashar et al., "READS: A Method for Display of 3'-End Fragments of Restriction Enzyme-Digested cDNAs for Analysis of Differential Gene Expression" Methods Enzymol. (1999) 303: 258-72.
Ravikumar et al., "Development of 2'-O-Methoxyethyl Phosphorothioate Oligonucleotides as Antisense Drugs under Stereochemical Control." Organic Process Research and Development (2002) 6:798-806.
Robeyns et al., "Structure of the Fully Modified Left-Handed Cyclohexene Nucleic Acid Sequence GTGTACAC" J. Am. Chem. Soc. (2008) 130(6): 1979-1984.
Robeyns et al., "Oligonucleotides with cyclohexene-nucleoside building blocks: crystallization and preliminary X-ray studies of a left-handed sequence GTGTACAC" Acta Clystallographica, Section F: Structural Biology and Crystallization Communications (2005) F61(6): 585-586.
Sanghvi, Y.S., "Heterocyclic base modifications in nucleic acids and their applicatins in antisense oligonucleotides." Chapter 15, Antisense Research and Applications, Crooke, S.T. and Lebleu, B., Eds., CRC Press, 1993, 273-288.
Searle et al., "On the stability of nucleic acid structures in solution: enthalpy—entropy compensations, internal rotations and reversibility" Nucleic Acids Res. (1993) 21: 2051-2056.

Seth et al., "Synthesis and biophysical characterization of R-6'-Me-α-L-LNA modified oligonucleotides" Bioorg. Med. Chem. (2011) 21(4): 1122-1125.
Seth et al., "Synthesis and Biophysical Evaluation of 2',4'-Constrained 2'O-Methoxyethyl and 2',4'-Constrained 2'O-Ethyl Nucleic Acid Analogues" (2010) 75: 1569-1581.
Seth et al., "Design, Synthesis and Evaluation of Constrained Methoxyethyl (cMOE) and Constrained Ethyl (cEt) Nucleoside Analogs" (2008) 52(1): 553-554.
Singh et al., "LNA (locked nucleic acids): synthesis and high-affinity nucleic acid recognition" Chem. Commun. (1998) 4: 455-456.
Singh et al., "Synthesis of 2'-Amino-LNA: A Novel Conformationally Restricted High-Affinity Oligonucleotide Analogue with a Handle" J. Org. Chem. (1998) 63: 10035-10039.
Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26): 8362-8379.
Sutcliffe, et al., "TOGA: An automated parsing technology for analyzing expression of nearly all genes" Proc. Natl. Acad. Sci. USA (2000) 97: 1976-81.
Swayze et al., "The Medicinal Chemistry of Oligonucleotides in Antisense a Drug Technology" Chapter 6, pp. 143-182 Crooke, S.T., ed., 2008.
Tabara et al., "RNAi in C. elegans: Soaking in the Genome Sequence" Science (1998) 282: 430-431.
Tijsterman et al., "RNA Helicase MUT-14-Dependent Gene Silencing Triggered in C. elegans by Short Antisense RNAs" Science (2002) 295: 694-697.
Timmons et al., "Specific interference by ingested dsRNA" Nature (1998) 395: 854.
Timmons et al., "Ingestion of bacterially expressed dsRNAs can produce specific and potent genetic interference in Caenorhabditis elegans" Gene (2001) 263: 103-112.
To, "Identification of Differential Gene Expression by High Throughput analysis." Comb. Chem. High Throughput Screen, 2000, 3, 235-41.
Tuschl et al., "Targeted mRNA degradation by double-stranded RNA in vitro" Genes Dev. (1999) 13: 3191-3197.
Verbeure et al., "Rnase H mediated cleavage of RNA by cyclohexene nucleic acid (CeNA)" Nucleic Acids Research (2001) 29(24): 4941-4947.
Wahlestedt et al., "Potent and nontoxic antisense oligonucleotides containing locked nucleic acids" Proc. Natl. Acad. Sci. U. S. A. (2000) 97: 5633-5638.
Wang et al., "Cyclohexene Nuclei Acids (CeNA): Serum Stable Oligonucleotides that Activate Rnase H and Increase Duplex Stability with Complementary RNA" J. Am. Chem. (2000) 122: 8595-8602.
Wang et al., "A Straightforward Stereoselective Synthesis of D- and L-5-Hydroxy-4-hydroxymethyl-2-cyclohexenylguanine" J. Org. Chem. (2001) 66: 8478-82.
Wang et al., "Stereocontrolled Synthesis of Ara-Type Cyclohexenyl Nucleosides" J. Org. Chem. (2003) 68: 4499-4505.
Wang et al., "Cyclohexene Nucleic Acids (CeNA) Form Stable Duplexes with RNA and Induce RNASE H Activity" Nucleosides, Nucleotides & Nucleic Acids (2001) 20(4-7): 785-788.
Wang et al., "A Stereoselective Synthesis of Dinucleotide Phosphorothioates, Using Chiral Indol-oxazaphosphorine Intermediates" Tetrahedron Letters (1997) 38(22): 3797-3800.
Wang et al., "A Stereoselective Synthesis of Dinucleotide Phosphorothioate Triesters through a Chiral Indol-oxazaphosphorine Intermediate" Tetrahedron Letters (1997) 38(5): 705-708.
Wilds et al., "2'-Deoxy-2'-fluoro-beta-D-arabinonucleosides and oligonucleotides (2'F-ANA): synthesis and physicochemical studies." Nucleic Acids Research (2000) 28(18): 3625-3635.
Zhang et al., "PowerBLAST: A New Network BLAST Application for Interactive or Automated Sequence Analysis and Annotation" Genome Res. (1997) 7: 649-656.

OLIGOMERIC COMPOUNDS COMPRISING ALPHA-BETA-CONSTRAINED NUCLEIC ACID

SEQUENCE LISTING

The present application is being filed along with a Sequence Listing in electronic format. The Sequence Listing is provided as a file entitled CHEM0092USASEQ_ST25.txt, created Sep. 28, 2016, which is 264 Kb in size. The information in the electronic format of the sequence listing is incorporated herein by reference in its entirety.

FIELD OF THE INVENTION

The present disclosure provides α-β-constrained nucleic acid and antisense oligomeric compounds prepared therefrom. More particularly, the α-β-constrained nucleic acid provided herein comprise a constrained cyclic phosphorus internucleoside linkage such as a cyclic phosphate that is attached to an optionally modified nucleoside at its 5' position to provide a modified nucleotide. Oligomeric compounds comprising one or more of the α-β-constrained nucleic as provided herein are expected to be useful for modulating gene expression pathways, including those relying on mechanisms of action such as RNaseH, RNAi and dsRNA enzymes, as well as other antisense mechanisms based on target degradation or target occupancy. In certain embodiments, the oligomeric compounds provided herein hybridize to a portion of a target RNA resulting in loss of normal function of the target RNA. One having skill in the art, once armed with this disclosure will be able, without undue experimentation, to identify, prepare and exploit antisense compounds for these uses.

BACKGROUND OF THE INVENTION

Antisense technology is an effective means for reducing the expression of one or more specific gene products and can therefore prove to be uniquely useful in a number of therapeutic, diagnostic, and research applications. Chemically modified nucleosides are routinely used for incorporation into antisense compounds to enhance one or more properties, such as nuclease resistance, pharmacokinetics or affinity for a target RNA. In 1998, the antisense compound, Vitravene® (fomivirsen; developed by Isis Pharmaceuticals Inc., Carlsbad, Calif.) was the first antisense drug to achieve marketing clearance from the U.S. Food and Drug Administration (FDA), and is currently a treatment of cytomegalovirus (CMV)-induced retinitis in AIDS patients. More recently, Kynamro™ (Mipomersen sodium injectable; developed by Isis Pharmaceuticals Inc., Carlsbad, Calif.) has achieved marketing clearance (2013) from the U.S. Food and Drug Administration (FDA), and is currently a treatment of homozygous familial hypercholesterolemia (HoFH).

New chemical modifications have improved the potency and efficacy of antisense compounds, uncovering the potential for oral delivery as well as enhancing subcutaneous administration, decreasing potential for side effects, and leading to improvements in patient convenience. Chemical modifications increasing potency of antisense compounds allow administration of lower doses, which reduces the potential for toxicity, as well as decreasing overall cost of therapy. Modifications increasing the resistance to degradation result in slower clearance from the body, allowing for less frequent dosing. Different types of chemical modifications can be combined in one compound to further optimize the compound's efficacy.

The diastereoselective synthesis and characterization of dinucleotides containing a cyclic phosphate or cyclic phosphonate internucleoside linkage have been reported (see Clezio et al., Organic Letters, 2003, 5(2), 161-164 Dupouy et al., Eur. J. Org. Chem., 2006, 5515-5525; and Catana, et al., Eur. J. Org. Chem., 2011, 34, 6857-6863).

The synthesis of DNA dinucleotides containing a cyclic phosphate internucleoside linkage has been described (see Clezio et al., Eur. J. Org. Chem., 2007, 1935-1941).

The synthesis of dinucleotides including 2'-H, 2'-OH and 2'-OCH$_3$ modified nucleosides and containing a cyclic phosphate internucleoside linkage has been described. The dimers were analyzed by X-ray crystallography and NMR spectroscopy (see Maturano et al., Eur. J. Org. Chem., 2012, 4, 721-730).

The diastereoselective synthesis and characterization of tetranucleotides containing a cyclic phosphate internucleoside linkage have been reported (see Clezio et al., Eur. J. Org. Chem., 2007, 3894-3900).

The introduction of α,β-D-CNA (constrained nucleic acid) within oligonucleotides has previously been shown to stabilize the duplex DNA (see Dupouy et al., Organic & Biomolecular Chemistry, 2008, 6(16), 2894-2851).

The synthesis of deoxyribo-dinucleotides containing a cyclic phosphate internucleoside linkage and their incorporation into oligomeric compounds has been described. The Tm values of the duplexes with their DNA or RNA complements have also been reported (see Dupouy et al., Angew. Chem. Int. Ed., 2006, 45, 3623-3627).

The synthesis of DNA with cyclic phosphate internucleoside linkages to study the effect such linkages would have on polymerase chain reaction (PCR, see Martinez et al., PLoS ONE, 2011, 6(10), published online, 1-8).

BRIEF SUMMARY OF THE INVENTION

Disclosed herein are novel α-β-constrained nucleic acid and antisense oligomeric compounds prepared therefrom. More particularly, the α-β-constrained nucleic acid provided herein comprise a constrained cyclic phosphorus internucleoside linkage such as a cyclic phosphate that is attached to an optionally modified nucleoside at the 5' position. The constrained cyclic phosphorus internucleoside linkage is further attached to a monomer subunit to facilitate incorporation of the modified nucleotide into an oligomeric compound. In certain embodiments, the oligomeric compounds provided herein are hybridize to a portion of a target RNA resulting in loss of normal function of the target RNA.

The variables are defined individually in further detail herein. It is to be understood that the oligomeric compounds comprising at least one region of α,β-constrained nucleic acid as provided herein include all combinations of the embodiments disclosed and variables defined herein.

In certain embodiments, oligomeric compounds are provided comprising at least one modified nucleotide having Formula I:

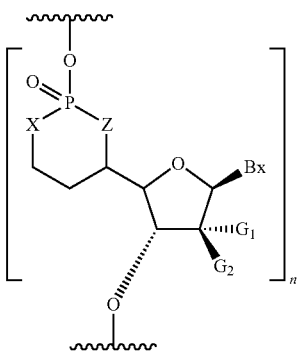

I wherein independently for each modified nucleotide having Formula I:
each Bx is a heterocyclic base moiety;
each $G_1$ and $G_2$ is, independently, H, OH or a 2'-sugar substituent group;
one of each X and each Z is $CJ_1J_2$, $NJ_2$, S or O and the other of each X and each Z is O;
each $J_1$ and $J_2$ is, independently, H, $C_1$-$C_6$ alkyl, $C_2$-$C_6$ alkenyl or $C_2$-$C_6$ alkynyl;
each n is, independently, from 1 to about 30; and
when Z is O and X is O then at least one $G_1$ and $G_2$ is other than H, OH or $OCH_3$ and when Z is O and X is $CH_2$ or S then at least one $G_1$ and $G_2$ is other than H.

In certain embodiments, oligomeric compounds are provided comprising from 8 to 40 linked monomer subunits wherein at least one of the monomer subunits is a modified nucleotide having Formula II:

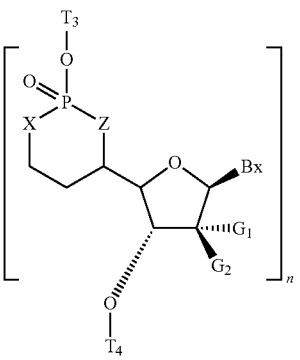

II wherein independently for each modified nucleotide having Formula II:
$T_3$ is attached to one of the linked monomer subunits;
$T_4$ is H, a hydroxyl protecting group, a linked conjugate group or an internucleoside linking group attached to one of the linked monomer subunits;
each Bx is a heterocyclic base moiety;
each $G_1$ and $G_2$ is, independently, H, OH or a 2'-sugar substituent group;
one of each X and each Z is $CJ_1J_2$, $NJ_2$, S or O and the other of each X and each Z is O;
each $J_1$ and $J_2$ is, independently, H, $C_1$-$C_6$ alkyl, $C_2$-$C_6$ alkenyl or $C_2$-$C_6$ alkynyl;
each n is, independently, from 1 to about 30; and
when Z is O and X is O then at least one $G_1$ and $G_2$ is other than H, OH or $OCH_3$ and when Z is O and X is $CH_2$ or S then at least one $G_1$ and $G_2$ is other than H.

In certain embodiments, each X is O. In certain embodiments, each X is $CJ_1J_2$. In certain embodiments, each X is $CH_2$. In certain embodiments, each X is S. In certain embodiments, each X is $NJ_1$. In certain embodiments, each $J_1$ is H or $CH_3$.

In certain embodiments, each Z is O. In certain embodiments, each Z is $CJ_1J_2$. In certain embodiments, each Z is $CH_2$. In certain embodiments, each Z is S. In certain embodiments, each Z is $NJ_1$. In certain embodiments, each $J_1$ is H or $CH_3$.

In certain embodiments, one of each $G_1$ and each $G_2$ is H and the other of each $G_1$ and each $G_2$ is, independently, selected from halogen and O—$[C(R_1)(R_2)]_i$—$[(C=O)_m$-$A]_j$-T;
each $R_1$ and $R_2$ is, independently, H, $C_1$-$C_6$ alkyl or halogen;
A is O, S or $N(E_1)$;
T is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;
$E_1$, $E_2$ and $E_3$ are each, independently, H, $C_1$-$C_6$ alkyl or substituted $C_1$-$C_6$ alkyl;
i is from 1 to about 6;
m is 0 or 1;
j is 0 or 1;
wherein each substituted group comprises one or more optionally protected substituent groups independently selected from halogen, $OJ_3$, $N(J_3)(J_4)$, =$NJ_3$, $SJ_3$, $N_3$, CN, $OC(=L_2)J_3$, $OC(=L_2)N(J_3)(J_4)$ and $C(=L_2)N(J_3)(J_4)$;
$L_2$ is O, S or $NJ_5$;
each $J_3$, $J_4$ and $J_5$ is, independently, H or $C_1$-$C_6$ alkyl; and
when j is 1 then T is other than halogen.

In certain embodiments, one of each $G_1$ and each $G_2$ is H and the other of each $G_1$ and each $G_2$ is, independently, selected from halogen, $OCH_3$, $OCH_2F$, $OCHF_2$, $OCF_3$, $OCH_2CH_3$, $O(CH_2)_2F$, $OCH_2CHF_2$, $OCH_2CF_3$, $OCH_2$—CH=$CH_2$, $O(CH_2)_2$—$OCH_3$, $O(CH_2)_2$—$SCH_3$, $O(CH_2)_2$—$OCF_3$, $O(CH_2)_3$—$N(R_3)(R_4)$, $O(CH_2)_2$—$ON(R_3)(R_4)$, $O(CH_2)_2$—$O(CH_2)_2$—$N(R_3)(R_4)$, $OCH_2C(=O)$—$N(R_4)(R_4)$, $OCH_2C(=O)$—$N(R_5)$—$(CH_2)_2$—$N(R_3)(R_4)$ and $O(CH_2)_2$—$N(R_5)$—$C(=NR_6)[N(R_3)(R_4)]$ wherein $R_3$, $R_4$, $R_5$ and $R_6$ are each, independently, H or $C_1$-$C_6$ alkyl. In certain embodiments, one of each $G_1$ and each $G_2$ is H and the other of each $G_1$ and each $G_2$ is, independently, selected from halogen, $OCH_3$, $OCF_3$, $OCH_2CH_3$, $OCH_2CF_3$, $OCH_2$—CH=$CH_2$, $O(CH_2)_2$—$OCH_3$, $O(CH_2)_2$—$O(CH_2)_2$—$N(CH_3)_2$, $OCH_2C(=O)$—$N(H)CH_3$, $OCH_2C(=O)$—$N(H)$—$(CH_2)_2$—$N(CH_3)_2$ and $OCH_2$—$N(H)$—$C(=NH)NH_2$. In certain embodiments, one of each $G_1$ and each $G_2$ is H and the other of each $G_1$ and each $G_2$ is, independently, selected from F, $OCH_3$, $O(CH_2)_2$—$OCH_3$ or $OCH_2C(=O)$—$N(H)CH_3$. In certain embodiments, each $G_1$ is $O(CH_2)_2$—$OCH_3$ and each $G_2$ is H. In certain embodiments, each $G_1$ and $G_2$ is H. In certain embodiments, each $G_2$ is H.

In certain embodiments, each Bx is, independently, an optionally protected pyrimidine, substituted pyrimidine, purine or substituted purine. In certain embodiments, each Bx is, independently, uracil, thymine, cytosine, 4-N-benzoylcytosine, 5-methylcytosine, 4-N-benzoyl-5-methylcytosine, adenine, 6-N-benzoyladenine, guanine or 2-N-isobutyrylguanine.

In certain embodiments, each of said at least one modified nucleotide having Formula I has the configuration of Formula Ia, Ib, Ic or Id:

Ia

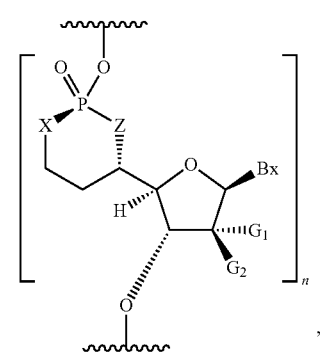

,

Ib

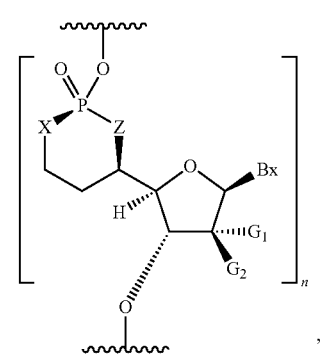

,

Ic

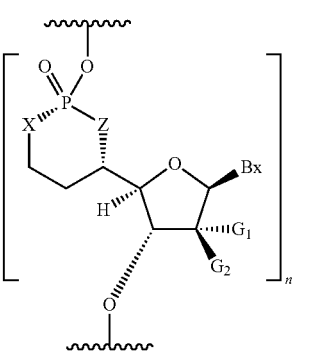

or

Id

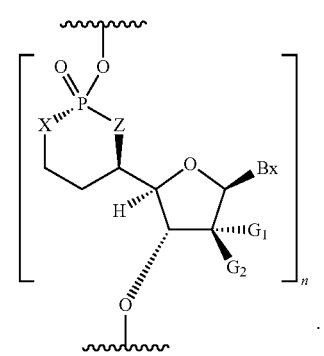

.

In certain embodiments, each of said at least one modified nucleotide having Formula I has the configuration of Formula Ia. In certain embodiments, each of said at least one modified nucleotide having Formula I has the configuration of Formula Ib. In certain embodiments, each of said at least one modified nucleotide having Formula I has the configuration of Formula Ic. In certain embodiments, each of said at least one modified nucleotide having Formula I has the configuration of Formula Id. In certain embodiments, each $G_1$ and $G_2$ is H, each X and Z is O, and each n is 1. In certain embodiments, oligomeric compounds are provided comprising only one modified nucleotide of Formula I.

In certain embodiments, the monomer subunits and the at least one modified nucleotide having Formula I are linked together by internucleoside linking groups selected from phosphodiester and phosphorothioate internucleoside linking groups. In certain embodiments, each internucleoside linking group is a phosphorothioate internucleoside linking group.

In certain embodiments, each of said at least one modified nucleotide having Formula II has the configuration of Formula IIa, IIb, IIc or IId:

IIa

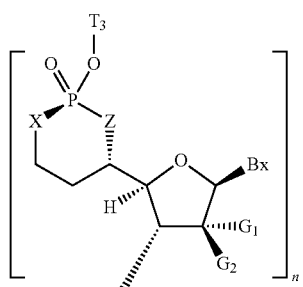

,

IIb

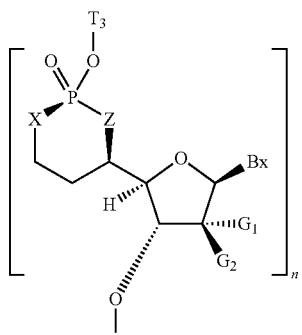

,

IIc

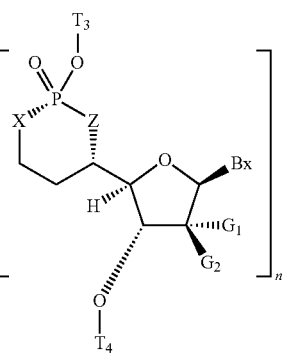

or

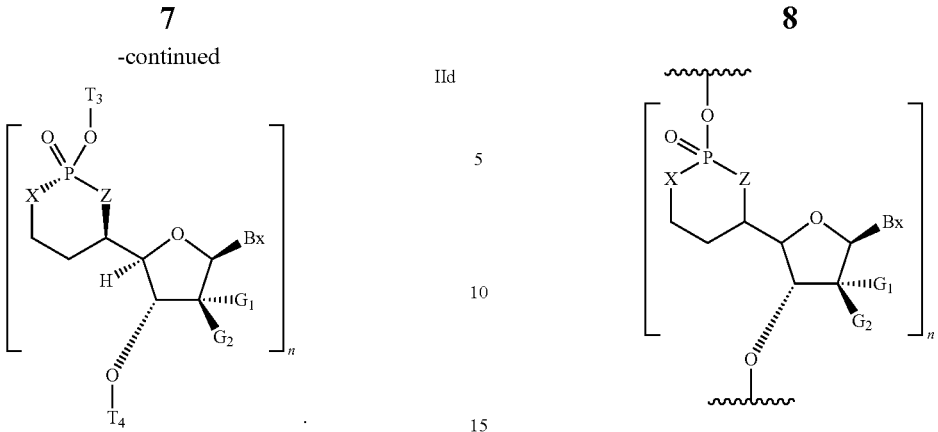

IId

In certain embodiments, each of said at least one modified nucleotide having Formula II has the configuration of Formula IIa. In certain embodiments, each of said at least one modified nucleotide having Formula II has the configuration of Formula IIb. In certain embodiments, each of said at least one modified nucleotide having Formula II has the configuration of Formula IIc In certain embodiments, each of said at least one modified nucleotide having Formula II has the configuration of Formula IId.

In certain embodiments, $T_3$ is attached to a 3'-position of a β-D-ribonucleoside, β-D-2'-deoxyribonucleoside or a modified nucleoside. In certain embodiments, $T_3$ is attached to a modified nucleoside comprising a substituted nucleoside or a bicyclic nucleoside. In certain embodiments, $T_3$ is attached to a modified nucleoside comprising a nucleoside having sugar surrogate.

In certain embodiments, $T_4$ is H, a hydroxyl protecting group or a linked conjugate group. In certain embodiments, $T_4$ is a phosphodiester or phosphorothioate internucleoside linkage attached to the terminal 5'-position of said one or more linked monomer subunits.

In certain embodiments, the monomer subunits and the at least one modified nucleotide having Formula II are linked together by internucleoside linking groups selected from phosphodiester and phosphorothioate internucleoside linking groups. In certain embodiments, each internucleoside linking group is a phosphorothioate internucleoside linking group.

In certain embodiments, methods of inhibiting gene expression are provided comprising contacting a cell with an oligomeric compound as provided herein wherein said oligomeric compound comprises from about 8 to about 40 monomeric subunits and is complementary to a target RNA.

In certain embodiments, antisense gapped oligomeric compounds are provided comprising:

a first region of from 1 to about 5 contiguous monomer subunits;

a second region of from 1 to about 5 contiguous monomer subunits; and a third region located between the first and second region comprising from 6 to about 14 monomer subunits;

wherein each monomer subunit in the first and second region is, independently, a modified nucleoside and each monomer subunit in the third region is, independently, a nucleoside or a modified nucleoside other than the modified nucleosides in the first and second region and wherein the third region comprises at least one modified nucleotide having Formula I:

wherein independently for each modified nucleotide having Formula I:

each Bx is a heterocyclic base moiety;

each $G_1$ and $G_2$ is, independently, H, OH or a 2'-sugar substituent group;

each X or each Z is $CJ_1J_2$, $NJ_1$, S or O and the other of each X or each Z is O;

each $J_1$ and $J_2$ is, independently, H, $C_1$-$C_6$ alkyl, $C_2$-$C_6$ alkenyl or $C_2$-$C_6$ alkynyl; and n is from 1 to about 3.

In certain embodiments, each X is O. In certain embodiments, each X is $CJ_1J_2$ In certain embodiments, each X is $CH_2$. In certain embodiments, each X is S. In certain embodiments, each X is $NJ_1$. In certain embodiments, each $J_1$ is H or $CH_3$.

In certain embodiments, antisense gapped oligomeric compounds are provided comprising:

a first region of from 1 to about 5 contiguous monomer subunits;

a second region of from 1 to about 5 contiguous monomer subunits; and a third region located between the first and second region comprising from 6 to about 14 monomer subunits;

wherein each monomer subunit in the first and second region is, independently, a modified nucleoside and each monomer subunit in the third region is, independently, a nucleoside or a modified nucleoside other than the modified nucleosides in the first and second region and wherein the third region comprises at least one modified nucleotide having Formula III:

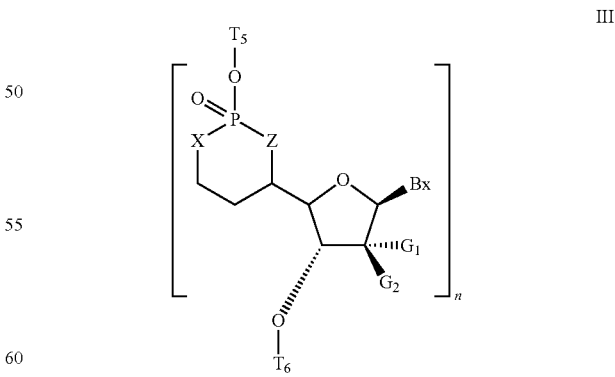

III wherein independently for each modified nucleotide having Formula III:

$T_5$ is attached to one of the monomer subunits;

$T_6$ is an internucleoside linking group attached to one of the monomer subunits;

each Bx is a heterocyclic base moiety;

each $G_1$ and $G_2$ is, independently, H, OH or a 2'-sugar substituent group;

each X or each Z is $CJ_1J_2$, $NJ_1$, S or O and the other of each X or each Z is O;

each $J_1$ and $J_2$ is, independently, H, $C_1$-$C_6$ alkyl, $C_2$-$C_6$ alkenyl or $C_2$-$C_6$ alkynyl; and n is from 1 to about 3.

In certain embodiments, each Z is O. In certain embodiments, each Z is $CJ_1J_2$. In certain embodiments, each Z is $CH_2$. In certain embodiments, each Z is S. In certain embodiments, each Z is $NJ_1$. In certain embodiments, each $J_1$ is H or $CH_3$.

In certain embodiments, one of $G_1$ and $G_2$ is H and the other of $G_1$ and $G_2$ is, independently, selected from halogen and O—$[C(R_1)(R_2)]_i$—$[(C=O)_m$-$A]_j$-T;

each $R_1$ and $R_2$ is, independently, H, $C_1$-$C_6$ alkyl or halogen;

A is O, S or $N(E_1)$;

T is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

i is from 1 to about 6;

m is 0 or 1;

j is 0 or 1;

wherein each substituted group comprises one or more optionally protected substituent groups independently selected from halogen, $OJ_3$, $N(J_3)(J_4)$, $=NJ_3$, $SJ_3$, $N_3$, CN, $OC(=L_2)J_3$, $OC(=L_2)N(J_3)(J_4)$ and $C(=L_2)N(J_3)(J_4)$;

$L_2$ is O, S or $NJ_5$;

each $J_3$, $J_4$ and $J_5$ is, independently, H or $C_1$-$C_6$ alkyl; and when j is 1 then T is other than halogen.

In certain embodiments, for each modified nucleotide of Formula I, one of $G_1$ and $G_2$ is H and the other of $G_1$ and $G_2$ is, independently, selected from F, $OCH_3$, $O(CH_2)_2$—$OCH_3$ or $OCH_2C(=O)$—$N(H)CH_3$. In certain embodiments, for each modified nucleotide of Formula I, $G_1$ is $O(CH_2)_2$—$OCH_3$ and $G_2$ is H. In certain embodiments, each $G_1$ and $G_2$ is H.

In certain embodiments, for each modified nucleotide of Formula III, one of $G_1$ and $G_2$ is H and the other of $G_1$ and $G_2$ is, independently, selected from halogen and O—$[C(R_1)(R_2)]_i$—$[(C=O)_m$-$A]_j$-T;

each $R_1$ and $R_2$ is, independently, H, $C_1$-$C_6$ alkyl or halogen;

A is O, S or $N(E_1)$;

T is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

i is from 1 to about 6;

m is 0 or 1;

j is 0 or 1;

wherein each substituted group comprises one or more optionally protected substituent groups independently selected from halogen, $OJ_3$, $N(J_3)(J_4)$, $=NJ_3$, $SJ_3$, $N_3$, CN, $OC(=L_2)J_3$, $OC(=L_2)N(J_3)(J_4)$ and $C(=L_2)N(J_3)(J_4)$;

$L_2$ is O, S or $NJ_5$;

each $J_3$, $J_4$ and $J_5$ is, independently, H or $C_1$-$C_6$ alkyl; and when j is 1 then T is other than halogen.

In certain embodiments, for each modified nucleotide of Formula III, one of $G_1$ and $G_2$ is H and the other of $G_1$ and $G_2$ is, independently, selected from F, $OCH_3$, $O(CH_2)_2$—$OCH_3$ or $OCH_2C(=O)$—$N(H)CH_3$. In certain embodiments, for each modified nucleotide of Formula III, $G_1$ is $O(CH_2)_2$—$OCH_3$ and $G_2$ is H. In certain embodiments, for each modified nucleotide of Formula III, X and Z are each O and $G_1$ and $G_2$ are each H.

In certain embodiments, gapped oligomeric compounds are provided comprising only one modified nucleotide of Formula III. In certain embodiments, gapped oligomeric compounds are provided wherein one modified nucleotide of Formula III is located at the 5' end of the third region. In certain embodiments, gapped oligomeric compounds are provided wherein one modified nucleotide of Formula III is located at the 3' end of the third region. In certain embodiments, gapped oligomeric compounds are provided wherein each monomer subunit in the third region that is not a modified nucleotide having Formula III is a β-D-2'-deoxyribonucleoside.

In certain embodiments, for each modified nucleotide of Formula I, X and Z are each O and $G_1$ and $G_2$ are each H.

In certain embodiments, each Bx is, independently, an optionally protected pyrimidine, substituted pyrimidine, purine or substituted purine. In certain embodiments, each Bx is, independently, uracil, thymine, cytosine, 4-N-benzoylcytosine, 5-methylcytosine, 4-N-benzoyl-5-methylcytosine, adenine, 6-N-benzoyladenine, guanine or 2-N-isobutyrylguanine.

In certain embodiments, gapped oligomeric compounds are provided comprising only one modified nucleotide of Formula I. In certain embodiments, gapped oligomeric compounds are provided comprising one modified nucleotide of Formula I located at the 5' end of the third region. In certain embodiments, gapped oligomeric compounds are provided comprising one modified nucleotide of Formula I located at the 3' end of the third region. In certain embodiments, each monomer subunit in the third region is a β-D-2'-deoxyribonucleoside.

In certain embodiments, gapped oligomeric compounds are provided wherein each n is 1.

In certain embodiments, gapped oligomeric compounds are provided wherein the third region comprises from 8 to 13 β-D-2'-deoxyribonucleosides. In certain embodiments, gapped oligomeric compounds are provided wherein the third region comprises from 8 to 9 β-D-2'-deoxyribonucleosides.

In certain embodiments, gapped oligomeric compounds are provided wherein the first and second regions each, independently, have from 2 to 3 monomer subunits. In certain embodiments, the first and second regions each, independently, have from 4 to 5 monomer subunits. In certain embodiments, the first and second regions each, independently, have from 3 to 5 monomer subunits and the third region has from 8 to 13 β-D-2'-deoxyribonucleosides.

In certain embodiments, the monomer subunits in the first and second regions are, each independently, selected from bicyclic nucleosides, 2'-modified nucleosides, 4'-thio modified nucleosides and 4'-thio-2'-modified nucleosides. In certain embodiments, each of the monomer subunits in the first and second regions are 2'-modified nucleosides having a 2'-substituent group independently selected from 2'-F, 2'-$OCH_3$ and 2'-$O(CH_2)_2$—$OCH_3$. In certain embodiments, each of the monomer subunits in the first and second regions are, independently, a 2'-modified nucleoside having a 2'-substituent group independently selected from 2'-F, 2'-$OCH_3$ and 2'-$O(CH_2)_2$—$OCH_3$ or a bicyclic nucleoside. In certain embodiments, each of the monomer subunits in the first and second regions are, independently, a 2'-O(CH$_2$)$_2$—OCH$_3$ modified nucleoside or a constrained ethyl bicyclic nucleoside having a 4'-CH—[(S)—CH$_3$)]—O-2' bridging group or a 4'-CH—[(R)—CH$_3$)]—O-2' bridging group.

In certain embodiments, gapped oligomeric compounds are provided comprising from 10 to about 21 monomer subunits. In certain embodiments, gapped oligomeric compounds are provided comprising from about 14 to about 19 monomer subunits.

In certain embodiments, gapped oligomeric compounds are provided wherein the monomer subunits and the at least one modified nucleotide having Formula I are linked together by internucleoside linking groups selected from phosphodiester and phosphorothioate internucleoside linking groups. In certain embodiments, each internucleoside linking group is a phosphorothioate internucleoside linking group.

In certain embodiments, gapped oligomeric compounds are provided wherein the monomer subunits and the at least one modified nucleotide having Formula III are linked together by internucleoside linking groups selected from phosphodiester and phosphorothioate internucleoside linking groups. In certain embodiments, gapped oligomeric compounds are provided wherein the monomer subunits and the at least one modified nucleotide having Formula III are linked together by phosphorothioate internucleoside linking groups.

In certain embodiments, gapped oligomeric compounds are provided wherein each of said at least one modified nucleotide having Formula I has the configuration of Formula Ia, Ib, Ic or Id:

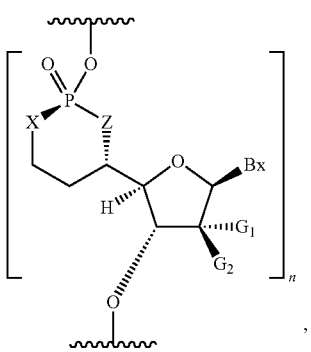

Ia

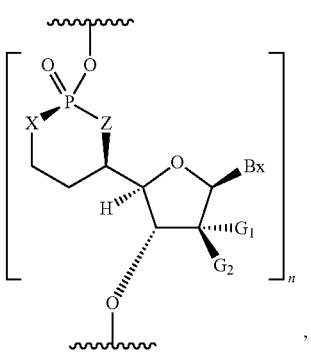

Ib

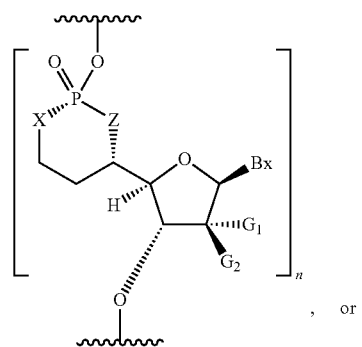

Ic, or

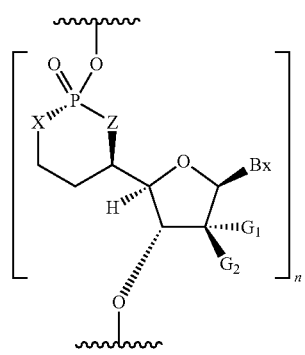

Id

In certain embodiments, gapped oligomeric compounds are provided wherein each of said at least one modified nucleotide having Formula I has the configuration of Formula Ia. In certain embodiments, each of said at least one modified nucleotide having Formula I has the configuration of Formula Ib. In certain embodiments, each of said at least one modified nucleotide having Formula I has the configuration of Formula Ic. In certain embodiments, each of said at least one modified nucleotide having Formula I has the configuration of Formula Id.

In certain embodiments, gapped oligomeric compounds are provided wherein each of said at least one modified nucleotide having Formula III has the configuration of Formula IIIa, IIIb, IIIc or IIId:

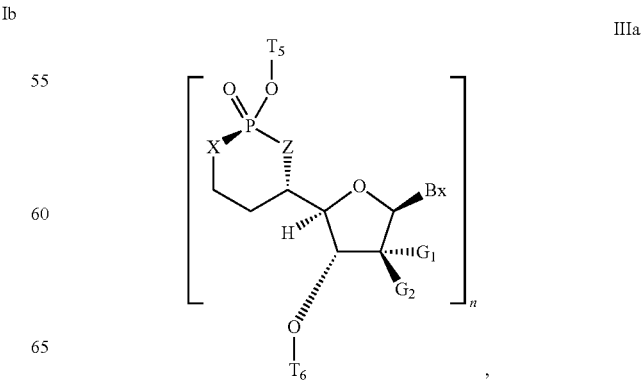

IIIa

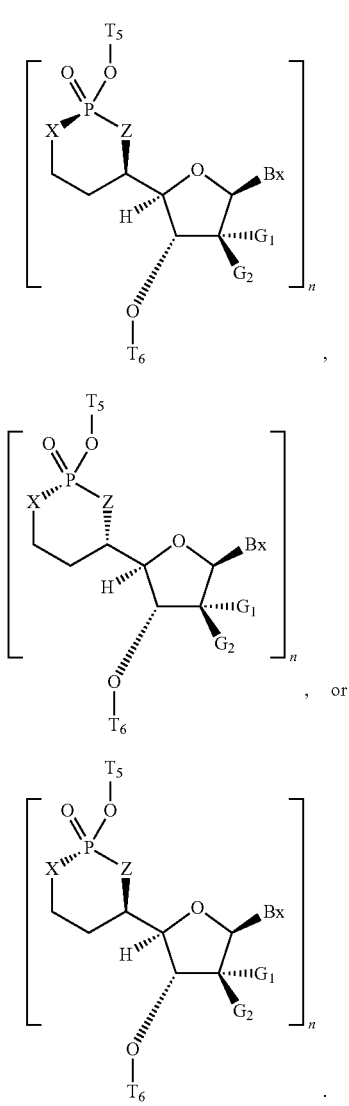

IIIb

IIIc

, or

IIId

In certain embodiments, each of said at least one modified nucleotide having Formula III has the configuration of Formula IIIa. In certain embodiments, each of said at least one modified nucleotide having Formula III has the configuration of Formula IIIb. In certain embodiments, each of said at least one modified nucleotide having Formula III has the configuration of Formula IIIc. In certain embodiments, each of said at least one modified nucleotide having Formula III has the configuration of Formula IIId.

In certain embodiments, gapped oligomeric compounds are provided comprising only one modified nucleotide of Formula III.

In certain embodiments, gapped oligomeric compounds are provided wherein each $G_1$ and $G_2$ is H, each X and Z is O, and each n is 1. In certain embodiments, gapped oligomeric compounds are provided wherein each $G_1$ and $G_2$ is H, each X and Z is O, and each n is 1.

In certain embodiments, gapped oligomeric compounds are provided comprising only one modified nucleotide of Formula I. In certain embodiments, gapped oligomeric compounds are provided comprising only one modified nucleotide of Formula I wherein each $G_1$ and $G_2$ is H, each X and Z is O, and each n is 1. In certain embodiments, gapped oligomeric compounds are provided comprising only one modified nucleotide of Formula I having the configuration of Formula Ia wherein each $G_1$ and $G_2$ is H, each X and Z is O, and each n is 1. In certain embodiments, gapped oligomeric compounds are provided comprising only one modified nucleotide of Formula I having the configuration of Formula Ib wherein each $G_1$ and $G_2$ is H, each X and Z is O, and each n is 1. In certain embodiments, gapped oligomeric compounds are provided comprising only one modified nucleotide of Formula I having the configuration of Formula Ic wherein each $G_1$ and $G_2$ is H, each X and Z is O, and each n is 1. In certain embodiments, gapped oligomeric compounds are provided comprising only one modified nucleotide of Formula I having the configuration of Formula Id wherein each $G_1$ and $G_2$ is H, each X and Z is O, and each n is 1.

In certain embodiments, methods of inhibiting gene expression are provided comprising contacting a cell with an oligomeric compound as provided herein. In certain embodiments, methods of inhibiting gene expression are provided comprising contacting a cell with an oligomeric compound as provided herein wherein said oligomeric compound comprises from about 8 to about 40 monomeric subunits and is complementary to a target RNA. In certain embodiments, the cell is in an animal. In certain embodiments, the cell is in a human. In certain embodiments, the target RNA is selected from mRNA, pre-mRNA and micro RNA. In certain embodiments, the target RNA is mRNA. In certain embodiments, the target RNA is human mRNA. In certain embodiments, the target RNA is cleaved thereby inhibiting its function. In certain embodiments, the method further comprises detecting the levels of target RNA.

In certain embodiments, an in vitro method of inhibiting gene expression is provided comprising contacting one or more cells or a tissue with an oligomeric compound as provided herein.

In certain embodiments, oligomeric compounds are provided for use in an in vivo method of inhibiting gene expression said method comprising contacting one or more cells, a tissue or an animal with an oligomeric compound as provided herein.

DETAILED DESCRIPTION OF THE INVENTION

Provided herein are novel α-β-constrained nucleic acid and oligomeric compounds prepared therefrom. The novel α-β-constrained nucleic acid are expected to be useful for enhancing one or more properties of the oligomeric compounds they are incorporated into such as for example nuclease resistance. In certain embodiments, the oligomeric compounds provided herein hybridize to a portion of a target RNA resulting in loss of normal function of the target RNA.

In certain embodiments, the α-β-constrained nucleic acid provided herein are incorporated into antisense oligomeric compounds which are used to reduce target RNA, such as messenger RNA, in vitro and in vivo. The reduction of target RNA can be effected via numerous pathways with a resultant modulation of gene expression. Such modulation can provide direct or indirect increase or decrease in a particular target (nucleic acid or protein). Such pathways include for example the steric blocking of transcription or translation and cleavage of mRNA using either single or double stranded oligomeric compounds. The oligomeric compounds provided herein are also expected to be useful as primers and probes in diagnostic applications. In certain embodiments, oligomeric compounds comprising at least one region of α-β-constrained nucleic acid as provided herein are expected to be useful as aptamers which are oligomeric compounds capable of binding to aberrant proteins in an in vivo setting.

In certain embodiments, oligomeric compounds are provided comprising at least one modified nucleotide having Formula I:

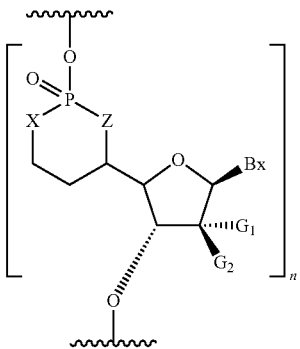

wherein independently for each modified nucleotide having Formula I:

each Bx is a heterocyclic base moiety;
each $G_1$ and $G_2$ is, independently, H, OH or a 2'-sugar substituent group;
one of each X and each Z is $CJ_1J_2$, $NJ_2$, S or O and the other of each X and each Z is O;
each $J_1$ and $J_2$ is, independently, H, $C_1$-$C_6$ alkyl, $C_2$-$C_6$ alkenyl or $C_2$-$C_6$ alkynyl;
each n is, independently, from 1 to about 30; and
when Z is O and X is O then at least one $G_1$ and $G_2$ is other than H, OH or $OCH_3$ and when Z is O and X is $CH_2$ or S then at least one $G_1$ and $G_2$ is other than H.

In certain embodiments, antisense gapped oligomeric compounds are provided comprising:

a first region of from 1 to about 5 contiguous monomer subunits;
a second region of from 1 to about 5 contiguous monomer subunits; and
a third region located between the first and second region comprising from 6 to about 14 monomer subunits;
wherein each monomer subunit in the first and second region is, independently, a modified nucleoside and each monomer subunit in the third region is, independently, a nucleoside or a modified nucleoside other than the modified nucleosides in the first and second region and wherein the third region comprises at least one modified nucleotide having Formula I:

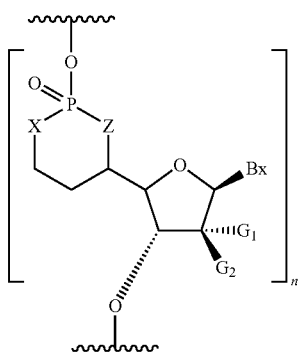

wherein independently for each modified nucleotide having Formula I:

each Bx is a heterocyclic base moiety;
each $G_1$ and $G_2$ is, independently, H, OH or a 2'-sugar substituent group;
each X or each Z is $CJ_1J_2$, $NJ_1$, S or O and the other of each X or each Z is O;
each $J_1$ and $J_2$ is, independently, H, $C_1$-$C_6$ alkyl, $C_2$-$C_6$ alkenyl or $C_2$-$C_6$ alkynyl; and
n is from 1 to about 3.

In certain embodiments, a modified nucleotide having Formula I is prepared by reaction of a phosphoramidite with an intermediate that will provide the cyclic internucleoside linkage and a 5' monomer subunit which is the residue of the phosphoramidite. The use of any phosphoramidite provides for inclusion of numerous different monomer subunits into a modified nucleotide having Formula I. In certain embodiments, other reactive phosphorus groups as known in the art can be used in place of a phosphoramidite group to affect the coupling. Numerous examples of such couplings are provided herein.

The modified nucleotides having Formula I can encompass the entirety of the oligomeric compound such that each internucleoside linkage is a cyclic constrained phosphate or analog thereof as provided herein or can be incorporated as dimers (single cyclic linkage), trimers (two cyclic linkages) or larger blocks at predetermined positions within an oligomeric compound. The variability of incorporation of the blocks having the cyclic internucleoside linkages coupled with the various chemical modifications that can be applied to each of these blocks provide a broad platform for the preparation of oligomeric compounds designed for specific applications. As illustrated in the example section, the stereochemistry of various sites can also be optimized for a specific target or application.

Incorporation of one or more region of α-β-constrained nucleic acid, as provided herein, into an oligomeric compound is expected to enhance one or more desired properties of the resulting oligomeric compound. Such properties include without limitation stability, nuclease resistance, binding affinity, specificity, absorption, cellular distribution, cellular uptake, charge, pharmacodynamics and pharmacokinetics.

As used herein the term "motif" refers to the pattern created by the relative positioning of monomer subunits within an oligomeric compound wherein the pattern is determined by comparing the sugar moieties of the linked monomer subunits. The only determinant for the motif of an oligomeric compound is the differences or lack of differences between the sugar moieties. The internucleoside linkages, heterocyclic bases and further groups such as terminal groups are not considered when determining the motif of an oligomeric compound. One or more region(s) of α-β-constrained nucleic acid as provided herein can be used in any portion of a motif. Only the 2'-sugar substituent groups present on the sugar groups of the α-β-constrained nucleic acid define the motif not the internucleoside linkages.

The preparation of motifs has been disclosed in various publications including without limitation, representative U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922; and published international applications WO 2005/121371 and WO 2005/121372 (both published on Dec. 22, 2005), certain of which are commonly owned with the instant application, and each of which is herein incorporated by reference in its entirety.

In certain embodiments, the α-β-constrained nucleic acid provided herein are incorporated into oligomeric compounds such that a motif results. The placement of α-β- constrained nucleic acid into oligomeric compounds to provide particular motifs can enhance the desired properties of the resulting oligomeric compounds for activity using various mechanisms such as for example RNaseH or RNAi. Such motifs include without limitation, gapmer motifs, hemimer motifs, blockmer motifs, uniformly fully modified motifs, positionally modified motifs and alternating motifs. In conjunction with these motifs a wide variety of internucleoside linkages can also be used including but not limited to phosphodiester and phosphorothioate internucleoside linkages which can be incorporated uniformly or in various combinations. The oligomeric compounds can further include terminal groups at one or both of the 5' and or 3' terminals such as a conjugate or reporter group. The positioning of the α-β-constrained nucleic acid provided herein, the use of linkage strategies and terminal groups can be easily optimized to enhance a desired activity for a selected target.

As used herein the term "alternating motif" refers to an oligomeric compound comprising a contiguous sequence of linked monomer subunits wherein the monomer subunits have two different types of sugar moieties that alternate for essentially the entire sequence of the oligomeric compound. Oligomeric compounds having an alternating motif can be described by the formula: 5'-A(-L-B-L-A)$_n$(-L-B)$_{nn}$-3' where A and B are monomer subunits that have different sugar moieties, each L is, independently, an internucleoside linking group, n is from about 4 to about 12 and nn is 0 or 1. The heterocyclic base and internucleoside linkage is independently variable at each position. The motif further optionally includes the use of one or more other groups including but not limited to capping groups, conjugate groups and other 5' and or 3'-terminal groups. This permits alternating oligomeric compounds from about 9 to about 26 monomer subunits in length. This length range is not meant to be limiting as longer and shorter oligomeric compounds are also amenable to oligomeric compounds provided herein. In certain embodiments, each A or each B comprise α-β-constrained nucleic acid as provided herein.

As used herein the term "uniformly fully modified motif" refers to an oligomeric compound comprising a contiguous sequence of linked monomer subunits that each have the same type of sugar moiety. The heterocyclic base and internucleoside linkage is independently variable at each position. The motif further optionally includes the use of one or more other groups including but not limited to capping groups, conjugate groups and other 5' and or 3'-terminal groups. In certain embodiments, the uniformly fully modified motif includes a contiguous sequence of α-β-constrained nucleic acid as provided herein. In certain embodiments, one or both of the 5' and 3'-ends of the contiguous sequence of α-β-constrained nucleic acid, comprise 5' and or 3'-terminal groups such as one or more unmodified nucleosides.

As used herein the term "hemimer motif" refers to an oligomeric compound comprising a contiguous sequence of monomer subunits that each have the same type of sugar moiety with a further short contiguous sequence of monomer subunits located at the 5' or the 3' end that have a different type of sugar moiety. The heterocyclic base and internucleoside linkage is independently variable at each position. The motif further optionally includes the use of one or more other groups including but not limited to capping groups, conjugate groups and other 5' and or 3'-terminal groups. In general, a hemimer is an oligomeric compound of uniform sugar moieties further comprising a short region (1, 2, 3, 4 or about 5 monomer subunits) having uniform but different sugar moieties located on either the 3' or the 5' end of the oligomeric compound.

In certain embodiments, the hemimer motif comprises a contiguous sequence of from about 10 to about 28 monomer subunits having one type of sugar moiety with from 1 to 5 or from 2 to about 5 monomer subunits having a second type of sugar moiety located at one of the termini. In certain embodiments, the hemimer is a contiguous sequence of from about 8 to about 20 β-D-2'-deoxyribonucleosides having a region of α-β-constrained nucleic acid comprising from 1-12 linked nucleosides located at one of the termini. In certain embodiments, the hemimer is a contiguous sequence of from about 8 to about 20 β-D-2'-deoxyribonucleosides having a region of α-β-constrained nucleic acid located at one of the termini. In certain embodiments, the hemimer is a contiguous sequence of from about 12 to about 18 β-D-2'-deoxyribonucleosides having a region of α-β-constrained nucleic acid located at one of the termini. In certain embodiments, the hemimer is a contiguous sequence of from about 10 to about 14 β-D-2'-deoxyribonucleosides having a region of α-β-constrained nucleic acid located at one of the termini.

As used herein the terms "blockmer motif" and "blockmer" refer to an oligomeric compound comprising an otherwise contiguous sequence of monomer subunits wherein the sugar moieties of each monomer subunit is the same except for an interrupting internal block of contiguous monomer subunits having a different type of sugar moiety. The heterocyclic base and internucleoside linkage is independently variable at each position of a blockmer. The motif further optionally includes the use of one or more other groups including but not limited to capping groups, conjugate groups and other 5' or 3'-terminal groups. A blockmer overlaps somewhat with a gapmer in the definition but typically only the monomer subunits in the block have non-naturally occurring sugar moieties in a blockmer and only the monomer subunits in the external regions have non-naturally occurring sugar moieties in a gapmer with the remainder of monomer subunits in the blockmer or gapmer being β-D-2'-deoxyribonucleosides or β-D-ribonucleosides. In certain embodiments, blockmers are provided herein wherein all of the monomer subunits comprise non-naturally occurring sugar moieties.

As used herein the term "positionally modified motif" is meant to include an otherwise contiguous sequence of monomer subunits having one type of sugar moiety that is interrupted with two or more regions of from 1 to about 5 contiguous monomer subunits having another type of sugar moiety. Each of the two or more regions of from 1 to about 5 contiguous monomer subunits are independently uniformly modified with respect to the type of sugar moiety. In certain embodiments, each of the two or more regions have the same type of sugar moiety. In certain embodiments, each of the two or more regions have a different type of sugar moiety. In certain embodiments, each of the two or more regions, independently, have the same or a different type of sugar moiety. The heterocyclic base and internucleoside linkage is independently variable at each position of a positionally modified oligomeric compound. The motif further optionally includes the use of one or more other groups including but not limited to capping groups, conjugate groups and other 5' or 3'-terminal groups. In certain embodiments, positionally modified oligomeric compounds are provided comprising a sequence of from 8 to 20 β-D-2'-deoxyribonucleosides that further includes two or three regions of α-β-constrained nucleic acid. Positionally modified oligomeric compounds are distinguished from gapped motifs, hemimer motifs, blockmer motifs and alternating motifs because the pattern of regional substitution defined by any positional motif does not fit into the definition provided herein for one of these other motifs. The term positionally modified oligomeric compound includes many different specific substitution patterns.

As used herein the term "gapmer" or "gapped oligomeric compound" refers to an oligomeric compound having two external regions or wings and an internal region or gap. The three regions form a contiguous sequence of monomer subunits with the sugar moieties of the external regions being different than the sugar moieties of the internal region and wherein the sugar moiety of each monomer subunit within a particular region is essentially the same. In certain embodiments, each monomer subunit within a particular region has the same sugar moiety. When the sugar moieties of the external regions are the same the gapmer is a symmetric gapmer and when the sugar moiety used in the 5'-external region is different from the sugar moiety used in the 3'-external region, the gapmer is an asymmetric gapmer. In certain embodiments, the external regions are small (each independently 1, 2, 3, 4 or about 5 monomer subunits) and the monomer subunits comprise non-naturally occurring sugar moieties with the internal region comprising β-D-2'-deoxyribonucleosides. In certain embodiments, the external regions each, independently, comprise from 1 to about 5 monomer subunits having non-naturally occurring sugar moieties and the internal region comprises from 6 to 18 unmodified nucleosides. The internal region or the gap generally comprises β-D-2'-deoxyribonucleosides but can comprise non-naturally occurring sugar moieties. The heterocyclic base and internucleoside linkage is independently variable at each position of a gapped oligomeric compound. The motif further optionally includes the use of one or more other groups including but not limited to capping groups, conjugate groups and other 5' or 3'-terminal groups.

In certain embodiments, gapped oligomeric compounds are provided having modified nucleosides in the wings and an internal region of β-D-2'-deoxyribonucleosides. Such a gapmer can include α-β-constrained nucleic acid in one or both wings and or in a portion of the gap or for the entirety of the gap. In certain embodiments, the gapped oligomeric compounds comprise an internal region of β-D-2'-deoxyribonucleosides with one of the external regions comprising α-β-constrained nucleic acid as disclosed herein and the other external region comprising modified nucleosides having different sugar groups than the α-β-constrained nucleic acid as disclosed herein. In certain embodiments, the gapped oligomeric compounds comprise an internal region of β-D-2'-deoxyribonucleosides with both of the external regions comprising α-β-constrained nucleic acid as provided herein. In certain embodiments, gapped oligomeric compounds are provided herein wherein all of the monomer subunits comprise non-naturally occurring sugar moieties.

In certain embodiments, gapped oligomeric compounds are provided comprising at least one region of the α-β-constrained nucleic acid as disclosed herein and one or two modified nucleosides at the 5'-end, two or three modified nucleosides at the 3'-end and an internal region of from 10 to 16 β-D-2'-deoxyribonucleosides. In certain embodiments, gapped oligomeric compounds are provided comprising at least one region of the α-β-constrained nucleic acid as disclosed herein and one modified nucleoside at the 5'-end, two modified nucleosides at the 3'-end and an internal region of from 10 to 16 β-D-2'-deoxyribonucleosides. In certain embodiments, gapped oligomeric compounds are provided comprising at least one region of the α-β-constrained nucleic acid as disclosed herein and one modified nucleoside at the 5'-end, two modified nucleosides at the 3'-end and an internal region of from 10 to 14 β-D-2'-deoxyribonucleosides.

In certain embodiments, gapped oligomeric compounds are provided that are from about 18 to about 21 monomer subunits in length. In certain embodiments, gapped oligomeric compounds are provided that are from about 16 to about 21 monomer subunits in length. In certain embodiments, gapped oligomeric compounds are provided that are from about 10 to about 21 monomer subunits in length. In certain embodiments, gapped oligomeric compounds are provided that are from about 12 to about 16 monomer subunits in length. In certain embodiments, gapped oligomeric compounds are provided that are from about 12 to about 14 monomer subunits in length. In certain embodiments, gapped oligomeric compounds are provided that are from about 14 to about 16 monomer subunits in length.

As used herein the term "alkyl," refers to a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred. The term "lower alkyl" as used herein includes from 1 to about 6 carbon atoms. Alkyl groups as used herein may optionally include one or more further substituent groups.

As used herein the term "alkenyl," refers to a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein the term "alkynyl," refers to a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein the term "aliphatic," refers to a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines. Aliphatic groups as used herein may optionally include further substituent groups.

As used herein the term "alicyclic" refers to a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

As used herein the term "alkoxy," refers to a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

As used herein the term "aminoalkyl" refers to an amino substituted $C_1$-$C_{12}$ alkyl radical. The alkyl portion of the radical forms a covalent bond with a parent molecule. The amino group can be located at any position and the aminoalkyl group can be substituted with a further substituent group at the alkyl and/or amino portions.

As used herein the terms "aryl" and "aromatic," refer to a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

As used herein the terms "aralkyl" and "arylalkyl," refer to an aromatic group that is covalently linked to a $C_1$-$C_{12}$ alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

As used herein the term "heterocyclic radical" refers to a radical mono-, or poly-cyclic ring system that includes at least one heteroatom and is unsaturated, partially saturated or fully saturated, thereby including heteroaryl groups. Heterocyclic is also meant to include fused ring systems wherein one or more of the fused rings contain at least one heteroatom and the other rings can contain one or more heteroatoms or optionally contain no heteroatoms. A heterocyclic radical typically includes at least one atom selected from sulfur, nitrogen or oxygen. Examples of heterocyclic radicals include, [1,3]dioxolanyl, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, tetrahydrofuryl and the like. Heterocyclic groups as used herein may optionally include further substituent groups.

As used herein the terms "heteroaryl," and "heteroaromatic," refer to a radical comprising a mono- or poly-cyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

As used herein the term "heteroarylalkyl," refers to a heteroaryl group as previously defined that further includes a covalently attached $C_1$-$C_{12}$ alkyl radical. The alkyl radical portion of the resulting heteroarylalkyl group is capable of forming a covalent bond with a parent molecule. Examples include without limitation, pyridinylmethylene, pyrimidinylethylene, napthyridinylpropylene and the like. Heteroarylalkyl groups as used herein may optionally include further substituent groups on one or both of the heteroaryl or alkyl portions.

As used herein the term "acyl," refers to a radical formed by removal of a hydroxyl group from an organic acid and has the general Formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

As used herein the term "hydrocarbyl" includes radical groups that comprise C, O and H. Included are straight, branched and cyclic groups having any degree of saturation. Such hydrocarbyl groups can include one or more additional heteroatoms selected from N and S and can be further mono or poly substituted with one or more substituent groups.

As used herein the term "mono or poly cyclic structure" is meant to include all ring systems selected from single or polycyclic radical ring systems wherein the rings are fused or linked and is meant to be inclusive of single and mixed ring systems individually selected from aliphatic, alicyclic, aryl, heteroaryl, aralkyl, arylalkyl, heterocyclic, heteroaryl, heteroaromatic and heteroarylalkyl. Such mono and poly cyclic structures can contain rings that each have the same level of saturation or each, independently, have varying degrees of saturation including fully saturated, partially saturated or fully unsaturated. Each ring can comprise ring atoms selected from C, N, O and S to give rise to heterocyclic rings as well as rings comprising only C ring atoms which can be present in a mixed motif such as for example benzimidazole wherein one ring has only carbon ring atoms and the fused ring has two nitrogen atoms. The mono or poly cyclic structures can be further substituted with substituent groups such as for example phthalimide which has two =O groups attached to one of the rings. Mono or poly cyclic structures can be attached to parent molecules using various strategies such as directly through a ring atom, fused through multiple ring atoms, through a substituent group or through a bifunctional linking moiety.

As used herein the terms "halo" and "halogen," refer to an atom selected from fluorine, chlorine, bromine and iodine.

As used herein the term "oxo" refers to the group (=O).

As used herein the term "protecting group," refers to a labile chemical moiety which is known in the art to protect reactive groups including without limitation, hydroxyl, amino and thiol groups, against undesired reactions during synthetic procedures. Protecting groups are typically used selectively and/or orthogonally to protect sites during reactions at other reactive sites and can then be removed to leave the unprotected group as is or available for further reactions. Protecting groups as known in the art are described generally in Greene's Protective Groups in Organic Synthesis, 4th edition, John Wiley & Sons, New York, 2007.

Groups can be selectively incorporated into oligomeric compounds as provided herein as precursors. For example an amino group can be placed into a compound as provided herein as an azido group that can be chemically converted to the amino group at a desired point in the synthesis. Generally, groups are protected or present as precursors that will be inert to reactions that modify other areas of the parent molecule for conversion into their final groups at an appropriate time. Further representative protecting or precursor groups are discussed in Agrawal et al., *Protocols for Oligonucleotide Conjugates*, Humana Press; New Jersey, 1994, 26, 1-72.

The term "orthogonally protected" refers to functional groups which are protected with different classes of protecting groups, wherein each class of protecting group can be removed in any order and in the presence of all other classes (see, Barany et al., *J. Am. Chem. Soc.*, 1977, 99, 7363-7365; Barany et al., *J. Am. Chem. Soc.*, 1980, 102, 3084-3095). Orthogonal protection is widely used in for example automated oligonucleotide synthesis. A functional group is deblocked in the presence of one or more other protected functional groups which is not affected by the deblocking procedure. This deblocked functional group is reacted in some manner and at some point a further orthogonal protecting group is removed under a different set of reaction conditions. This allows for selective chemistry to arrive at a desired compound or oligomeric compound.

Examples of hydroxyl protecting groups include without limitation, acetyl, t-butyl, t-butoxymethyl, methoxymethyl, tetrahydropyranyl, 1-ethoxyethyl, 1-(2-chloroethoxy)ethyl, p-chlorophenyl, 2,4-dinitrophenyl, benzyl, 2,6-dichlorobenzyl, diphenylmethyl, p-nitrobenzyl, bis(2-acetoxyethoxy)methyl (ACE), 2-trimethylsilylethyl, trimethylsilyl, triethylsilyl, t-butyldimethylsilyl, t-butyldiphenylsilyl, triphenylsilyl, [(triisopropylsilyl)oxy]methyl (TOM), benzoylformate, chloroacetyl, trichloroacetyl, trifluoroacetyl, pivaloyl, benzoyl, p-phenylbenzoyl, 9-fluorenylmethyl carbonate, mesylate, tosylate, triphenylmethyl (trityl), monomethoxytrityl, dimethoxytrityl (DMT), trimethoxytrityl, 1(2-fluorophenyl)-4-methoxypiperidin-4-yl (FPMP), 9-phenylxanthine-9-yl (Pixyl) and 9-(p-methoxyphenyl)xanthine-9-yl (MOX). Wherein more commonly used hydroxyl protecting groups include without limitation, benzyl, 2,6-dichlorobenzyl, t-butyldimethylsilyl, t-butyldiphenylsilyl, benzoyl, mesylate, tosylate, dimethoxytrityl (DMT), 9-phenylxanthine-9-yl (Pixyl) and 9-(p-methoxyphenyl)xanthine-9-yl (MOX).

Examples of amino protecting groups include without limitation, carbamate-protecting groups, such as 2-trimethylsilylethoxycarbonyl (Teoc), 1-methyl-1-(4-biphenylyl)ethoxycarbonyl (Bpoc), t-butoxycarbonyl (BOC), allyloxycarbonyl (Alloc), 9-fluorenylmethyloxycarbonyl (Fmoc), and benzyl-oxycarbonyl (Cbz); amide-protecting groups, such as formyl, acetyl, trihaloacetyl, benzoyl, and nitrophenylacetyl; sulfonamide-protecting groups, such as 2-nitrobenzenesulfonyl; and imine- and cyclic imide-protecting groups, such as phthalimido and dithiasuccinoyl.

Examples of thiol protecting groups include without limitation, triphenylmethyl (trityl), benzyl (Bn), and the like.

The compounds described herein contain one or more asymmetric centers and thus give rise to enantiomers, diastereomers, and other stereoisomeric forms that may be defined, in terms of absolute stereochemistry, as (R)- or (S)-, α or β, or as (D)- or (L)- such as for amino acids. Included herein are all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions*, John Wiley & Sons, 1981. When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to limit a particular configuration unless the text so states.

The terms "substituent" and "substituent group," as used herein, are meant to include groups that are typically added to other groups or parent compounds to enhance desired properties or provide other desired effects. Substituent groups can be protected or unprotected and can be added to one available site or to many available sites in a parent compound. Substituent groups may also be further substituted with other substituent groups and may be attached directly or via a linking group such as an alkyl or hydrocarbyl group to a parent compound.

Substituent groups amenable herein include without limitation, halogen, hydroxyl, alkyl, alkenyl, alkynyl, acyl (—C(O)$R_{aa}$), carboxyl (—C(O)O—$R_{aa}$), aliphatic groups, alicyclic groups, alkoxy, substituted oxy (—O—$R_{aa}$), aryl, aralkyl, heterocyclic radical, heteroaryl, heteroarylalkyl, amino (—N($R_{bb}$)($R_{cc}$)), imino(=N$R_{bb}$), amido (—C(O)N($R_{bb}$)($R_{cc}$) or —N($R_{bb}$)C(O)$R_{aa}$), azido (—N$_3$), nitro (—NO$_2$), cyano (—CN), carbamido (—OC(O)N($R_{bb}$)($R_{cc}$) or —N($R_{bb}$)C(O)O$R_{aa}$), ureido (—N($R_{bb}$)C(O)N($R_{bb}$)($R_{cc}$)), thioureido (—N($R_{bb}$)C(S)N($R_{bb}$)—($R_{cc}$)), guanidinyl (—N($R_{bb}$)C(=N$R_{bb}$)N($R_{bb}$)($R_{cc}$)), amidinyl (—C(=N$R_{bb}$)N($R_{bb}$)($R_{cc}$) or —N($R_{bb}$)C(=N$R_{bb}$)($R_{aa}$)), thiol (—S$R_{bb}$), sulfinyl (—S(O)$R_{bb}$), sulfonyl (—S(O)$_2R_{bb}$) and sulfonamidyl (—S(O)$_2$N($R_{bb}$($R_{cc}$) or —N($R_{bb}$)S—(O)$_2$$R_{bb}$). Wherein each $R_{aa}$, $R_{bb}$ and $R_{cc}$ is, independently, H, an optionally linked chemical functional group or a further substituent group with a preferred list including without limitation, H, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

In this context, "recursive substituent" means that a substituent may recite another instance of itself. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by way of example and not limitation, physical properties such as molecular weight, solubility or log P, application properties such as activity against the intended target and practical properties such as ease of synthesis.

Recursive substituents are an intended aspect of the invention. One of ordinary skill in the art of medicinal and organic chemistry understands the versatility of such substituents. To the degree that recursive substituents are present in a claim of the invention, the total number will be determined as set forth above.

The terms "stable compound" and "stable structure" as used herein are meant to indicate a compound that is sufficiently robust to survive isolation to a useful degree of purity from a reaction mixture, and formulation into an efficacious therapeutic agent. Only stable compounds are contemplated herein.

As used herein, the term "nucleobase" refers to unmodified or naturally occurring nucleobases which include, but are not limited to, the purine bases adenine (A) and guanine (G), and the pyrimidine bases thymine (T), cytosine (C) and uracil (U).

As used herein the term "heterocyclic base moiety" refers to unmodified or naturally occurring nucleobases as well as modified or non-naturally occurring nucleobases and synthetic mimetics thereof (such as for example phenoxazines). In one embodiment, a heterocyclic base moiety is any heterocyclic system that contains one or more atoms or groups of atoms capable of hydrogen bonding to a heterocyclic base of a nucleic acid.

In certain embodiments, heterocyclic base moieties include without limitation modified nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein.

In certain embodiments, heterocyclic base moieties include without limitation tricyclic pyrimidines such as 1,3-diazaphenoxazine-2-one, 1,3-diazaphenothiazine-2-one and 9-(2-aminoethoxy)-1,3-diazaphenoxazine-2-one (G-clamp). Heterocyclic base moieties also include those in which the purine or pyrimidine base is replaced with other heterocycles, for example 7-deaza-adenine, 7-deazaguanosine, 2-aminopyridine and 2-pyridone. Further heterocyclic base moieties include without limitation those known to the art skilled (see for example: U.S. Pat. No. 3,687,808; Swayze et al., *The Medicinal Chemistry of Oligonucleotides* in Antisense a Drug Technology, Chapter 6, pages 143-182, Crooke, S. T., ed., 2008); *The Concise Encyclopedia Of Polymer Science And Engineering*, Kroschwitz, J. I., Ed., John Wiley & Sons, 1990, 858-859; Englisch et al., *Angewandte Chemie*, International Edition, 1991, 30, 613; Sanghvi, Y. S., Chapter 15. Antisense Research and Applications, Crooke, S. T. and Lebleu, B., Eds., CRC Press, 1993, 273-302). Modified polycyclic heterocyclic compounds useful as heterocyclic base moieties are disclosed in the above noted U.S. Pat. No. 3,687,808, as well as U.S. Pat. Nos. 4,845,205; 5,130,302; 5,134,066; 5,175,273; 5,367,066; 5,432,272; 5,434,257; 5,457,187; 5,459,255; 5,484,908; 5,502,177; 5,525,711; 5,552,540; 5,587,469; 5,594,121; 5,596,091; 5,614,617; 5,645,985; 5,646,269; 5,681,941; 5,750,692; 5,763,588; 5,830,653; 6,005,096; and U.S. Patent Application Publication 20030158403, each of which is incorporated herein by reference in its entirety.

As used herein the term "sugar moiety" refers to naturally occurring sugars having a furanose ring, synthetic or non-naturally occurring sugars having a modified furanose ring and sugar surrogates wherein the furanose ring has been replaced with a cyclic ring system such as for example a morpholino or hexitol ring system or a non-cyclic sugar surrogate such as that used in peptide nucleic acids. Illustrative examples of sugar moieties useful in the preparation of oligomeric compounds include without limitation, β-D-ribose, β-D-2'-deoxyribose, substituted sugars (such as 2', 5' and bis substituted sugars), 4'-S-sugars (such as 4'-S-ribose, 4'-S-2'-deoxyribose and 4'-S-2'-substituted ribose wherein the ring oxygen atom has been replaced with a sulfur atom), bicyclic modified sugars (such as the 2'-O—CH$_2$-4' or 2'-O—(CH$_2$)$_2$-4' bridged ribose derived bicyclic sugars) and sugar surrogates (such as for example when the ribose ring has been replaced with a morpholino, a hexitol ring system or an open non-cyclic system).

As used herein the term "sugar substituent group" refers to groups that are covalently attached to sugar moieties. In certain embodiments, examples of sugar substituent groups include without limitation halogen, alkyl, substituted alkyl, alkoxy, substituted alkoxy, alkenyl, substituted alkenyl, alkynyl, substituted alkynyl, amino, substituted amino, thio, substituted thio and azido. In certain embodiments the alkyl and alkoxy groups are $C_1$ to $C_6$. In certain embodiments, the alkenyl and alkynyl groups are $C_2$ to $C_6$. In certain embodiments, examples of sugar substituent groups include without limitation 2'-F, 2'-allyl, 2'-amino, 2'-azido, 2'-thio, 2'-O-allyl, 2'-OCF$_3$, 2'-O—$C_1$-$C_{10}$ alkyl, 2'-OCH$_3$, 2'-O(CH$_2$)$_n$CH$_3$, 2'-OCH$_2$CH$_3$, 2'-O—(CH$_2$)$_2$CH$_3$, 2'-O—(CH$_2$)$_2$—O—CH$_3$ (MOE), 2'-O[(CH$_2$)$_n$O]$_m$CH$_3$, 2'-O(CH$_2$)$_2$SCH$_3$, 2'-O—(CH$_2$)$_3$—N(R$_p$)(R$_q$), 2'-O(CH$_2$)$_n$NH$_2$, 2'-O—(CH$_2$)$_2$—O—N(R$_p$)(R$_q$), O(CH$_2$)$_n$ON[(CH$_2$)$_n$CH$_3$]$_2$, 2'-O(CH$_2$)$_n$ONH$_2$, 2'-O—(CH$_2$)$_2$—O—(CH$_2$)$_2$—N(R$_p$)(R$_q$), 2'-O—CH$_2$C(=O)—N(R$_p$)(R$_q$), 2'-OCH$_2$C(=O)N(H)CH$_3$, 2'-O—CH$_2$C(=O)—N(H)—(CH$_2$)$_2$—N(R$_p$)(R$_q$) and 2'-O—CH$_2$—N(H)—C(=NR$_r$)[N(R$_p$)(R$_q$)], wherein each R$_p$, R$_q$ and R$_r$ is, independently, H, substituted or unsubstituted $C_1$-$C_{10}$ alkyl or a protecting group and where n and m are from 1 to about 10.

In certain embodiments, examples of substituent groups useful for modifying furanose sugar moieties (e.g., sugar substituent groups used for modified nucleosides), include without limitation 2'-F, 2'-allyl, 2'-amino, 2'-azido, 2'-thio, 2'-O-allyl, 2'-OCF$_3$, 2'-O—$C_1$-$C_{10}$ alkyl, 2'-O—CH$_3$, OCF$_3$, 2'-O—CH$_2$CH$_3$, 2'-O—(CH$_2$)$_2$CH$_3$, 2'-O—(CH$_2$)$_2$—O—CH$_3$ (MOE), 2'-O(CH$_2$)$_2$SCH$_3$, 2'-O—CH$_2$CH=CH$_2$, 2'-O—(CH$_2$)$_3$—N(R$_m$)(R$_n$), 2'-O—(CH$_2$)$_2$—O—N(R$_m$)(R$_n$), 2'-O—(CH$_2$)$_2$—O—(CH$_2$)$_2$—N(R$_m$)(R$_n$), 2'-O—CH$_2$C(=O)—N(R$_m$)(R$_n$), 2'-O—CH$_2$C(=O)—N(H)—(CH$_2$)$_2$—N(R$_m$)(R$_n$) and 2'-O—CH$_2$—N(H)—C(=NR$_m$)[N(R$_m$)(R$_n$)] wherein each R$_m$ and R$_n$ is, independently, H, substituted or unsubstituted $C_1$-$C_{10}$ alkyl or a protecting group. In certain embodiments, examples of 2,-sugar substituent groups include without limitation fluoro, —O—CH$_3$, —O—CH$_2$CH$_3$, —O—(CH$_2$)$_2$CH$_3$, —O—(CH$_2$)$_2$—O—CH$_3$, —O—CH$_2$—CH=CH$_2$, —O—(CH$_2$)$_3$—N(R$_1$)(R$_2$), O—(CH$_2$)$_2$—O—N(R$_1$)(R$_2$), —O—(CH$_2$)$_2$—O—(CH$_2$)$_2$—N(R$_1$)(R$_2$), —O—CH$_2$C(=O)—N(R$_1$)(R$_2$), —O—CH$_2$C(=O)—N(H)—(CH$_2$)$_2$—N(R$_1$)(R$_2$) and —O—CH$_2$—N(H)—C(=NR$_1$)[N(R$_1$)(R$_2$)] wherein R$_1$ and R$_2$ are each independently, H or $C_1$-$C_2$ alkyl. In certain embodiments, examples of sugar substituent groups include without limitation fluoro, —O—CH$_3$, —O—(CH$_2$)$_2$—O—CH$_3$, —O—CH$_2$C(=O)—N(H)(CH$_3$), —O—CH$_2$C(=O)—N(H)—(CH$_2$)$_2$—N(CH$_3$)$_2$ and —O—CH$_2$—N(H)—C(=NCH$_3$)[N(CH$_3$)$_2$]. In certain embodiments, examples of sugar substituent groups include without limitation fluoro, —O—CH$_3$, —O—(CH$_2$)$_2$—O—CH$_3$, —O—CH$_2$C(=O)—N(H)(CH$_3$) and —O—CH$_2$C(=O)—N(H)—(CH$_2$)$_2$—N(CH$_3$)$_2$. Further examples of modified sugar moieties include without limitation bicyclic sugars (e.g. bicyclic nucleic acids or bicyclic nucleosides discussed below).

In certain embodiments, examples of sugar substituent groups include without limitation one or two 5'-sugar substituent groups independently selected from $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl and halogen. In certain embodiments, examples of sugar substituent groups include without limitation one or two 5'-sugar substituent groups independently selected from vinyl, 5'-methyl, 5'-(S)-methyl and 5'-(R)-methyl. In certain embodiments, examples of sugar substituent groups include without limitation one 5'-sugar substituent group selected from vinyl, 5'-(S)-methyl and 5'-(R)-methyl.

In certain embodiments, examples of sugar substituent groups include without limitation substituted silyl, an RNA cleaving group, a reporter group, an intercalator, a group for improving pharmacokinetic properties, or a group for improving the pharmacodynamic properties of an oligomeric compound, and other substituents having similar properties. In certain embodiments, oligomeric compounds include modified nucleosides comprising 2'-MOE substituent groups (Baker et al., J. Biol. Chem., 1997, 272, 11944-12000). Such 2'-MOE substitution has been described as having improved binding affinity compared to unmodified nucleosides and to other modified nucleosides, such as 2'-O-methyl, 2'-O-propyl, and 2'-O-aminopropyl. Oligonucleotides having the 2'-MOE substituent also have been shown to be antisense inhibitors of gene expression with promising features for in vivo use (Martin, P., *Helv. Chim. Acta*, 1995, 78, 486-504; Altmann et al., Chimia, 1996, 50, 168-176; Altmann et al., *Biochem. Soc. Trans.*, 1996, 24, 630-637; and Altmann et al., *Nucleosides Nucleotides*, 1997, 16, 917-926).

Sugar moieties can be substituted with combinations of sugar substituent groups including without limitation 2'-F-5'-methyl substituted nucleosides (see PCT International Application WO 2008/101157, published on Aug. 21, 2008 for other disclosed 5', 2'-bis substituted nucleosides). Other combinations are also possible, including without limitation, replacement of the ribosyl ring oxygen atom with S and further substitution at the 2'-position (see published U.S. Patent Application US2005-0130923, published on Jun. 16, 2005) and 5'-substitution of a bicyclic nucleoside (see PCT International Application WO 2007/134181, published on Nov. 22, 2007 wherein a 4'-$CH_2$—O-2' bicyclic nucleoside is further substituted at the 5' position with a 5'-methyl or a 5'-vinyl group).

As used herein, the term "nucleoside" refers to a nucleobase-sugar combination. The two most common classes of such nucleobases are purines and pyrimidines.

As used herein, the term "nucleotide" refers to a nucleoside further comprising a modified or unmodified phosphate internucleoside linking group or a non-phosphate internucleoside linking group. For nucleotides that include a pentofuranosyl sugar, the internucleoside linking group can be linked to either the 2', 3' or 5' hydroxyl moiety of the sugar. The phosphate and or a non-phosphate internucleoside linking groups are routinely used to covalently link adjacent nucleosides to one another to form a linear polymeric compound.

The term "nucleotide mimetic" as used herein is meant to include monomers that incorporate into oligomeric compounds with sugar and linkage surrogate groups, such as for example peptide nucleic acids (PNA) or morpholinos (linked by —N(H)—C(=O)—O—). In general, the heterocyclic base at each position is maintained for hybridization to a nucleic acid target but the sugar and linkage is replaced with surrogate groups that are expected to function similar to native groups but have one or more enhanced properties.

As used herein the term "nucleoside mimetic" is intended to include those structures used to replace the sugar and the base at one or more positions of an oligomeric compound. Examples of nucleoside mimetics include without limitation nucleosides wherein the heterocyclic base moiety is replaced with a phenoxazine moiety (for example the 9-(2-aminoethoxy)-1,3-diazaphenoxazine-2-one group, also referred to as a G-clamp which forms four hydrogen bonds when hybridized with a guanosine base) and further replacement of the sugar moiety with a group such as for example a morpholino, a cyclohexenyl or a bicyclo[3.1.0]hexyl.

As used herein the term "modified nucleoside" is meant to include all manner of modified nucleosides that can be incorporated into an oligomeric compound using oligomer synthesis. The term is intended to include modifications made to a nucleoside such as modified stereochemical configurations, one or more substitutions, and deletion of groups as opposed to the use of surrogate groups which are described elsewhere herein. The term includes nucleosides having a furanose sugar (or 4'-S analog) portion and can include a heterocyclic base or can be an abasic nucleoside. One group of representative modified nucleosides includes without limitation, substituted nucleosides (such as 2', 5', and/or 4' substituted nucleosides) 4'-S-modified nucleosides, (such as 4'-S-ribonucleosides, 4'-S-2'-deoxyribonucleosides and 4'-S-2'-substituted ribonucleosides), bicyclic modified nucleosides (such as for example, bicyclic nucleosides wherein the sugar moiety has a 2'-O—$CHR_a$-4' bridging group, wherein R, is H, alkyl or substituted alkyl) and base modified nucleosides. The sugar can be modified with more than one of these modifications listed such as for example a bicyclic modified nucleoside further including a 5'-substitution or a 5' or 4' substituted nucleoside further including a 2' substituent. The term modified nucleoside also includes combinations of these modifications such as base and sugar modified nucleosides. These modifications are meant to be illustrative and not exhaustive as other modifications are known in the art and are also envisioned as possible modifications for the modified nucleosides described herein.

As used herein the term "monomer subunit" is meant to include all manner of monomer units that are amenable to oligomer synthesis with one preferred list including monomer subunits such as β-D-ribonucleosides, β-D-2'-deoxyribnucleosides, modified nucleosides, including substituted nucleosides (such as 2', 5' and bis substituted nucleosides), 4'-S-modified nucleosides, (such as 4'-S-ribonucleosides, 4'-S-2'-deoxyribonucleosides and 4'-S-2'-substituted ribonucleosides), bicyclic modified nucleosides (such as bicyclic nucleosides wherein the sugar moiety has a 2'-O—$CHR_a$-4' bridging group, wherein R, is H, alkyl or substituted alkyl), other modified nucleosides, nucleoside mimetics, nucleosides having sugar surrogates and regions of α-β-constrained nucleic acid as provided herein.

As used herein the term "bicyclic nucleoside" refers to a nucleoside comprising at least a bicyclic sugar moiety. Examples of bicyclic nucleosides include without limitation nucleosides having a furanosyl sugar that comprises a bridge between two of the non-geminal carbons, preferably the 4' and the 2' carbon atoms. In certain embodiments, oligomeric compounds provided herein include one or more 4' to 2' bridged bicyclic nucleosides. Examples of such 4' to 2' bridged bicyclic nucleosides, include but are not limited to one of formulae: 4'-($CH_2$)—O-2' (LNA); 4'-($CH_2$)—S-2'; 4'-($CH_2$)$_2$—O-2' (ENA); 4'-CH($CH_3$)—O- 2' and 4'-C—H($CH_2OCH_3$)—O-2' (and analogs thereof see U.S. Pat. No.

7,399,845, issued on Jul. 15, 2008); 4'-C(CH$_3$)(CH$_3$)—O-2' (and analogs thereof see published International Application WO/2009/006478, published Jan. 8, 2009); 4'-CH$_2$—N(OCH$_3$)-2' (and analogs thereof see published International Application WO/2008/150729, published Dec. 11, 2008); 4'-CH$_2$—O—N(CH$_3$)-2' (see published U.S. Patent Application US2004-0171570, published Sep. 2, 2004); 4'-CH$_2$—N(R)—O-2', wherein R is H, C$_1$-C$_{12}$ alkyl, or a protecting group (see U.S. Pat. No. 7,427,672, issued on Sep. 23, 2008); 4'-CH$_2$—C(H)(CH$_3$)-2' (see Chattopadhyaya, et al., J. Org. Chem., 2009, 74, 118-134); and 4'-CH$_2$—C(=CH$_2$)-2' (and analogs thereof see published International Application WO 2008/154401, published on Dec. 8, 2008). Further bicyclic nucleosides have been reported in published literature (see for example: Srivastava et al., J. Am. Chem. Soc., 2007, 129(26) 8362-8379; Frieden et al., Nucleic Acids Research, 2003, 21, 6365-6372; Elayadi et al., Curr. Opinion Invens. Drugs. 2001, 2, 558-561; Braasch et al., Chem. Biol., 2001, 8, 1-7; Orum et al., Curr. Opinion Mol. Ther., 2001, 3, 239-243; Wahlestedt et al., Proc. Natl. Acad. Sci. U.S.A, 2000, 97, 5633-5638; Singh et al., Chem. Commun., 1998, 4, 455-456; Koshkin et al., Tetrahedron, 1998, 54, 3607-3630; Kumar et al., Bioorg. Med. Chem. Lett., 1998, 8, 2219-2222; Singh et al., J. Org. Chem., 1998, 63, 10035-10039; U.S. Pat. Nos. 7,399,845; 7,053,207; 7,034,133; 6,794,499; 6,770,748; 6,670,461; 6,525,191; 6,268,490; U.S. Patent Publication Nos.: US2008-0039618; US2007-0287831; US2004-0171570; U.S. patent application Ser. No. 12/129,154; 61/099,844; 61/097,787; 61/086,231; 61/056,564; 61/026,998; 61/026,995; 60/989,574; International applications WO 2007/134181; WO 2005/021570; WO 2004/106356; WO 94/14226; and PCT International Applications Nos.: PCT/US2008/068922; PCT/US2008/066154; and PCT/US2008/064591). Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

In certain embodiments, bicyclic nucleosides comprise a bridge between the 4' and the 2' carbon atoms of the pentofuranosyl sugar moiety including without limitation, bridges comprising 1 or from 1 to 4 linked groups independently selected from —[C(R$_a$)(R$_b$)$_n$]—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—; wherein: x is 0, 1, or 2; n is 1, 2, 3, or 4; each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl or a protecting group.

In certain embodiments, the bridge of a bicyclic sugar moiety is, —[C(R$_a$)(R$_b$)$_n$]—, —[C(R$_a$)(R$_b$)]$_n$—O—, —C(R$_a$R$_b$)—N(R)—O— or —C(R$_a$R$_b$)—O—N(R)—. In certain embodiments, the bridge is 4'-CH$_2$-2', 4'-(CH$_2$)$_2$-2', 4'-(CH$_2$)$_3$-2', 4'-CH$_2$—O-2', 4'-(CH$_2$)$_2$—O-2', 4'-CH$_2$—O—N(R)-2' and 4'-CH$_2$—N(R)—O-2'- wherein each R is, independently, H, a protecting group or C$_1$-C$_{12}$ alkyl.

In certain embodiments, bicyclic nucleosides are further defined by isomeric configuration. For example, a nucleoside comprising a 4'-(CH$_2$)—O-2' bridge, may be in the α-L configuration or in the β-D configuration. Previously, α-L-methyleneoxy (4'-CH$_2$—O-2') BNA's have been incorporated into antisense oligonucleotides that showed antisense activity (Frieden et al., Nucleic Acids Research, 2003, 21, 6365-6372).

In certain embodiments, bicyclic nucleosides include those having a 4' to 2' bridge wherein such bridges include without limitation, α-L-4'-(CH$_2$)—O-2', β-D-4'-CH$_2$—O-2', 4'-(CH$_2$)$_2$—O-2', 4'-CH$_2$—O—N(R)-2', 4'-CH$_2$—N(R)—O-2', 4'-CH(CH$_3$)—O-2', 4'-CH$_2$—S-2', 4'-CH$_2$—N(R)-2', 4'-CH$_2$—CH(CH$_3$)-2', and 4'-(CH$_2$)$_3$-2', wherein R is H, a protecting group or C$_1$-C$_{12}$ alkyl.

In certain embodiments, bicyclic nucleosides have the formula:

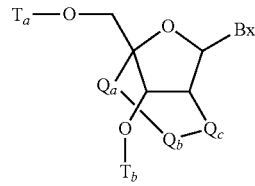

wherein:
Bx is a heterocyclic base moiety;
-Q$_a$-Q$_b$-Q$_c$- is —CH$_2$—N(R$_c$)—CH$_2$—, —C(=O)—N(R$_c$)—CH$_2$—, —CH$_2$—O—N(R$_c$)—, —CH$_2$—N(R$_c$)—O— or —N(R$_c$)—O—CH$_2$;
R$_c$ is C$_1$-C$_{12}$ alkyl or an amino protecting group; and
T$_a$ and T$_b$ are each, independently, H, a hydroxyl protecting group, a conjugate group, a reactive phosphorus group, a phosphorus moiety or a covalent attachment to a support medium.

In certain embodiments, bicyclic nucleosides have the formula:

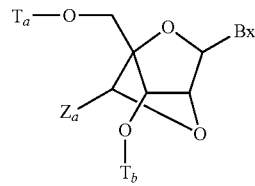

wherein:
Bx is a heterocyclic base moiety;
T$_a$ and T$_b$ are each, independently, H, a hydroxyl protecting group, a conjugate group, a reactive phosphorus group, a phosphorus moiety or a covalent attachment to a support medium;
Z$_a$ is C$_1$-C$_6$ alkyl, C$_2$-C$_6$ alkenyl, C$_2$-C$_6$ alkynyl, substituted C$_1$-C$_6$ alkyl, substituted C$_2$-C$_6$ alkenyl, substituted C$_2$-C$_6$ alkynyl, acyl, substituted acyl, substituted amide, thiol or substituted thiol.

In one embodiment, each of the substituted groups, is, independently, mono or poly substituted with substituent groups independently selected from halogen, oxo, hydroxyl, OJ$_c$, NJ$_c$J$_d$, SJ$_c$, N$_3$, OC(=X)J$_c$, and NJ$_e$C(=X)NJ$_c$J$_d$, wherein each $J_c$, $J_d$ and $J_e$ is, independently, H, $C_1$-$C_6$ alkyl, or substituted $C_1$-$C_6$ alkyl and X is O or $NJ_c$.

In certain embodiments, bicyclic nucleosides have the formula:

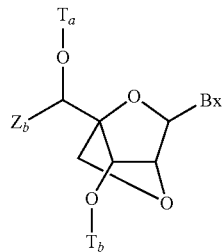

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl or substituted acyl (C(=O)—).

In certain embodiments, bicyclic nucleosides have the formula:

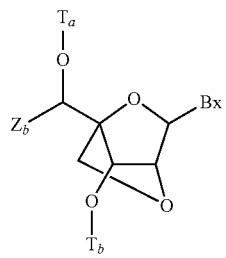

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

In certain embodiments, bicyclic nucleosides have the formula:

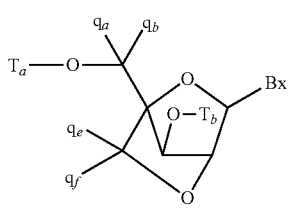

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SO_2J_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$;

or $q_e$ and $q_f$ together are =C($q_g$)($q_h$);

$q_g$ and $q_h$ are each, independently, H, halogen, $C_1$-$C_{12}$ alkyl or substituted $C_1$-$C_{12}$ alkyl.

The synthesis and preparation of adenine, cytosine, guanine, 5-methyl-cytosine, thymine and uracil bicyclic nucleosides having a 4'-CH$_2$—O-2' bridge, along with their oligomerization, and nucleic acid recognition properties have been described (Koshkin et al., *Tetrahedron*, 1998, 54, 3607-3630). The synthesis of bicyclic nucleosides has also been described in WO 98/39352 and WO 99/14226.

Analogs of various bicyclic nucleosides that have 4' to 2' bridging groups such as 4'-CH$_2$—O-2' and 4'-CH$_2$—S-2', have also been prepared (Kumar et al., *Bioorg. Med Chem. Lett.*, 1998, 8, 2219-2222). Preparation of oligodeoxyribonucleotide duplexes comprising bicyclic nucleosides for use as substrates for nucleic acid polymerases has also been described (Wengel et al., WO 99/14226). Furthermore, synthesis of 2'-amino-BNA, a novel conformationally restricted high-affinity oligonucleotide analog has been described in the art (Singh et al., *J. Org. Chem.*, 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleosides have the formula:

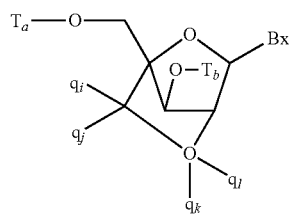

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SO_2J_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$; and $q_i$ and $q_j$ or $q_l$ and $q_k$ together are =C($q_g$)($q_h$), wherein $q_g$ and $q_h$ are each, independently, H, halogen, $C_1$-$C_{12}$ alkyl or substituted $C_1$-$C_{12}$ alkyl.

One carbocyclic bicyclic nucleoside having a 4'-(CH$_2$)$_3$-2' bridge and the alkenyl analog bridge 4'-CH=CH—CH$_2$-2' have been described (Frier et al., *Nucleic Acids Research*, 1997, 25(22), 4429-4443 and Albaek et al., *J. Org. Chem.*, 2006, 71, 7731-7740). The synthesis and preparation of carbocyclic bicyclic nucleosides along with their oligomerization and biochemical studies have also been described (Srivastava et al., *J. Am. Chem. Soc.* 2007, 129(26), 8362-8379).

In certain embodiments, bicyclic nucleosides include, but are not limited to, (A) α-L-methyleneoxy (4'-CH$_2$—O-2') BNA, (B) β-D-methyleneoxy (4'-CH$_2$—O-2') BNA, (C) ethyleneoxy (4'-(CH$_2$)$_2$—O-2') BNA, (D) aminooxy (4'-CH$_2$—O—N(R)-2') BNA, (E) oxyamino (4'-CH$_2$—N(R)—O-2') BNA, (F) methyl(methyleneoxy) (4'-CH(CH$_3$)—O-2') BNA (also referred to as constrained ethyl or cEt), (G) methylene-thio (4'-CH$_2$—S-2') BNA, (H) methylene-amino (4'-CH$_2$—N(R)-2') BNA, (I) methyl carbocyclic (4'-CH$_2$—CH(CH$_3$)-2') BNA, (J) propylene carbocyclic (4'-(CH$_2$)$_3$-2') BNA, and (K) vinyl BNA as depicted below.

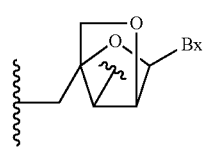
(A)

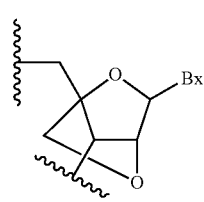
(B)

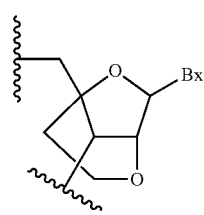
(C)

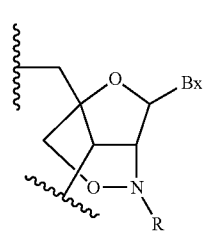
(D)

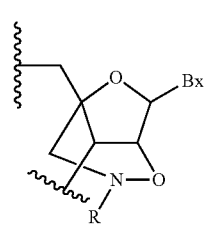
(E)

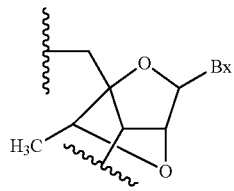
(F)

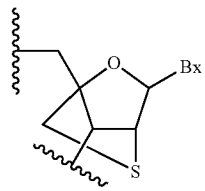
(G)

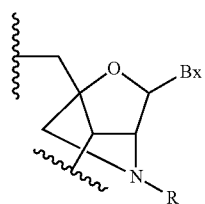
(H)

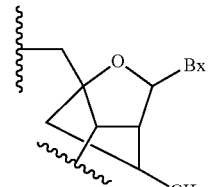
(I)

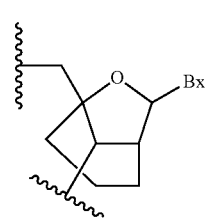
(J)

(K)

wherein Bx is the base moiety and R is, independently, H, a protecting group, C$_1$-C$_6$ alkyl or C$_1$-C$_6$ alkoxy.

As used herein the term "sugar surrogate" refers to replacement of the nucleoside furanose ring with a non-furanose (or 4'-substituted furanose) group with another structure such as another ring system or open system. Such structures can be as simple as a six membered ring as opposed to the five membered furanose ring or can be more complicated such as a bicyclic or tricyclic ring system or a non-ring system used in peptide nucleic acid. In certain embodiments, sugar surrogates include without limitation sugar surrogate groups such as morpholinos, cyclohexenyls and cyclohexitols. In general the heterocyclic base is maintained even when the sugar moiety is a sugar surrogate so that the resulting monomer subunit will be able to hybridize.

In certain embodiments, nucleosides having sugar surrogate groups include without limitation, replacement of the ribosyl ring with a sugar surrogate such as a tetrahydropyranyl ring system (also referred to as hexitol) as illustrated below:

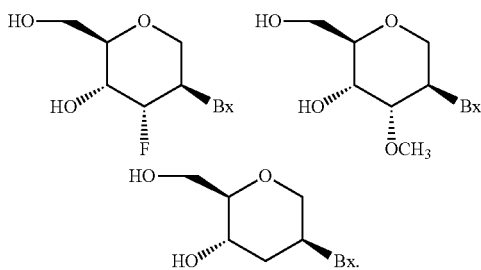

In certain embodiments, sugar surrogates are selected having the formula:

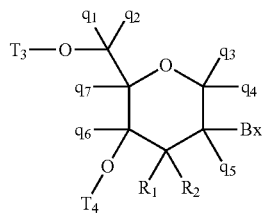

wherein:

Bx is a heterocyclic base moiety;

$T_3$ and $T_4$ are each, independently, an internucleoside linking group linking the tetrahydropyran nucleoside analog to the oligomeric compound or one of $T_3$ and $T_4$ is an internucleoside linking group linking the tetrahydropyran nucleoside analog to an oligomeric compound or oligonucleotide and the other of $T_3$ and $T_4$ is H, a hydroxyl protecting group, a linked conjugate group or a 5' or 3'-terminal group;

$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and one of $R_1$ and $R_2$ is hydrogen and the other is selected from halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$ and CN, wherein X is O, S or $NJ_1$ and each $J_1$, $J_2$ and $J_3$ is, independently, H or $C_1$-$C_6$ alkyl.

In certain embodiments, $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides are provided wherein one of $R_1$ and $R_2$ is F. In certain embodiments, $R_1$ is fluoro and $R_2$ is H; $R_1$ is methoxy and $R_2$ is H, and $R_1$ is methoxyethoxy and $R_2$ is H.

Such sugar surrogates can be referred to as a "modified tetrahydropyran nucleoside" or "modified THP nucleoside". Modified THP nucleosides include, but are not limited to, what is referred to in the art as hexitol nucleic acid (HNA), altritol nucleic acid (ANA), and mannitol nucleic acid (MNA) (see Leumann, C. J., *Bioorg. & Med. Chem.*, 2002, 10, 841-854).

In certain embodiments, oligomeric compounds comprise one or more modified cyclohexenyl nucleosides, which is a nucleoside having a six-membered cyclohexenyl in place of the pentofuranosyl residue in naturally occurring nucleosides. Modified cyclohexenyl nucleosides include, but are not limited to those described in the art (see for example commonly owned, published PCT Application WO 2010/036696, published on Apr. 10, 2010, Robeyns et al., *J. Am. Chem. Soc.*, 2008, 130(6), 1979-1984; Horváth et al., *Tetrahedron Letters.* 2007, 48, 3621-3623; Nauwelaerts et al., *J. Am. Chem. Soc.*, 2007, 129(30), 9340-9348; Gu et al., *Nucleosides. Nucleotides & Nucleic Acids,* 2005, 24(5-7), 993-998; Nauwelaerts et al., *Nucleic Acids Research.* 2005, 33(8), 2452-2463; Robeyns et al., Acta Crystallographica, Section F: Structural Biology and Crystallization Communications, 2005, F61(6), 585-586; Gu et al., Tetrahedron, 2004, 60(9), 2111-2123; Gu et al., Oligonucleotides, 2003, 13(6), 479-489; Wang et al., *J. Org. Chem.*, 2003, 68, 4499-4505; Verbeure et al., Nucleic Acids Research, 2001, 29(24), 4941-4947; Wang et al., *J. Org. Chem.,* 2001, 66, 8478-82; Wang et al., *Nucleosides. Nucleotides & Nucleic Acids,* 2001, 20(4-7), 785-788; Wang et al., *J. Am. Chem.,* 2000, 122, 8595-8602; Published PCT application, WO 06/047842; and Published PCT Application WO 01/049687; the text of each is incorporated by reference herein, in their entirety). Certain modified cyclohexenyl nucleosides have Formula X.

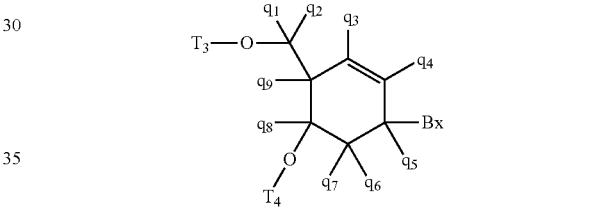

wherein independently for each of said at least one cyclohexenyl nucleoside analog of Formula X:

Bx is a heterocyclic base moiety;

$T_3$ and $T_4$ are each, independently, an internucleoside linking group linking the cyclohexenyl nucleoside analog to an antisense compound or one of $T_3$ and $T_4$ is an internucleoside linking group linking the tetrahydropyran nucleoside analog to an antisense compound and the other of $T_3$ and $T_4$ is H, a hydroxyl protecting group, a linked conjugate group, or a 5'- or 3'-terminal group; and $q_1$, $q_2$, $q_3$, $q_4$, $q_5$, $q_6$, $q_7$, $q_8$ and $q_9$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or other sugar substituent group.

Many other monocyclic, bicyclic and tricyclic ring systems are known in the art and are suitable as sugar surrogates that can be used to modify nucleosides for incorporation into oligomeric compounds as provided herein (see for example review article: Leumann, Christian J. *Bioorg. & Med. Chem.,* 2002, 10, 841-854). Such ring systems can undergo various additional substitutions to further enhance their activity.

Some representative U.S. patents that teach the preparation of such modified sugars include without limitation, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,670,633; 5,700,920; 5,792,847 and 6,600,032 and International Application PCT/

US2005/019219, filed Jun. 2, 2005 and published as WO 2005/121371 on Dec. 22, 2005 certain of which are commonly owned with the instant application, and each of which is herein incorporated by reference in its entirety.

The α-β-constrained nucleic acid as provided herein can be prepared by any of the applicable techniques of organic synthesis, as, for example, illustrated in the examples below. Many such techniques are well known in the art. However, many of the known techniques are elaborated in *Compendium of Organic Synthetic Methods*, John Wiley & Sons, New York: Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade Jr., 1980; Vol. 5, Leroy G. Wade Jr., 1984; and Vol. 6, Michael B. Smith; as well as March, J., *Advanced Organic Chemistry*, 3rd Edition, John Wiley & Sons, New York, 1985; *Comprehensive Organic Synthesis. Selectivity. Strategy & Efficiency in Modern Organic Chemistry*, in 9 Volumes, Barry M. Trost, Editor-in-Chief, Pergamon Press, New York, 1993; *Advanced Organic Chemistry. Part B: Reactions and Synthesis*, 4th Edition; Carey and Sundberg, Kluwer Academic/Plenum Publishers, New York, 2001; *Advanced Organic Chemistry, Reactions, Mechanisms, and Structure*, 2nd Edition, March, McGraw Hill, 1977; Greene, T. W., and Wutz, P. G. M., *Protecting Groups in Organic Synthesis*, 4th Edition, John Wiley & Sons, New York, 1991; and Larock, R. C., *Comprehensive Organic Transformations*, 2nd Edition, John Wiley & Sons, New York, 1999.

As used herein the term "reactive phosphorus" is meant to include groups that are covalently linked to a monomer subunit that can be further attached to an oligomeric compound that are useful for forming internucleoside linkages including for example phosphodiester and phosphorothioate internucleoside linkages. Such reactive phosphorus groups are known in the art and contain phosphorus atoms in $P^{III}$ or $P^{V}$ valence state including, but not limited to, phosphoramidite, H-phosphonate, phosphate triesters and phosphorus containing chiral auxiliaries. In certain embodiments, reactive phosphorus groups are selected from diisopropylcyanoethoxy phosphoramidite (—O*—P[N[(CH(CH$_3$)$_2$]$_2$]O(CH$_2$)$_2$CN) and H-phosphonate (—O*—P(=O)(H)OH), wherein the O* is provided from the Markush group for the monomer. A preferred synthetic solid phase synthesis utilizes phosphoramidites ($P^{III}$ chemistry) as reactive phosphites. The intermediate phosphite compounds are subsequently oxidized to the phosphate or thiophosphate ($P^{V}$ chemistry) using known methods to yield, phosphodiester or phosphorothioate internucleoside linkages. Chiral auxiliaries are known in the art (see for example: Wang et al., *Tetrahedron Letters*, 1997, 38(5), 705-708; Jin et al., *J. Org. Chem*, 1997, 63, 3647-3654; Wang et al., *Tetrahedron Letters*, 1997, 38(22), 3797-3800; and U.S. Pat. No. 6,867,294, issued Mar. 15, 2005). Additional reactive phosphates and phosphites are disclosed in Tetrahedron Report Number 309 (Beaucage and Iyer, *Tetrahedron*, 1992, 48, 2223-2311).

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

The term "oligonucleoside" refers to a sequence of nucleosides that are joined by internucleoside linkages that do not have phosphorus atoms. Internucleoside linkages of this type include short chain alkyl, cycloalkyl, mixed heteroatom alkyl, mixed heteroatom cycloalkyl, one or more short chain heteroatomic and one or more short chain heterocyclic. These internucleoside linkages include without limitation, siloxane, sulfide, sulfoxide, sulfone, acetyl, formacetyl, thioformacetyl, methylene formacetyl, thioformacetyl, alkenyl, sulfamate, methyleneimino, methylenehydrazino, sulfonate, sulfonamide, amide and others having mixed N, O, S and CH$_2$ component parts.

As used herein, the term "oligomeric compound" refers to a contiguous sequence of linked monomer subunits. Each linked monomer subunit normally includes a heterocyclic base moiety but monomer subunits also includes those without a heterocyclic base moiety such as abasic monomer subunits. At least some and generally most if not essentially all of the heterocyclic bases in an oligomeric compound are capable of hybridizing to a nucleic acid molecule, normally a preselected RNA target. The term "oligomeric compound" therefore includes oligonucleotides, oligonucleotide analogs and oligonucleosides. It also includes polymers having one or a plurality of nucleoside mimetics and or nucleosides having sugar surrogate groups.

In certain embodiments, oligomeric compounds comprise a plurality of monomer subunits independently selected from naturally occurring nucleosides, non-naturally occurring nucleosides, modified nucleosides, nucleoside mimetics, and nucleosides having sugar surrogate groups. In certain embodiments, oligomeric compounds are single stranded. In certain embodiments, oligomeric compounds are double stranded comprising a double-stranded duplex. In certain embodiments, oligomeric compounds comprise one or more conjugate groups and/or terminal groups.

When preparing oligomeric compounds having specific motifs as disclosed herein it can be advantageous to mix non-naturally occurring monomer subunits with the α-β-constrained nucleic acid as provided herein with other non-naturally occurring monomer subunits, naturally occurring monomer subunits (nucleosides) or mixtures thereof. In certain embodiments, oligomeric compounds are provided herein comprising a contiguous sequence of linked monomer subunits including at least one region of α-β-constrained nucleic acid as provided. In certain embodiments, oligomeric compounds are provided comprising at least two regions of α-β-constrained nucleic acid as provided herein.

Oligomeric compounds are routinely prepared linearly but can also be joined or otherwise prepared to be circular and/or can be prepared to include branching. Oligomeric compounds can form double stranded constructs such as for example two strands hybridized to form a double stranded composition. Double stranded compositions can be linked or separate and can include various other groups such as conjugates and/or overhangs on the ends.

As used herein, "antisense compound" refers to an oligomeric compound, at least a portion of which is at least partially complementary to a target nucleic acid to which it hybridizes. In certain embodiments, an antisense compound modulates (increases or decreases) expression or amount of a target nucleic acid. In certain embodiments, an antisense compound alters splicing of a target pre-mRNA resulting in a different splice variant. In certain embodiments, an antisense compound modulates expression of one or more different target proteins. Antisense mechanisms contemplated herein include, but are not limited to an RNase H mechanism, RNAi mechanisms, splicing modulation, translational arrest, altering RNA processing, inhibiting microRNA function, or mimicking microRNA function.

As used herein, "antisense activity" refers to any detectable and/or measurable activity attributable to the hybridization of an antisense compound to its target nucleic acid. In certain embodiments, such activity may be an increase or decrease in an amount of a nucleic acid or protein. In certain embodiments, such activity may be a change in the ratio of splice variants of a nucleic acid or protein. Detection and/or measuring of antisense activity may be direct or indirect. For example, in certain embodiments, antisense activity is assessed by detecting and/or measuring the amount of target protein or the relative amounts of splice variants of a target protein. In certain embodiments, antisense activity is assessed by detecting and/or measuring the amount of target nucleic acids and/or cleaved target nucleic acids and/or alternatively spliced target nucleic acids. In certain embodiments, antisense activity is assessed by observing a phenotypic change in a cell or animal.

As used herein the term "internucleoside linkage" or "internucleoside linking group" is meant to include all manner of internucleoside linking groups known in the art including but not limited to, phosphorus containing internucleoside linking groups such as phosphodiester and phosphorothioate, and non-phosphorus containing internucleoside linking groups such as formacetyl and methyleneimino. Internucleoside linkages also includes neutral non-ionic internucleoside linkages such as amide-3 (3'-$CH_2$—C(=O)—N(H)-5'), amide-4 (3'-$CH_2$—N(H)—C(=O)-5) and methylphosphonate wherein a phosphorus atom is not always present.

In certain embodiments, oligomeric compounds as provided herein can be prepared having one or more internucleoside linkages containing modified e.g. non-naturally occurring internucleoside linkages. The two main classes of internucleoside linkages are defined by the presence or absence of a phosphorus atom. Modified internucleoside linkages having a phosphorus atom include without limitation, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity can comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative U.S. patents that teach the preparation of the above phosphorus containing linkages include without limitation, U.S. Pat. Nos. 3,687,808; 4,469,863; 4,476,301; 5,023,243; 5,177,196; 5,188,897; 5,194,599; 5,264,423; 5,276,019; 5,278,302; 5,286,717; 5,321,131; 5,399,676; 5,405,939; 5,453,496; 5,455,233; 5,466,677; 5,476,925; 5,519,126; 5,527,899; 5,536,821; 5,541,306; 5,550,111; 5,563,253; 5,565,555; 5,571,799; 5,587,361; 5,625,050; 5,672,697 and 5,721,218, certain of which are commonly owned with this application, and each of which is herein incorporated by reference.

In certain embodiments, oligomeric compounds as provided herein can be prepared having one or more non-phosphorus containing internucleoside linkages. Such oligomeric compounds include without limitation, those that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include without limitation, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; 5,677,439; 5,646,269 and 5,792,608, certain of which are commonly owned with this application, and each of which is herein incorporated by reference.

As used herein "neutral internucleoside linkage" is intended to include internucleoside linkages that are non-ionic. Neutral internucleoside linkages include without limitation, phosphotriesters, methylphosphonates, MMI (3'-$CH_2$—N($CH_3$)—O-5'), amide-3 (3'-$CH_2$—C(=O)—N(H)-5), amide-4 (3'-$CH_2$—N(H)—C(=O)-5), formacetal (3'-O—$CH_2$—O-5'), and thioformacetal (3'-S—$CH_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and $CH_2$ component parts.

In certain embodiments, oligomeric compounds as provided herein can be prepared having one or more optionally protected phosphorus containing internucleoside linkages. Representative protecting groups for phosphorus containing internucleoside linkages such as phosphodiester and phosphorothioate linkages include β-cyanoethyl, diphenylsilylethyl, δ-cyanobutenyl, cyano p-xylyl (CPX), N-methyl-N-trifluoroacetyl ethyl (META), acetoxy phenoxy ethyl (APE) and butene-4-yl groups. See for example U.S. Pat. No. 4,725,677 and Re. 34,069 (β-cyanoethyl); Beaucage et al., *Tetrahedron*, 1993, 49(10), 1925-1963; Beaucage et al., *Tetrahedron*, 1993, 49(46), 10441-10488; Beaucage et al., *Tetrahedron*, 1992, 48(12), 2223-2311.

As used herein the terms "linking groups" and "bifunctional linking moieties" are meant to include groups known in the art that are useful for attachment of chemical functional groups, conjugate groups, reporter groups and other groups to selective sites in a parent compound such as for example an oligomeric compound. In general, a bifunctional linking moiety comprises a hydrocarbyl moiety having two functional groups. One of the functional groups is selected to bind to a parent molecule or compound of interest and the other is selected to bind to essentially any selected group such as a chemical functional group or a conjugate group. In some embodiments, the linker comprises a chain structure or a polymer of repeating units such as ethylene glycols or amino acid units. Examples of functional groups that are routinely used in bifunctional linking moieties include without limitation, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like. Some nonlimiting examples of bifunctional linking moieties include 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other linking groups include without limitation, substituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, the oligomeric compounds as provided herein can be modified by covalent attachment of one or more conjugate groups. In general, conjugate groups modify one or more properties of the oligomeric compounds they are attached to. Such oligonucleotide properties include without limitation, pharmacodynamics, pharmacokinetics, binding, absorption, cellular distribution, cellular uptake, charge and clearance. Conjugate groups are routinely used in the chemical arts and are linked directly or via an optional linking moiety or linking group to a parent compound such as an oligomeric compound. A preferred list of conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes.

In certain embodiments, the oligomeric compounds as provided herein can be modified by covalent attachment of one or more terminal groups to the 5' or 3'-terminal groups. A terminal group can also be attached at any other position at one of the terminal ends of the oligomeric compound. As used herein the terms "5'-terminal group", "3'-terminal group", "terminal group" and combinations thereof are meant to include useful groups known to the art skilled that can be placed on one or both of the terminal ends, including but not limited to the 5' and 3'-ends of an oligomeric compound respectively, for various purposes such as enabling the tracking of the oligomeric compound (a fluorescent label or other reporter group), improving the pharmacokinetics or pharmacodynamics of the oligomeric compound (such as for example: uptake and/or delivery) or enhancing one or more other desirable properties of the oligomeric compound (a group for improving nuclease stability or binding affinity). In certain embodiments, 5' and 3'-terminal groups include without limitation, modified or unmodified nucleosides; two or more linked nucleosides that are independently, modified or unmodified; conjugate groups; capping groups; phosphate moieties; and protecting groups.

As used herein the term "phosphate moiety" refers to a terminal phosphate group that includes phosphates as well as modified phosphates. The phosphate moiety can be located at either terminus but is preferred at the 5'-terminal nucleoside. In one aspect, the terminal phosphate is unmodified having the formula —O—P(=OH)(OH)OH. In another aspect, the terminal phosphate is modified such that one or more of the O and OH groups are replaced with H, O, S, N(R) or alkyl where R is H, an amino protecting group or unsubstituted or substituted alkyl. In certain embodiments, the 5' and or 3' terminal group can comprise from 1 to 3 phosphate moieties that are each, independently, unmodified (di or tri-phosphates) or modified.

As used herein, the term "phosphorus moiety" refers to a group having the formula:

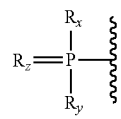

wherein:

$R_x$ and $R_y$ are each, independently, hydroxyl, protected hydroxyl group, thiol, protected thiol group, $C_1$-$C_6$ alkyl, substituted $C_1$-$C_6$ alkyl, $C_1$-$C_6$ alkoxy, substituted $C_1$-$C_6$ alkoxy, a protected amino or substituted amino; and $R_z$ is O or S.

As a monomer such as a phosphoramidite or H-phosphonate the protected phosphorus moiety is preferred to maintain stability during oligomer synthesis. After incorporation into an oligomeric compound the phosphorus moiety can include deprotected groups.

Phosphorus moieties included herein can be attached to a monomer, which can be used in the preparation of oligomeric compounds, wherein the monomer may be attached using O, S, $NR_d$ or $CR_eR_f$, wherein $R_d$ includes without limitation H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, substituted $C_2$-$C_6$ alkynyl or substituted acyl, and $R_e$ and $R_f$ each, independently, include without limitation, H, halogen, $C_1$-$C_6$ alkyl, substituted $C_1$-$C_6$ alkyl, $C_1$-$C_6$ alkoxy or substituted $C_1$-$C_6$ alkoxy. Such linked phosphorus moieties include without limitation, phosphates, modified phosphates, thiophosphates, modified thiophosphates, phosphonates, modified phosphonates, phosphoramidates and modified phosphoramidates.

RNA duplexes exist in what has been termed "A Form" geometry while DNA duplexes exist in "B Form" geometry. In general, RNA:RNA duplexes are more stable, or have higher melting temperatures ($T_m$) than DNA:DNA duplexes (Sanger et al., *Principles of Nucleic Acid Structure.* 1984, Springer-Verlag; New York, N.Y.; Lesnik et al., *Biochemistry*, 1995, 34, 10807-10815; Conte et al., *Nucleic Acids Res.*, 1997, 25, 2627-2634). The increased stability of RNA has been attributed to several structural features, most notably the improved base stacking interactions that result from an A-form geometry (Searle et al., *Nucleic Acids Res.*, 1993, 21, 2051-2056). The presence of the 2' hydroxyl in RNA biases the sugar toward a C3' endo pucker, i.e., also designated as Northern pucker, which causes the duplex to favor the A-form geometry. In addition, the 2' hydroxyl groups of RNA can form a network of water mediated hydrogen bonds that help stabilize the RNA duplex (Egli et al., *Biochemistry*, 1996, 35, 8489-8494). On the other hand, deoxy nucleic acids prefer a C2' endo sugar pucker, i.e., also known as Southern pucker, which is thought to impart a less stable B-form geometry (Sanger, W. (1984) *Principles of Nucleic Acid Structure*, Springer-Verlag, New York, N.Y.).

The relative ability of a chemically-modified oligomeric compound to bind to complementary nucleic acid strands, as compared to natural oligonucleotides, is measured by obtaining the melting temperature of a hybridization complex of said chemically-modified oligomeric compound with its complementary unmodified target nucleic acid. The melting temperature ($T_m$), a characteristic physical property of double helixes, denotes the temperature in degrees centigrade at which 50% helical versus coiled (unhybridized) forms are present. $T_m$ (also commonly referred to as binding affinity) is measured by using the UV spectrum to determine the formation and breakdown (melting) of hybridization. Base stacking, which occurs during hybridization, is accompanied by a reduction in UV absorption (hypochromicity). Consequently a reduction in UV absorption indicates a higher $T_m$.

It is known in the art that the relative duplex stability of an antisense compound:RNA target duplex can be modulated through incorporation of chemically-modified nucleosides into the antisense compound. Sugar-modified nucleosides have provided the most efficient means of modulating the $T_m$ of an antisense compound with its target RNA. Sugar-modified nucleosides that increase the population of or lock the sugar in the C3'-endo (Northern, RNA-like sugar pucker) configuration have predominantly provided a per modification $T_m$ increase for antisense compounds toward a complementary RNA target. Sugar-modified nucleosides that increase the population of or lock the sugar in the C2'-endo (Southern, DNA-like sugar pucker) configuration predominantly provide a per modification $T_m$ decrease for antisense compounds toward a complementary RNA target. The sugar pucker of a given sugar-modified nucleoside is not the only factor that dictates the ability of the nucleoside to increase or decrease an antisense compound's $T_m$ toward complementary RNA. For example, the sugar-modified nucleoside tricycloDNA is predominantly in the C2'-endo conformation, however it imparts a 1.9 to 3° C. per modification increase in $T_m$ toward a complementary RNA. Another example of a sugar-modified high-affinity nucleoside that does not adopt the C3'-endo conformation is α-L-LNA (described in more detail herein).

As used herein, "$T_m$" means melting temperature which is the temperature at which the two strands of a duplex nucleic acid separate. $T_m$ is often used as a measure of duplex stability or the binding affinity of an antisense compound toward a complementary strand such as an RNA molecule.

As used herein, "complementarity" in reference to nucleobases refers to a nucleobase that is capable of base pairing with another nucleobase. For example, in DNA, adenine (A) is complementary to thymine (T). For example, in RNA, adenine (A) is complementary to uracil (U). In certain embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases or more broadly, heterocyclic base moieties, comprising certain modifications may maintain the ability to pair with a counterpart nucleobase and thus, are still capable of complementarity.

As used herein, "non-complementary"" in reference to nucleobases refers to a pair of nucleobases that do not form hydrogen bonds with one another or otherwise support hybridization.

As used herein, "complementary" in reference to linked nucleosides, oligonucleotides, oligomeric compounds, or nucleic acids, refers to the capacity of an oligomeric compound to hybridize to another oligomeric compound or nucleic acid through nucleobase or more broadly, heterocyclic base, complementarity. In certain embodiments, an antisense compound and its target are complementary to each other when a sufficient number of corresponding positions in each molecule are occupied by nucleobases that can bond with each other to allow stable association between the antisense compound and the target. One skilled in the art recognizes that the inclusion of mismatches is possible without eliminating the ability of the oligomeric compounds to remain in association. Therefore, described herein are antisense compounds that may comprise up to about 20% nucleotides that are mismatched (i.e., are not nucleobase complementary to the corresponding nucleotides of the target). Preferably the antisense compounds contain no more than about 15%, more preferably not more than about 10%, most preferably not more than about 5% or no mismatches. The remaining nucleotides are nucleobase complementary or otherwise do not disrupt hybridization (e.g., universal bases). One of ordinary skill in the art would recognize the compounds provided herein are at least 80%, at least 85%, at least 90%, at least 95%, at least 96%, at least 97%, at least 98%, at least 99% or 100% complementary to a target nucleic acid.

It is understood in the art that the sequence of an oligomeric compound need not be 100% complementary to that of its target nucleic acid to be specifically hybridizable. Moreover, an oligomeric compound may hybridize over one or more segments such that intervening or adjacent segments are not involved in the hybridization event (e.g., a loop structure or hairpin structure). In certain embodiments, oligomeric compounds can comprise at least about 70%, at least about 80%, at least about 90%, at least about 95%, or at least about 99% sequence complementarity to a target region within the target nucleic acid sequence to which they are targeted. For example, an oligomeric compound in which 18 of 20 nucleobases of the oligomeric compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an oligomeric compound which is 18 nucleobases in length having 4 (four) noncomplementary nucleobases which are flanked by two regions of complete complementarity with the target nucleic acid would have 77.8% overall complementarity with the target nucleic acid and would thus fall within this scope. Percent complementarity of an oligomeric compound with a region of a target nucleic acid can be determined routinely using BLAST programs (basic local alignment search tools) and PowerBLAST programs known in the art (Altschul et al., *J. Mol. Biol.*, 1990, 215, 403-410; Zhang and Madden, *Genome Res.*, 1997, 7, 649-656).

As used herein, "hybridization" refers to the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleoside or nucleotide bases (nucleobases). For example, the natural base adenine is nucleobase complementary to the natural nucleobases thymidine and uracil which pair through the formation of hydrogen bonds. The natural base guanine is nucleobase complementary to the natural bases cytosine and 5-methyl cytosine. Hybridization can occur under varying circumstances.

As used herein, "target nucleic acid" refers to any nucleic acid molecule the expression, amount, or activity of which is capable of being modulated by an antisense compound. In certain embodiments, the target nucleic acid is DNA or RNA. In certain embodiments, the target RNA is mRNA, pre-mRNA, non-coding RNA, pri-microRNA, pre-microRNA, mature microRNA, promoter-directed RNA, or natural antisense transcripts. For example, the target nucleic acid can be a cellular gene (or mRNA transcribed from the gene)

whose expression is associated with a particular disorder or disease state, or a nucleic acid molecule from an infectious agent. In certain embodiments, target nucleic acid is a viral or bacterial nucleic acid.

Further included herein are oligomeric compounds such as antisense oligomeric compounds, antisense oligonucleotides, ribozymes, external guide sequence (EGS) oligonucleotides, alternate splicers, primers, probes, and other oligomeric compounds which hybridize to at least a portion of the target nucleic acid. As such, these oligomeric compounds may be introduced in the form of single-stranded, double-stranded, circular or hairpin oligomeric compounds and may contain structural elements such as internal or terminal bulges or loops. Once introduced to a system, the oligomeric compounds provided herein may elicit the action of one or more enzymes or structural proteins to effect modification of the target nucleic acid. Alternatively, the oligomeric compound may inhibit the activity the target nucleic acid through an occupancy-based method, thus interfering with the activity of the target nucleic acid.

One non-limiting example of such an enzyme is RNAse H, a cellular endonuclease which cleaves the RNA strand of an RNA:DNA duplex. It is known in the art that single-stranded oligomeric compounds which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While one form of oligomeric compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

As used herein, "modulation" refers to a perturbation of amount or quality of a function or activity when compared to the function or activity prior to modulation. For example, modulation includes the change, either an increase (stimulation or induction) or a decrease (inhibition or reduction) in gene expression. As a further example, modulation of expression can include perturbing splice site selection of pre-mRNA processing, resulting in a change in the amount of a particular splice-variant present compared to conditions that were not perturbed. As a further example, modulation includes perturbing translation of a protein.

As used herein, the term "pharmaceutically acceptable salts" refers to salts that retain the desired activity of the compound and do not impart undesired toxicological effects thereto. The term "pharmaceutically acceptable salt" includes a salt prepared from pharmaceutically acceptable non-toxic acids or bases, including inorganic or organic acids and bases.

Pharmaceutically acceptable salts of the oligomeric compounds described herein may be prepared by methods well-known in the art. For a review of pharmaceutically acceptable salts, see Stahl and Wermuth, Handbook of Pharmaceutical Salts: Properties, Selection and Use (Wiley-VCH, Weinheim, Germany, 2002). Sodium salts of antisense oligonucleotides are useful and are well accepted for therapeutic administration to humans. Accordingly, in one embodiment the oligomeric compounds described herein are in the form of a sodium salt.

In certain embodiments, oligomeric compounds provided herein comprise from about 8 to about 80 monomer subunits in length. One having ordinary skill in the art will appreciate that this embodies oligomeric compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 monomer subunits in length, or any range therewithin.

In certain embodiments, oligomeric compounds provided herein comprise from about 8 to 40 monomer subunits in length. One having ordinary skill in the art will appreciate that this embodies oligomeric compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 monomer subunits in length, or any range therewithin.

In certain embodiments, oligomeric compounds provided herein comprise from about 8 to 20 monomer subunits in length. One having ordinary skill in the art will appreciate that this embodies oligomeric compounds of 8, 9, 10, 11, 12, 13, 14, 15, 16, 17, 18, 19 or 20 monomer subunits in length, or any range therewithin.

In certain embodiments, oligomeric compounds provided herein comprise from about 8 to 16 monomer subunits in length. One having ordinary skill in the art will appreciate that this embodies oligomeric compounds of 8, 9, 10, 11, 12, 13, 14, 15 or 16 monomer subunits in length, or any range therewithin.

In certain embodiments, oligomeric compounds provided herein comprise from about 10 to 14 monomer subunits in length. One having ordinary skill in the art will appreciate that this embodies oligomeric compounds of 10, 11, 12, 13 or 14 monomer subunits in length, or any range therewithin.

In certain embodiments, oligomeric compounds provided herein comprise from about 10 to 18 monomer subunits in length. One having ordinary skill in the art will appreciate that this embodies oligomeric compounds of 10, 11, 12, 13, 14, 15, 16, 17 or 18 monomer subunits in length, or any range therewithin.

In certain embodiments, oligomeric compounds provided herein comprise from about 10 to 21 monomer subunits in length. One having ordinary skill in the art will appreciate that this embodies oligomeric compounds of 10, 11, 12, 13, 14, 15, 16, 17, 18, 19, 20 or 21 monomer subunits in length, or any range therewithin.

In certain embodiments, oligomeric compounds provided herein comprise from about 12 to 14 monomer subunits in length. One having ordinary skill in the art will appreciate that this embodies oligomeric compounds of 12, 13 or 14 monomer subunits in length, or any range therewithin.

In certain embodiments, oligomeric compounds provided herein comprise from about 12 to 18 monomer subunits in length. One having ordinary skill in the art will appreciate that this embodies oligomeric compounds of 12, 13, 14, 15, 16, 17 or 18 monomer subunits in length, or any range therewithin.

In certain embodiments, oligomeric compounds provided herein comprise from about 12 to 21 monomer subunits in length. One having ordinary skill in the art will appreciate that this embodies oligomeric compounds of 12, 13, 14, 15, 16, 17, 18, 19, 20 or 21 monomer subunits in length, or any range therewithin.

In certain embodiments, oligomeric compounds provided herein comprise from about 14 to 18 monomer subunits in length. One having ordinary skill in the art will appreciate that this embodies oligomeric compounds of 14, 15, 16, 17 or 18 monomer subunits in length, or any range therewithin.

In certain embodiments, oligomeric compounds of any of a variety of ranges of lengths of linked monomer subunits are provided. In certain embodiments, oligomeric compounds are provided consisting of X-Y linked monomer subunits, where X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X<Y. For example, in certain embodiments, this provides oligomeric compounds comprising: 8-9, 8-10, 8-11, 8-12, 8-13, 8-14, 8-15, 8-16, 8-17, 8-18, 8-19, 8-20, 8-21, 8-22, 8-23, 8-24, 8-25, 8-26, 8-27, 8-28, 8-29, 8-30, 9-10, 9-11, 9-12, 9-13, 9-14, 9-15, 9-16, 9-17, 9-18, 9-19, 9-20, 9-21, 9-22, 9-23, 9-24, 9-25, 9-26, 9-27, 9-28, 9-29, 9-30, 10-11, 10-12, 10-13, 10-14, 10-15, 10-16, 10-17, 10-18, 10-19, 10-20, 10-21, 10-22, 10-23, 10-24, 10-25, 10-26, 10-27, 10-28, 10-29, 10-30, 11-12, 11-13, 11-14, 11-15, 11-16, 11-17, 11-18, 11-19, 11-20, 11-21, 11-22, 11-23, 11-24, 11-25, 11-26, 11-27, 11-28, 11-29, 11-30, 12-13, 12-14, 12-15, 12-16, 12-17, 12-18, 12-19, 12-20, 12-21, 12-22, 12-23, 12-24, 12-25, 12-26, 12-27, 12-28, 12-29, 12-30, 13-14, 13-15, 13-16, 13-17, 13-18, 13-19, 13-20, 13-21, 13-22, 13-23, 13-24, 13-25, 13-26, 13-27, 13-28, 13-29, 13-30, 14-15, 14-16, 14-17, 14-18, 14-19, 14-20, 14-21, 14-22, 14-23, 14-24, 14-25, 14-26, 14-27, 14-28, 14-29, 14-30, 15-16, 15-17, 15-18, 15-19, 15-20, 15-21, 15-22, 15-23, 15-24, 15-25, 15-26, 15-27, 15-28, 15-29, 15-30, 16-17, 16-18, 16-19, 16-20, 16-21, 16-22, 16-23, 16-24, 16-25, 16-26, 16-27, 16-28, 16-29, 16-30, 17-18, 17-19, 17-20, 17-21, 17-22, 17-23, 17-24, 17-25, 17-26, 17-27, 17-28, 17-29, 17-30, 18-19, 18-20, 18-21, 18-22, 18-23, 18-24, 18-25, 18-26, 18-27, 18-28, 18-29, 18-30, 19-20, 19-21, 19-22, 19-23, 19-24, 19-25, 19-26, 19-27, 19-28, 19-29, 19-30, 20-21, 20-22, 20-23, 20-24, 20-25, 20-26, 20-27, 20-28, 20-29, 20-30, 21-22, 21-23, 21-24, 21-25, 21-26, 21-27, 21-28, 21-29, 21-30, 22-23, 22-24, 22-25, 22-26, 22-27, 22-28, 22-29, 22-30, 23-24, 23-25, 23-26, 23-27, 23-28, 23-29, 23-30, 24-25, 24-26, 24-27, 24-28, 24-29, 24-30, 25-26, 25-27, 25-28, 25-29, 25-30, 26-27, 26-28, 26-29, 26-30, 27-28, 27-29, 27-30, 28-29, 28-30, or 29-30 linked monomer subunits.

In certain embodiments, the ranges for the oligomeric compounds listed herein are meant to limit the number of monomer subunits in the oligomeric compounds, however such oligomeric compounds may further include 5' and/or 3'-terminal groups including but not limited to protecting groups such as hydroxyl protecting groups, optionally linked conjugate groups and/or other substituent groups.

In certain embodiments, the preparation of oligomeric compounds as disclosed herein is performed according to literature procedures for DNA: Protocols for Oligonucleotides and Analogs, Agrawal, Ed., Humana Press, 1993, and/or RNA: Scaringe, *Methods,* 2001, 23, 206-217; Gait et al., *Applications of Chemically synthesized RNA in RNA: Protein Interactions*, Smith, Ed., 1998, 1-36; Gallo et al., *Tetrahedron,* 2001, 57, 5707-5713. Additional methods for solid-phase synthesis may be found in Caruthers U.S. Pat. Nos. 4,415,732; 4,458,066; 4,500,707; 4,668,777; 4,973, 679; and 5,132,418; and Koster U.S. Pat. No. 4,725,677 and Re. 34,069.

Oligomeric compounds are routinely prepared using solid support methods as opposed to solution phase methods. Commercially available equipment commonly used for the preparation of oligomeric compounds that utilize the solid support method is sold by several vendors including, for example, Applied Biosystems (Foster City, Calif.). Any other means for such synthesis known in the art may additionally or alternatively be employed. Suitable solid phase techniques, including automated synthesis techniques, are described in *Oligonucleotides and Analogues, a Practical Approach*, F. Eckstein, Ed., Oxford University Press, New York, 1991.

The synthesis of RNA and related analogs relative to the synthesis of DNA and related analogs has been increasing as efforts in RNA interference and micro RNA increase. The primary RNA synthesis strategies that are presently being used commercially include 5'-O-DMT-2'-O-t-butyldimethylsilyl (TBDMS), 5'-O-DMT-2'-O-[1(2-fluorophenyl)-4-methoxypiperidin-4-yl] (FPMP), 2'-O-[(triisopropylsilyl) oxy]methyl (2'-O—$CH_2$—O—$Si(iPr)_3$ (TOM) and the 5'-O-silyl ether-2'-ACE (5'-O-bis(trimethylsiloxy) cyclododecyloxysilyl ether (DOD)-2'-O-bis(2-acetoxyethoxy)methyl (ACE). A current list of some of the major companies currently offering RNA products include Pierce Nucleic Acid Technologies, Dharmacon Research Inc., Ameri Biotechnologies Inc., and Integrated DNA Technologies, Inc. One company, Princeton Separations, is marketing an RNA synthesis activator advertised to reduce coupling times especially with TOM and TBDMS chemistries. The primary groups being used for commercial RNA synthesis are: TBDMS: 5'-O-DMT-2'-O-t-butyldimethylsilyl; TOM: 2'-O-[(triisopropylsilyl)oxy]methyl; DOD/ACE: (5'-O-bis(trimethylsiloxy)cyclododecyloxysilyl ether-2'-O-bis(2-acetoxyethoxy)methyl; and FPMP: 5'-O-DMT-2'-O-[1 (2-fluorophenyl)-4-ethoxypiperidin-4-yl]. In certain embodiments, each of the aforementioned RNA synthesis strategies can be used herein. In certain embodiments, the aforementioned RNA synthesis strategies can be performed together in a hybrid fashion e.g. using a 5'-protecting group from one strategy with a 2'-O-protecting from another strategy.

In some embodiments, "suitable target segments" may be employed in a screen for additional oligomeric compounds that modulate the expression of a selected protein. "Modulators" are those oligomeric compounds that decrease or increase the expression of a nucleic acid molecule encoding a protein and which comprise at least an 8-nucleobase portion which is complementary to a suitable target segment. The screening method comprises the steps of contacting a suitable target segment of a nucleic acid molecule encoding a protein with one or more candidate modulators, and selecting for one or more candidate modulators which decrease or increase the expression of a nucleic acid molecule encoding a protein. Once it is shown that the candidate modulator or modulators are capable of modulating (e.g. either decreasing or increasing) the expression of a nucleic acid molecule encoding a peptide, the modulator may then be employed herein in further investigative studies of the function of the peptide, or for use as a research, diagnostic, or therapeutic agent. In the case of oligomeric compounds targeted to microRNA, candidate modulators may be evaluated by the extent to which they increase the expression of a microRNA target RNA or protein (as interference with the activity of a microRNA will result in the increased expression of one or more targets of the microRNA).

As used herein, "expression" refers to the process by which a gene ultimately results in a protein. Expression includes, but is not limited to, transcription, splicing, post-transcriptional modification, and translation.

Suitable target segments may also be combined with their respective complementary oligomeric compounds provided herein to form stabilized double-stranded (duplexed) oligonucleotides. Such double stranded oligonucleotide moieties have been shown in the art to modulate target expression and regulate translation as well as RNA processing via an antisense mechanism. Moreover, the double-stranded moieties may be subject to chemical modifications (Fire et al., Nature, 1998, 391, 806-811; Timmons and Fire, Nature, 1998, 395, 854; Timmons et al., Gene, 2001, 263, 103-112; Tabara et al., Science, 1998, 282, 430-431; Montgomery et al., Proc. Natl. Acad. Sci. USA, 1998, 95, 15502-15507; Tuschl et al., Genes Dev., 1999, 13, 3191-3197; Elbashir et al., Nature, 2001, 411, 494-498; Elbashir et al., Genes Dev., 2001, 15, 188-200). For example, such double-stranded moieties have been shown to inhibit the target by the classical hybridization of antisense strand of the duplex to the target, thereby triggering enzymatic degradation of the target (Tijsterman et al., Science, 2002, 295, 694-697).

The oligomeric compounds provided herein can also be applied in the areas of drug discovery and target validation. In certain embodiments, provided herein is the use of the oligomeric compounds and targets identified herein in drug discovery efforts to elucidate relationships that exist between proteins and a disease state, phenotype, or condition. These methods include detecting or modulating a target peptide comprising contacting a sample, tissue, cell, or organism with one or more oligomeric compounds provided herein, measuring the nucleic acid or protein level of the target and/or a related phenotypic or chemical endpoint at some time after treatment, and optionally comparing the measured value to a non-treated sample or sample treated with a further oligomeric compound as provided herein. These methods can also be performed in parallel or in combination with other experiments to determine the function of unknown genes for the process of target validation or to determine the validity of a particular gene product as a target for treatment or prevention of a particular disease, condition, or phenotype. In certain embodiments, oligomeric compounds are provided for use in therapy. In certain embodiments, the therapy is reducing target messenger RNA.

As used herein, the term "dose" refers to a specified quantity of a pharmaceutical agent provided in a single administration. In certain embodiments, a dose may be administered in two or more boluses, tablets, or injections. For example, in certain embodiments, where subcutaneous administration is desired, the desired dose requires a volume not easily accommodated by a single injection. In such embodiments, two or more injections may be used to achieve the desired dose. In certain embodiments, a dose may be administered in two or more injections to minimize injection site reaction in an individual.

In certain embodiments, chemically-modified oligomeric compounds are provided herein that may have a higher affinity for target RNAs than does non-modified DNA. In certain such embodiments, higher affinity in turn provides increased potency allowing for the administration of lower doses of such compounds, reduced potential for toxicity, improvement in therapeutic index and decreased overall cost of therapy.

Effect of nucleoside modifications on RNAi activity is evaluated according to existing literature (Elbashir et al., Nature, 2001, 411, 494-498; Nishikura et al., Cell, 2001, 107, 415-416; and Bass et al., Cell, 2000, 101, 235-238.)

In certain embodiments, oligomeric compounds provided herein can be utilized for diagnostics, therapeutics, prophylaxis and as research reagents and kits. Furthermore, antisense oligonucleotides, which are able to inhibit gene expression with exquisite specificity, are often used by those of ordinary skill to elucidate the function of particular genes or to distinguish between functions of various members of a biological pathway. In certain embodiments, oligomeric compounds provided herein can be utilized either alone or in combination with other oligomeric compounds or other therapeutics as tools in differential and/or combinatorial analyses to elucidate expression patterns of a portion or the entire complement of genes expressed within cells and tissues. Oligomeric compounds can also be effectively used as primers and probes under conditions favoring gene amplification or detection, respectively. These primers and probes are useful in methods requiring the specific detection of nucleic acid molecules encoding proteins and in the amplification of the nucleic acid molecules for detection or for use in further studies. Hybridization of oligomeric compounds as provided herein, particularly the primers and probes, with a nucleic acid can be detected by means known in the art. Such means may include conjugation of an enzyme to the oligonucleotide, radiolabelling of the oligonucleotide or any other suitable detection means. Kits using such detection means for detecting the level of selected proteins in a sample may also be prepared.

As one nonlimiting example, expression patterns within cells or tissues treated with one or more of the oligomeric compounds provided herein are compared to control cells or tissues not treated with oligomeric compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds and or oligomeric compounds which affect expression patterns.

Examples of methods of gene expression analysis known in the art include DNA arrays or microarrays (Brazma and Vilo, FEBS Lett., 2000, 480, 17-24; Celis, et al., FEBS Lett., 2000, 480, 2-16), SAGE (serial analysis of gene expression) (Madden, et al., Drug Discov. Today, 2000, 5, 415-425), READS (restriction enzyme amplification of digested cDNAs) (Prashar and Weissman, Methods Enzymol., 1999, 303, 258-72), TOGA (total gene expression analysis) (Sutcliffe, et al., Proc. Natl. Acad. Sci. USA, 2000, 97, 1976-81), protein arrays and proteomics (Celis, et al., FEBS Lett., 2000, 480, 2-16; Jungblut, et al., Electrophoresis, 1999, 20, 2100-10), expressed sequence tag (EST) sequencing (Celis, et al., FEBS Lett., 2000, 480, 2-16; Larsson, et al., J. Biotechnol., 2000, 80, 143-57), subtractive RNA fingerprinting (SuRF) (Fuchs, et al., Anal. Biochem., 2000, 286, 91-98; Larson, et al., Cytometry, 2000, 41, 203-208), subtractive cloning, differential display (DD) (Jurecic and Belmont, Curr. Opin. Microbiol., 2000, 3, 316-21), comparative genomic hybridization (Carulli, et al., J. Cell Biochem. Suppl., 1998, 31, 286-96), FISH (fluorescent in situ hybridization) techniques (Going and Gusterson, Eur. J. Cancer, 1999, 35, 1895-904) and mass spectrometry methods (To, Comb. Chem. High Throughput Screen, 2000, 3, 235-41).

Those skilled in the art, having possession of the present disclosure will be able to prepare oligomeric compounds, comprising a contiguous sequence of linked monomer subunits, of essentially any viable length to practice the methods disclosed herein. Such oligomeric compounds will include at least one region of α-β-constrained nucleic acid as provided herein and may also include other monomer subunits including but not limited to nucleosides, modified nucleosides, nucleosides comprising sugar surrogate groups and nucleoside mimetics.

While in certain embodiments, oligomeric compounds provided herein can be utilized as described, the following examples serve only to illustrate and are not intended to be limiting.

EXAMPLES (GENERAL)

$^1$H and $^{13}$C NMR spectra were recorded on a 300 MHz and 75 MHz Bruker spectrometer, respectively.

Example 1 Synthesis of Nucleoside Phosphoramidites

The preparation of nucleoside phosphoramidites is performed following procedures that are illustrated herein and in the art such as but not limited to U.S. Pat. No. 6,426,220 and published PCT WO 02/36743.

Example 2 Synthesis of Oligomeric Compounds

The oligomeric compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as alkylated derivatives and those having phosphorothioate linkages.

Oligomeric compounds: Unsubstituted and substituted phosphodiester (P=O) oligomeric compounds, including without limitation, oligonucleotides can be synthesized on an automated DNA synthesizer (Applied Biosystems model 394) using standard phosphoramidite chemistry with oxidation by iodine.

In certain embodiments, phosphorothioate internucleoside linkages (P=S) are synthesized similar to phosphodiester internucleoside linkages with the following exceptions: thiation is effected by utilizing a 10% w/v solution of 3,H-1,2-benzodithiole-3-one 1,1-dioxide in acetonitrile for the oxidation of the phosphite linkages. The thiation reaction step time is increased to 180 sec and preceded by the normal capping step. After cleavage from the CPG column and deblocking in concentrated ammonium hydroxide at 55° C. (12-16 hr), the oligomeric compounds are recovered by precipitating with greater than 3 volumes of ethanol from a 1 M NH$_4$OAc solution. Phosphinate internucleoside linkages can be prepared as described in U.S. Pat. No. 5,508,270.

Alkyl phosphonate internucleoside linkages can be prepared as described in U.S. Pat. No. 4,469,863.

3'-Deoxy-3'-methylene phosphonate internucleoside linkages can be prepared as described in U.S. Pat. No. 5,610,289 or U.S. Pat. No. 5,625,050.

Phosphoramidite internucleoside linkages can be prepared as described in U.S. Pat. No. 5,256,775 or U.S. Pat. No. 5,366,878.

Alkylphosphonothioate internucleoside linkages can be prepared as described in published PCT applications PCT/US94/00902 and PCT/US93/06976 (published as WO 94/17093 and WO 94/02499, respectively).

3'-Deoxy-3'-amino phosphoramidate internucleoside linkages can be prepared as described in U.S. Pat. No. 5,476,925.

Phosphotriester internucleoside linkages can be prepared as described in U.S. Pat. No. 5,023,243.

Borano phosphate internucleoside linkages can be prepared as described in U.S. Pat. Nos. 5,130,302 and 5,177,198.

Oligomeric compounds having one or more non-phosphorus containing internucleoside linkages including without limitation methylenemethylimino linked oligonucleosides, also identified as MMI linked oligonucleosides, methylenedimethylhydrazo linked oligonucleosides, also identified as MDH linked oligonucleosides, methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone oligomeric compounds having, for instance, alternating MMI and P=O or P=S linkages can be prepared as described in U.S. Pat. Nos. 5,378,825, 5,386,023, 5,489,677, 5,602,240 and 5,610,289.

Formacetal and thioformacetal internucleoside linkages can be prepared as described in U.S. Pat. Nos. 5,264,562 and 5,264,564.

Ethylene oxide internucleoside linkages can be prepared as described in U.S. Pat. No. 5,223,618.

Example 3 Isolation and Purification of Oligomeric Compounds

After cleavage from the controlled pore glass solid support or other support medium and deblocking in concentrated ammonium hydroxide at 55° C. for 12-16 hours, the oligomeric compounds, including without limitation oligonucleotides and oligonucleosides, are recovered by precipitation out of 1 M NH$_4$OAc with >3 volumes of ethanol. Synthesized oligomeric compounds are analyzed by electrospray mass spectroscopy (molecular weight determination) and by capillary gel electrophoresis. The relative amounts of phosphorothioate and phosphodiester linkages obtained in the synthesis is determined by the ratio of correct molecular weight relative to the −16 amu product (+/−32+/−48). For some studies oligomeric compounds are purified by HPLC, as described by Chiang et al., J. Biol. Chem. 1991, 266, 18162-18171. Results obtained with HPLC-purified material are generally similar to those obtained with non-HPLC purified material.

Example 4 Synthesis of Oligomeric Compounds Using the 96 Well Plate Format

Oligomeric compounds, including without limitation oligonucleotides, can be synthesized via solid phase P(III) phosphoramidite chemistry on an automated synthesizer capable of assembling 96 sequences simultaneously in a 96-well format. Phosphodiester internucleoside linkages are afforded by oxidation with aqueous iodine. Phosphorothioate internucleoside linkages are generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites can be purchased from commercial vendors (e.g. PE-Applied Biosystems, Foster City, Calif., or Pharmacia, Piscataway, N.J.). Non-standard nucleosides are synthesized as per standard or patented methods and can be functionalized as base protected beta-cyanoethyldiisopropyl phosphoramidites.

Oligomeric compounds can be cleaved from support and deprotected with concentrated NH$_4$OH at elevated temperature (55-60° C.) for 12-16 hours and the released product then dried in vacuo. The dried product is then re-suspended in sterile water to afford a master plate from which all analytical and test plate samples are then diluted utilizing robotic pipettors.

Example 5 Analysis of Oligomeric Compounds Using the 96-Well Plate Format

The concentration of oligomeric compounds in each well can be assessed by dilution of samples and UV absorption spectroscopy. The full-length integrity of the individual products can be evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition is confirmed by mass analysis of the oligomeric compounds utilizing electrospray-mass spectroscopy. All assay test plates are diluted from the master plate using single and multi-channel robotic pipettors. Plates are judged to be acceptable if at least 85% of the oligomeric compounds on the plate are at least 85% full length.

Example 6 In Vitro Treatment of Cells with Oligomeric Compounds

The effect of oligomeric compounds on target nucleic acid expression is tested in any of a variety of cell types provided that the target nucleic acid is present at measurable levels. This can be routinely determined using, for example, PCR or Northern blot analysis. Cell lines derived from multiple tissues and species can be obtained from American Type Culture Collection (ATCC, Manassas, Va.).

The following cell type is provided for illustrative purposes, but other cell types can be routinely used, provided that the target is expressed in the cell type chosen. This can be readily determined by methods routine in the art, for example Northern blot analysis, ribonuclease protection assays or RT-PCR.

b.END cells: The mouse brain endothelial cell line b.END was obtained from Dr. Werner Risau at the Max Plank Institute (Bad Nauheim, Germany). b.END cells are routinely cultured in DMEM, high glucose (Invitrogen Life Technologies, Carlsbad, Calif.) supplemented with 10% fetal bovine serum (Invitrogen Life Technologies, Carlsbad, Calif.). Cells are routinely passaged by trypsinization and dilution when they reached approximately 90% confluence. Cells are seeded into 96-well plates (Falcon-Primaria #353872, BD Biosciences, Bedford, Mass.) at a density of approximately 3000 cells/well for uses including but not limited to oligomeric compound transfection experiments.

Experiments involving treatment of cells with oligomeric compounds:

When cells reach appropriate confluency, they are treated with oligomeric compounds using a transfection method as described.

LIPOFECTIN™

When cells reached 65-75% confluency, they are treated with one or more oligomeric compounds. The oligomeric compound is mixed with LIPOFECTIN™ Invitrogen Life Technologies, Carlsbad, Calif.) in Opti-MEM™-1 reduced serum medium (Invitrogen Life Technologies, Carlsbad, Calif.) to achieve the desired concentration of the oligomeric compound(s) and a LIPOFECTIN™ concentration of 2.5 or 3 µg/mL per 100 nM oligomeric compound(s). This transfection mixture is incubated at room temperature for approximately 0.5 hours. For cells grown in 96-well plates, wells are washed once with 100 µL OPTI-MEM™-1 and then treated with 130 µL of the transfection mixture. Cells grown in 24-well plates or other standard tissue culture plates are treated similarly, using appropriate volumes of medium and oligomeric compound(s). Cells are treated and data are obtained in duplicate or triplicate. After approximately 4-7 hours of treatment at 37° C., the medium containing the transfection mixture is replaced with fresh culture medium. Cells are harvested 16-24 hours after treatment with oligomeric compound(s).

Other suitable transfection reagents known in the art include, but are not limited to, CYTOFECTIN™, LIPOFECTAMINE™, OLIGOFECTAMINE™, and FUGENE™. Other suitable transfection methods known in the art include, but are not limited to, electroporation.

Example 7 Real-Time Quantitative PCR Analysis of Target mRNA Levels

Quantitation of target mRNA levels is accomplished by real-time quantitative PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

RT and PCR reagents are obtained from Invitrogen Life Technologies (Carlsbad, Calif.). RT, real-time PCR is carried out by adding 20 µL PCR cocktail (2.5×PCR buffer minus $MgCl_2$, 6.6 mM $MgCl_2$, 375 M each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5×ROX dye) to 96-well plates containing 30 µL total RNA solution (20-200 ng). The RT reaction is carried out by incubation for 30 minutes at 48° C. Following a 10 minute incubation at 95° C. to activate the PLATINUM® Taq, 40 cycles of a two-step PCR protocol are carried out: 95° C. for 15 seconds (denaturation) followed by 60° C. for 1.5 minutes (annealing/extension).

Gene target quantities obtained by RT, real-time PCR are normalized using either the expression level of GAPDH, a gene whose expression is constant, or by quantifying total RNA using RIBOGREEN™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent (Molecular Probes, Inc. Eugene, Oreg.). Methods of RNA quantification by RIBOGREEN™ are taught in Jones, L. J., et al, (Analytical Biochemistry, 1998, 265, 368-374).

In this assay, 170 µL of RIBOGREEN™ working reagent (RIBOGREEN™ reagent diluted 1:350 in 10 mM Tris-HCl, 1 mM EDTA, pH 7.5) is pipetted into a 96-well plate containing 30 µL purified, cellular RNA. The plate is read in a CytoFluor 4000 (PE Applied Biosystems) with excitation at 485 nm and emission at 530 nm.

Example 8 Analysis of Inhibition of Target Expression

Antisense modulation of a target expression can be assayed in a variety of ways known in the art. For example, a target mRNA levels can be quantitated by, e.g., Northern blot analysis, competitive polymerase chain reaction (PCR), or real-time PCR. Real-time quantitative PCR is presently desired. RNA analysis can be performed on total cellular RNA or poly(A)+ mRNA. One method of RNA analysis of the present disclosure is the use of total cellular RNA as described in other examples herein. Methods of RNA isolation are well known in the art. Northern blot analysis is also routine in the art. Real-time quantitative (PCR) can be conveniently accomplished using the commercially available ABI PRISM™ 7600, 7700, or 7900 Sequence Detection System, available from PE-Applied Biosystems, Foster City, Calif. and used according to manufacturer's instructions.

Protein levels of a target can be quantitated in a variety of ways well known in the art, such as immunoprecipitation, Western blot analysis (immunoblotting), enzyme-linked immunosorbant assay (ELISA) or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Methods for preparation of polyclonal antisera are taught in, for example, Ausubel, F. M. et al., *Current Protocols in Molecular Biology*, Volume 2, pp. 11.12.1-11.12.9, John Wiley & Sons, Inc., 1997. Preparation of monoclonal antibodies is taught in, for example, Ausubel, F. M. et al., *Current Protocols in Molecular Biology*, Volume 2, pp. 11.4.1-11.11.5, John Wiley & Sons, Inc., 1997.

Immunoprecipitation methods are standard in the art and can be found at, for example, Ausubel, F. M. et al., *Current Protocols in Molecular Biology*, Volume 2, pp. 10.16.1-10.16.11, John Wiley & Sons, Inc., 1998. Western blot (immunoblot) analysis is standard in the art and can be found at, for example, Ausubel, F. M. et al., *Current Protocols in Molecular Biology*, Volume 2, pp. 10.8.1-10.8.21, John Wiley & Sons, Inc., 1997. Enzyme-linked immunosorbant assays (ELISA) are standard in the art and can be found at, for example, Ausubel, F. M. et al., *Current Protocols in Molecular Biology*, Volume 2, pp. 11.2.1-11.2.22, John Wiley & Sons, Inc., 1991.

Example 9 Design of Phenotypic Assays and In Vivo Studies for the Use of Target Inhibitors Phenotypic Assays Once target inhibitors have been identified by the methods disclosed herein, the oligomeric compounds are further investigated in one or more phenotypic assays, each having measurable endpoints predictive of efficacy in the treatment of a particular disease state or condition.

Phenotypic assays, kits and reagents for their use are well known to those skilled in the art and are herein used to investigate the role and/or association of a target in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with a target inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Measurement of the expression of one or more of the genes of the cell after treatment is also used as an indicator of the efficacy or potency of the target inhibitors. Hallmark genes, or those genes suspected to be associated with a specific disease state, condition, or phenotype, are measured in both treated and untreated cells.

In Vivo Studies

The individual subjects of the in vivo studies described herein are warm-blooded vertebrate animals, which includes humans.

Example 10 RNA Isolation

Poly(A)+ mRNA Isolation

Poly(A)+ mRNA is isolated according to Miura et al., (Clin. Chem., 1996, 42, 1758-1764). Other methods for poly(A)+ mRNA isolation are routine in the art. Briefly, for cells grown on 96-well plates, growth medium is removed from the cells and each well is washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) is added to each well, the plate is gently agitated and then incubated at room temperature for five minutes. 55 µL of lysate is transferred to Oligo d(T) coated 96-well plates (AGCT Inc., Irvine Calif.). Plates are incubated for 60 minutes at room temperature, washed 3 times with 200 µL of wash buffer (10 mM Tris-HCl pH 7.6, 1 mM EDTA, 0.3 M NaCl). After the final wash, the plate is blotted on paper towels to remove excess wash buffer and then air-dried for 5 minutes. 60 µL of elution buffer (5 mM Tris-HCl pH 7.6), preheated to 70° C., is added to each well, the plate is incubated on a 90° C. hot plate for 5 minutes, and the eluate is then transferred to a fresh 96-well plate.

Cells grown on 100 mm or other standard plates may be treated similarly, using appropriate volumes of all solutions.

Total RNA Isolation

Total RNA is isolated using an RNEASY 96™ kit and buffers purchased from Qiagen Inc. (Valencia, Calif.) following the manufacturer's recommended procedures. Briefly, for cells grown on 96-well plates, growth medium is removed from the cells and each well is washed with 200 µL cold PBS. 150 µL Buffer RLT is added to each well and the plate vigorously agitated for 20 seconds. 150 µL of 70% ethanol is then added to each well and the contents mixed by pipetting three times up and down. The samples are then transferred to the RNEASY 96™ well plate attached to a QIAVAC™ manifold fitted with a waste collection tray and attached to a vacuum source. Vacuum is applied for 1 minute. 500 µL of Buffer RW1 is added to each well of the RNEASY 96™ plate and incubated for 15 minutes and the vacuum is again applied for 1 minute. An additional 500 µL of Buffer RW1 is added to each well of the RNEASY 96™ plate and the vacuum is applied for 2 minutes. 1 mL of Buffer RPE is then added to each well of the RNEASY 96™ plate and the vacuum applied for a period of 90 seconds. The Buffer RPE wash is then repeated and the vacuum is applied for an additional 3 minutes. The plate is then removed from the QIAVAC™ manifold and blotted dry on paper towels. The plate is then re-attached to the QIAVAC™ manifold fitted with a collection tube rack containing 1.2 mL collection tubes. RNA is then eluted by pipetting 140 µL of RNAse free water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 11 Target-Specific Primers and Probes

Probes and primers may be designed to hybridize to a target sequence, using published sequence information.

For example, for human PTEN, the following primer-probe set was designed using published sequence information (GENBANK™ accession number U92436.1, SEQ ID NO: 1).

```
Forward primer:
                                  (SEQ ID NO: 2)
AATGGCTAAGTGAAGATGACAATCAT Reverse primer:
                                  (SEQ ID NO: 3)
TGCACATATCATTACACCAGTTCGT
```

And the PCR probe:

FAM-TTGCAGCAATTCACTGTAAAGCTG-GAAAGG-TAMRA (SEQ ID NO: 4), where FAM is the fluorescent dye and TAMRA is the quencher dye.

Example 12 Western Blot Analysis of Target Protein Levels

Western blot analysis (immunoblot analysis) is carried out using standard methods. Cells are harvested 16-20 h after oligonucleotide treatment, washed once with PBS, suspended in Laemmli buffer (100 µl/well), boiled for 5 minutes and loaded on a 16% SDS-PAGE gel. Gels are run for 1.5 hours at 150 V, and transferred to membrane for western blotting. Appropriate primary antibody directed to a target is used, with a radiolabeled or fluorescently labeled secondary antibody directed against the primary antibody species. Bands are visualized using a PHOSPHORIMAGER™ (Molecular Dynamics, Sunnyvale Calif.).

Example 13 Preparation of Phosphoramidites 1-15

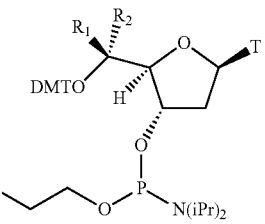

1 $R_1 = H, R_2 = H$
2 $R_1 = CH_3, R_2 = H$
3 $R_1 = H, R_2 = CH_3$

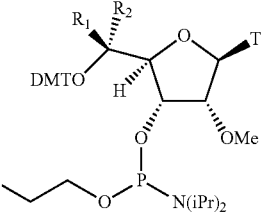

3a $R_1 = H, R_2 = H$
3b $R_1 = CH_3, R_2 = H$
3c $R_1 = H, R_2 = CH_3$

59

-continued

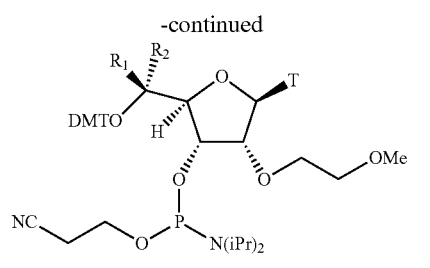

4 R₁ = H, R₂ = H
5 R₁ = CH₃, R₂ = H
6 R₁ = H, R₂ = CH₃

7 R₁ = H, R₂ = H
8 R₁ = CH₃, R₂ = H
9 R₁ = H, R₂ = CH₃

10 R₁ = H, R₂ = H
11 R₁ = CH₃, R₂ = H
12 R₁ = H, R₂ = CH₃

13 R₁ = H, R₂ = H
14 R₁ = CH₃, R₂ = H
15 R₁ = H, R₂ = CH₃

Phosphoramidites 1-15 are prepared using procedures similar to published procedures (see Wilds et al., *Nucleic Acids Research*, 2000, 28(18), 3625-3635; Prakash et al., *Org. Lett.*, 2003, 5(4), 403-406; Ravikumar et al., *Process Research and Development*, 2002, 6(6), 798-806; Martin, P., *Helvetica Chimica Acta*, 1995, 78(2), 486-504; WO 2011/123621; WO 2010/101951; WO 2010/048549; WO 2010/048585; WO 2008/101157; WO 1994/22890 and US patent U.S. Pat. No. 6,147,200).

60

Example 14 General Method for the Preparation of Phosphoramidites 16-31b

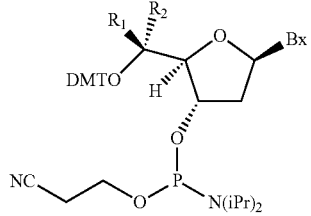

16 R₁ = H, R₂ = H
17 R₁ = CH₃, R₂ = H
18 R₁ = H, R₂ = CH₃

18a R₁ = H, R₂ = H
18b R₁ = CH₃, R₂ = H
18c R₁ = H, R₂ = CH₃

19 R₁ = H, R₂ = H
20 R₁ = CH₃, R₂ = H
21 R₁ = H, R₂ = CH₃

22 R₁ = H, R₂ = H
23 R₁ = CH₃, R₂ = H
24 R₁ = H, R₂ = CH₃

25 R₁ = H, R₂ = H
26 R₁ = CH₃, R₂ = H
27 R₁ = H, R₂ = CH₃

-continued

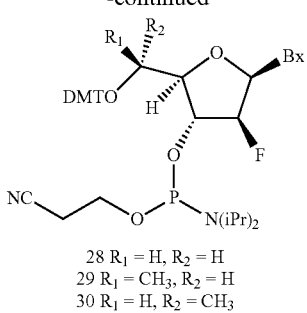

28 R₁ = H, R₂ = H
29 R₁ = CH₃, R₂ = H
30 R₁ = H, R₂ = CH₃

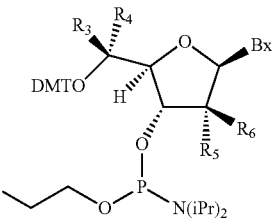

31

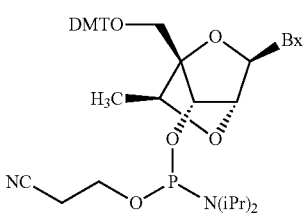

31a

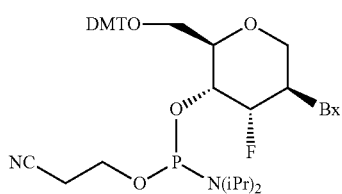

31b

Bx is a heterocyclic base moiety;
$R_3$ and $R_4$ are each independently H, alkyl, substituted alkyl, alkoxy, substituted alkoxy, alkenyl, substituted alkenyl, alkynyl or substituted alkynyl, aryl or substituted aryl; and
$R_5$ and $R_6$ are each independently H, OH or a 2'-sugar substituent group.

Phosphoramidites 16-31 are prepared as per the procedures well known in the art as described in the specification herein and also as per the procedures illustrated in Example 13. Compounds 31a and 31b are prepared using similar procedures as described in published literature (see Seth et al., *Bioorg. Med. Chem.*, 2011, 21(4), 1122-1125, *J. Org. Chem.*, 2010, 75(5), 1569-1581, *Nucleic Acids Symposium Series*, 2008, 52(1), 553-554; and Martin et al., *J. Am. Chem. Soc.* 2011, 133(41), 16642-16649; also see published PCT International Applications (WO 2011/115818, WO 2010/091308, WO 2010/077578, WO2010/036698, WO2009/143369, WO 2009/006478, WO 2009/023855, and WO 2007/090071), and U.S. Pat. No. 7,569,686).

Example 15 Preparation of Compounds 40 (RC5', $S_P$) and 41 (RC5', $R_P$)

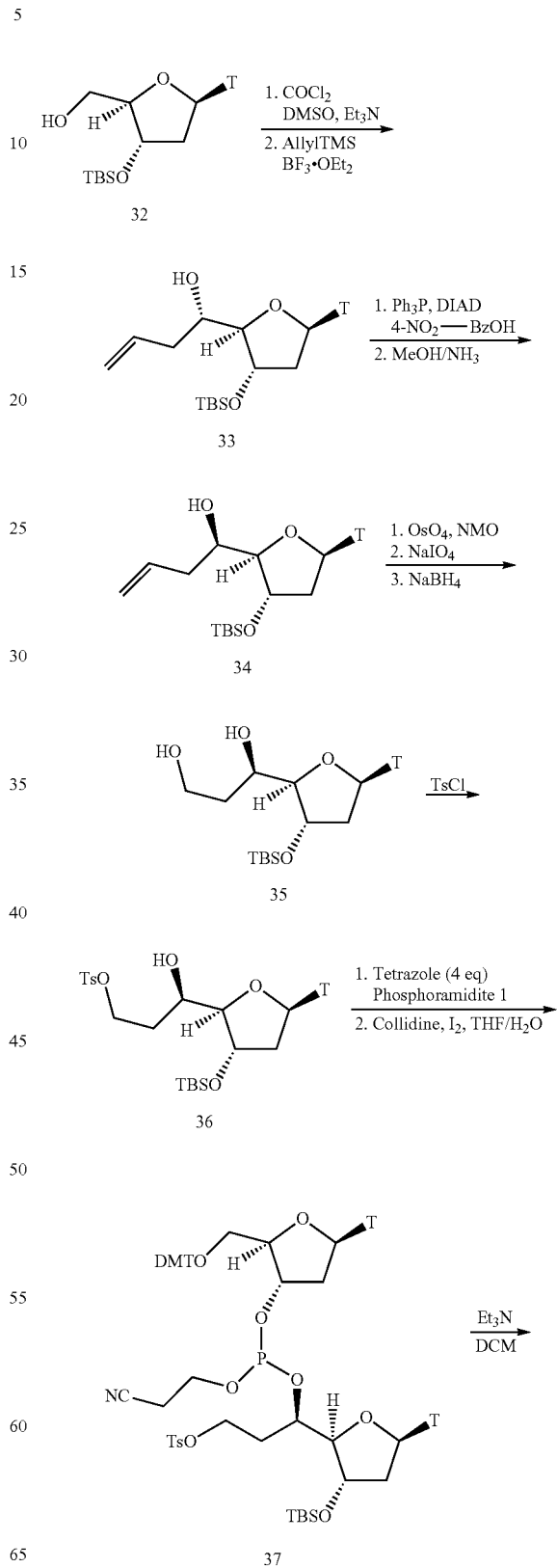

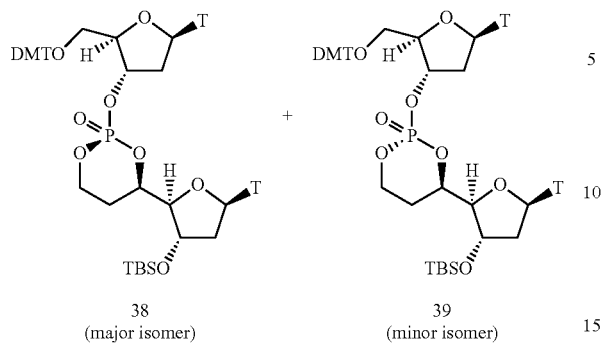

38 (major isomer)  +  39 (minor isomer)

1. TBAF
2. Phosphitylation

1. TBAF
2. Phosphitylation

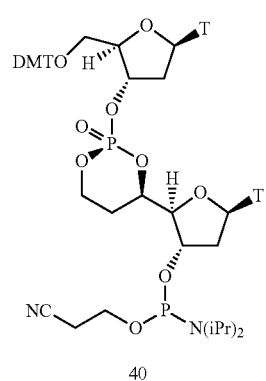

40    41

Compound 32 is available from commercial sources. Compounds 38 and 39 were separated by column chromatography. Either isomer can be used for the subsequent phosphitylation reaction.

The major isomer, Compound 38 was treated with TBAF to remove the TBS protecting group followed by a phosphitylation reaction to provide the desired phosphoramidite, Compound 40 which was used as building blocks for oligonucleotide synthesis. The structural analysis of Compound 40 was confirmed by $^1$H and $^{31}$P NMR spectroscopy.

Example 16 Preparation of Compounds 45-45e ($RC5'$, $S_P$) and 46-46e ($RC5'$, $R_P$)

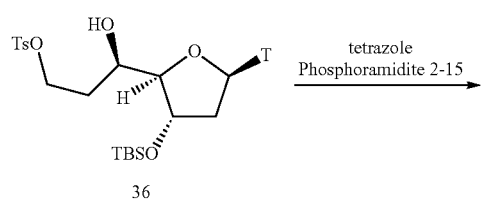

36 → tetrazole Phosphoramidite 2-15 →

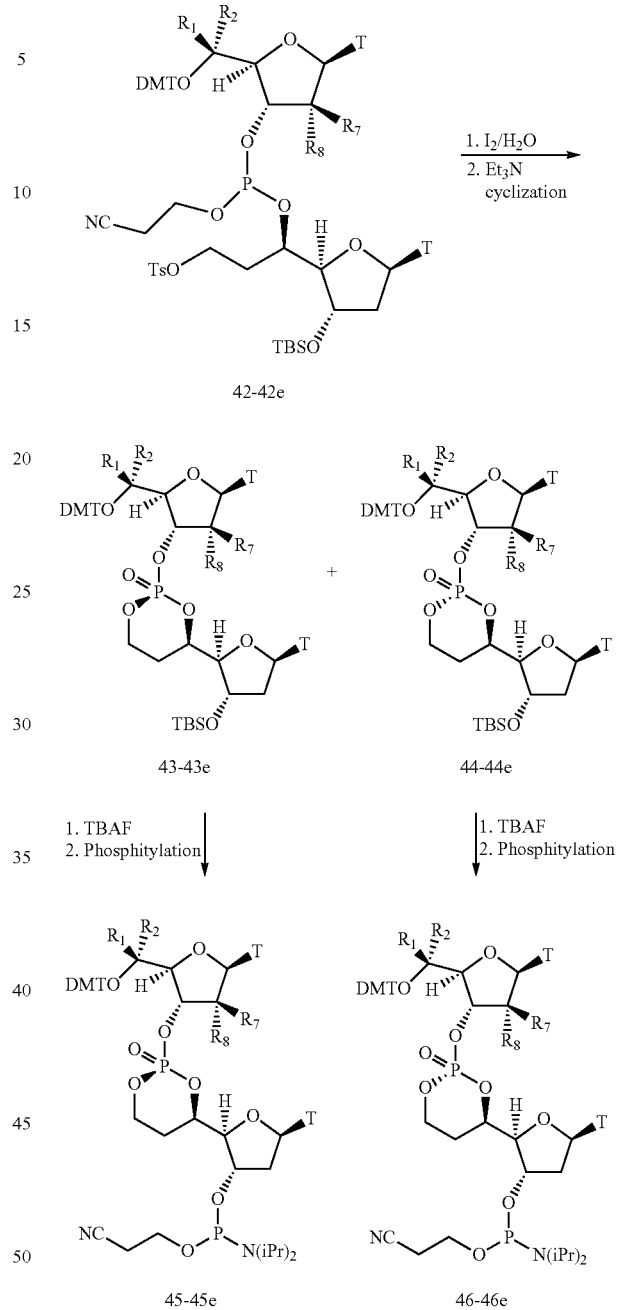

42-42e

1. $I_2/H_2O$
2. $Et_3N$ cyclization 43-43e + 44-44e

1. TBAF
2. Phosphitylation

1. TBAF
2. Phosphitylation 45-45e    46-46e 42-46 $R_1$, $R_2$ and $R_8$ = H, $R_7$ = F
42a-46a $R_1$ = $CH_3$, $R_2$ and $R_8$ = H, $R_7$ = F
42b-46b $R_1$ and $R_8$ = H, $R_2$ = $CH_3$, $R_7$ = F
42c-46c $R_1$, $R_2$ and $R_7$ = H, $R_8$ = $OCH_3$, $O(CH_2)_2OCH_3$, $OCH_2(CO)NHCH_3$, or F
42d-46d $R_1$ and $R_7$ = H, $R_2$ = $CH_3$, $R_8$ = $OCH_3$, $O(CH_2)_2OCH_3$, $OCH_2(CO)NHCH_3$ or F
42e-46e $R_1$ = $CH_3$, $R_2$ and $R_7$ = H, $R_8$ = $OCH_3$, $O(CH_2)_2OCH_3$, $OCH_2(CO)NHCH_3$ or F Phosphoramidites 2-15 and Compound 36 are prepared as per the procedures illustrated in Examples 13 and 15. The diastereomeric mixture obtained after cyclization is separated by column chromatography to provide the desired product as a single diastereomer (e.g. Compounds 43-43e or 44-44e).

Example 17 General Method for the Preparation of Compounds 50-50e (RC5', $S_P$) and 51-51e (RC5', $R_P$)

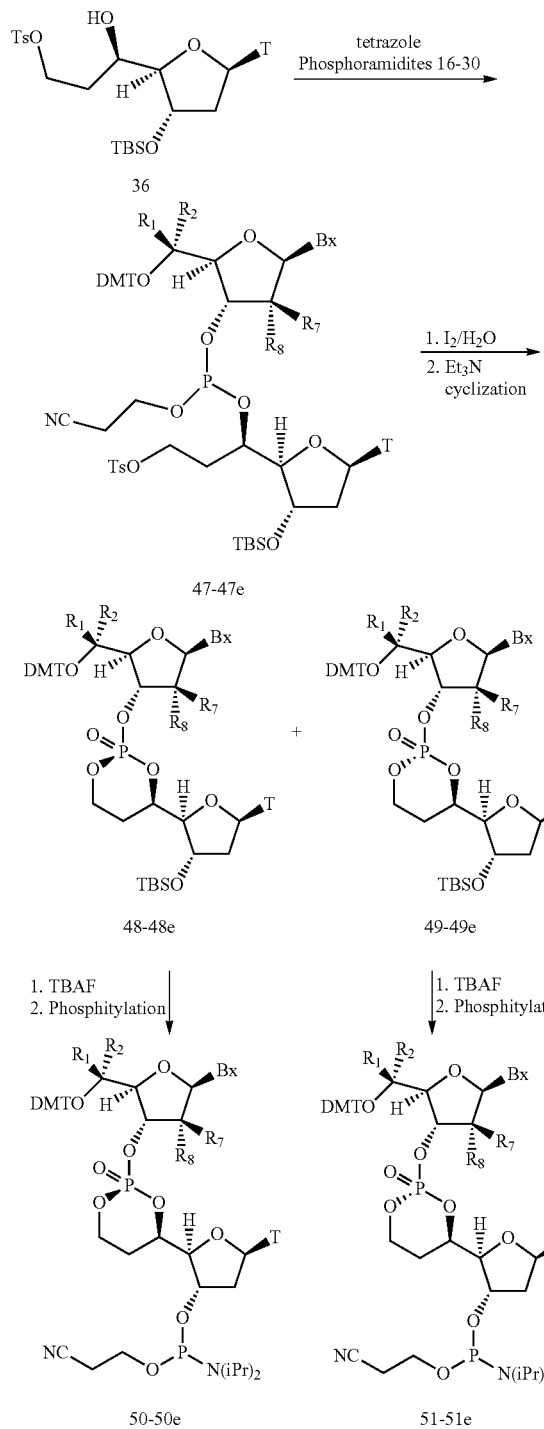

Example 18 General Method for the Preparation of Compounds 55 (RC5', $S_P$) and 56 (RC5', $R_P$)

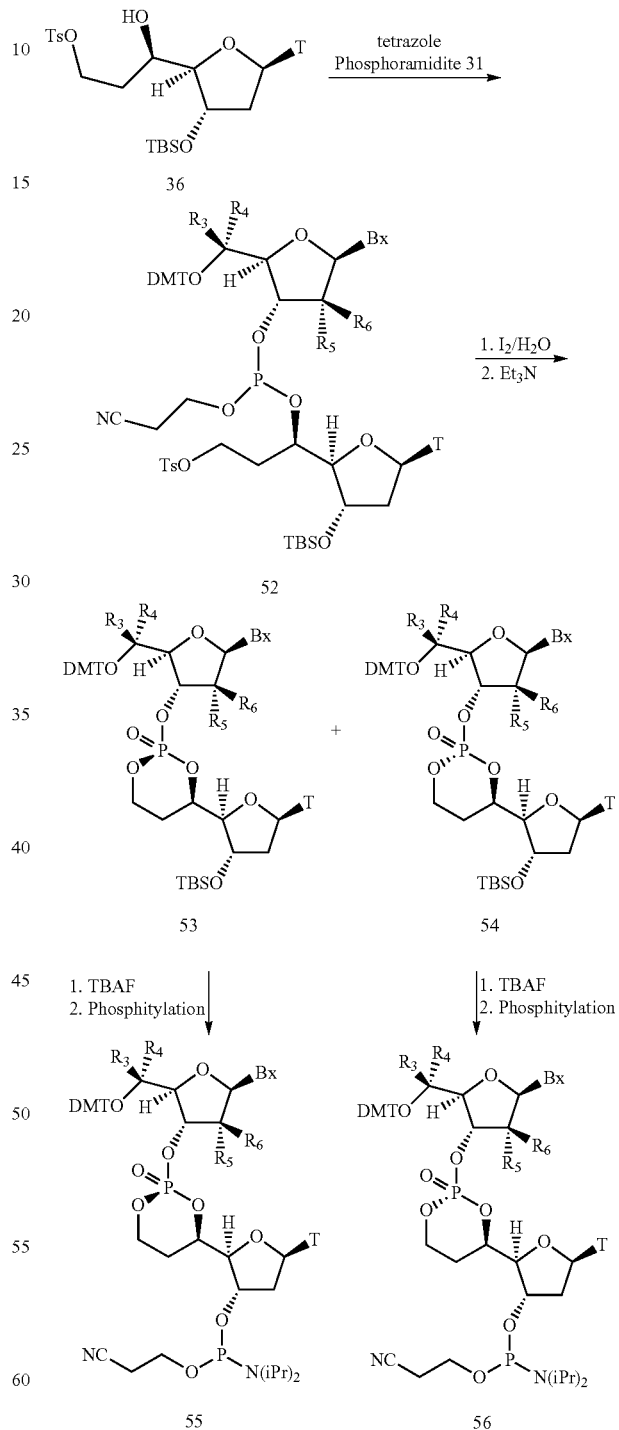

Phosphoramidites 16-30 and Compound 36 are prepared as per the procedures illustrated in Examples 14 and 15. The diastereomeric mixture obtained after cyclization is separated by column chromatography to provide the desired product as a single diastereomer (e.g. Compounds 48-48e or 49-49e).

Bx = heterocyclic base moiety
47-51 $R_1$, $R_2$ and $R_8$ = H, $R_7$ = F
47a-51a $R_1$ = $CH_3$, $R_2$ and $R_8$ = H, $R_7$ = F
47b-51b $R_1$ and $R_8$ = H, $R_2$ = $CH_3$, $R_7$ = F
47c-51c $R_1$, $R_2$ and $R_7$ = H, $R_8$ = $OCH_3$, $O(CH_2)_2OCH_3$, $OCH_2(CO)NHCH_3$, or F
47d-51d $R_1$ and $R_7$ = H, $R_2$ = $CH_3$, $R_8$ = $OCH_3$, $O(CH_2)_2OCH_3$, $OCH_2(CO)NHCH_3$ or F
47e-51e $R_1$ = $CH_3$, $R_2$ and $R_7$ = H, $R_8$ = $OCH_3$, $O(CH_2)_2OCH_3$, $OCH_2(CO)NHCH_3$ or F Bx is a heterocyclic base moiety;
$R_3$ and $R_4$ are each independently H, alkyl, substituted alkyl, alkoxy, substituted alkoxy, alkenyl, substituted alkenyl, alkynyl or substituted alkynyl, aryl or substituted aryl;
and $R_5$ and $R_6$ are each independently H, OH or 2'-sugar substituent group Phosphoramidite 31 and Compound 36 are prepared as per the procedures illustrated in Examples 14 and 15. Compounds 53 and 54 are separated by column chromatography.

Example 19 Preparation of Compounds 63 (RC5', S$_P$) and 64 (RC5', R$_P$)

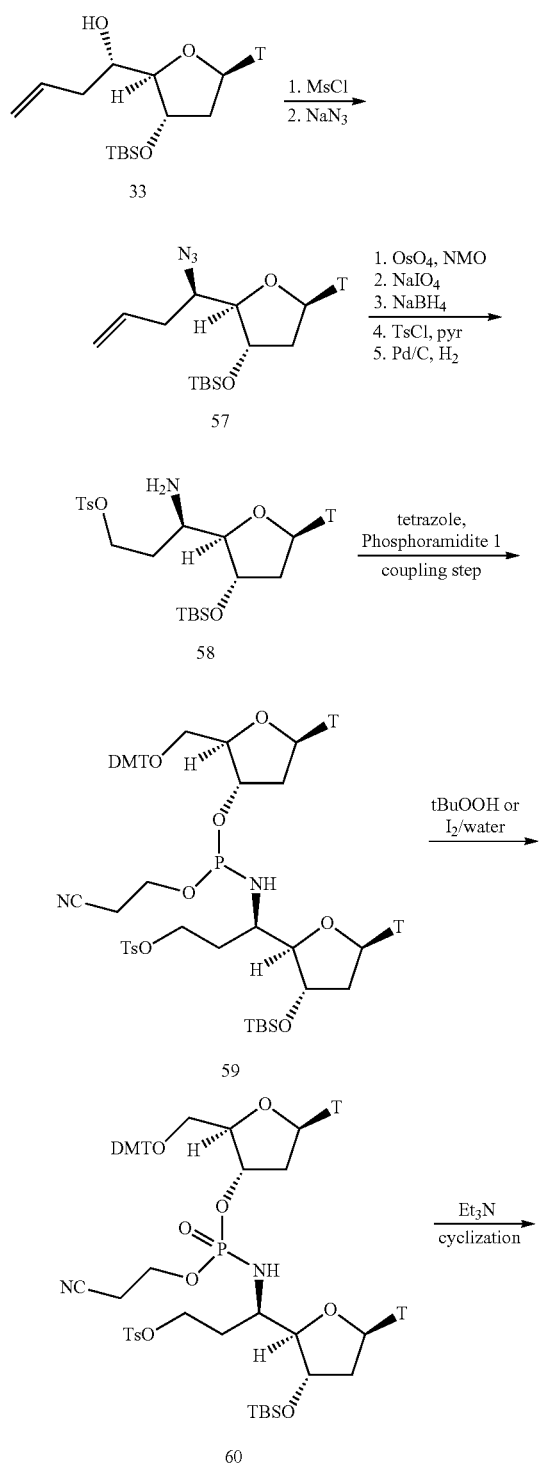

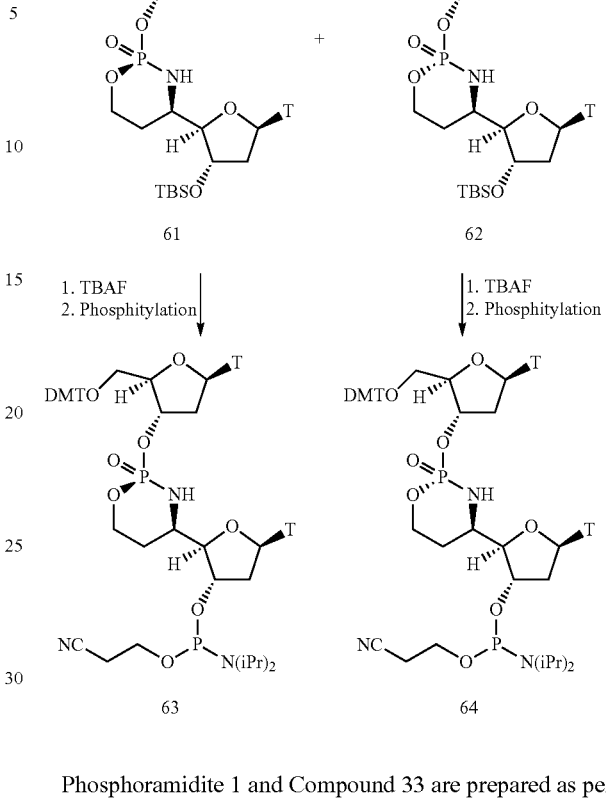

Phosphoramidite 1 and Compound 33 are prepared as per the procedures illustrated in Examples 13 and 15.

Phosphoramidite 1 used in the coupling step serves only to illustrate the compounds described herein and is not intended to be limiting. Various phosphoramidites as illustrated in Examples 13 and 14 (e.g. Compounds 2-31) can also be used to couple with the tosylate precursor (e.g. Compound 58) in the same manner as exemplified in Examples 15-18 to provide the desired dimer (e.g. Compound 59).

Oxidation followed by cyclization in the presence of Et$_3$N provides the cyclic phosphoramidate as a diastereomeric mixture, which is separated by column chromatography to provide Compounds 61 and 62. TBS deprotection followed by phosphitylation provides the desired dimer phosphoramidites Compounds 63 and 64, which are used as building blocks in oligonucleotide synthesis.

Example 20 Preparation of Compounds 71 (RC5', S$_P$) and 72 (RC5', R$_P$)

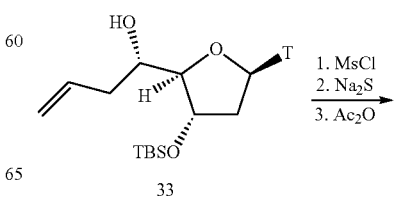

33

69
-continued

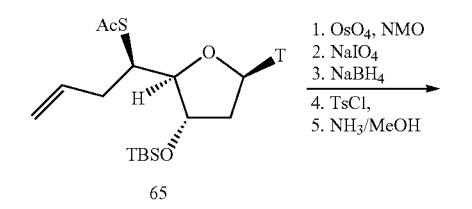

65

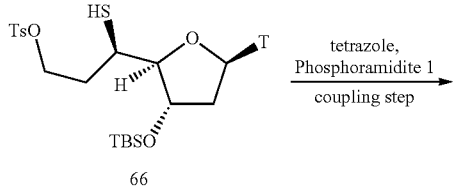

66

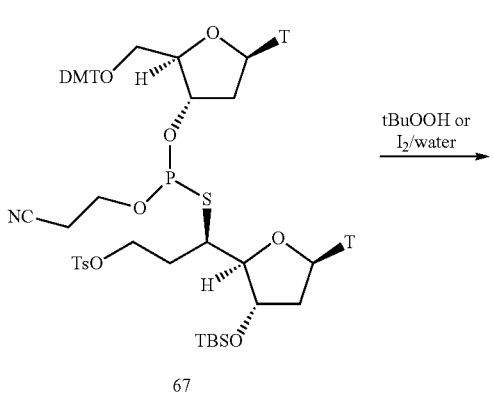

67

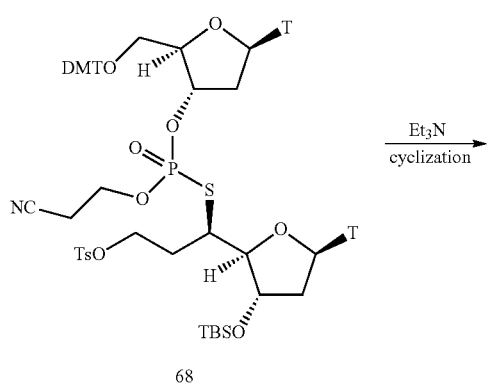

68

70
-continued

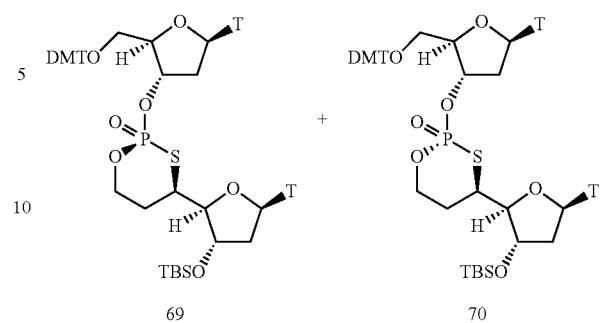

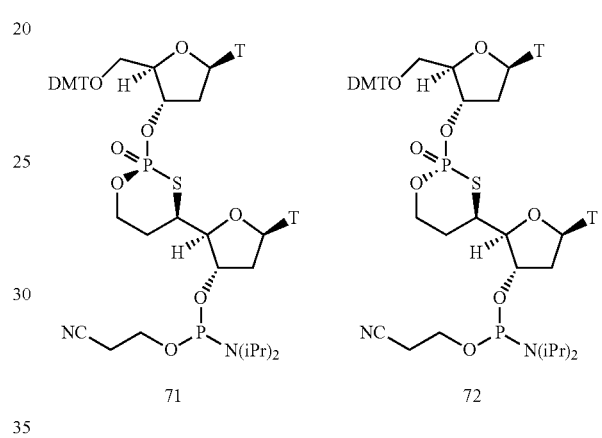

Phosphoramidite 1 and Compound 33 are prepared as per the procedures illustrated in Examples 13 and 15.

Phosphoramidite 1 used in the coupling step serves only to illustrate the compounds described herein and is not intended to be limiting. Various phosphoramidites as illustrated in Examples 13 and 14 (e.g. Compounds 2-31) can also be used to couple with the thio tosylate precursor (e.g. Compound 66) in the same manner as exemplified in Examples 15-18 to provide the desired dimer (e.g. Compound 67).

Oxidation followed by cyclization in the presence of $Et_3N$ provides the cyclic phosphorothioate as a diastereomeric mixture, which is separated by column chromatography to provide Compounds 69 and 70. TBS deprotection followed by phosphitylation provides the desired dimer phosphoramidites Compounds 71 and 72, which are used as building blocks in oligonucleotide synthesis.

Example 21 Preparation of Compounds 79 and 80

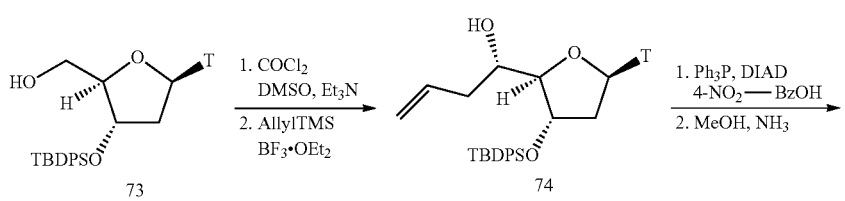

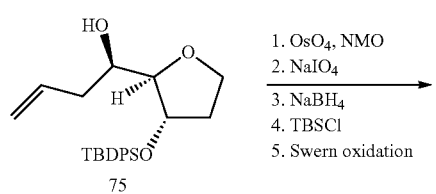
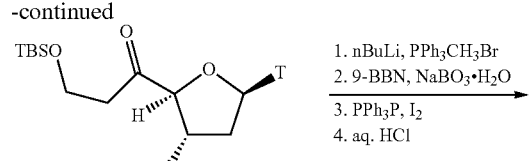
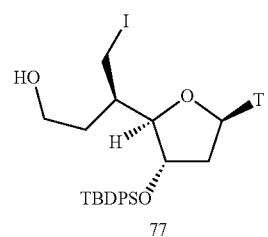
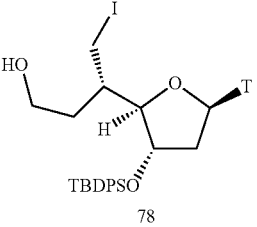
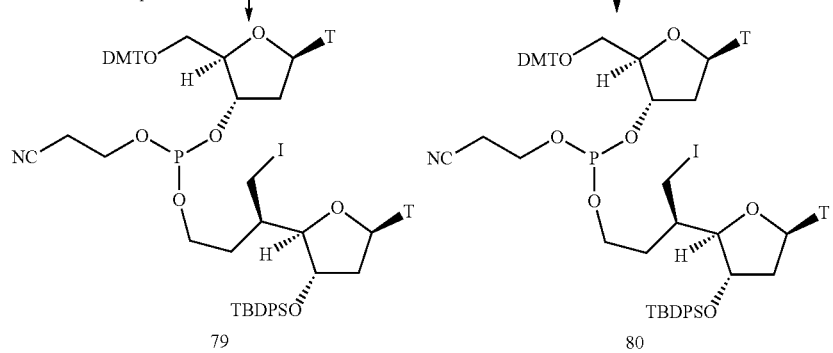

Compound 73 is available from commercial sources. Phosphoramidite 1 is prepared as per the procedures illustrated in Example 13. Compounds 77 and 78 are separated by column chromatography.

Phosphoramidite 1 used in the coupling step serves only to illustrate the compounds described herein and is not intended to be limiting. Various phosphoramidites as illustrated in Examples 13 and 14 (e.g. Compounds 2-31) can also be used to couple with the iodo precursor (e.g. Compound 77 or 78) in the same manner as exemplified in Examples 15-18 to provide the desired dimer (e.g. Compound 79 or 80).

Example 22 Preparation of Compounds 83 (RC5', $S_P$), 83a (RC5', $R_P$), 84 (SC5', $S_P$) and 84a (SC5', $R_P$)

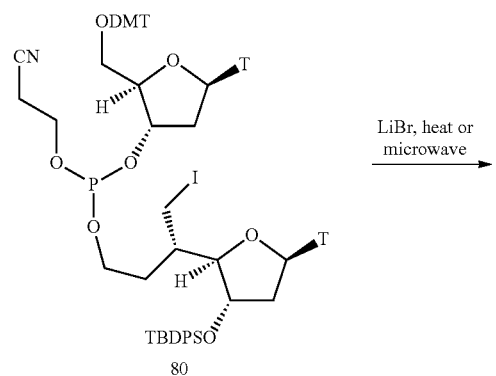

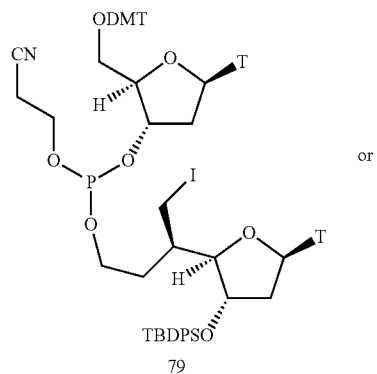

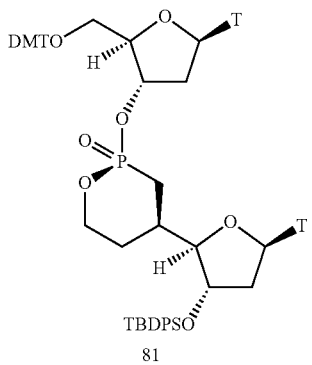

73
-continued

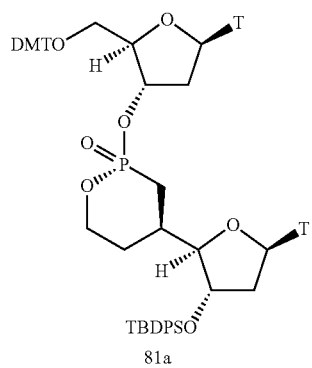
81a

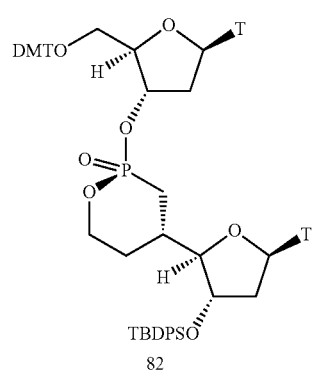
82

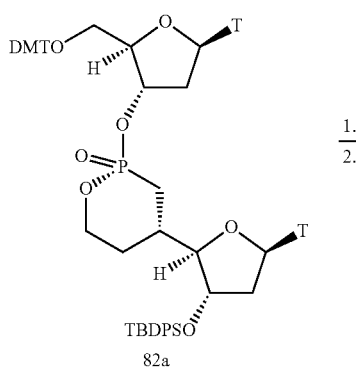

1. TBAF
2. Phosphitylation →

82a

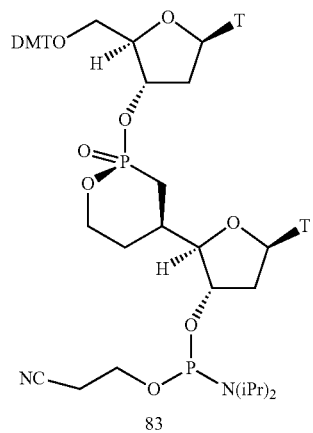
83 or

+ or

74
-continued

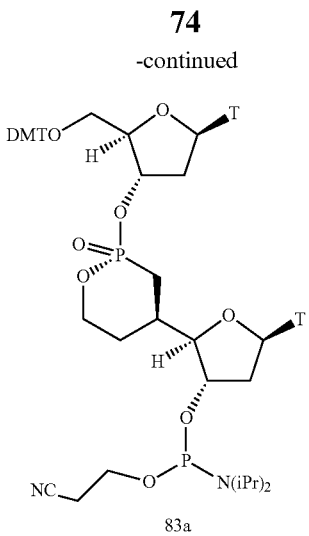
83a

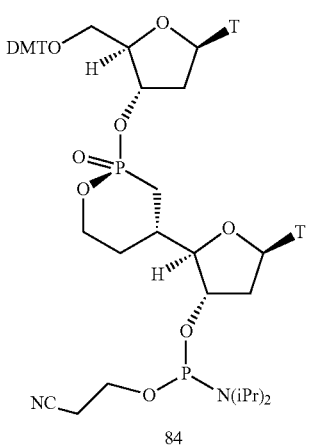
84

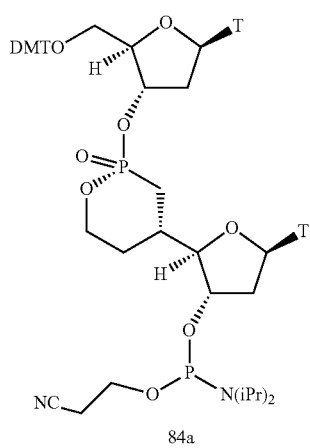
84a or or

Compounds 79 and 80 are prepared as per the procedures illustrated in Example 21. Compounds 81 and 81a, or 82 and 82a are separated by column chromatography to provide the cyclic dimer as a single diastereomer. Either isomer, Compound 81, 81a, 82 or 82a can be used for a phosphitylation reaction to provide the desired phosphoramidites, Compounds 83-84a.

Example 23 Preparation of Compounds 89 (RC5', S$_P$) and 90 (RC5', R$_P$)

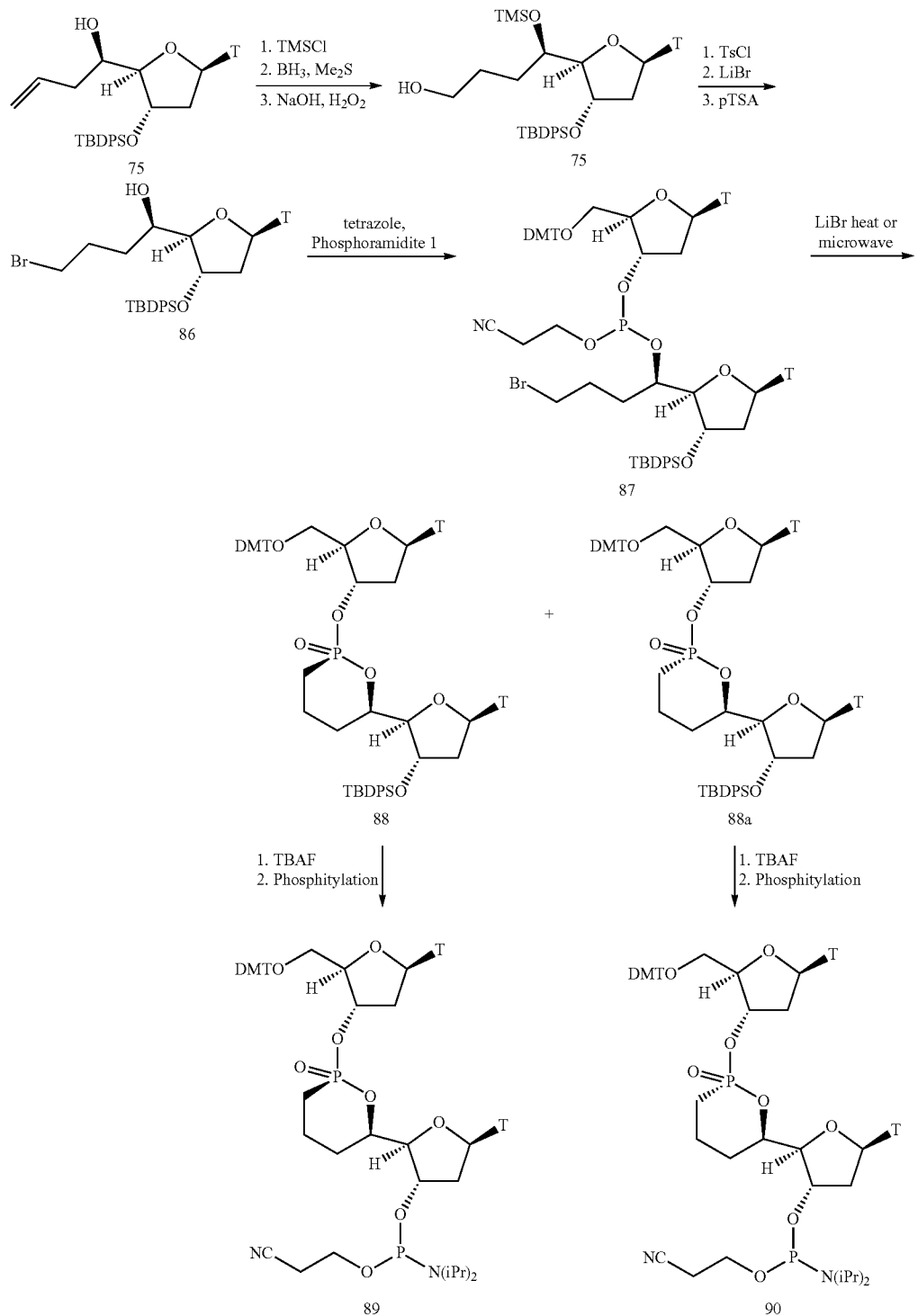

Phosphoramidite 1 and Compound 75 are prepared as per the procedures illustrated in Examples 13 and 21.

Phosphoramidite 1 used in the coupling step serves only to illustrate the compounds described herein and is not intended to be limiting. Various phosphoramidites as illustrated in Examples 13 and 14 (e.g. Compounds 2-31) can also be used to couple with the bromide precursor (e.g. Compound 86) in the same manner as exemplified in Examples 15-18 to provide the desired dimer (e.g. Compound 87). Compounds 88 and 88a are separated by column chromatography.

Example 24 Preparation of Compounds 97 (RC5', S$_P$) and 98 (RC5', R$_P$)
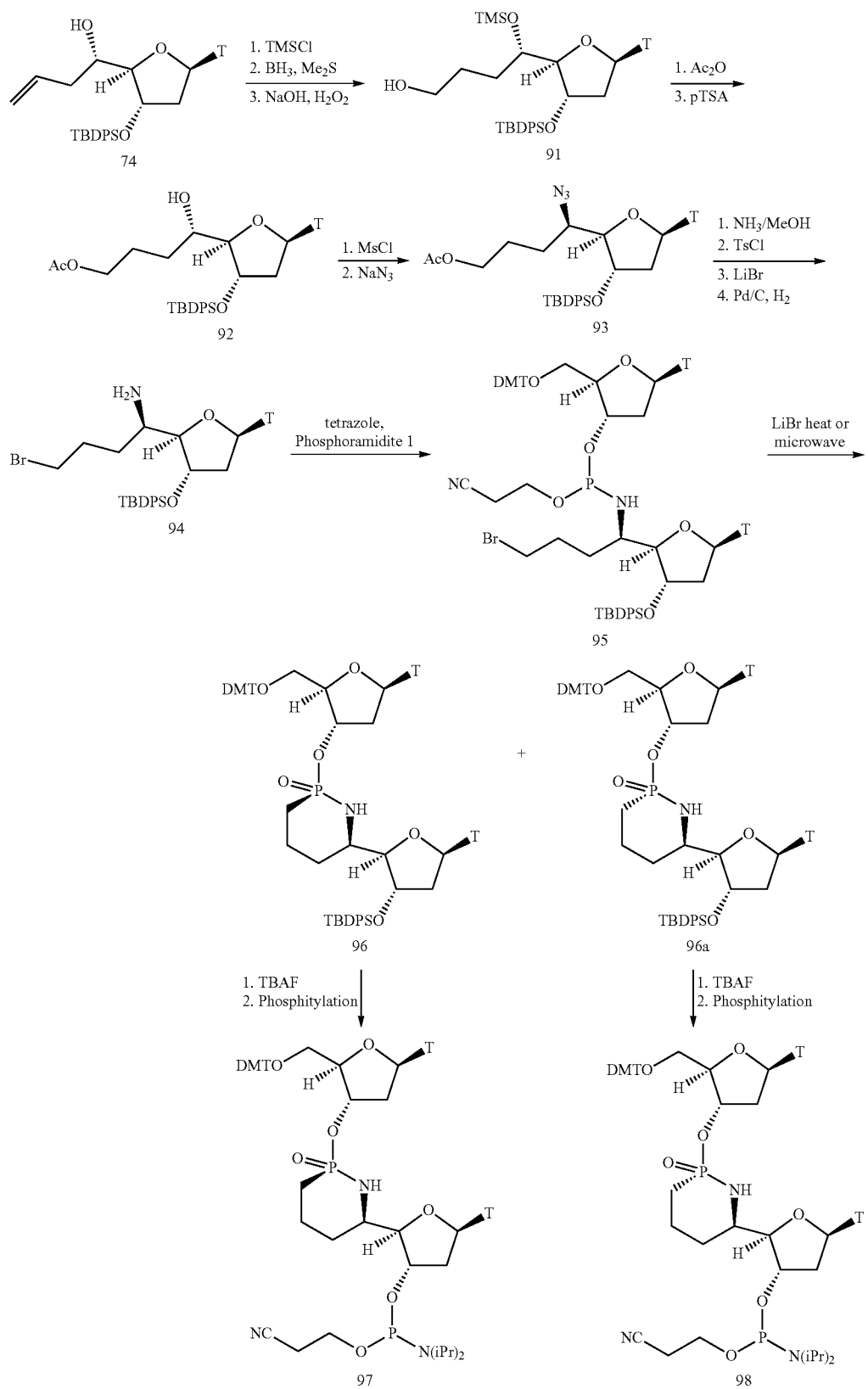

Phosphoramidite 1 and Compound 74 are prepared as per the procedures illustrated in Examples 13 and 21.

Phosphoramidite 1 used in the coupling step serves only to illustrate the compounds described herein and is not intended to be limiting. Various phosphoramidites as illustrated in Examples 13 and 14 (e.g. Compounds 2-31) can also be used to couple with the bromo amine precursor (e.g. Compound 94) in the same manner as exemplified in Examples 15-18 to provide the desired dimer (e.g. Compound 95). Compounds 96 and 96a are separated by column chromatography.

Example 25 Preparation of Compounds 103 (RC5', S$_P$) and 104 (RC5', R$_P$)

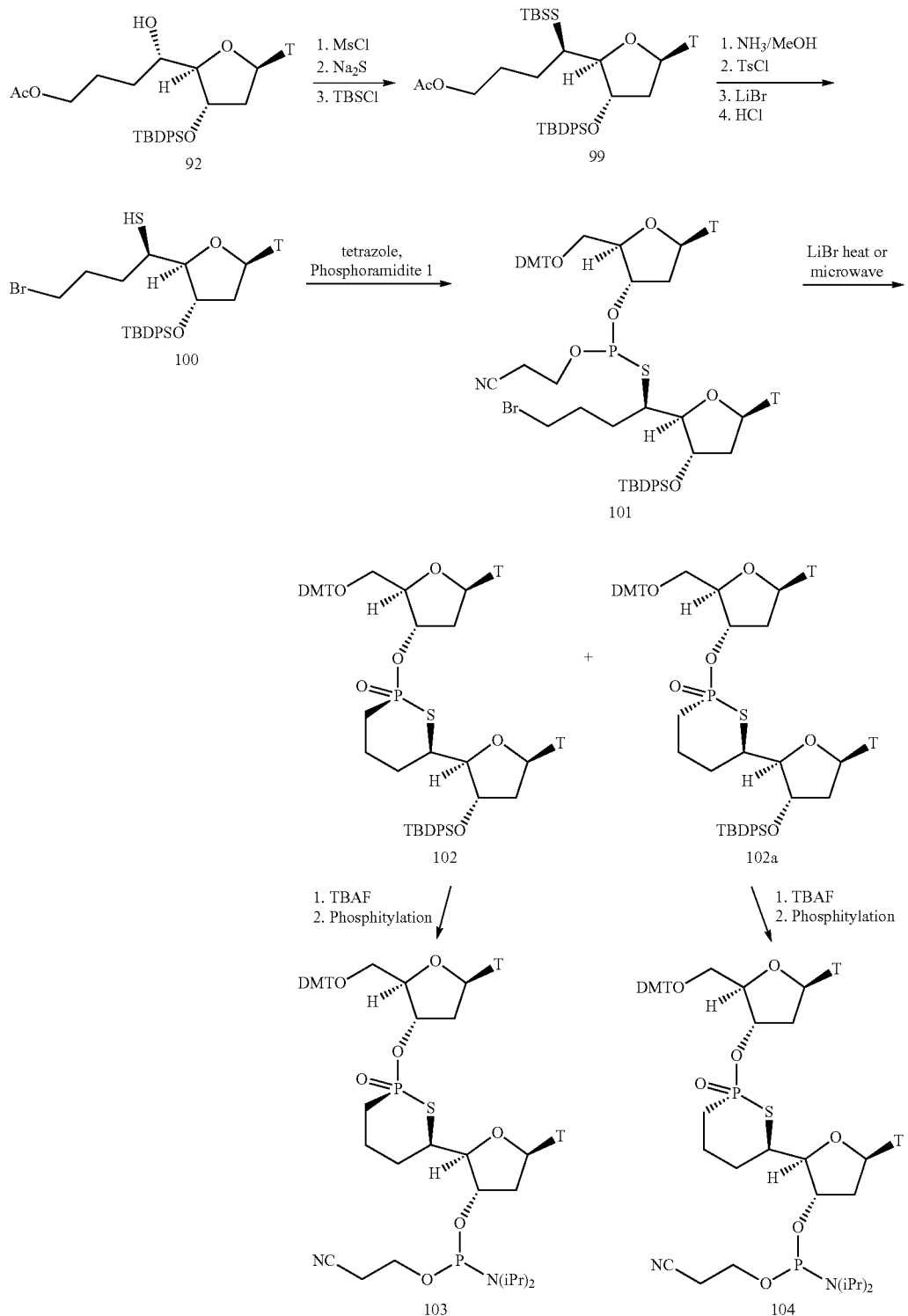

Phosphoramidite 1 and Compound 92 are prepared as per the procedures illustrated in Examples 13 and 24. Compounds 102 and 102a are separated by column chromatography.
Example 26 Preparation of Compounds 113 (RC5', S$_P$) and 114 (RC5', R$_P$)
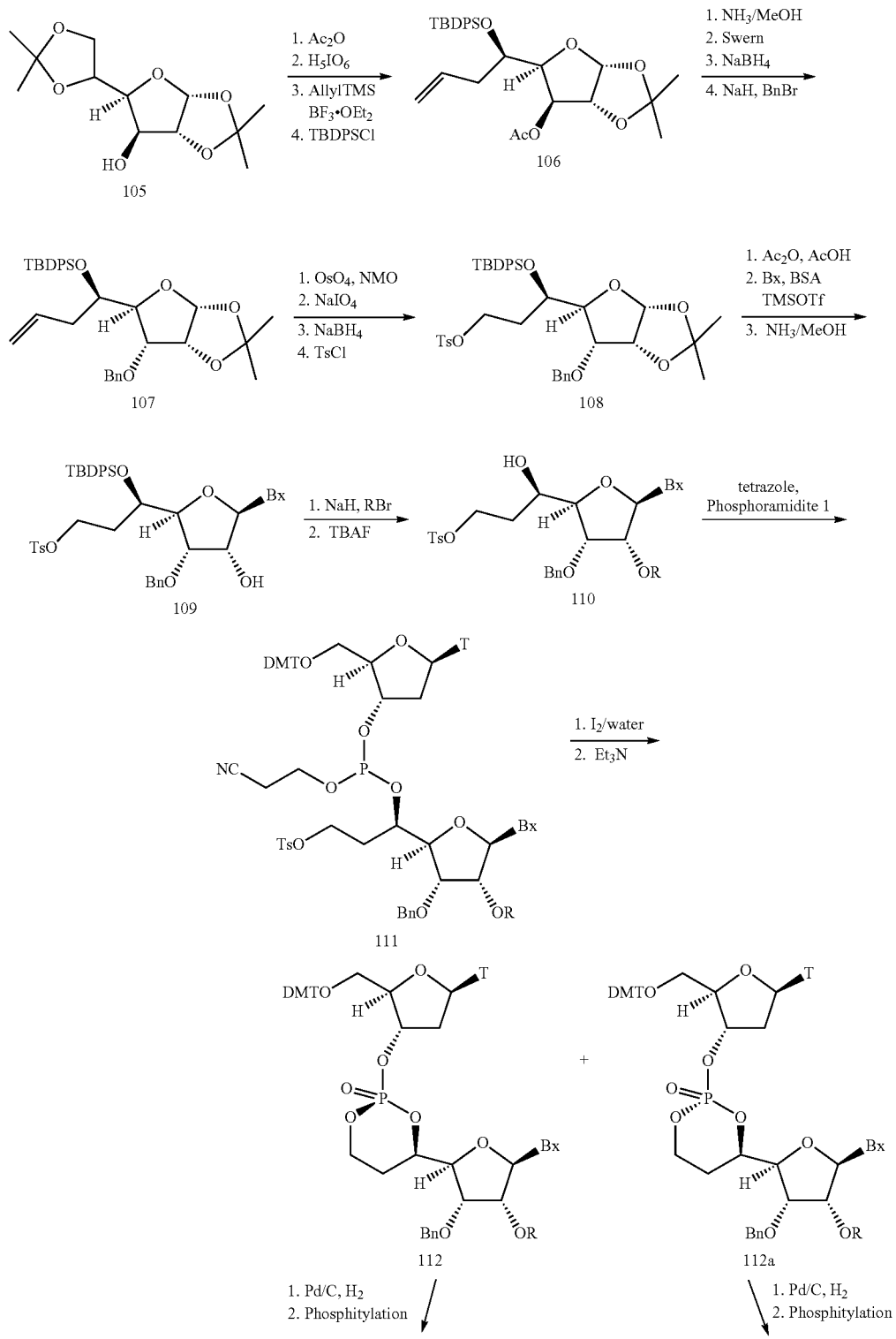

-continued

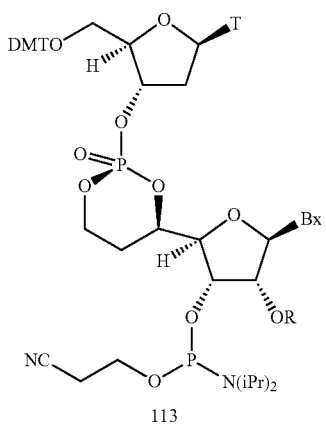

113

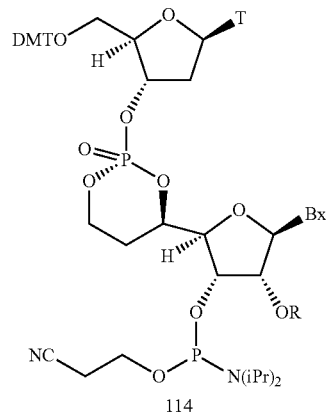

114

Bx = heterocyclic base moiety
R = —CH₃, —(CH₂)₂—OCH₃, or
—CH₂(CO)NHCH₃

Compound 105 is available from commercial sources. Phosphoramidite 1 is prepared as per the procedures illustrated in Example 13.

Phosphoramidite 1 used in the coupling step serves only to illustrate the compounds described herein and is not intended to be limiting. Various phosphoramidites as illustrated in Examples 13 and 14 (e.g. Compounds 2-31) can also be used to couple with the tosylate precursor (e.g. Compound 110) in the same manner as exemplified in Examples 15-18 to provide the desired dimer (e.g. Compound 111). Compounds 112 and 112a are separated by column chromatography.

Example 27 General Method for the Preparation of Compounds 123 (SC5', S$_P$) and 124 (SC5', R$_P$)

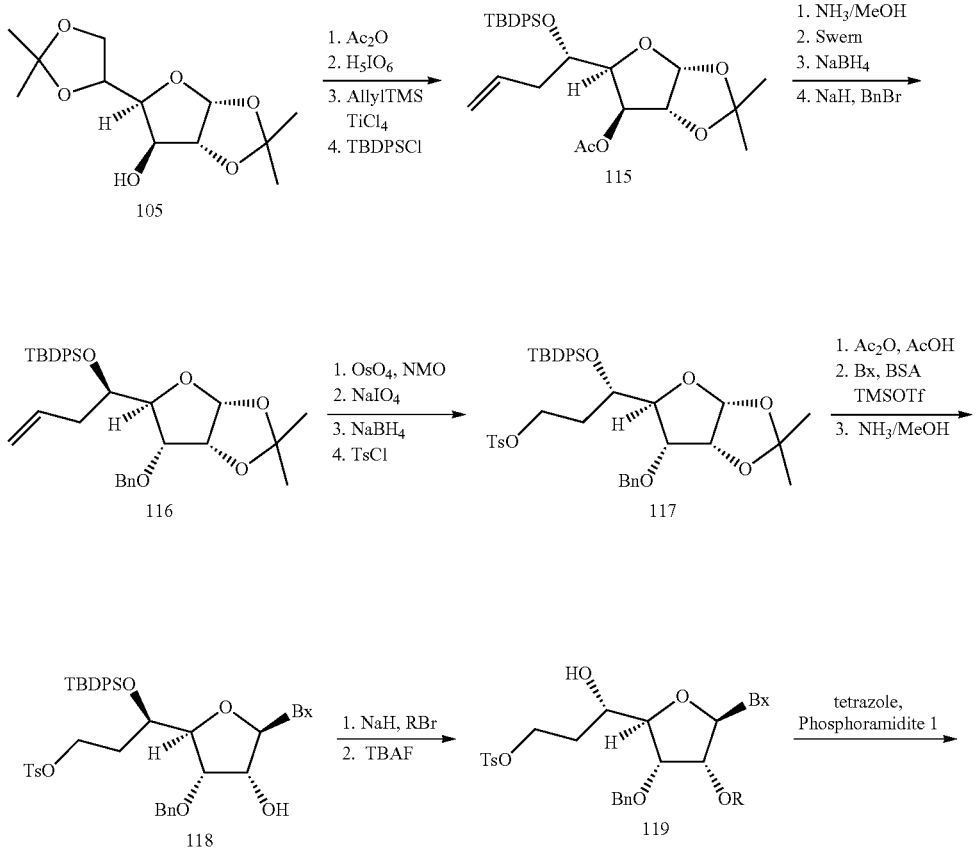

-continued

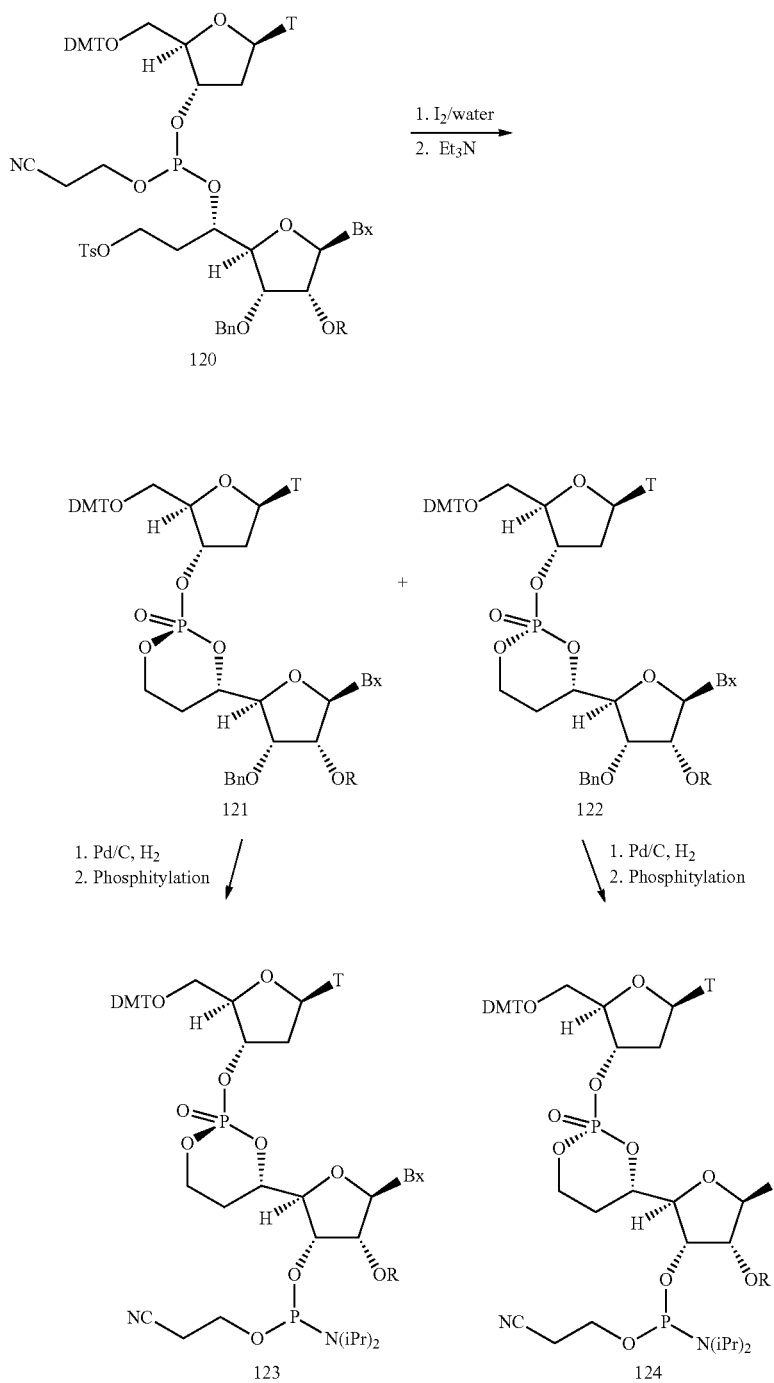

Bx = heterocyclic base moiety
R = —CH₃, —(CH₂)₂—OCH₃, or
—CH₂(CO)NHCH₃

Compound 105 is available from commercial sources. Phosphoramidite 1 is prepared as per the procedures illustrated in Example 13.

Phosphoramidite 1 used in the coupling step serves only to illustrate the compounds described herein and is not intended to be limiting. Various phosphoramidites as illustrated in Examples 13 and 14 (e.g. Compounds 2-31) can also be used to couple with the tosylate precursor (e.g. Compound 119) in the same manner as exemplified in Examples 15-18 to provide the desired dimer (e.g. Compound 120). Compounds 121 and 122 are separated by column chromatography.

Example 28 General Method for the Preparation of Compounds 131 (RC5', S$_P$) and 132 (SRC5', R$_P$)
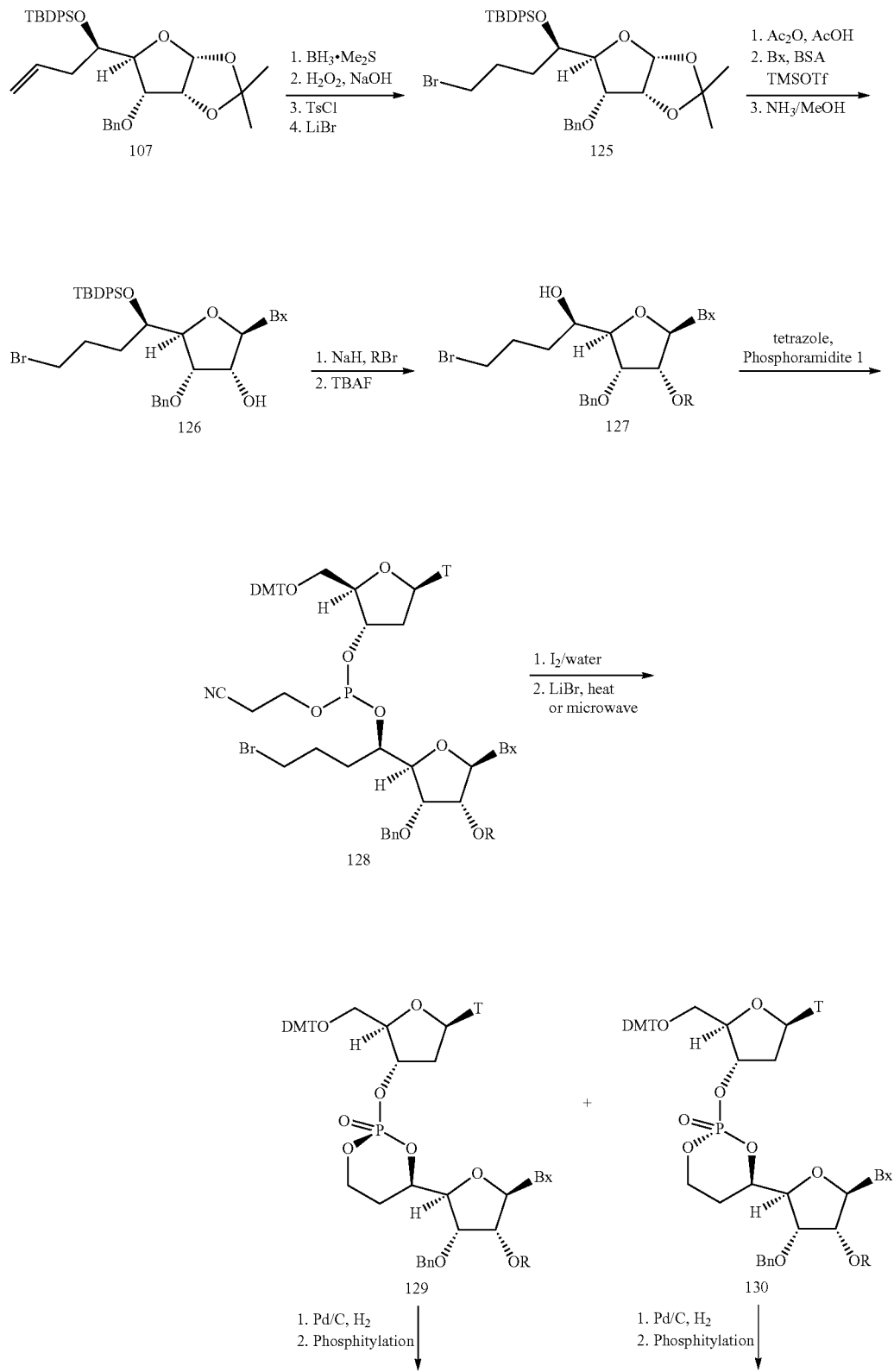

-continued

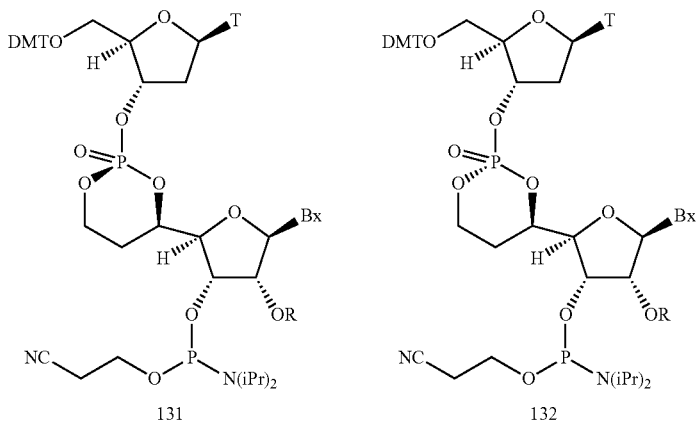

131   132

Bx = heterocyclic base moiety
R = —CH₃, —(CH₂)₂—OCH₃, or
—CH₂(CO)NHCH₃

Phosphoramidite 1 and Compound 107 are prepared as per the procedures illustrated in Examples 13 and 26.

Phosphoramidite 1 used in the coupling step serves only to illustrate the compounds described herein and is not intended to be limiting. Various phosphoramidites as illustrated in Examples 13 and 14 (e.g. Compounds 2-31) can also be used to couple with the bromo precursor (e.g. Compound 127) in the same manner as exemplified in Examples 15-18 to provide the desired dimer (e.g. Compound 128). Compounds 129 and 130 are separated by column chromatography.

Example 29 General Method for the Preparation of Compounds 139 (SC5', S$_P$) and 140 (SC5', R$_P$)

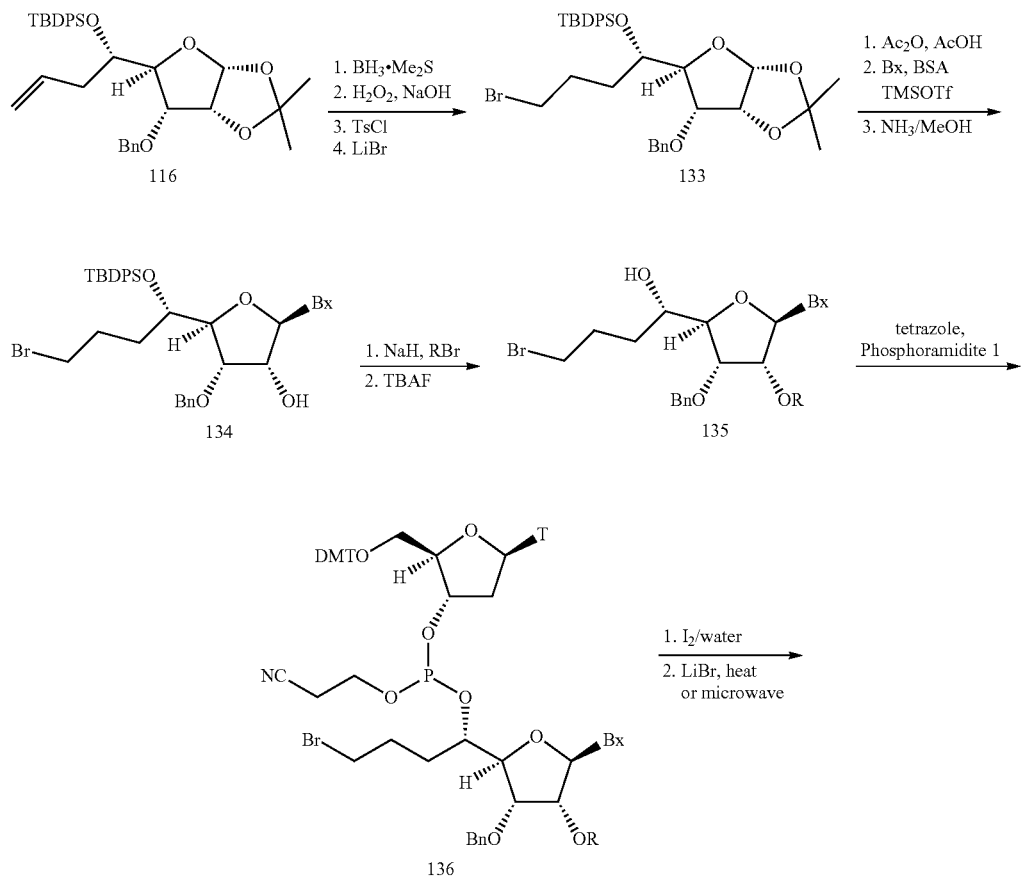

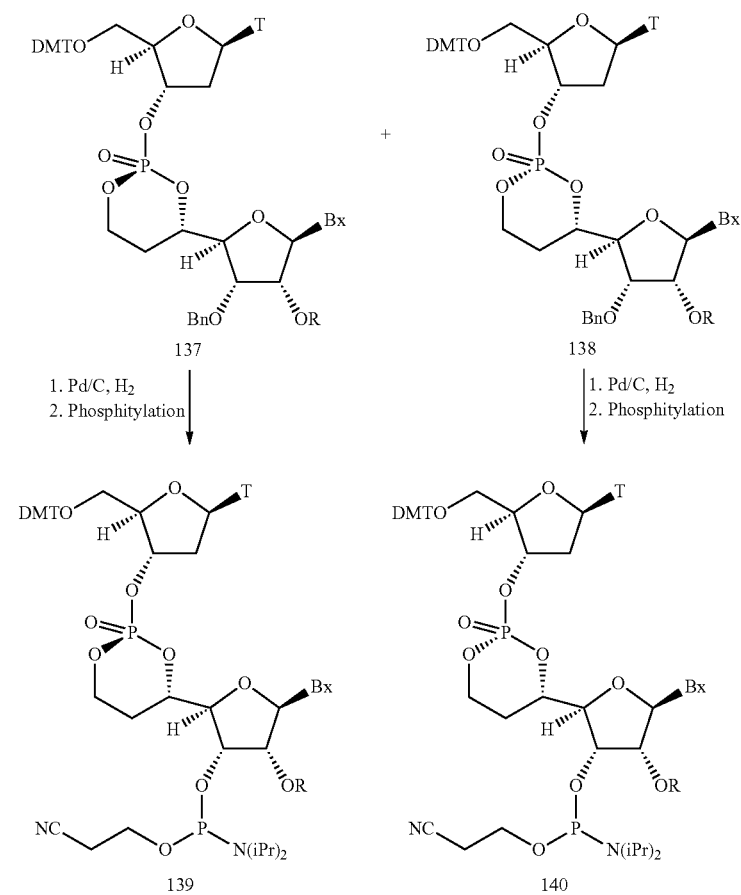

137138

1. Pd/C, H₂
2. Phosphitylation

1. Pd/C, H₂
2. Phosphitylation

139140

Bx = heterocyclic base moiety
R = —CH₃, —(CH₂)₂—OCH₃, or
—CH₂(CO)NHCH₃

Phosphoramidite 1 and Compound 116 are prepared as per the procedures illustrated in Examples 13 and 27.

Phosphoramidite 1 used in the coupling step serves only to illustrate the compounds described herein and is not intended to be limiting. Various phosphoramidites as illustrated in Examples 13 and 14 (e.g. Compounds 2-31) can also be used to couple with the bromo precursor (e.g. Compound 135) in the same manner as exemplified in Examples 15-18 to provide the desired dimer (e.g. Compound 136). Compounds 137 and 138 are separated by column chromatography.

Example 30 Preparation of Compounds 157-158 (RC5', $S_P$) and 159-160 (RC5', $R_P$)

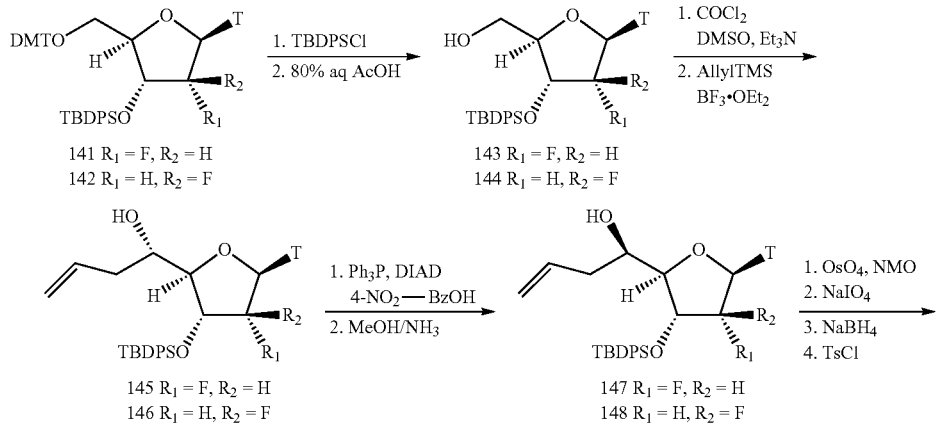

141 R₁ = F, R₂ = H
142 R₁ = H, R₂ = F

143 R₁ = F, R₂ = H
144 R₁ = H, R₂ = F

145 R₁ = F, R₂ = H
146 R₁ = H, R₂ = F

147 R₁ = F, R₂ = H
148 R₁ = H, R₂ = F

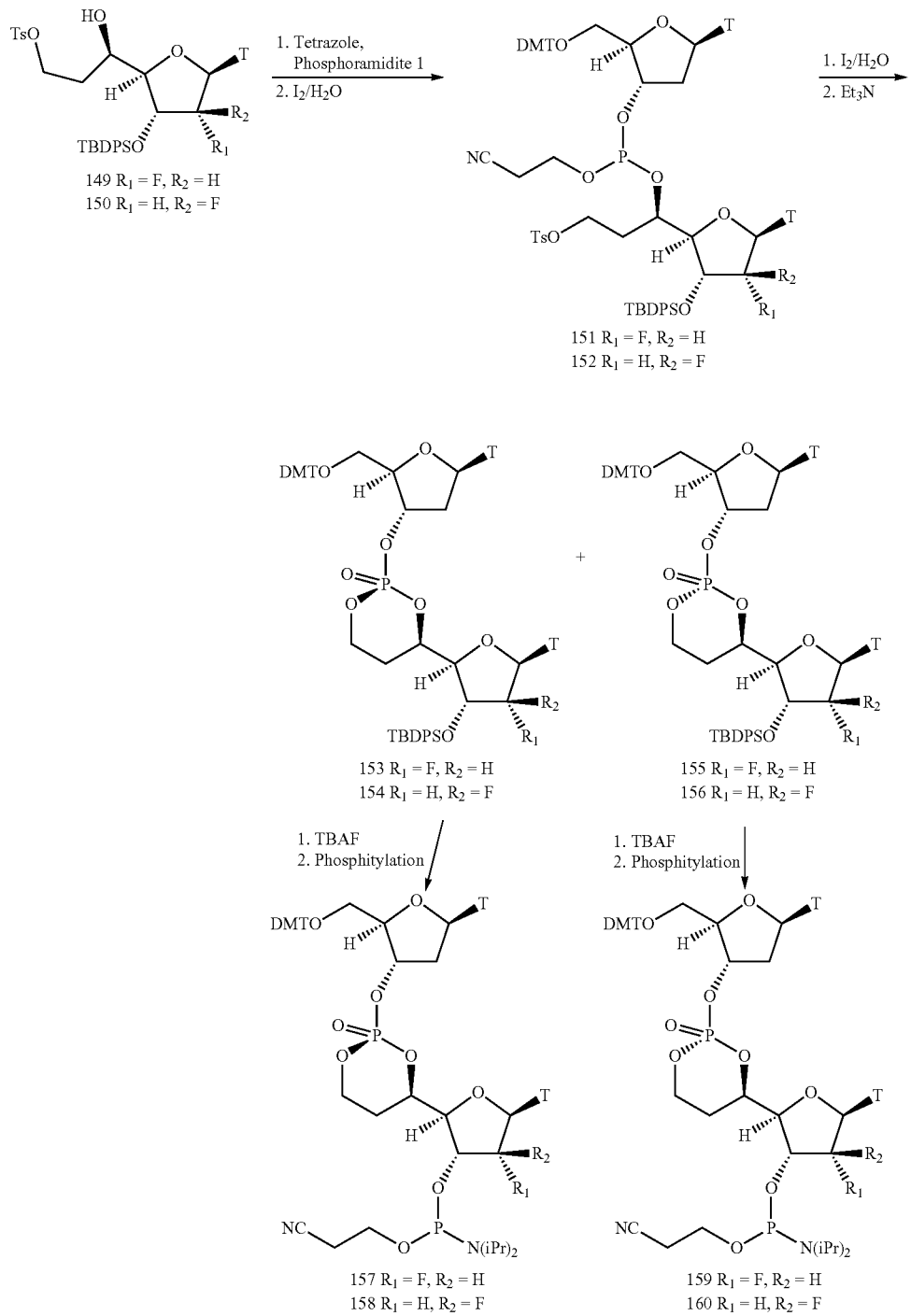

Compounds 141 and 142 are prepared using procedures similar to published procedures (see Wilds et al., *Nucleic Acids Research*, 2000, 28(18), 3625-3635; Prakash et al., *Org. Lett.*, 2003, 5(4), 403-406; Ravikumar et al., *Process Research and Development* 2002, 6(6), 798-806; Martin, P., *Helvetica Chimica Acta*, 1995, 78(2), 486-504; WO 2011/123621; WO 2010/101951; WO 2010/048549; WO 2010/048585; WO 2008/101157; WO 1994/22890 and US patent U.S. Pat. No. 6,147,200). Phosphoramidite 1 is prepared as per the procedures illustrated in Example 13.

Phosphoramidite 1 used in the coupling step serves only to illustrate the compounds described herein and is not intended to be limiting. Various phosphoramidites as illustrated in Examples 13 and 14 (e.g. Compounds 2-31) can also be used to couple with the tosylate precursor (e.g. Compound 149 or 150) in the same manner as exemplified in Examples 15-18 to provide the desired dimer (e.g. Compound 151 or 152). Compounds 157-160 are separated by column chromatography.

Example 31 Preparation of Compounds 169-170 (RC5', S$_P$) and 171-172 (RC5', R$_P$)
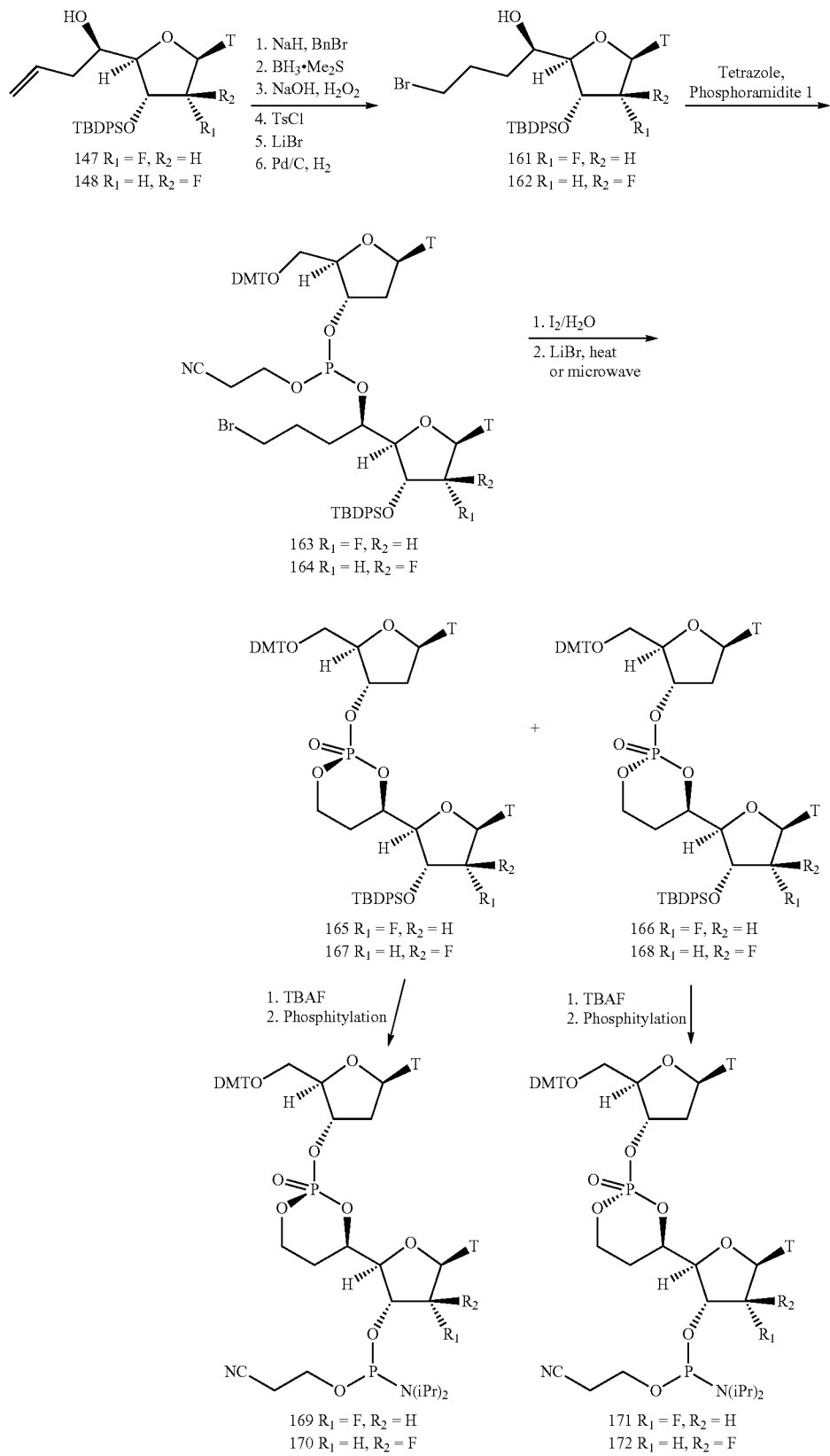

Phosphoramidite 1, Compounds 147 and 148 are prepared as per the procedures illustrated in Examples 13 and 30.

Phosphoramidite 1 used in the coupling step serves only to illustrate the compounds described herein and is not intended to be limiting. Various phosphoramidites as illustrated in Examples 13 and 14 (e.g. Compounds 2-31) can also be used to couple with the bromo precursor (e.g. Compound 161 or 162) in the same manner as exemplified in Examples 15-18 to provide the desired dimer (e.g. Compound 163 or 164). Compounds 165 and 166, or 167 and 168 are separated by column chromatography.

Example 32 Preparation of Compounds 174 and 175

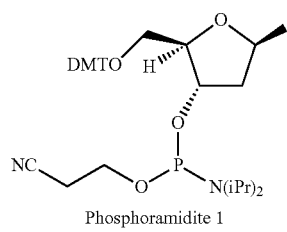

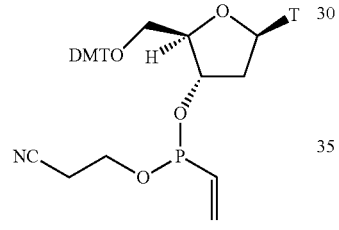

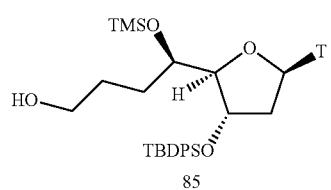

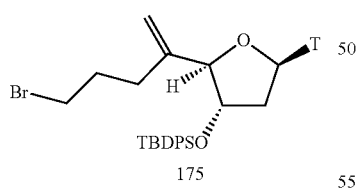

Phosphoramidite 1 and Compound 85 are prepared as per the procedures illustrated in Examples 13 and 23. Trimethylsilyl acetylene, Compound 173 is available from commercial sources.

Phosphoramidite 1 used in this example serve only to illustrate the compounds described herein and is not intended to be limiting. Various phosphoramidites as illustrated in Examples 13 and 14 (e.g. Compounds 2-31) can also be used to synthesize additional analogs of Compound 174.

Example 33 Preparation of Compounds 182 (RC5', S$_P$), 183 (RC5', R$_P$), 184 (SC5', S$_P$) and 185 (SC5', R$_P$)

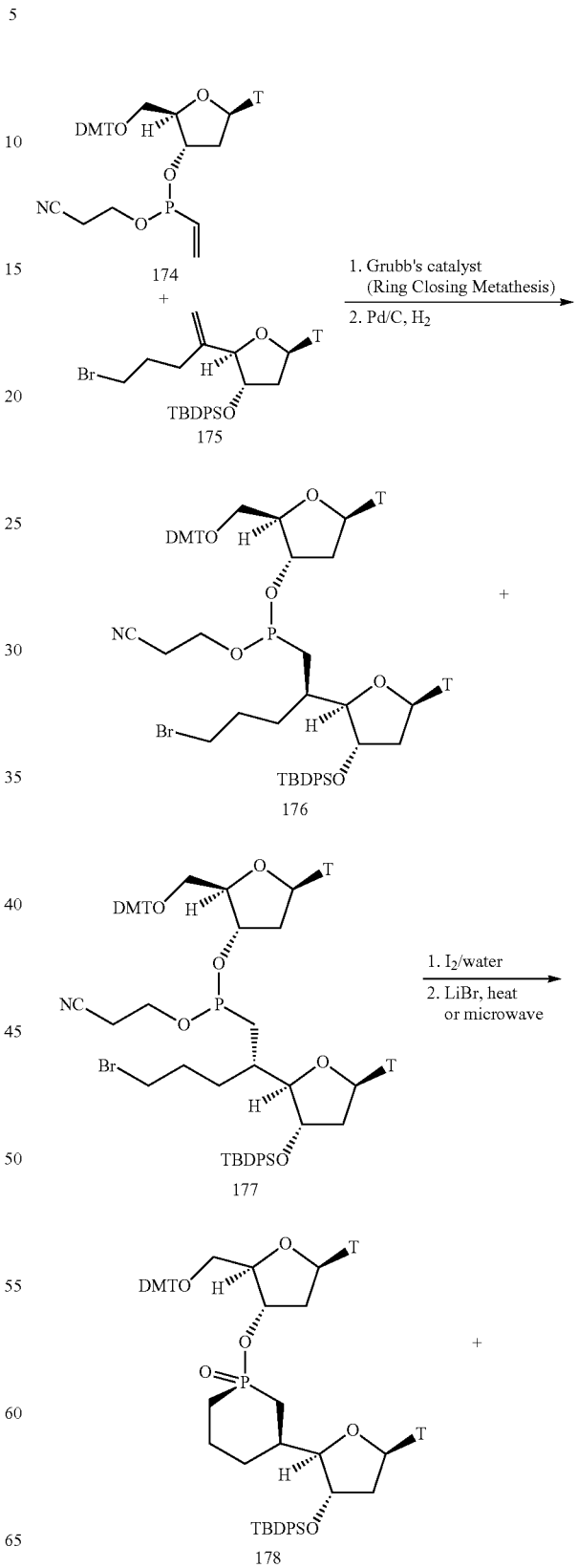

99
-continued

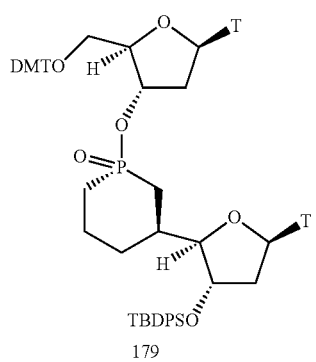
179

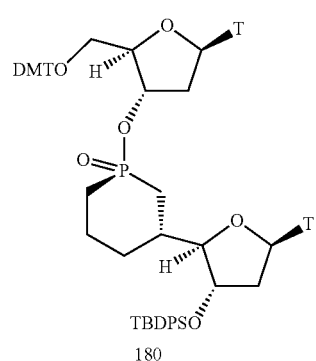
180

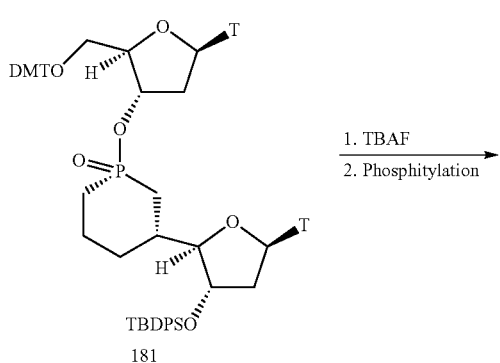
181

1. TBAF
2. Phosphitylation

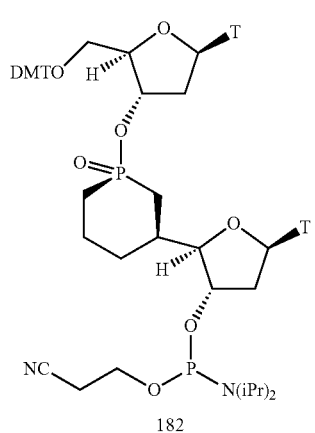
182

100
-continued

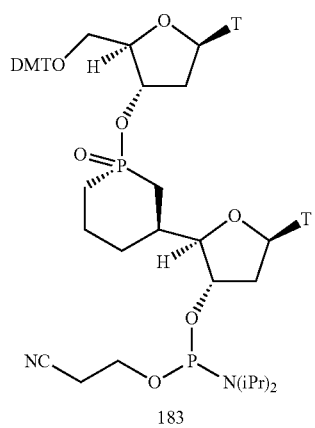
183

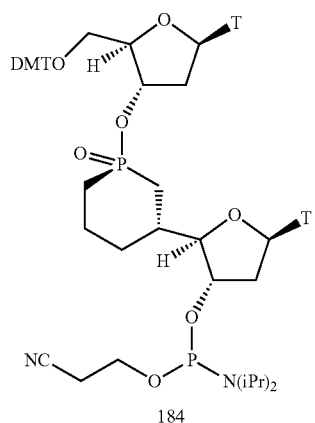
184

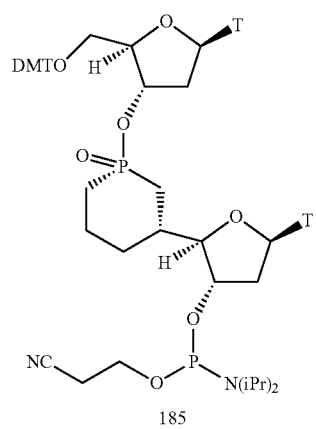
185

Compounds 174 and 175 are prepared as per the procedures illustrated in Example 32. Ring closing metathesis followed by palladium-catalyzed hydrogenation provides a diastereomeric mixture of Compounds 176 and 177, which is separated by column chromatography to provide the desired product as a single diastereomer. Either isomer can be used for the subsequent reactions. Similarly, the diastereomeric mixtures of Compounds 178 and 179, or 180 and 181 obtained after cyclization are also chromatographically separated. Either isomer can be used for a phosphitylation reaction to provide the desired phosphoramidites, Compounds 182-185.

Example 34 Preparation of Compounds 194-195 (SC5', $S_P$) and 196-197 (SC5', $R_P$)
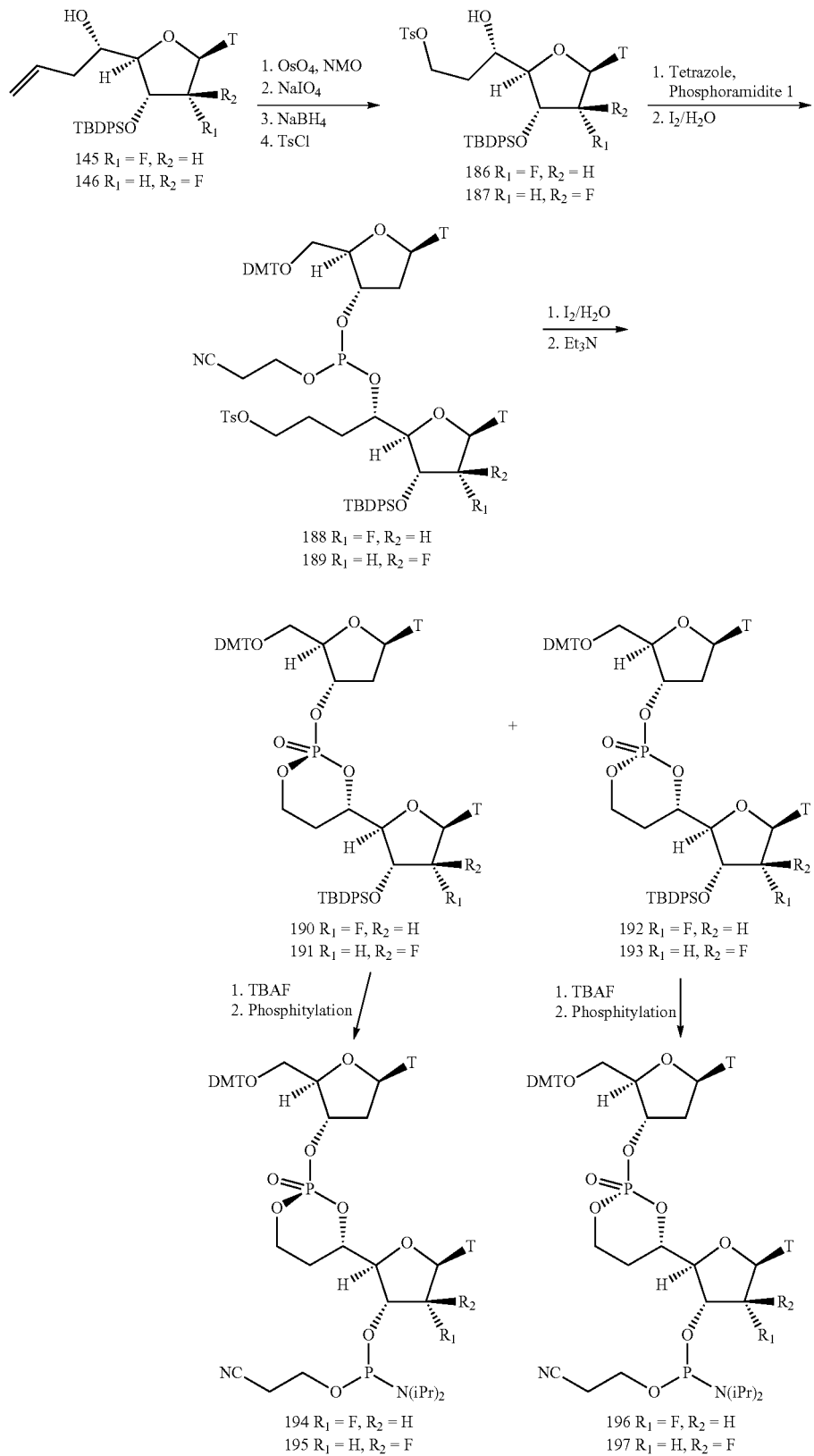

Compounds 145 and 146 are prepared as per the procedures illustrated in Example 30. Compounds 190 and 192, or 191 and 193 are separated by column chromatography.
Example 35 Preparation of Compounds 206-207 (SC5', $S_P$) and 208-209 (SC5', $R_P$)
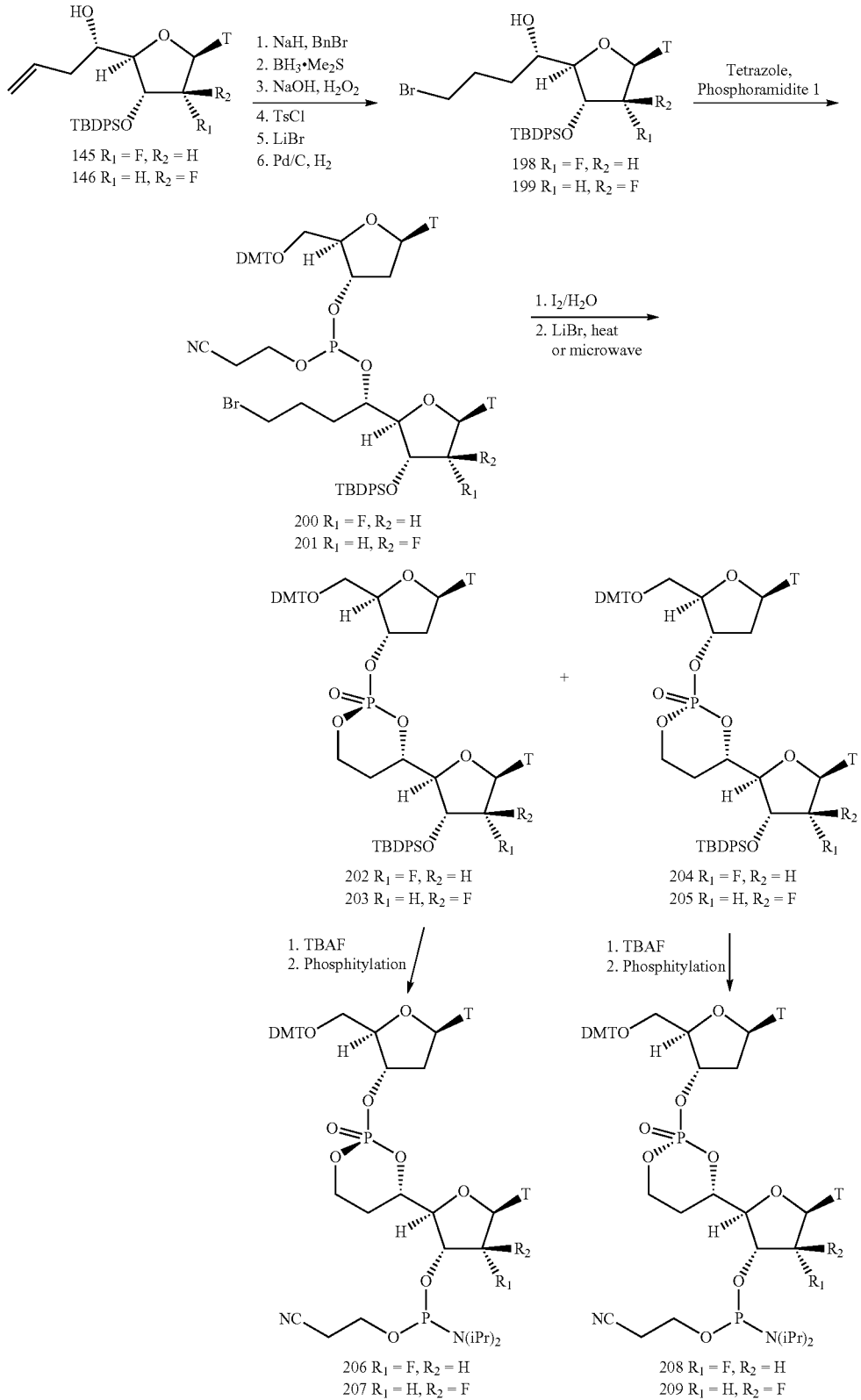

Compounds 145 and 146 are prepared as per the procedures illustrated in Example 30. Compounds 202 and 204, or 203 and 205 are separated by column chromatography.

Example 36 General Method for the Preparation of Compounds 214 (RC5', $S_P$) and 215 (RC5', $R_P$)

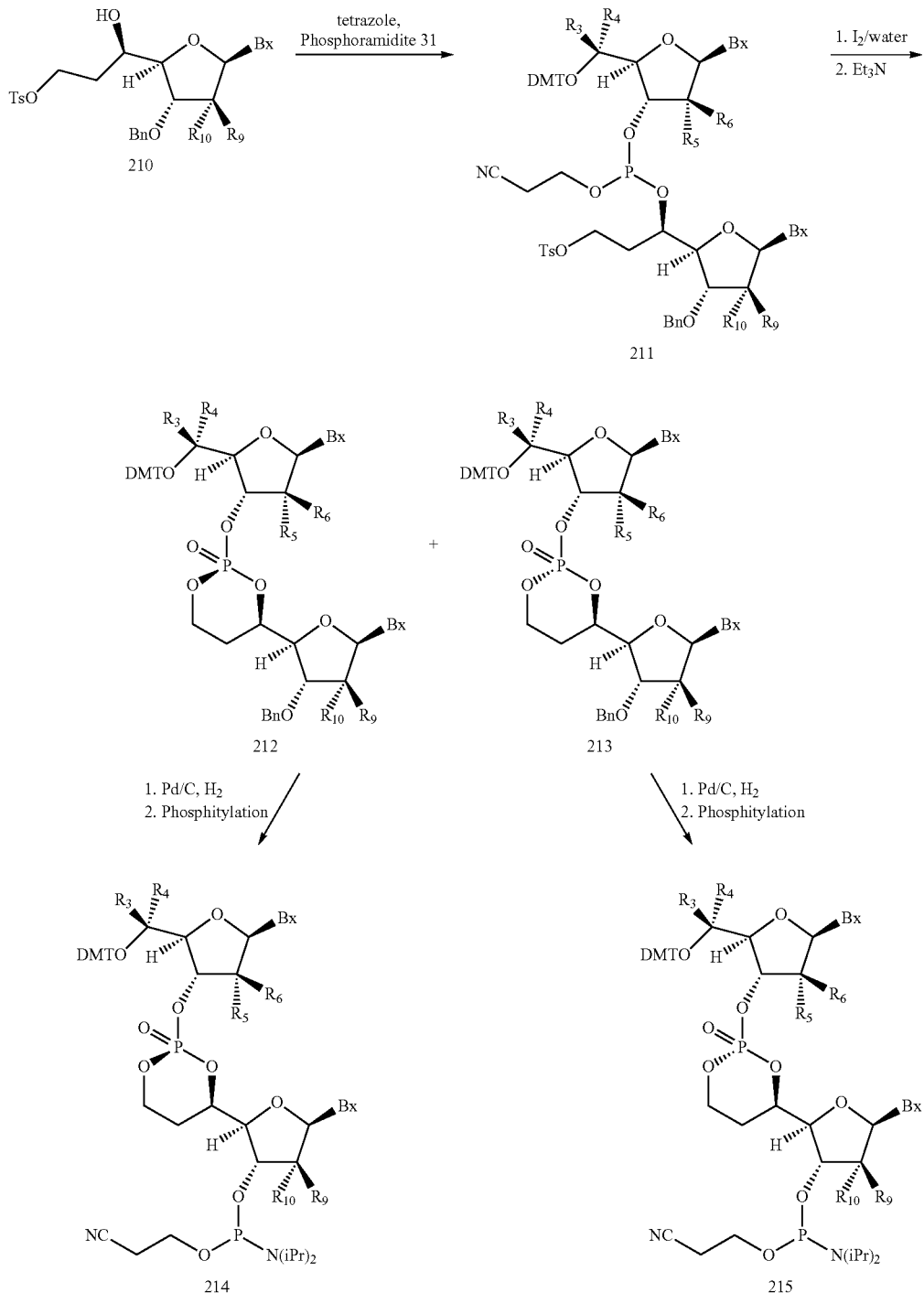

Bx is a heterocyclic base moiety;
$R_3$ and $R_4$ are each independently H, alkyl, substituted alkyl, alkoxy, substituted alkoxy, alkenyl, substituted alkenyl, alkynyl or substituted alkynyl, aryl or substituted aryl; and
$R_5$, $R_6$, $R_9$ and $R_{10}$ are each independently H, OH, or a 2'-sugar substituent group Phosphoramidite 31 and Compound 210 are prepared using similar procedures as described in Examples 13-15, 26, and 30. Compounds 212 and 213 are separated by column chromatography.

Example 37 General Method for the Preparation of Compounds 220 (SC5', $S_P$) and 221 (SC5', $R_P$)

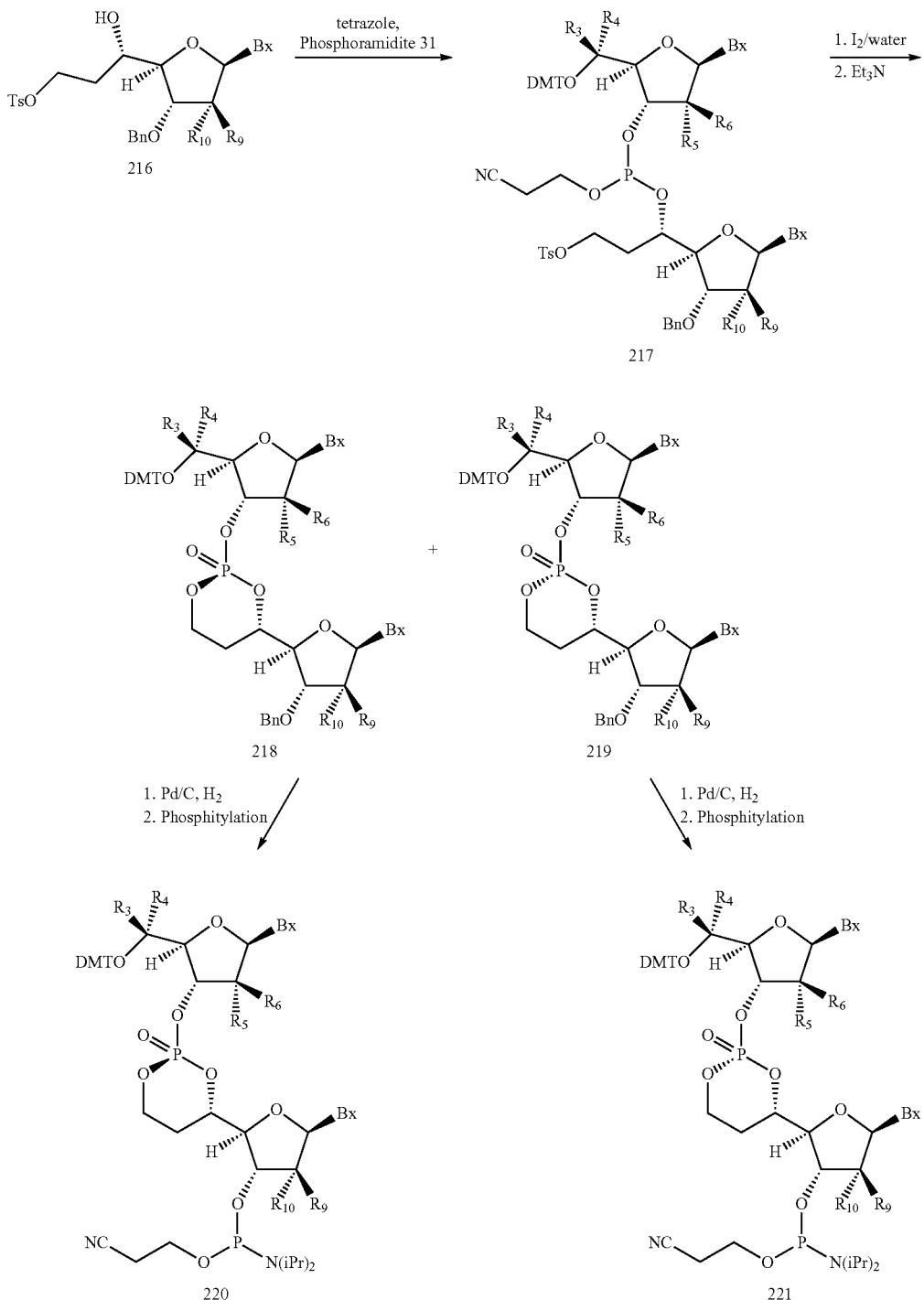

Bx is a heterocyclic base moiety;
$R_3$ and $R_4$ are each independently H, alkyl, substituted alkyl, alkoxy, substituted alkoxy, alkenyl, substituted alkenyl, alkynyl or substituted alkynyl, aryl or substituted aryl; and
$R_5$, $R_6$, $R_9$ and $R_{10}$ are each independently H, OH, or a 2'-sugar substituent group Phosphoramidite 31 and Compound 216 are prepared using similar procedures as described in Examples 13-15, 27, and 34. Compounds 218 and 219 are separated by column chromatography.

Example 38 General Method for the Preparation of Compounds 226 (RC5', $S_P$) and 227 (RC5', $R_P$)

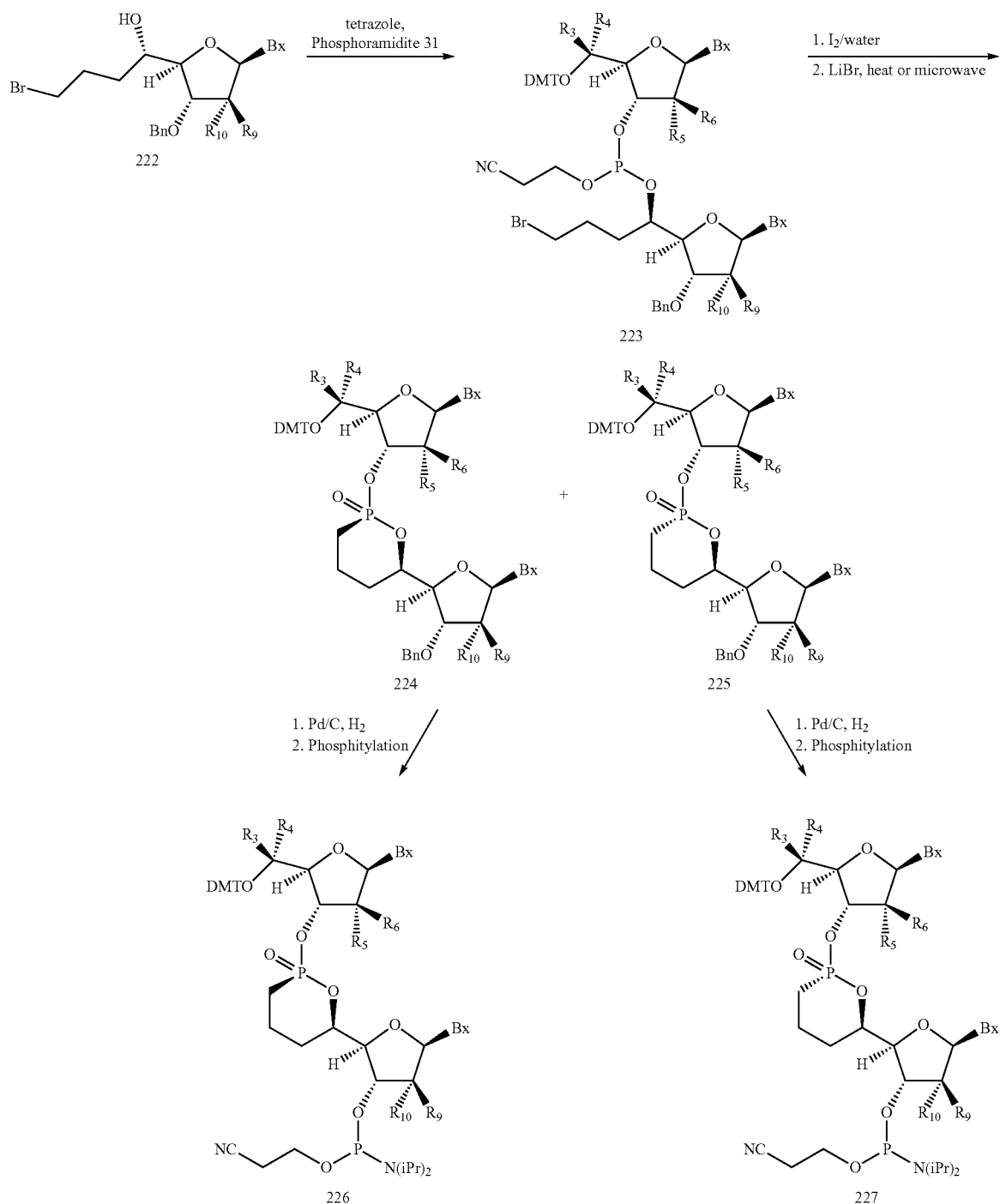

Bx is a heterocyclic base moiety;
$R_3$ and $R_4$ are each independently H, alkyl, substituted alkyl, alkoxy, substituted alkoxy, alkenyl, substituted alkenyl, alkynyl or substituted alkynyl, aryl or substituted aryl; and
$R_5$, $R_6$, $R_9$ and $R_{10}$ are each independently H, OH, or a 2'-sugar substituent group Phosphoramidite 31 and Compound 222 are prepared using similar procedures as described in Examples 13-15, 28 and 31. Compounds 224 and 225 are separated by column chromatography.

Example 39 General Method for the Preparation of Compounds 232 (SC5', $S_P$) and 233 (SC5', $R_P$)

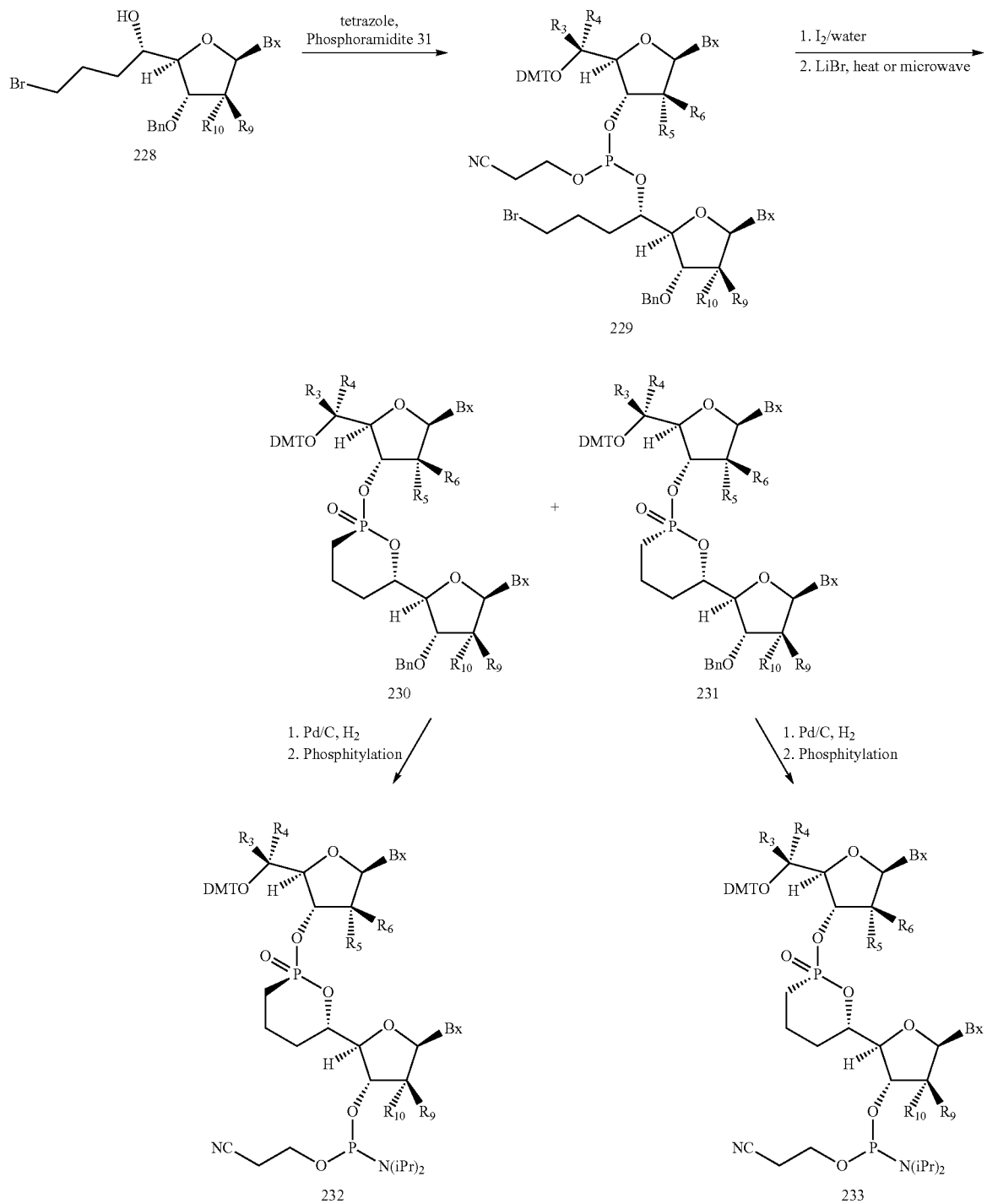

Bx is a heterocyclic base moiety;
$R_3$ and $R_4$ are each independently H, alkyl, substituted alkyl, alkoxy, substituted alkoxy, alkenyl, substituted alkenyl, alkynyl or substituted alkynyl, aryl or substituted aryl; and
$R_5$, $R_6$, $R_9$ and $R_{10}$ are each independently H, OH, or a 2'-sugar substituent group Phosphoramidite 31 and Compound 228 are prepared using similar procedures as described in Examples 13-15, 29 and 35. Compounds 230 and 231 are separated by column chromatography.

Example 40 General Method for the Preparation of Compounds 237 (RC5', $S_P$) and 238 (RC5', $R_P$)

and 30. Compounds 235 and 236 are separated by column chromatography.

Phosphoramidite 31a used in the coupling step serves only to illustrate the compounds described herein and is not intended to be limiting. Additional bicyclic phosphoramidites known in the art as described in the specification herein can also be employed to generate various dimeric phosphoramidite analogs of Compounds 237 and 238. These

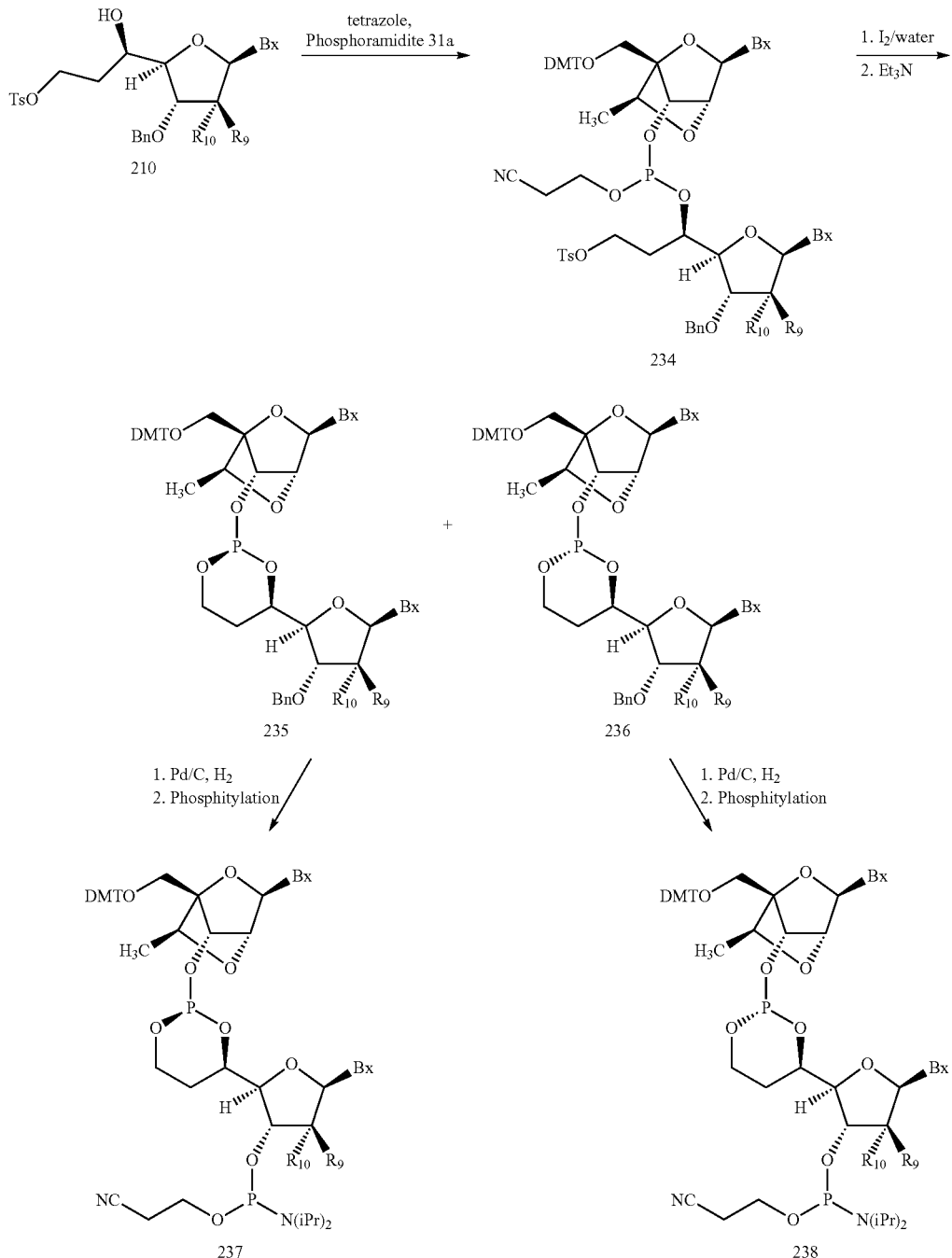

Bx is a heterocyclic base moiety;
$R_9$ and $R_{10}$ are each independently H, OH, or a 2'-sugar substituent group Phosphoramidite 31a and Compound 210 are prepared using similar procedures as described in Examples 14, 26 dimers are used as phosphoramidite building blocks for oligonucleotide synthesis.

Example 41 General Method for the Preparation of Compounds 242 (RC5', $S_P$) and 243 (RC5', $R_P$)

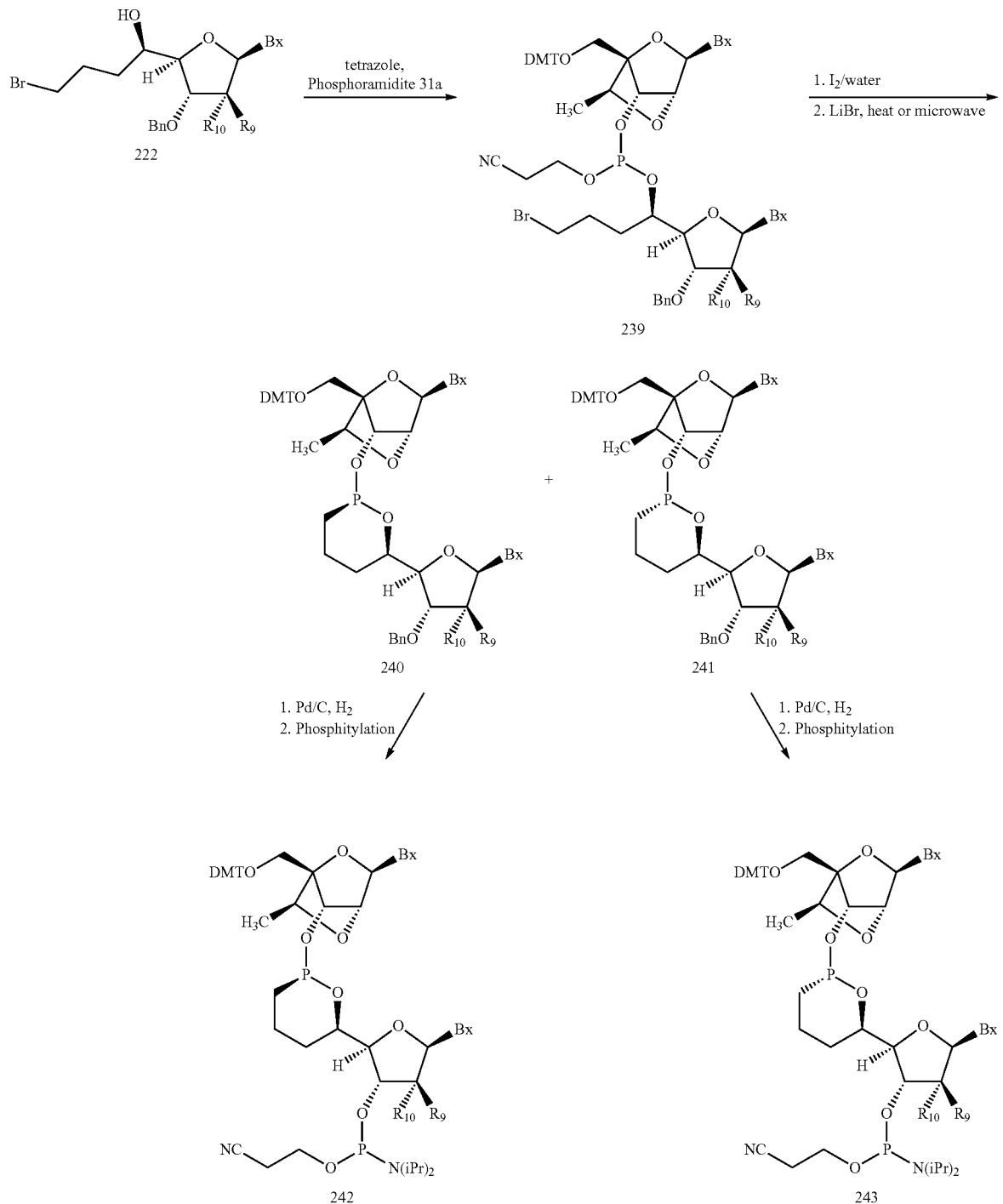

Bx is a heterocyclic base moiety;
$R_9$ and $R_{10}$ are each independently H, OH, or a 2'-sugar substituent group Phosphoramidite 31a and Compound 222 are prepared using similar procedures as described in Examples 14, 28 and 38. Compounds 240 and 241 are separated by column chromatography.

Phosphoramidite 31a used in the coupling step serves only to illustrate the compounds described herein and is not intended to be limiting. Additional bicyclic phosphoramidites known in the art as described in the specification herein can also be employed to generate various dimeric phosphoramidite analogs of Compounds 242 and 243. These dimers are used as phosphoramidite building blocks for oligonucleotide synthesis.

Example 42 General Method for the Preparation of Compounds 247 (RC5', S$_P$) and 248 (RC5', R$_P$)

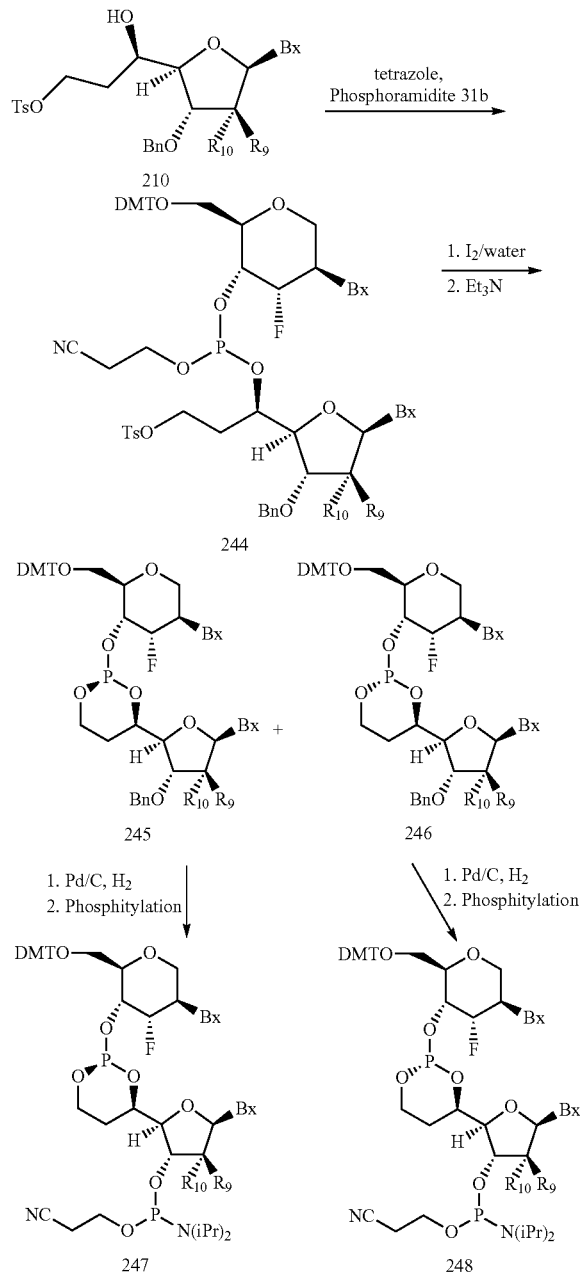

Bx is a heterocyclic base moiety;
R$_9$ and R$_{10}$ are each independently H, OH, or a 2'-sugar substituent group Phosphoramidite 31b and Compound 210 are prepared using similar procedures as described in Examples 14, 26 and 30. Compounds 245 and 246 are separated by column chromatography.

Phosphoramidite 31b used in the coupling step serves only to illustrate the compounds described herein and is not intended to be limiting. Additional sugar surrogate groups known in the art as described in the specification herein can also be employed to generate various dimeric phosphoramidite analogs of Compounds 247 and 248. These dimers are used as phosphoramidite building blocks for oligonucleotide synthesis.

Example 43 General Method for the Preparation of Compounds 252 (RC5', S$_P$) and 253 (RC5', R$_P$)

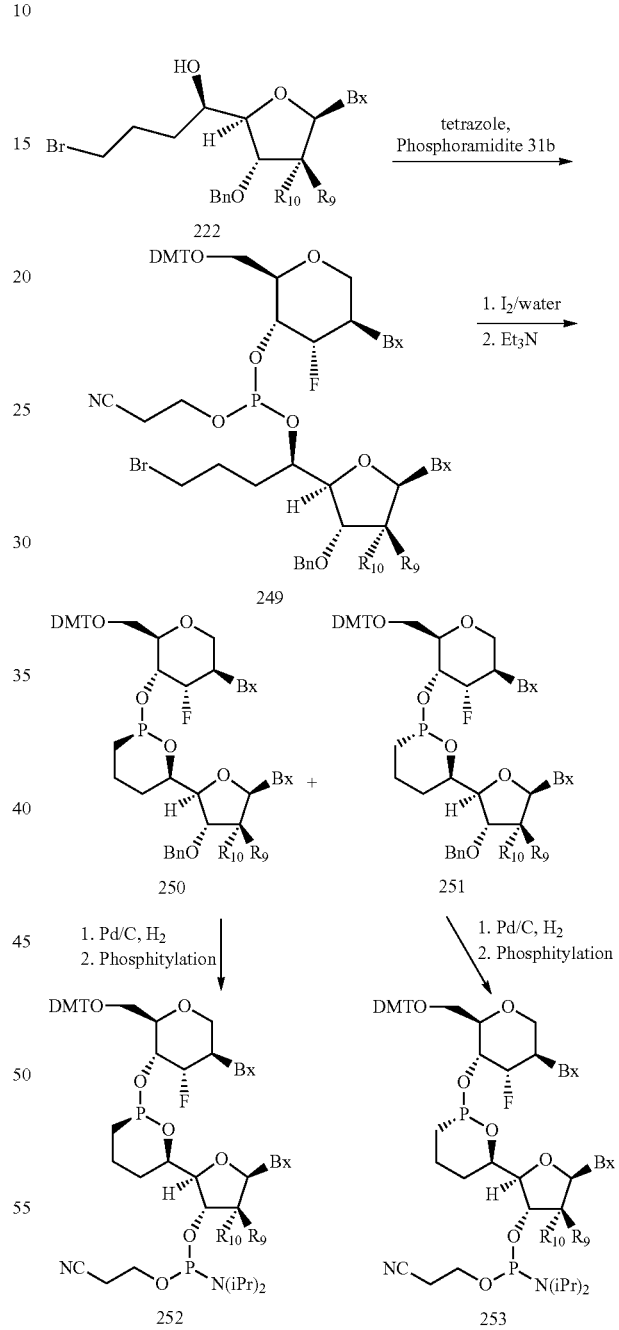

Bx is a heterocyclic base moiety;
R$_9$ and R$_{10}$ are each independently H, OH, or a 2'-sugar substituent group Phosphoramidite 31b and Compound 222 are prepared using similar procedures as described in Examples 14, 28 and 38. Compounds 250 and 251 are separated by column chromatography.

Phosphoramidite 31b used in the coupling step serves only to illustrate the compounds described herein and is not intended to be limiting. Additional sugar surrogate groups known in the art as described in the specification herein can also be employed to generate various dimeric phosphoramidite analogs of Compounds 252 and 253. These dimers are used as phosphoramidite building blocks for oligonucleotide synthesis.

Example 44 General Method for the Preparation of Trimeric Phosphoramidites, Compounds 258 (RC5'S$_P$)$_2$ and 259 (RC5', S$_P$)-(RC5', R$_P$)

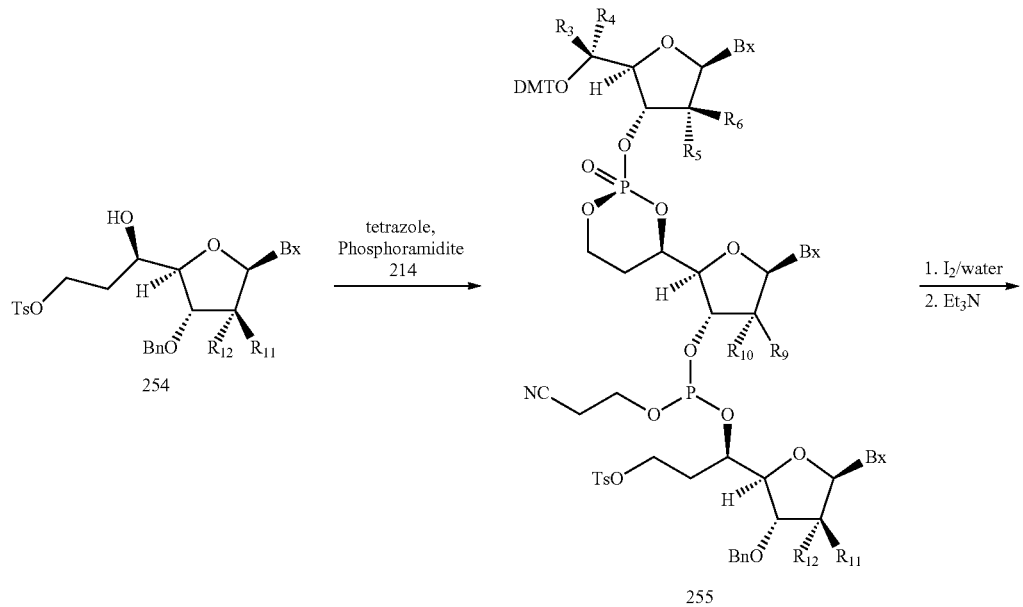

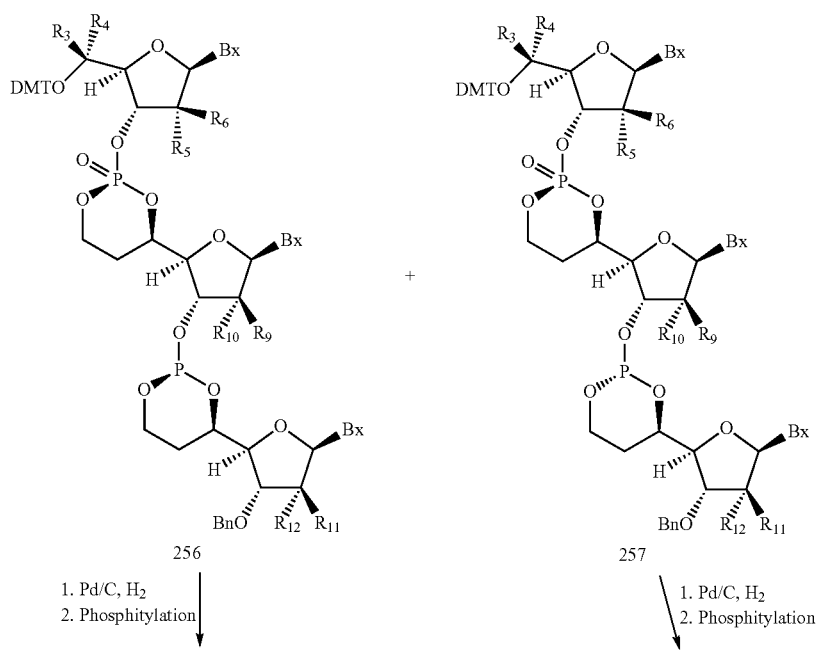

121

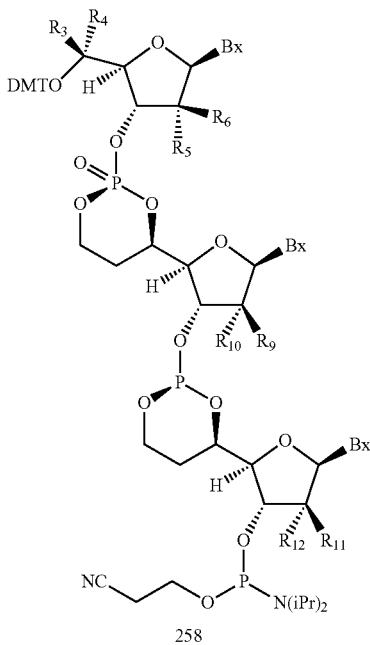

258

-continued

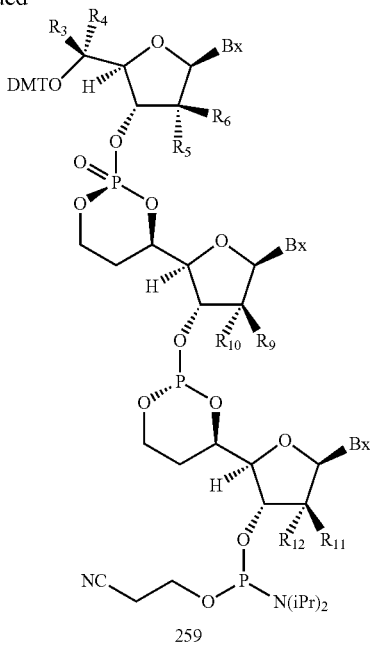

259

Bx is a heterocyclic base moiety;

$R_3$ and $R_4$ are each independently H, alkyl, substituted alkyl, alkoxy, substituted alkoxy, alkenyl, substituted alkenyl, alkynyl or substituted alkynyl, aryl or substituted aryl;

and $R_5$, $R_6$, $R_9$, $R_{10}$, $R_{11}$, and $R_{12}$ are each independently H, OH, or a 2′-sugar substituent group Dimeric phosphoramidite 214 and the tosylate precursor, Compound 254 are prepared using similar procedures as described in Example 26, 30 and 36, respectively. Compounds 256 and 257 are separated by column chromatography.

Dimeric phosphoramidite 214 and the tosylate precursor, Compound 254 used in the coupling step serve only to illustrate the compounds described herein and are not intended to be limiting. Additional precursors and dimeric phosphoramidite subunits as illustrated in Examples 15-43 can also be employed to construct trimers, tetramers or multiple monomer subunits that are used as building blocks in oligonucleotide synthesis.

Example 45 General Method for the Preparation of Trimeric Phosphoramidites, Compounds 264 (RC5′, $S_P$)$_2$ and 265 (RC5′, $S_P$)-(RC5′, $R_P$)

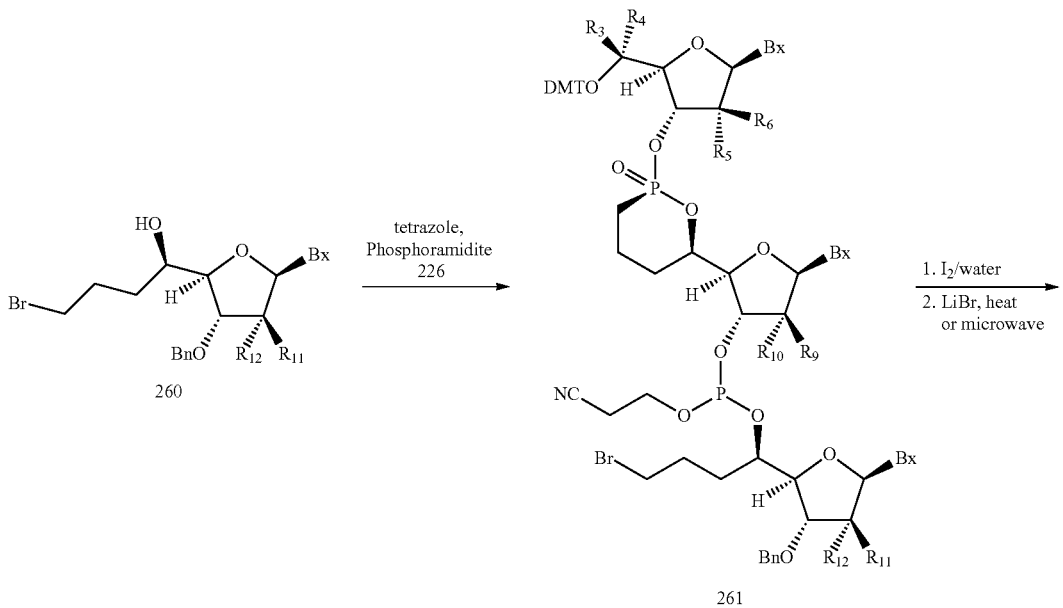

-continued

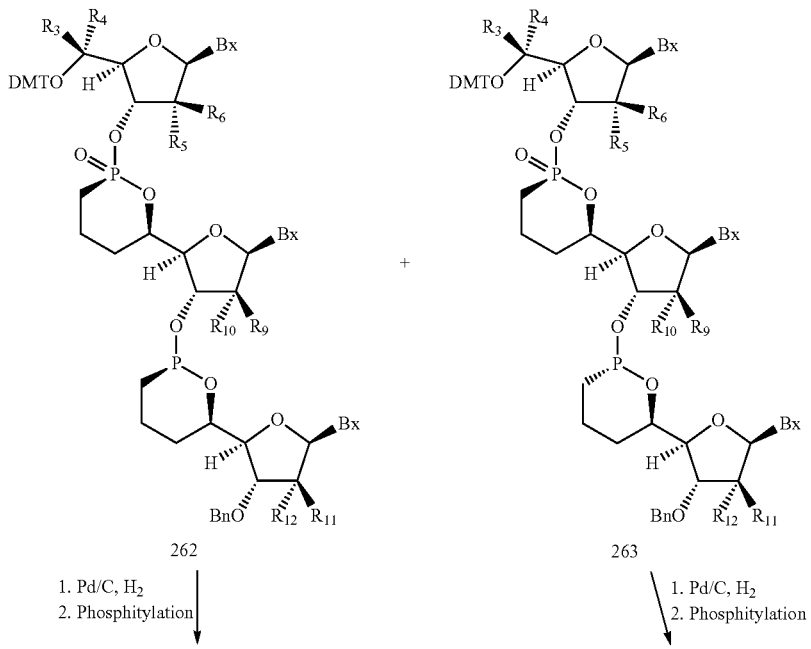

262 + 263

1. Pd/C, H₂
2. Phosphitylation

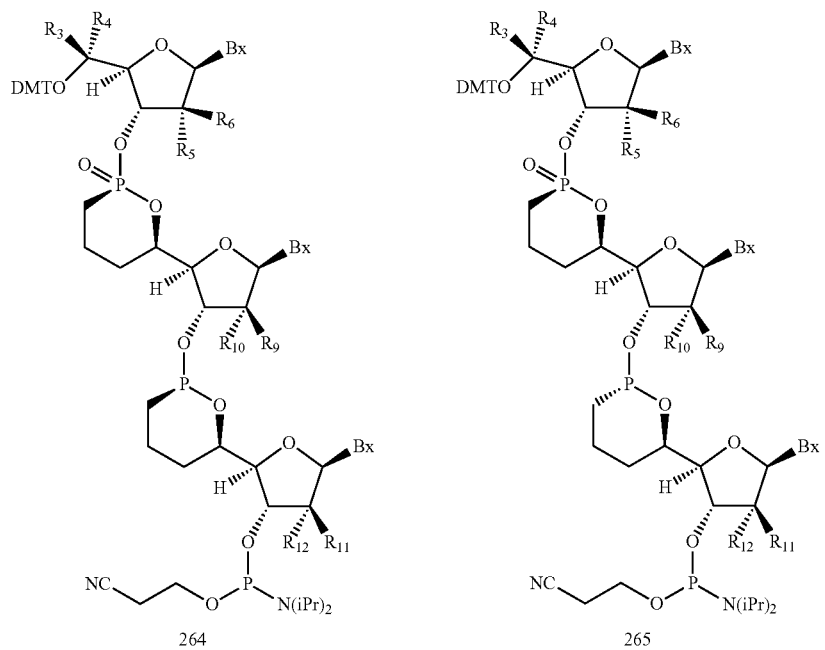

264   265

Bx is a heterocyclic base moiety;
R₃ and R₄ are each independently H, alkyl, substituted alkyl, alkoxy,
substituted alkoxy, alkenyl, substituted alkenyl, alkynyl or substituted alkynyl, aryl or substituted aryl;
and R₅, R₆, R₉, R₁₀, R₁₁, and R₁₂ are each independently H, OH, or a 2′-sugar substituent group Dimeric phosphoramidite 226 and the bromo precursor, Compound 260 are prepared using similar procedures as described in Example 38. Compounds 262 and 263 are separated by column chromatography.

Dimeric phosphoramidite 226 and the bromo precursor, Compound 260 used in the coupling step serve only to illustrate the compounds described herein and are not intended to be limiting. Additional precursors and dimeric phosphoramidite subunits as illustrated in Examples 15-43 can also be employed to construct trimers, tetramers or multiple monomer subunits that are used as building blocks in oligonucleotide synthesis.

Example 46 General Method for the Preparation of Trimeric Phosphoramidites, Compounds 269 (RC5', S$_P$) and 270 (RC5', S$_P$)-(RC5', R$_P$)
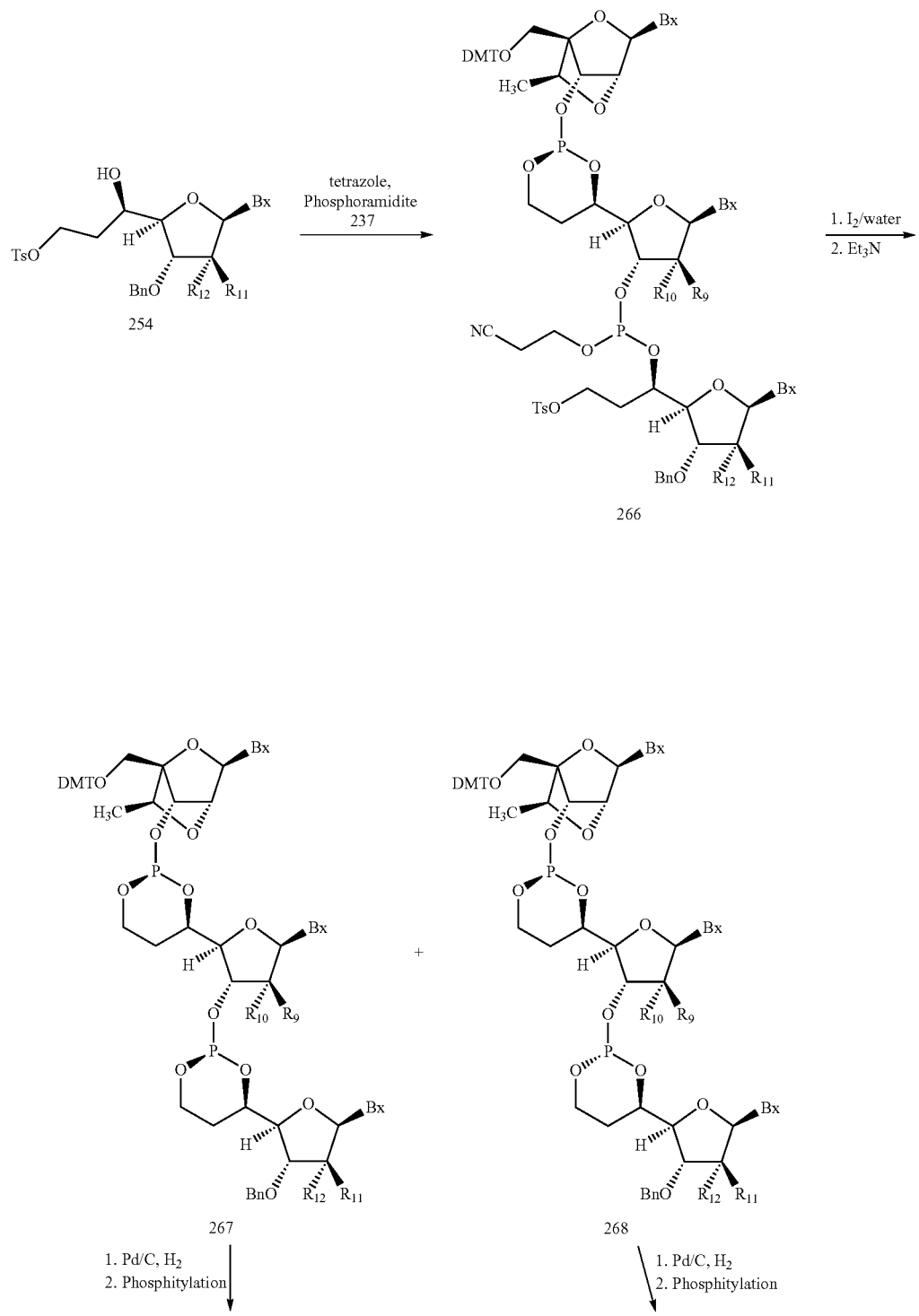

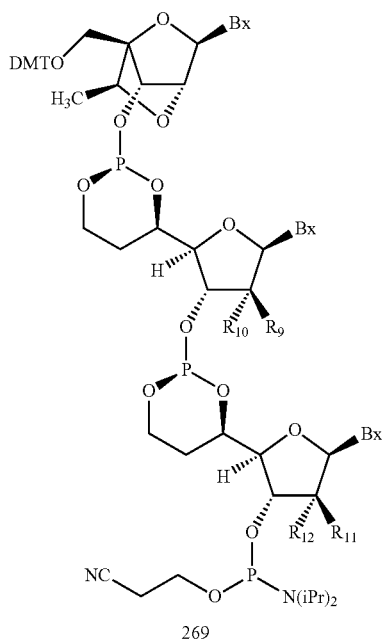
269

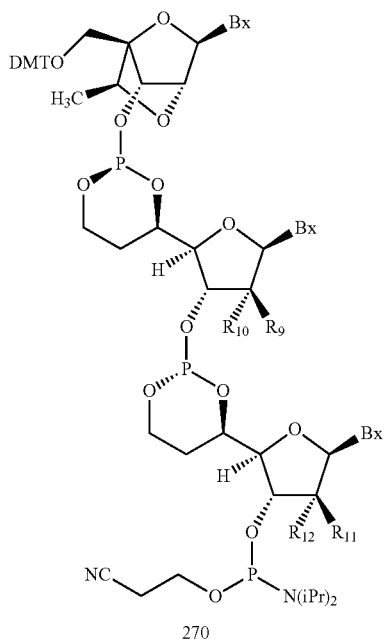
270

Bx is a heterocyclic base moiety;

$R_9$, $R_{10}$, $R_{11}$, and $R_{12}$ are each independently H, OH, or a 2'-sugar substituent group Dimeric phosphoramidite 237 and the tosylate precursor, Compound 254 are prepared using similar procedures as described in Example 40 and 44, respectively. Compounds 267 and 268 are separated by column chromatography.

Dimeric phosphoramidite 237 and the tosylate precursor, Compound 254 used in the coupling step serve only to illustrate the compounds described herein and are not intended to be limiting. Additional precursors and dimeric phosphoramidite subunits as illustrated in Examples 15-43 can also be employed to construct trimers, tetramers or multiple monomer subunits that are used as building blocks in oligonucleotide synthesis.

Example 47 General Method for the Preparation of Trimeric Phosphoramidites, Compounds 274 (RC5', $S_P$)$_2$ and 275 (RC5', $S_P$)-(RC5', $R_P$)

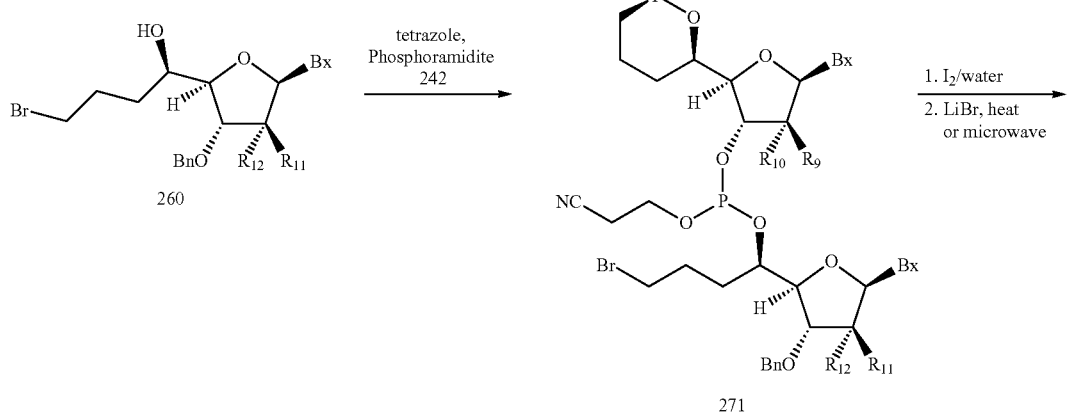

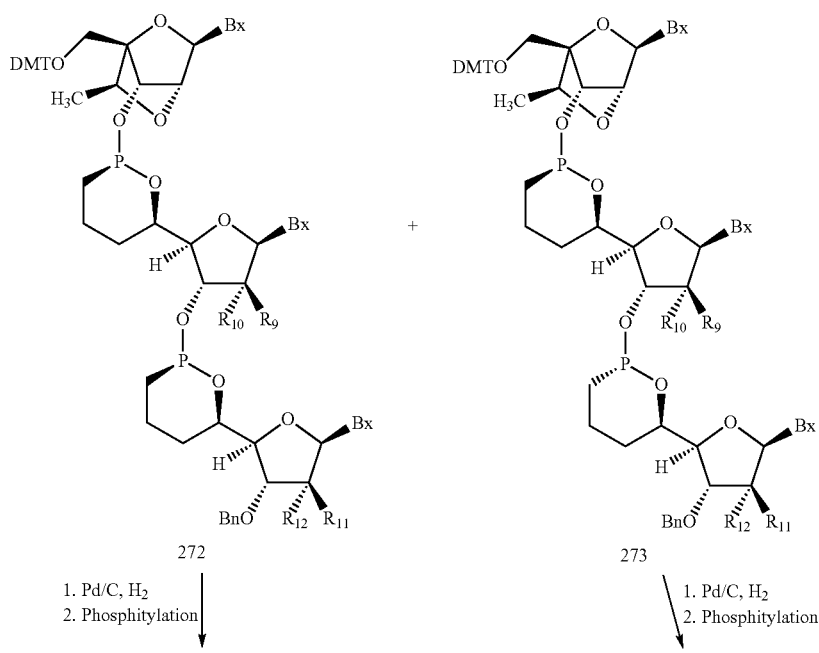

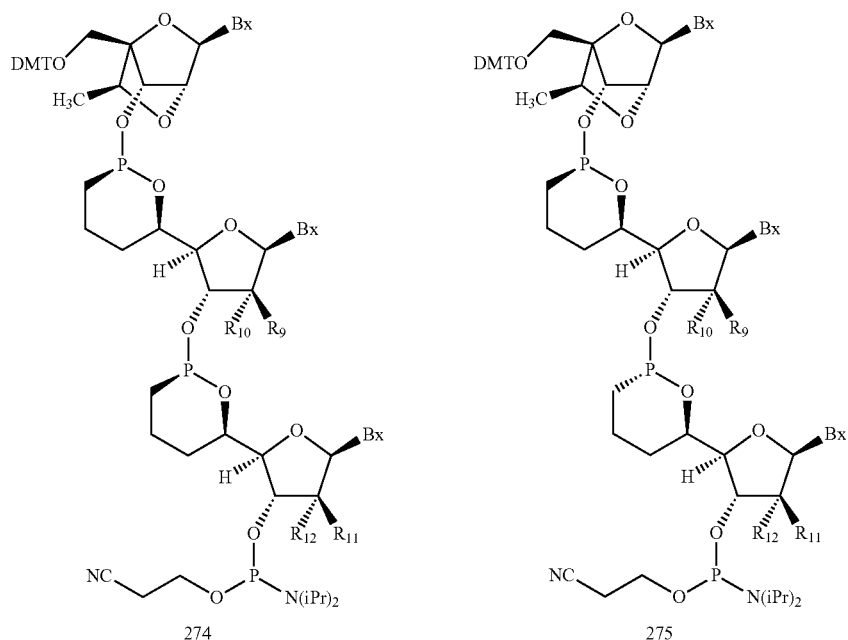

Bx is a heterocyclic base moiety;
$R_9$, $R_{10}$, $R_{11}$, and $R_{12}$ are each independently H, OH, or a 2′-sugar substituent group Dimeric phosphoramidite 242 and the bromo precursor, Compound 260 are prepared using similar procedures as described in Example 41 and 45, respectively. Compounds 272 and 273 are separated by column chromatography.

Dimeric phosphoramidite 242 and the bromo precursor, Compound 260 used in the coupling step serve only to illustrate the compounds described herein and are not intended to be limiting. Additional precursors and dimeric phosphoramidite subunits as illustrated in Examples 15-43 can also be employed to construct trimers, tetramers or multiple monomer subunits that are used as building blocks in oligonucleotide synthesis.

Example 48 General Method for the Preparation of Trimeric Phosphoramidites, Compounds 279 (RC5', $S_P$)$_2$ and 280 (RC5', $S_P$)-(RC5', $R_P$)
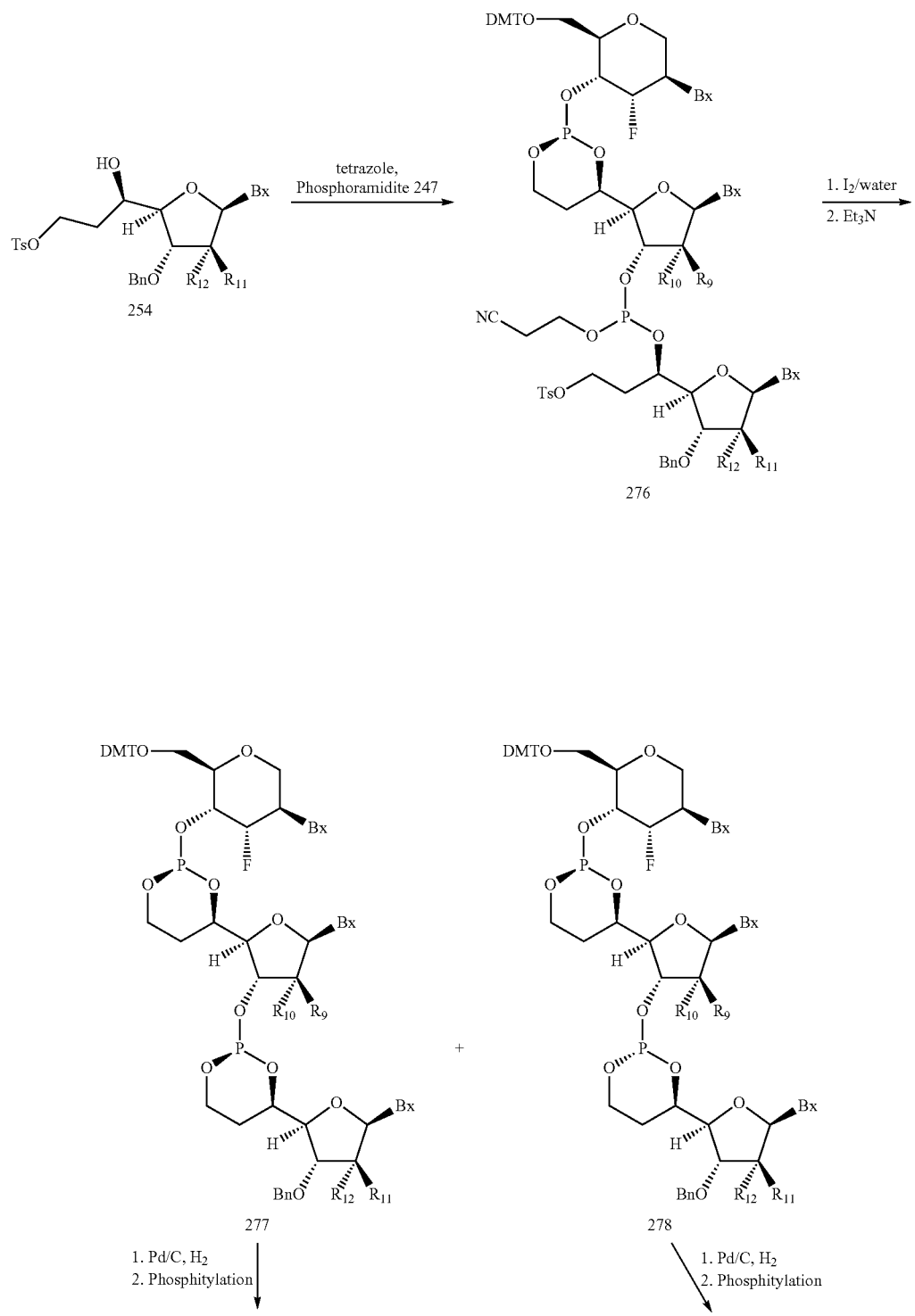

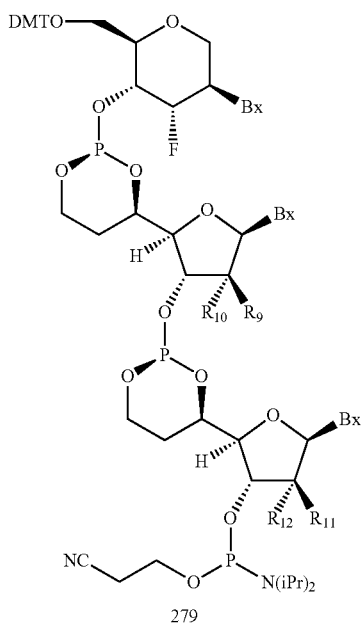
279

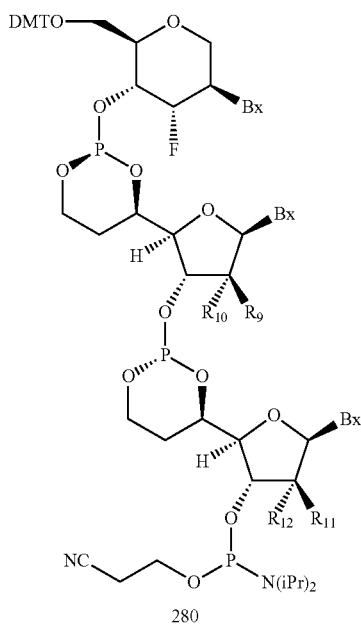
280

Bx is a heterocyclic base moiety;
$R_9$, $R_{10}$, $R_{11}$ and $R_{12}$ are each independently H, OH, or a 2'-sugar substituent group Dimeric phosphoramidite 247 and the tosylate precursor, Compound 254 are prepared using similar procedures as described in Example 42 and 44, respectively. Compounds 277 and 278 are separated by column chromatography.

Dimeric phosphoramidite 247 and the tosylate precursor, Compound 254 used in the coupling step serve only to illustrate the compounds described herein and are not intended to be limiting. Additional precursors and dimeric phosphoramidite subunits as illustrated in Examples 15-43 can also be employed to construct trimers, tetramers or multiple monomer subunits that are used as building blocks in oligonucleotide synthesis.

Example 49 General Method for the Preparation of Trimeric Phosphoramidites, Compounds 284 (RC5', $S_P$) and 285 (RC5', $S_P$)-(RC5', $R_P$)

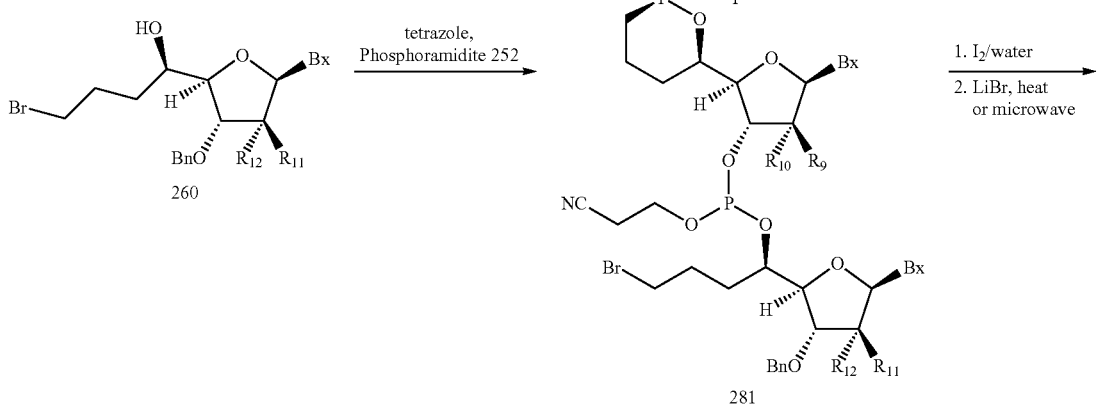
281

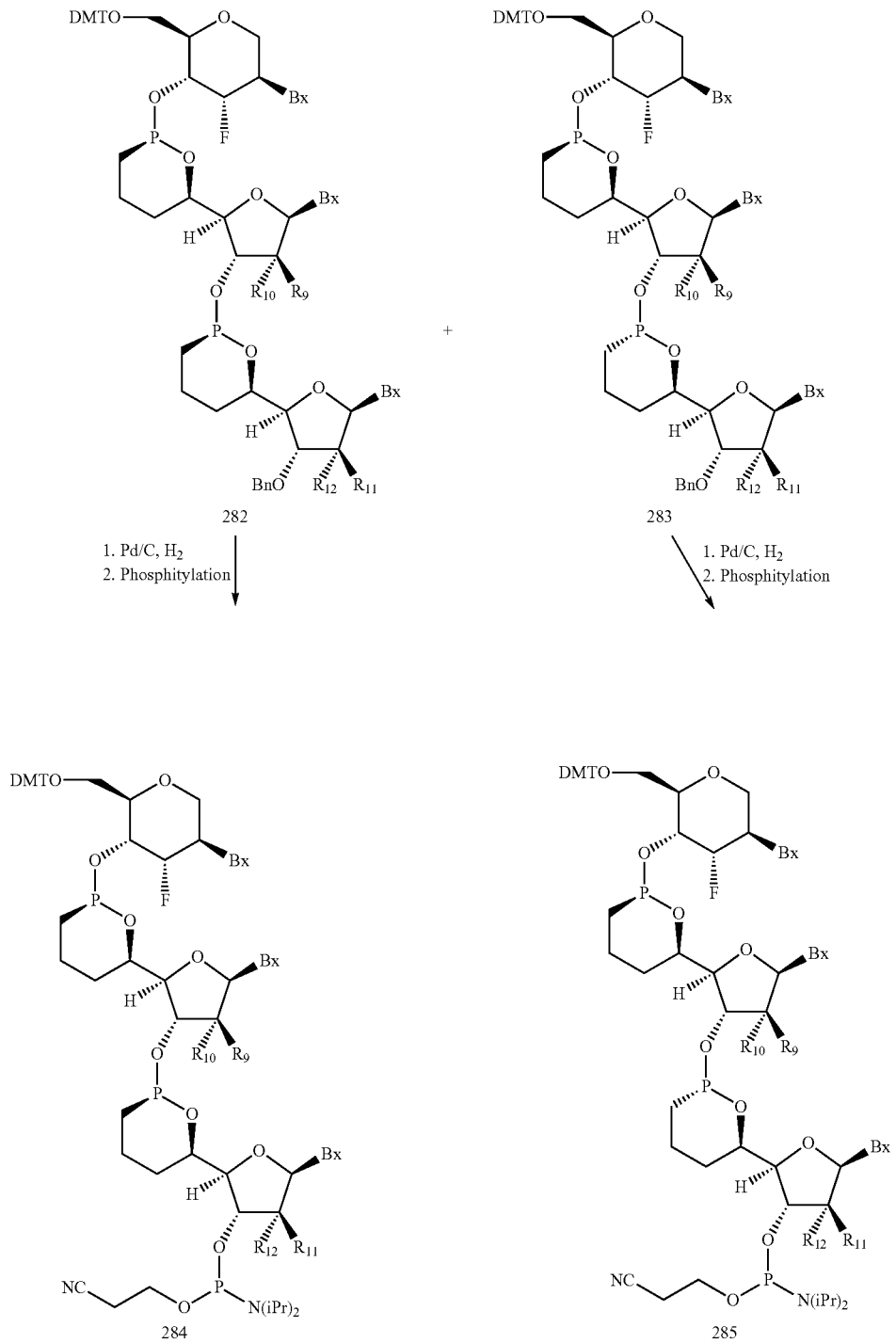

Bx is a heterocyclic base moiety;
R$_9$, R$_{10}$, R$_{11}$ and R$_{12}$ are each independently H, OH, or a 2′-sugar substituent group Dimeric phosphoramidite 252 and the bromo precursor, Compound 260 are prepared using similar procedures as described in Example 43 and 47, respectively. Compounds 282 and 283 are separated by column chromatography.

Dimeric phosphoramidite 252 and the bromo precursor, Compound 260 used in the coupling step serve only to illustrate the compounds described herein and are not intended to be limiting. Additional precursors and dimeric phosphoramidite subunits as illustrated in Examples 15-43 can also be employed to construct trimers, tetramers or multiple monomer subunits that are used as building blocks in oligonucleotide synthesis.

Example 50 General Method for the Preparation of Trimeric Phosphoramidites, Compounds 289 (RC5', $S_P$) and 290 (RC5', $S_P$)-(RC5', $R_P$)
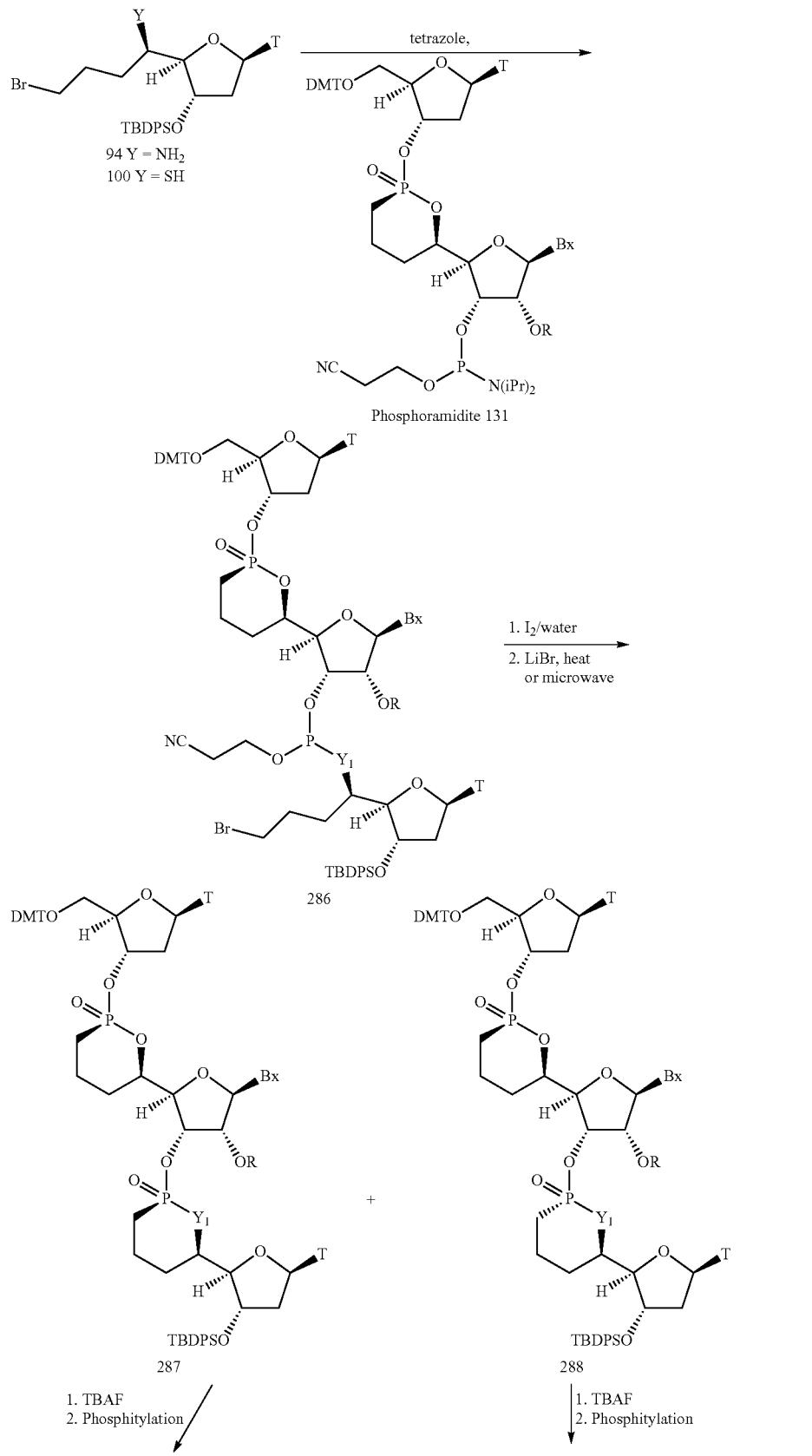

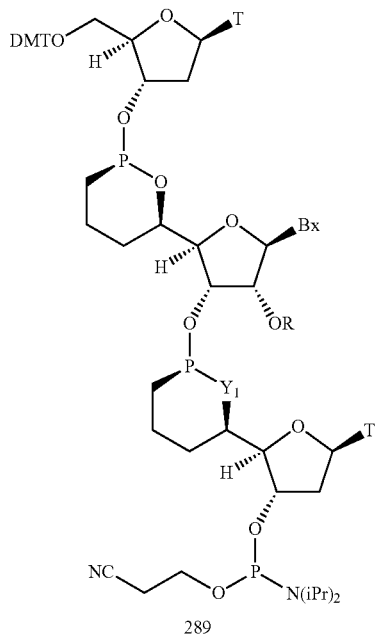

289

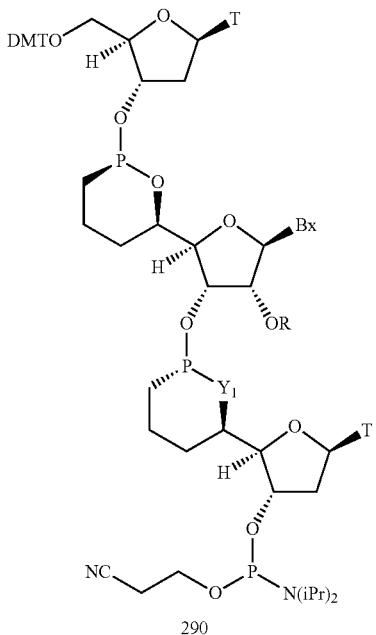

290

Y₁ = NH or S
R = —CH₃, —(CH₂)₂OCH₃, or —(CH₂)NHCH₃
Bx = heterocyclic base moiety Compounds 94, 100 and 131 are prepared as per the procedures illustrated in Examples 24, 26 and 28. The amino and thio precursors along with Phosphoramidite 131 used in the coupling step serve only to illustrate the compounds described herein and are not intended to be limiting. Additional precursors and phosphoramidites as illustrated in Examples 13-43 can also be employed to construct trimers, tetramers or multiple monomer subunits that are used as building blocks in oligonucleotide synthesis. Compounds 287 and 288 are separated by column chromatography.

Example 51 General Meth of for the Preparation of Trimeric Phosphoramidites, Compounds 294 (SRC5', S$_P$) and 295 (RC5', S$_P$)-(RC5', R$_P$)

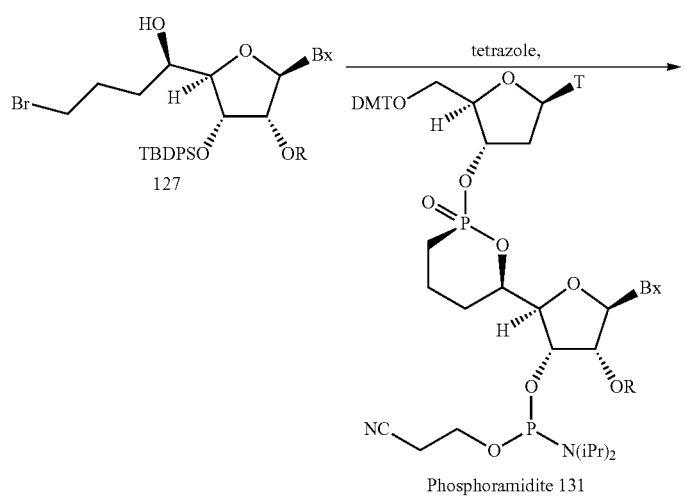

Phosphoramidite 131

-continued
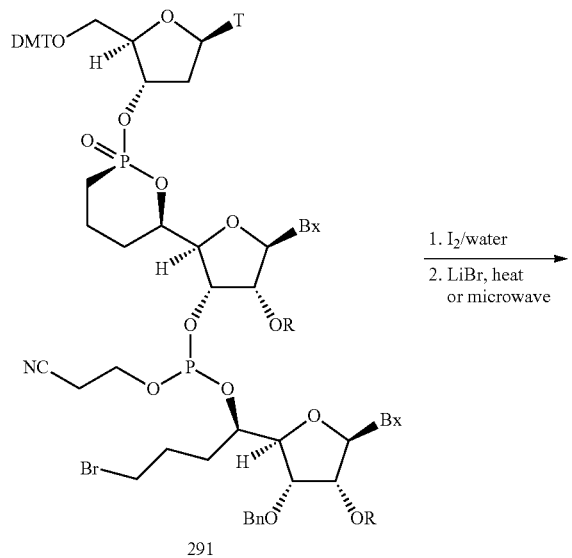
1. I₂/water
2. LiBr, heat or microwave
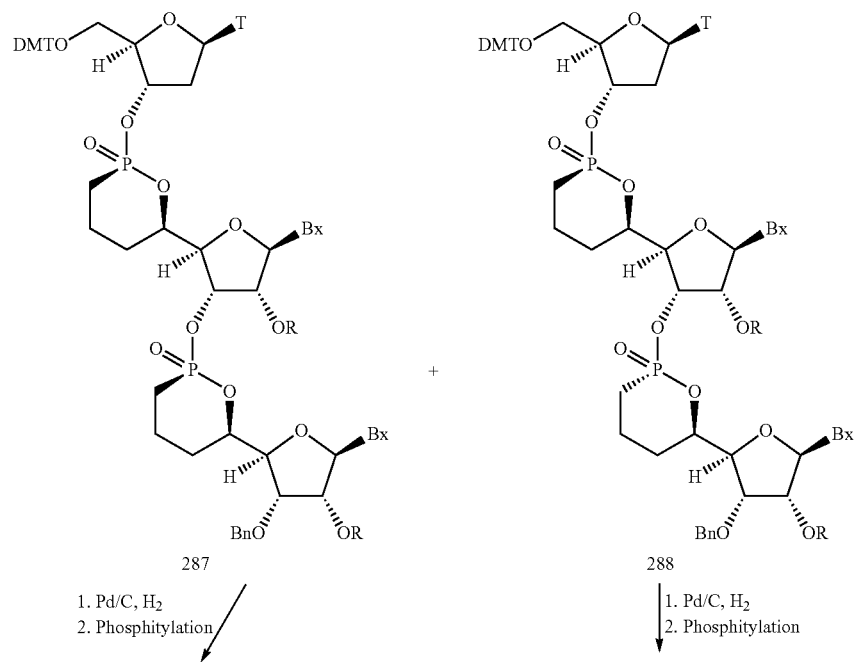
287
1. Pd/C, H₂
2. Phosphitylation
288
1. Pd/C, H₂
2. Phosphitylation

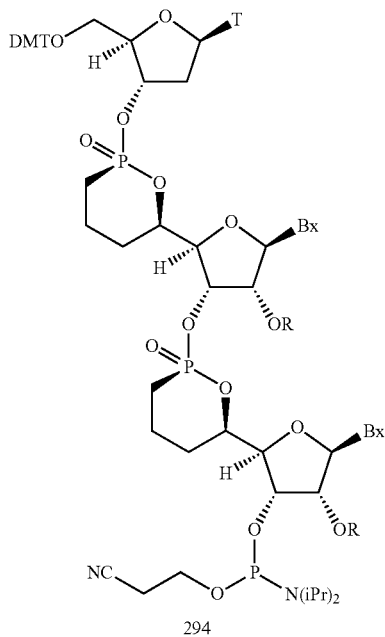

294

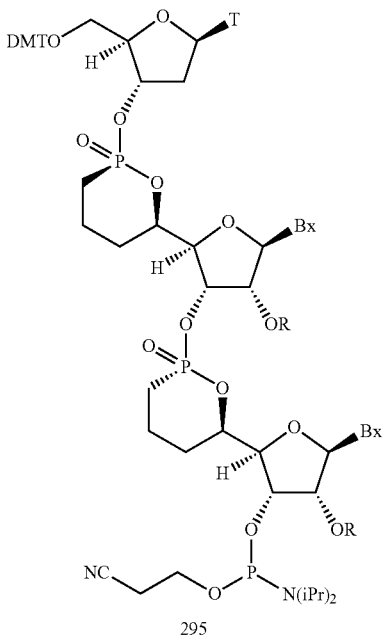

295

R = —CH₃, —(CH₂)₂OCH₃ or —(CH₂)NHCH₃
Bx = heterocyclic base moiety

Compounds 127 and 131 are prepared as per the procedures illustrated in Example 28. The bromo precursor and Phosphoramidite 131 used in the coupling step serve only to illustrate the compounds described herein and are not intended to be limiting. Additional precursors and phosphoramidites as illustrated in Examples 13-43 can also be employed to construct trimers, tetramers or multiple building block subunits that are used in oligonucleotide synthesis. Compounds 292 and 293 are separated by column chromatography.

Example 52 General Method for the Preparation of Trimeric Phosphoramidites, Compounds 303 (RC5', $S_P$)-(SC5', $S_P$) and 304 (RC5', $S_P$)-(SC5', $R_P$)

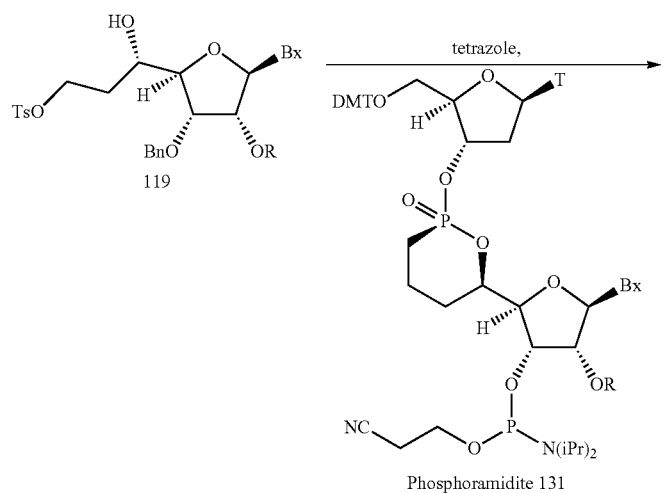

Phosphoramidite 131

-continued
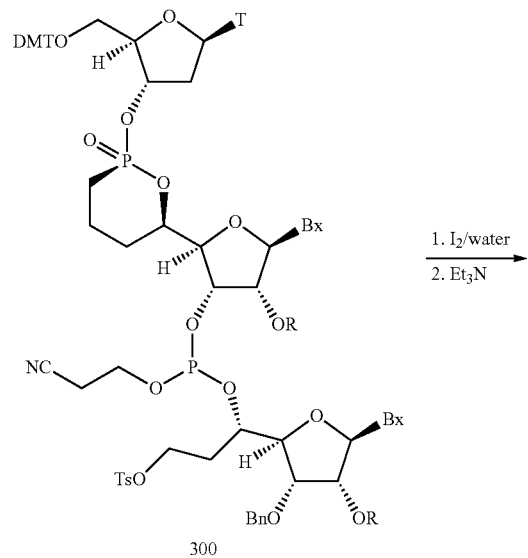
300
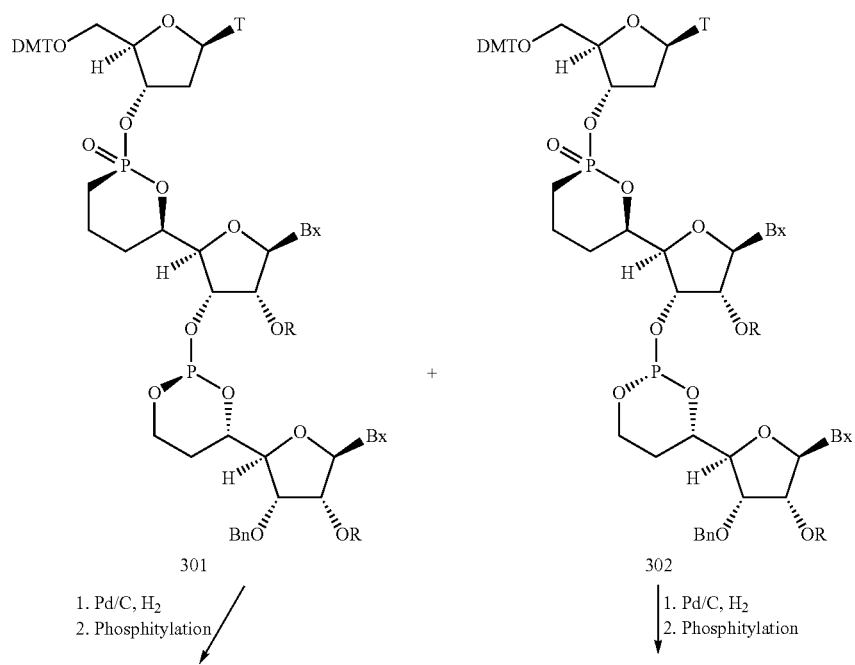
301        302
1. Pd/C, H₂
2. Phosphitylation
1. Pd/C, H₂
2. Phosphitylation

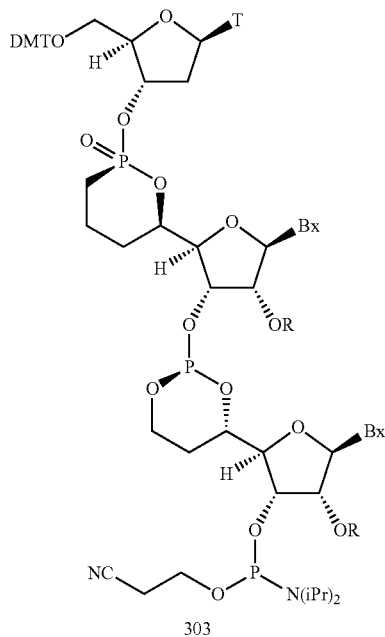

303

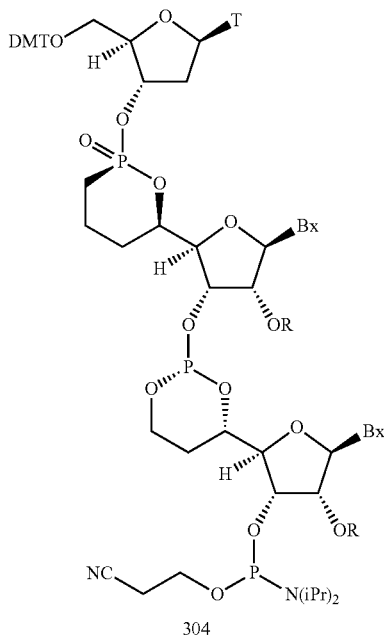

304

R = ―CH₃, ―(CH₂)₂OCH₃ or ―(CH₂)NHCH₃
Bx = heterocyclic base moiety

Compounds 119 and 131 are prepared as per the procedures illustrated in Examples 27 and 28. The tosylate precursor and Phosphoramidite 131 used in the coupling step serve only to illustrate the compounds described herein and are not intended to be limiting. Additional precursors and phosphoramidites as illustrated in Examples 13-43 can also be employed to construct trimers, tetramers or multiple building block subunits that are used in oligonucleotide synthesis. Compounds 301 and 302 are separated by column chromatography.

Example 53 General Method for the Preparation of Trimeric Phosphoramidites, Compounds 308 (RC5', S$_P$)₂ and 309 (RC5', S$_P$)-(RC5', R$_P$)

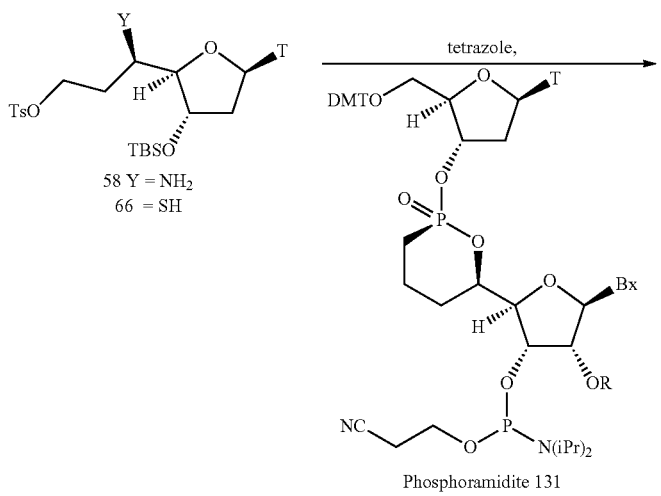

Phosphoramidite 131

-continued
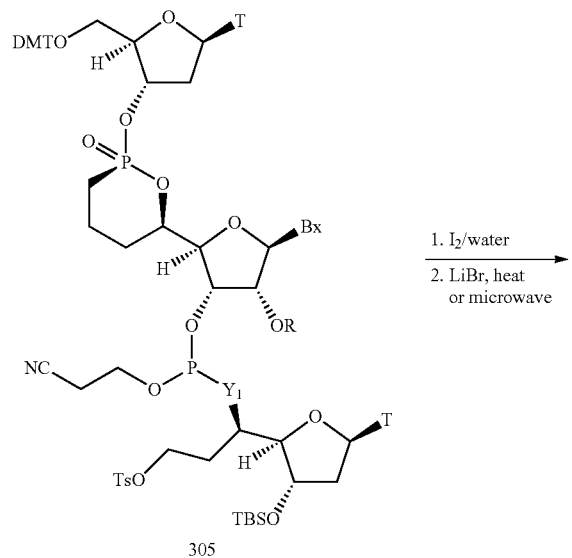
305
1. I₂/water
2. LiBr, heat or microwave
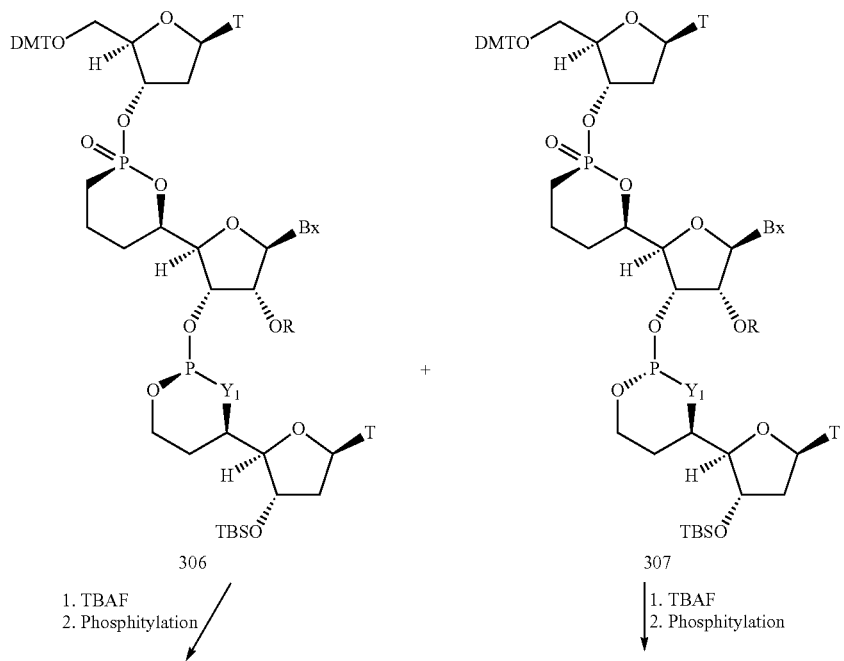
306
1. TBAF
2. Phosphitylation
307
1. TBAF
2. Phosphitylation -continued

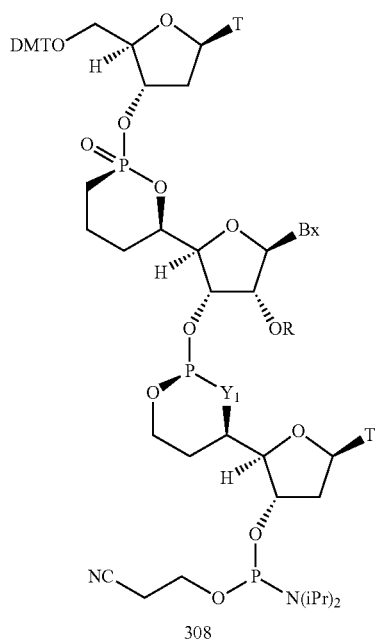

308

$Y_1$ = NH or S
R = —CH$_3$, —(CH$_2$)$_2$OCH$_3$, or —(CH$_2$)NHCH$_3$
Bx = heterocyclic base moiety

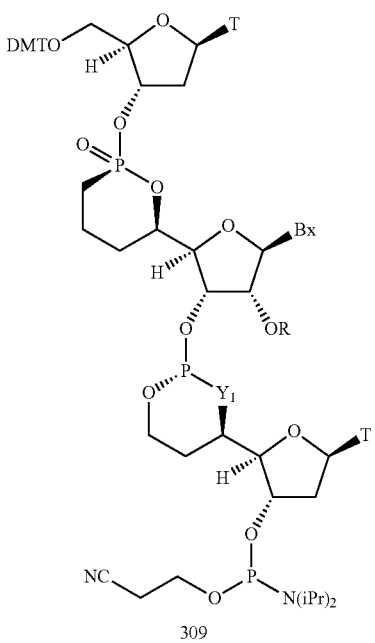

309

Compounds 58, 66 and 131 are prepared as per the procedures illustrated in Examples 19, 20 and 28. The amino and thio tosylate precursors along with Phosphoramidite 131 used in the coupling step serve only to illustrate the compounds described herein and are not intended to be limiting. Additional precursors and phosphoramidites as illustrated in Examples 13-43 can also be employed to construct trimers, tetramers or multiple building block subunits that are used in oligonucleotide synthesis. Compounds 306 and 307 are separated by column chromatography.

Example 54 General Preparation of Oligomeric Compound 312 (RC5', S$_P$)

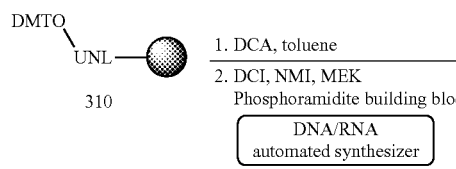

310

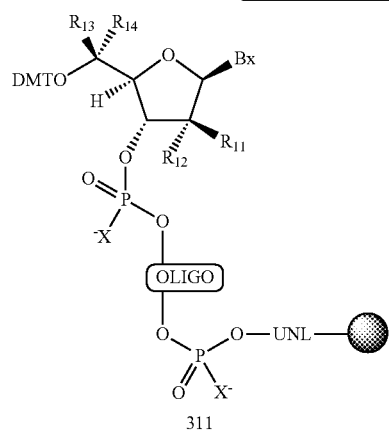

311

-continued

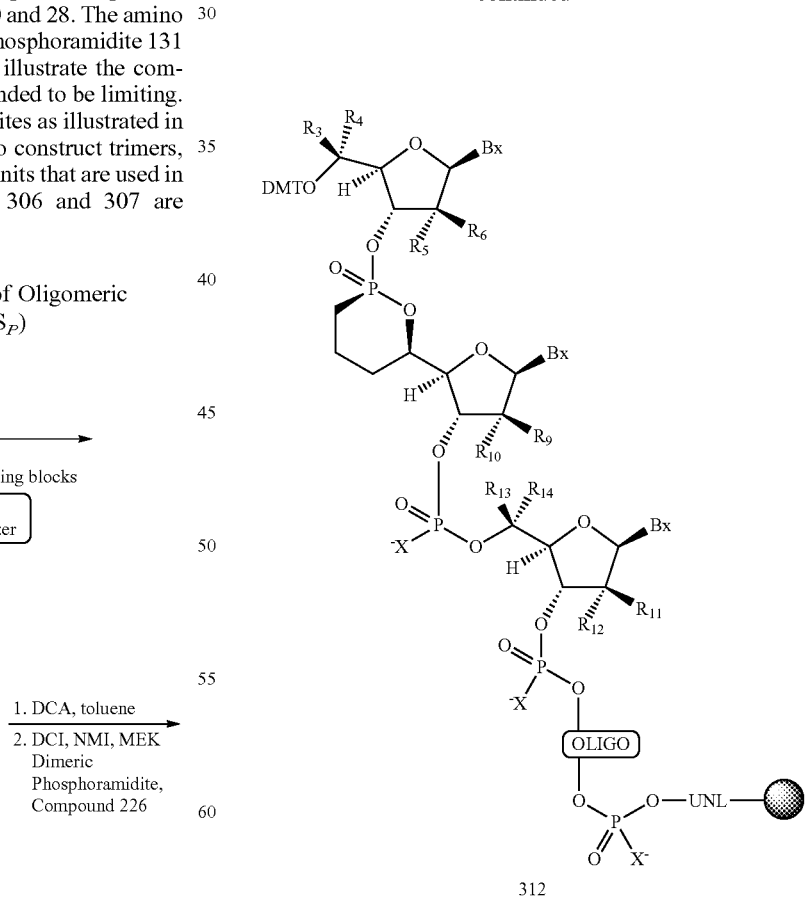

312

-continued

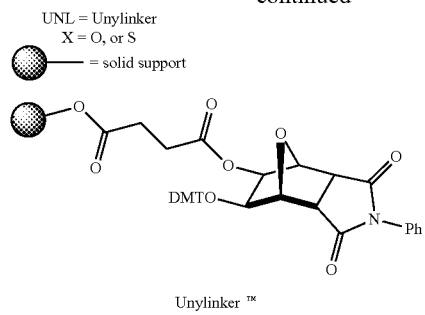

Unylinker ™

Bx is heterocyclic base moiety
$R_3$, $R_4$, $R_{13}$ and $R_{14}$ are each independently H, alkyl, substituted alkyl, substituted alkoxy, alkenyl, substituted alkenyl, alkynyl, substituted alkynyl, aryl or substituted aryl; and
$R_5$, $R_6$, $R_9$, $R_{10}$, $R_{11}$ and $R_{12}$ are each independently H, OH or a 2'-sugar substituent group The Unylinker™ 310 is commercially available. Oligomeric Compound 312 comprising a cyclic phosphonate internucleoside linkage is prepared using standard procedures in automated DNA/RNA synthesis (see Dupouy et al., Angew. Chem. Int. Ed., 2006, 45, 3623-3627). Phosphoramidite building block Compound 226 is prepared as per the procedures illustrated in Example 38. The synthetic steps illustrated are meant to be representative and not limiting as other dimers and trimers or longer building blocks which are disclosed in examples 13 to 43 can be used in place of Compound 226 to prepare an oligomeric compound having a predetermined sequence and composition such as a specific motif. The order of addition to the solid support can also be altered to provide for a region of α-β-constrained nucleic acid or multiple regions located at predetermined positions within an oligomeric compound.

The synthetic methods described herein (e.g. Examples 13-53) are versatile and allow for the incorporation of cyclic phosphorus containing internucleoside linkage(s) to be introduced at any position of the oligonucleotide.

Example 55 General Method for the Preparation of Oligomeric Compounds Comprising a Cyclic Phosphate Internucleoside Linkage Via Solid Phase Techniques (Preparation of 460209, 575149 and 626304)

Unless otherwise stated, all reagents and solutions used for the synthesis of oligomeric compounds are purchased from commercial sources. Standard phosphoramidite building blocks and solid support are used for incorporation nucleoside residues which include for example T, A, U, G, C and $^m$C residues. A 0.2 M solution of phosphoramidite in anhydrous acetonitrile was used for 2'-O-MOE, β-D-2'-deoxyribonucleoside monomers and cyclic phosphate containing β-D-2'-deoxyribonucleoside dimers. For constrained ethyl (cEt) BNA phosphoramidite, a 0.2 M solution in a 1:1 (v/v) mixture of acetonitrile and toluene was used.

The oligomeric compound was synthesized on VIMAD UnyLinker™ solid support and the appropriate amounts of solid support were packed in the column for synthesis. Dichloroacetic acid (3%) in DCM was used as detritylating reagent. 4,5-Dicyanoimidazole in the presence of N-methylimidazole or 1H-tetrazole in $CH_3CN$ was used as activator during the coupling step. The synthesis of oligomeric compounds was performed on an ABI394 synthesizer (Applied Biosystems) on a 2 μmol scale using the procedures set forth below.

A solid support preloaded with the Unylinker™ was loaded into a synthesis column after closing the column bottom outlet and $CH_3CN$ was added to form a slurry. The swelled support-bound Unylinker™ was treated with a detritylating reagent containing 3% dichloroacetic acid in DCM to provide the free hydroxyl groups. During the coupling step, four to fourteen equivalents of phosphoramidite solutions were delivered with coupling for 10 minutes. All of the other steps followed standard protocols. Phosphorothioate linkages were introduced by sulfurization with PADS (0.2 M) in 1:1 pyridine/$CH_3CN$ for a contact time of 5 minutes.

After the desired sequence was assembled, the cyanoethyl phosphate protecting groups were deprotected using a 1:1 (v/v) mixture of triethylamine and acetonitrile. The solid support bound oligomeric compound was washed with acetonitrile and dried under high vacuum. The solid-support bound oligomeric compound was then suspended in ammonia (28-30 wt %) at room temperature for 48 h to remove nucleobase protecting groups and to cleave from the solid support.

The unbound oligomeric compound was then filtered and the support was rinsed and filtered with water:ethanol (1:1) followed by water. The filtrate was combined and concentrated to dryness. The residue obtained was purified by cationic ion exchange HPLC (Source 30Q resin, A—50 mM sodium bicarbonate in $CH_3CN:H_2O$ 3:7 (v/v), B—50 mM sodium bicarbonate, 1.5 M sodium bromide in $CH_3CN:H_2O$ 3:7 (v/v), 0-30% in 110 min, flow 6 mL/min, λ=260 nm). Fractions containing full-length oligomeric compound were pooled together (assessed by LC/MS analysis >95%). The residue was desalted by HPLC on a reverse phase cartridge to yield the desired oligomeric compound. ISIS 460209 was also synthesized and analyzed in the same manner as described herein.

The modified oligomeric compounds were evaluated in a thermal stability ($T_m$) assay. A Cary 100 Bio spectrophotometer with the Cary Win UV Thermal program was used to measure absorbance vs. temperature. For the $T_m$ experiments, oligomeric compounds were prepared at a concentration of 8 μM in a buffer of 100 mM Na+, 10 mM phosphate, 0.1 mM EDTA, pH 7. The concentration of the oligonucleotides was determined at 85° C. The concentration of each oligomeric compound was 4 μM after mixing of equal volumes of test oligomeric compound and complimentary RNA strand (or the RNA strand having a single base mismatch). Oligomeric compounds were hybridized with the complimentary RNA strand by heating the duplex to 90° C. for 5 minutes followed by cooling to room temperature. Using the spectrophotometer, $T_m$ measurements were taken by heating the duplex solution at a rate of 0.5 C/min in cuvette starting @ 15° C. and heating to 85° C. $T_m$ values were determined using Vant Hoff calculations ($A_{260}$ vs temperature curve) using non self-complementary sequences where the minimum absorbance which relates to the duplex and the maximum absorbance which relates to the non-duplex single strand are manually integrated into the program. The oligomeric compounds are hybridized to a complementary region of 30mer RNA SEQ ID NO.: 07 ($Tm^1$), and also to a single base mismatch 30mer RNA SEQ ID NO.: 08 ($Tm^2$). The results are presented below.

| SEQ ID NO./ ISIS NO. | Composition (5' to 3') | ΔTm¹ (RNA $^{mu}$) | ΔTm² (RNA $^{wt}$) |
|---|---|---|---|
| 06/460209 | $T_eA_kA_kA_dT_dT_dG_dT_d{}^mC_dA_dT_d{}^mC_d A_k{}^mC_k{}^mC_e$ | (53.7) | (52.2) |
| 06/575149 | $T_eA_kA_kA_dT_xTG_dT_d{}^mC_dA_dT_d{}^mC_d A_k{}^mC_k{}^mC_e$ | 2.7 | 1.3 |
| 06/626304 | $T_eA_kA_kA_dT_yTG_dT_d{}^mC_dA_dT_d{}^mC_d A_k{}^mC_k{}^mC_e$ | -2.3 | -2.3 |

| SEQ ID NO. | RNA Complementary Strands (5' to 3') | |
|---|---|---|
| 07/539568 | AGACUUUUUCUGGUGAUGACAA UUUAUUAA | complementary mutant (mu) |
| 08/539569 | AGACUUUUUCUGGUGAUGGCAA UUUAUUAA | single base mismatch wild type (wt) |

Each internucleoside linkage for the modified oligonucleotides is a phosphorothioate internucleoside linkage except for the dimers $T_xT$ and $T_yT$, the internucleoside linkages of which are shown below. Each internucleoside linkage for the RNA complementary strands is a phosphodiester internucleoside linkage. Each nucleoside followed by a subscript "e" indicates a 2'-O-methoxyethyl (MOE) modified nucleoside. Each nucleoside followed by a subscript "k" indicates an (S)-cEt modified nucleoside (constrained ethyl bicyclic nucleoside having a 4'-CH—[(S)—CH₃)]—O-2' bridging group) as shown below. Each nucleoside followed by a subscript "d" is a β-D-2'-deoxyribonucleoside. Each "$^mC$" is a 5-methyl cytosine modified nucleoside.

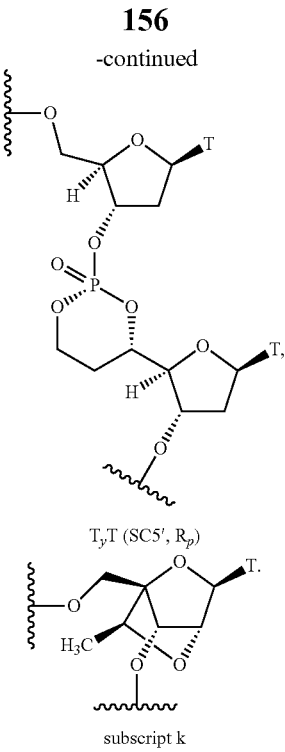

$T_xT\ (RC5',\ S_p)$ $T_yT\ (SC5',\ R_p)$ subscript k

Example 56 Single Nucleotide Polymorphisms (SNPs) in the Huntingtin (HTT) Gene Sequence SNP positions (identified by Hayden et al, WO/2009/135322) associated with the HTT gene were mapped to the HTT genomic sequence, designated herein as SEQ ID NO: 5 (NT_006081.18 truncated from nucleotides 1566000 to 1768000). The chart below provides SNP positions associated with the HTT gene and a reference SNP ID number from the Entrez SNP database at the National Center for Biotechnology Information (NCBI, http://www.ncbi.nlm.nih.gov/sites/entrez?db=snp), incorporated herein by reference. The chart below furnishes further details on each SNP. The 'Reference SNP ID number' or 'RS number' is the number designated to each SNP from the Entrez SNP database at NCBI, incorporated herein by reference. 'SNP position' refers to the nucleotide position of the SNP on SEQ ID NO: 5. 'Polymorphism' indicates the nucleotide variants at that SNP position. 'Major allele' indicates the nucleotide associated with the major allele, or the nucleotide present in a statistically significant proportion of individuals in the human population. 'Minor allele' indicates the nucleotide associated with the minor allele, or the nucleotide present in a relatively small proportion of individuals in the human population.

Single Nuclear Polymorphisms (SNPs) and their Positions on SEQ ID NO: 5

| RS No. | SNP position | Polymorphism | Major allele | Minor allele |
|---|---|---|---|---|
| rs2857936 | 1963 | C/T | C | T |
| rs12506200 | 3707 | A/G | G | A |
| rs762855 | 14449 | A/G | G | A |
| rs3856973 | 19826 | G/A | G | A |

-continued

| RS No. | SNP position | Polymorphism | Major allele | Minor allele |
|---|---|---|---|---|
| rs2285086 | 28912 | G/A | A | G |
| rs7659144 | 37974 | C/G | C | G |
| rs16843804 | 44043 | C/T | C | T |
| rs2024115 | 44221 | G/A | A | G |
| rs10015979 | 49095 | A/G | A | G |
| rs7691627 | 51063 | A/G | G | A |
| rs2798235 | 54485 | G/A | G | A |
| rs4690072 | 62160 | G/T | T | G |
| rs6446723 | 66466 | C/T | T | C |
| rs363081 | 73280 | G/A | G | A |
| rs363080 | 73564 | T/C | C | T |
| rs363075 | 77327 | G/A | G | A |
| rs363064 | 81063 | T/C | C | T |
| rs3025849 | 83420 | A/G | A | G |
| rs6855981 | 87929 | A/G | G | A |
| rs363102 | 88669 | G/A | A | G |
| rs11731237 | 91466 | C/T | C | T |
| rs4690073 | 99803 | A/G | G | A |
| rs363144 | 100948 | T/G | T | G |
| rs3025838 | 101099 | C/T | C | T |
| rs34315806 | 101687 | A/G | G | A |
| rs363099 | 101709 | T/C | C | T |
| rs363096 | 119674 | T/C | T | C |
| rs2298967 | 125400 | C/T | T | C |
| rs2298969 | 125897 | A/G | G | A |
| rs6844859 | 130139 | C/T | T | C |
| rs363092 | 135682 | C/A | C | A |
| rs7685686 | 146795 | A/G | A | G |
| rs363088 | 149983 | A/T | A | T |
| rs362331 | 155488 | C/T | T | C |
| rs916171 | 156468 | G/C | C | G |
| rs362322 | 161018 | A/G | A | G |
| rs362275 | 164255 | T/C | C | T |
| rs362273 | 167080 | A/G | A | G |
| rs2276881 | 171314 | G/A | G | A |
| rs3121419 | 171910 | T/C | C | T |
| rs362272 | 174633 | G/A | G | A |
| rs362271 | 175171 | G/A | G | A |
| rs3775061 | 178407 | C/T | C | T |
| rs362310 | 179429 | A/G | G | A |
| rs362307 | 181498 | T/C | C | T |
| rs362306 | 181753 | G/A | G | A |
| rs362303 | 181960 | T/C | C | T |
| rs362296 | 186660 | C/A | C | A |
| rs1006798 | 198026 | A/G | A | G |

Example 57 Modified Oligonucleotides Targeting Huntingtin (HTT) Single Nucleotide Polymorphism (SNP)

A modified oligonucleotide was designed based on a parent gapmer, ISIS 460209 wherein the central gap region contains nine β-D-2'-deoxyribonucleosides. The modified oligonucleotide was designed by introducing a cyclic phosphate internucleoside linkage within the central gap region of the gapmer. The cyclic phosphate containing oligonucleotide (ISIS 575149) was tested for its ability to selectively inhibit mutant (mut) HTT mRNA expression levels targeting rs7685686 while leaving the expression of the wild-type (wt) intact. The potency and selectivity of the modified oligonucleotide (ISIS 575149) was evaluated and compared to the parent gapmer (ISIS 460209).

The composition and motif for the modified oligonucleotide is described previously in Example 55. The position on the oligonucleotides opposite to the SNP position, as counted from the 5'-terminus is position 8.

Cell Culture and Transfection

The modified oligonucleotide was tested in vitro. Heterozygous fibroblast GM04022 cell line was used (from Coriell Institute). Cultured GM04022 cells at a density of 25,000 cells per well were transfected using electroporation with 0.12, 0.37, 1.1, 3.3 and 10 μM concentrations of modified oligonucleotides. After a treatment period of approximately 24 hours, cells were washed with DPBS buffer and lysed. RNA was extracted using Qiagen RNeasy purification and mRNA levels were measured by quantitative real-time PCR using ABI assay C_2229297_10 which measures at dbSNP rs362303. RT-PCR method in short; A mixture was made using 2020 uL 2×PCR buffer, 101 uL primers (300 uM from ABI), 1000 uL water and 40.4 uL RT MIX. To each well was added 15 uL of this mixture and 5 uL of purified RNA. The mutant and wild-type HTT mRNA levels were measured simultaneously by using two different fluorophores, FAM for mutant allele and VIC for wild-type allele. The HTT mRNA levels were adjusted according to total RNA content, as measured by RIBOGREEN and the results are presented below.

Analysis of $IC_{50}$'s

The half maximal inhibitory concentration ($IC_{50}$) of each oligonucleotide is presented below and was calculated by plotting the concentrations of oligonucleotides used versus the percent inhibition of HTT mRNA expression achieved at each concentration, and noting the concentration of oligonucleotide at which 50% inhibition of HTT mRNA expression was achieved compared to the control. The $IC_{50}$ at which each oligonucleotide inhibits the mutant HTT mRNA expression is denoted as 'mut $IC_{50}$'. The $IC_{50}$ at which each oligonucleotide inhibits the wild-type HTT mRNA expression is denoted as 'wt $IC_{50}$'. Selectivity was calculated by dividing the $IC_{50}$ for inhibition of the wild-type HTT versus the $IC_{50}$ for inhibiting expression of the mutant HTT mRNA. The results are presented below.

The parent gapmer, ISIS 460209 is included in the study as a benchmark oligonucleotide against which the potency and selectivity of the modified oligonucleotide is compared. As illustrated below, the oligonucleotide containing a cyclic phosphate internucleoside linkage in the central gap region exhibited enhanced potency and selectivity as compared to the parent gapmer having a full deoxy gap.

| SEQ ID NO./ ISIS NO. | Composition (5' to 3') |
|---|---|
| 06/460209 | $T_eA_kA_kA_dT_dT_dG_dT_d{}^mC_dA_dT_d{}^mC_dA_k{}^mC_k{}^mC_e$ |
| 06/575149 | $T_eA_kA_kA_dT_xTG_dT_d{}^mC_dA_dT_d{}^mC_dA_k{}^mC_k{}^mC_e$ |
| 06/626304 | $T_eA_kA_kA_dT_yTG_dT_d{}^mC_dA_dT_d{}^mC_dA_k{}^mC_k{}^mC_e$ |

(see Example 55 for description of oligonucleotide modifications)

| SEQ ID NO./ ISIS NO. | Mut $IC_{50}$ (μM) | Selectivity (mut vs. wt) | Gap Chemistry |
|---|---|---|---|
| 06/460209 | 0.33 | 4.2 | 2'-deoxy gap |
| 06/575149 | 0.14 | 7.2-paper | single cyclic P=O, $T_xT$ |
| 06/626304 | 0.25 | 27 | single cyclic P=O, $T_yT$ |

All publications, patents, and patent applications referenced herein are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. An oligomeric compound comprising from 8 to 40 linked monomer subunits wherein at least one of the monomer subunits is a modified nucleotide having Formula II:

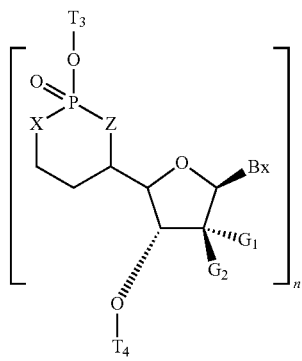

II wherein independently for each modified nucleotide having Formula II:
  $T_3$ is attached to one of the linked monomer subunits;
  $T_4$ is H, a hydroxyl protecting group, a linked conjugate group or an internucleoside linking group attached to one of the linked monomer subunits;
  each Bx is a heterocyclic base moiety;
  each $G_1$ and $G_2$ is, independently, H, OH or a 2'-sugar substituent group selected from halogen and O—[C$(R_1)(R_2)]_j$—[(C=O)$_m$-A]$_j$-T;
  wherein each $R_1$ and $R_2$ is, independently, H, $C_1$-$C_6$ alkyl or halogen;
  A is O, S or N($E_1$);
  T is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or N($E_2$)($E_3$);
  $E_1$, $E_2$ and $E_3$ are each, independently, H, $C_1$-$C_6$ alkyl or substituted $C_1$-$C_6$ alkyl;
  i is from 1 to about 6;
  m is 0 or 1;
  j is 0 or 1;

wherein each substituted group comprises one or more optionally protected substituent groups independently selected from halogen, $OJ_3$, $N(J_3)_4$), $=NJ_3$, $SJ_3$, $N_3$, CN, $OC(=L_2)J_3$, $OC(=L_2)N(J_3)(J_4)$ and $C(=L_2)N(J_3)(J_4)$;

$L_2$ is O, S or $NJ_5$;

each $J_3$, $J_4$ and $J_5$ is, independently, H or $C_1$-$C_6$ alkyl; and when j is 1 then T is other than halogen;

one of each X and each Z is $CJ_1J_2$, $NJ_2$, S or O and the other of each X and each Z is O;

each $J_1$ and $J_2$ is, independently, H, $C_1$-$C_6$ alkyl, $C_2$-$C_6$ alkenyl or $C_2$-$C_6$ alkynyl;

each n is, independently, from 1 to about 30; and when Z is O and X is O then at least one $G_1$ and $G_2$ is other than H, OH or $OCH_3$ and when Z is O and X is $CH_2$ or S then at least one $G_1$ and $G_2$ is other than H.

2. The oligomeric compound of claim 1 wherein each X is O.

3. The oligomeric compound of claim 1 wherein each X is $CH_2$.

4. The oligomeric compound of claim 1 wherein each Z is O.

5. The oligomeric compound of claim 1 wherein each Z is $CH_2$.

6. The oligomeric compound of claim 1 wherein each Z is S.

7. The oligomeric compound of claim 1 wherein each Z is NH or $NCH_3$.

8. The oligomeric compound of claim 1 wherein one of each $G_1$ and each $G_2$ is H and the other of each $G_1$ and each $G_2$ is, independently, selected from halogen, $OCH_3$, $OCF_3$, $OCH_2CH_3$, $OCH_2CF_3$, $OCH_2$—CH=$CH_2$, $O(CH_2)_2$—$OCH_3$, $O(CH_2)_2$—$O(CH_2)_2$—$N(CH_3)_2$, $OCH_2C(=O)$—N(H)$CH_3$, $OCH_2C(=O)$—N(H)—$(CH_2)_2$—$N(CH_3)_2$ and $OCH_2$—N(H)—C(=NH)$NH_2$.

9. The oligomeric compound of claim 1 wherein each $G_1$ is $O(CH_2)_2$—$OCH_3$ and each $G_2$ is H.

10. The oligomeric compound of claim 1 wherein each $G_1$ and $G_2$ is H.

11. The oligomeric compound of claim 1 wherein each Bx is, independently, uracil, thymine, cytosine, 4-N-benzoylcytosine, 5-methyl-cytosine, 4-N-benzoyl-5-methylcytosine, adenine, 6-N-benzoyl adenine, guanine or 2-N-isobutyrylguanine.

12. The oligomeric compound of claim 1 wherein each modified nucleotide having Formula II has the configuration of one of formulas IIa, IIb, IIc or IId:

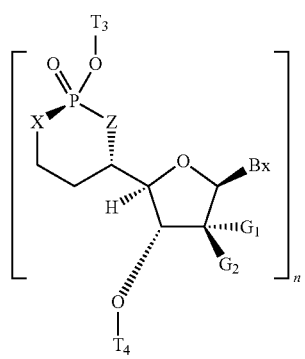

IIa

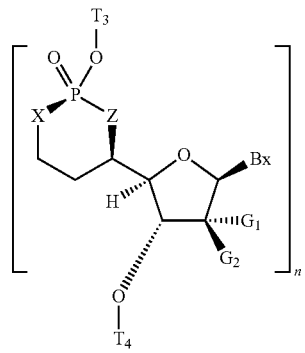

IIb

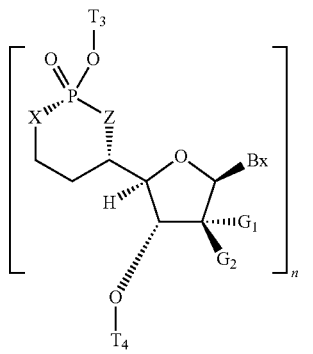

IIc or

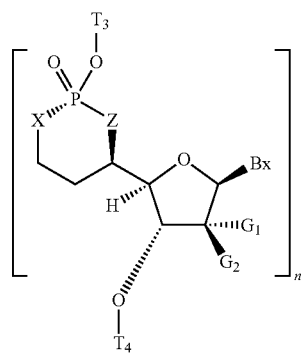

IId

13. The oligomeric compound of claim 12 wherein each modified nucleotide has the configuration of Formula IIa.

14. The oligomeric compound of claim 12 wherein each modified nucleotide has the configuration of Formula IIb.

15. The oligomeric compound of claim 12 wherein each modified nucleotide has the configuration of Formula IIc.

16. The oligomeric compound of claim 12 wherein each modified nucleotide has the configuration of Formula IId.

17. The oligomeric compound of claim 12 wherein each $G_1$ and $G_2$ is H, each X and Z is O, and n is 1.

18. The oligomeric compound of claim 1 wherein $T_3$ is attached to a 3'-position of a β-D-ribonucleoside, β-D-2'-deoxyribonucleoside or a modified nucleoside.

19. The oligomeric compound of claim 1 wherein $T_3$ is attached to a modified nucleoside comprising a substituted nucleoside or a bicyclic nucleoside.

20. The oligomeric compound of claim 1 wherein $T_4$ is H, a hydroxyl protecting group or a linked conjugate group.

21. The oligomeric compound of claim 1 comprising only one modified nucleotide of Formula II.

22. The oligomeric compound of claim 1 wherein the monomer subunits and each modified nucleotide having Formula II are linked together by internucleoside linking groups selected from phosphodiester and phosphorothioate internucleoside linking groups.

23. The oligomeric compound of claim 22 wherein each internucleoside linking group is a phosphorothioate internucleoside linking group.

24. A method of inhibiting gene expression comprising contacting a cell with an oligomeric compound of claim 1 wherein said oligomeric compound is complementary to a target RNA.

* * * * *

SEQUENCE LISTING

<160> NUMBER OF SEQ ID NOS: 8

<210> SEQ ID NO 1
<211> LENGTH: 3160
<212> TYPE: DNA
<213> ORGANISM: Homo sapien

<400> SEQUENCE: 1

| | | | | | |
|---|---|---|---|---|---|
| cctcccctcg | cccggcgcgg | tcccgtccgc | ctctcgctcg | cctcccgcct | ccctcggtc | 60 |
| ttccgaggcg | cccgggctcc | cggcgcggcg | gcggaggggg | cgggcaggcc | ggcgggcggt | 120 |
| gatgtggcag | gactctttat | gcgctgcggc | aggatacgcg | ctcggcgctg | ggacgcgact | 180 |
| gcgctcagtt | ctctcctctc | ggaagctgca | gccatgatgg | aagtttgaga | gttgagccgc | 240 |
| tgtgaggcga | ggccgggctc | aggcgaggga | gatgagagac | ggcggcggcc | gcggcccgga | 300 |
| gccctctca | gcgcctgtga | gcagccgcgg | gggcagcgcc | ctcggggagc | cggccggcct | 360 |
| gcggcggcgg | cagcggcggc | gtttctcgcc | tcctcttcgt | cttttctaac | cgtgcagcct | 420 |
| cttcctcggc | ttctcctgaa | agggaaggtg | gaagccgtgg | gctcgggcgg | gagccggctg | 480 |
| aggcgcggcg | gcggcggcgg | cggcacctcc | cgctcctgga | gcgggggga | gaagcggcgg | 540 |
| cggcggcggc | cgcggcggct | gcagctccag | ggaggggtc | tgagtcgcct | gtcaccattt | 600 |
| ccagggctgg | gaacgccgga | gagttggtct | ctcccttct | actgcctcca | acacggcggc | 660 |
| ggcggcggcg | gcacatccag | ggacccgggc | cggttttaaa | cctcccgtcc | gccgccgccg | 720 |
| caccccccgt | ggcccgggct | ccggaggccg | ccggcggagg | cagccgttcg | gaggattatt | 780 |
| cgtcttctcc | ccattccgct | gccgccgctg | ccaggcctct | ggctgctgag | gagaagcagg | 840 |
| cccagtcgct | gcaaccatcc | agcagccgcc | gcagcagcca | ttacccggct | gcggtccaga | 900 |
| gccaagcggc | ggcagagcga | ggggcatcag | ctaccgccaa | gtccagagcc | atttccatcc | 960 |
| tgcagaagaa | gccccgccac | cagcagcttc | tgccatctct | ctcctccttt | tcttcagcc | 1020 |
| acaggctccc | agacatgaca | gccatcatca | agagatcgt | tagcagaaac | aaaaggagat | 1080 |
| atcaaggaga | tggattcgac | ttagacttga | cctatattta | tccaaacatt | attgctatgg | 1140 |
| gatttcctgc | agaaagactt | gaaggcgtat | acaggaacaa | tattgatgat | gtagtaaggt | 1200 |
| ttttggattc | aaagcataaa | aaccattaca | agatatacaa | tctttgtgct | gaaagacatt | 1260 |
| atgacaccgc | caaatttaat | tgcagagttg | cacaatatcc | ttttgaagac | cataacccac | 1320 |
| cacagctaga | acttatcaaa | ccctttttgtg | aagatcttga | ccaatggcta | agtgaagatg | 1380 |
| acaatcatgt | tgcagcaatt | cactgtaaag | ctggaaaggg | acgaactggt | gtaatgatat | 1440 |
| gtgcatattt | attacatcgg | ggcaaatttt | taaaggcaca | agaggcccta | gatttctatg | 1500 |
| gggaagtaag | gaccagagac | aaaaagggag | taactattcc | cagtcagagg | cgctatgtgt | 1560 |
| attattatag | ctacctgtta | aagaatcatc | tggattatag | accagtggca | ctgttgtttc | 1620 |
| acaagatgat | gtttgaaact | attccaatgt | tcagtggcgg | aacttgcaat | cctcagtttg | 1680 |
| tggtctgcca | gctaaaggtg | aagatatatt | cctccaattc | aggacccaca | cgacgggaag | 1740 |
| acaagttcat | gtactttgag | ttccctcagc | cgttacctgt | gtgtggtgat | atcaaagtag | 1800 |
| agttcttcca | caaacagaac | aagatgctaa | aaaaggacaa | aatgtttcac | ttttgggtaa | 1860 |
| atacattctt | cataccagga | ccagaggaaa | cctcagaaaa | agtagaaaat | ggaagtctat | 1920 |
| gtgatcaaga | aatcgatagc | atttgcagta | tagagcgtgc | agataatgac | aaggaatatc | 1980 |
| tagtacttac | tttaacaaaa | aatgatcttg | acaaagcaaa | taagacaaa | gccaaccgat | 2040 |
| actttttctcc | aaatttttaag | gtgaagctgt | acttcacaaa | aacagtagag | gagccgtcaa | 2100 |

-continued

```
atccagaggc tagcagttca acttctgtaa caccagatgt tagtgacaat gaacctgatc    2160
attatagata ttctgacacc actgactctg atccagagaa tgaacctttt gatgaagatc    2220
agcatacaca aattacaaaa gtctgaattt ttttttatca agagggataa aacaccatga    2280
aaataaactt gaataaactg aaaatggacc tttttttttt taatggcaat aggacattgt    2340
gtcagattac cagttatagg aacaattctc ttttcctgac caatcttgtt ttaccctata    2400
catccacagg gttttgacac ttgttgtcca gttgaaaaaa ggttgtgtag ctgtgtcatg    2460
tatatacctt tttgtgtcaa aaggacattt aaaattcaat taggattaat aaagatggca    2520
ctttcccgtt ttattccagt tttataaaaa gtggagacag actgatgtgt atacgtagga    2580
attttttcct tttgtgttct gtcaccaact gaagtggcta aagagctttg tgatatactg    2640
gttcacatcc tacccctttg cacttgtggc aacagataag tttgcagttg gctaagagag    2700
gtttccgaaa ggttttgcta ccattctaat gcatgtattc gggttagggc aatggagggg    2760
aatgctcaga aaggaaataa ttttatgctg gactctggac catataccat ctccagctat    2820
ttacacacac ctttctttag catgctacag ttattaatct ggacattcga ggaattggcc    2880
gctgtcactg cttgttgttt gcgcattttt ttttaaagca tattggtgct agaaaaggca    2940
gctaaaggaa gtgaatctgt attggggtac aggaatgaac cttctgcaac atcttaagat    3000
ccacaaatga agggatataa aaataatgtc ataggtaaga aacacagcaa caatgactta    3060
accatataaa tgtggaggct atcaacaaag aatgggcttg aaacattata aaaattgaca    3120
atgatttatt aaatatgttt tctcaattgt aaaaaaaaaa                          3160
```

```
<210> SEQ ID NO 2
<211> LENGTH: 26
<212> TYPE: DNA
<213> ORGANISM: Artificial Sequence
<220> FEATURE:
<223> OTHER INFORMATION: Forward primer

<400> SEQUENCE: 2
aatggctaag tgaagatgac aatcat                                         26

<210> SEQ ID NO 3
<211> LENGTH: 25
<212> TYPE: DNA
<213> ORGANISM: Artificial Sequence
<220> FEATURE:
<223> OTHER INFORMATION: Reverse  primer

<400> SEQUENCE: 3
tgcacatatc attacaccag ttcgt                                          25

<210> SEQ ID NO 4
<211> LENGTH: 30
<212> TYPE: DNA
<213> ORGANISM: Artificial Sequence
<220> FEATURE:
<223> OTHER INFORMATION: Probe

<400> SEQUENCE: 4
ttgcagcaat tcactgtaaa gctggaaagg                                     30

<210> SEQ ID NO 5
<211> LENGTH: 202001
<212> TYPE: DNA
<213> ORGANISM: Homo sapien
```

<400> SEQUENCE: 5

```
gcccagcagg tgtcagcctc attttacccc gccccctattc aagatgaagt tgttctggtt      60
ccaacgcctc tgacatatta gctgcatcat tttacatttc ttttttttt ttccttttaa       120
atggggtctt gctctgtcac ccaggctgga gtgctgtggt atgatctcgg ctcactgcaa      180
tctccacctc cgaggttcca gcgattctct tgcctcagcc tcccgagtag ctgggactac      240
aggcacccac catcatactg gctaattttt tgtgttttta gtagagatgg ggtttcccca      300
tgttgcccag gctgatctca aactcctggg cttaagcaat acagccgcgt tggcctccca      360
aagtgttggg attacaagca tgagctaccc cacccagctc attttacatt tccacttgtt      420
aaactgaaaa ctggcccgag aaagcttctg tactgccatc cttgcgtcct tgcagatgaa      480
tcgtaaccta gcatagtagg taggcagact gaaaacctaa cttagcagta ggcttctgta      540
acaacagctg tgtctcagcc agttcctgca gccagacttc aaccactcac aggccgcaaa      600
ctgttcaaac tgtgttcgga gaaggcgaat tcatctggct gttaacgtgc ctcacttctg      660
cttttctgtg gccactttcc ttttctgtcc ataaatttgc tttgaccaca cagcatccct      720
agagtctccc tgaatctgct gtgattctgg gacctgcacc atttgtgaat tgttttttt      780
ttccttgatc agctaaactc tgttcaattc aatttgttgg aagttttaa cataccaatg      840
gtgcaccaag gttccaattt ctccacttcc tcataaataa gtcattttaa atggcttttc      900
agtattccaa tatttggaag tattaatgtt ctaccaatt ttctattttt ggacattgag      960
gttgtttcat ttttttttc tttttttgag acagagtctc gctccgtcac ccaggctgga     1020
gtgcagtggc ctgatcccgg cccactgcaa cctccacctc cctcctcagc ctcctgagta     1080
gctgggatta caggtgcatg caccaccaca cccagctaat ttttgtattt ttagtagaga     1140
tggggtttca ccatgttggt caggctggtc tcaaactcct gacctcaggt ggtccacctg     1200
ccttggcctc ccaaaatgct gggattacag gcctgagcca ctgcgcctgg cctcatcttc     1260
ttgatattaa tgttgcttta acatctttgt ccctgtgttt tttgtttttt ttttgagac     1320
ggagtctcat tcattctgtc acccaggctg gagttcagtg gcgtgatctc agctcactgc     1380
aacctctgtc tcctgggttc cagtgattct cctgcgtcgg tctcctgagt agctgtgttc     1440
ctgggtcttt cgatggttat ttaatacttc cctacagtaa tgccctgtgc gtacatgcta     1500
agtgtgatga aatggttggc acagttaaat cttttgaaag acattgccaa gtcactcttc     1560
agaaaagtga taggaggtca tagcaatttt aagaagtcct catttctaca tttccttact     1620
aatctcggtt ggtgtctctt caatctttcc tcacacttttt cttgggtttt tcctgaatca     1680
tgagtctact acatttacac attttaaagc atctttagaa acaggatctc attttgttgc     1740
ccaggctaga gtttggtggc atgattatag ctcctcatac tcctgggctc aagtgatcct     1800
tccacctctg aaacccccaaa atttgagaaa ggtctcattt aatttagaaa gtttatttg     1860
ccaaggttga gggtgcacac ctgtgatgat atacgagtta aaagaaaatt atttaggcag     1920
atactgaggg taagaaagtc ctcggtaagg ttttcttttc aatgaaaagc agcccccaag     1980
cattttctttt tctaacaaag agcagcctgt aaaatcgagc tgcagacata cacaagcaag     2040
ctggaagctt gcacaggtga atgctggcag ctgtgccaat aagaaaaggc tacctggggc     2100
caggcagatc caacatggcg gctccatctt cccttttcctt gtcaaccatg tgcacagtaa     2160
ggagcaggca acatagtgtc ccccgagtag agaccaattt gcataataaa aggtgagggt     2220
agggtgggca gcttctttgc atgctatgta aacattatgc ctggtccaac caatctttgg     2280
gccctgtgta aattagacac cacctcctca agcctgtcta taaaaccctg tccattctgc     2340
```

```
cgcaggctgg aagacccact ggggcacccc tctctctcta taggagacag ctattcattt    2400
ttctctttct ttcacctatt aaagctccac tcttaacccc actccgtgtg tatctatgtt    2460
cttgatttcc ttggcatgag gcaatgaacc ttgggtatta ccccagaacc ttgggtatta    2520
tgccacttca gtgacacagc ctcaggaaat cctgatgaca tgttcccaag atggtcgggg    2580
cacagcttgg ttttatacat tttagggaga catgagacgt caattcatat atgtaagaag    2640
tacattggtt ccgtccagaa aggcggggac aacttgaggc aggagagag cttctaggtc     2700 acaggtagac aaatggttgc attcttttga atctccgata agcctttcca aaggaggcaa    2760
tcagaatatg cgtctattga ctgggcgcag tggctcatgc ctgtaatgcc agcactttgg    2820
gaggcggagg tgggtggatc acctgaggtc aggagtttga gagcagcccg gccaacatgg    2880
tgaaaccctg tctctactaa aaatacaaaa aattagctgg gcgtggtggc gggcgcctgt    2940
aatcccagct actcgggagg ctgaggcagg agaatagctt gaacccagaa ggaagaggtt    3000
gcagtgagct gagatggtgc cattgcactc cagcctgggc aacaagagtg aaactccatc    3060
tcagaaaaaa aaaaaaaagg cctgggcaaa gtggctcacg cctgtaatcc cagcactttg    3120
ggaagccgag gcgggcaggt cacaaagtca ggagattgag accatcctgg ctaacatgat    3180 gaaacccat ctctactaaa aaatacaaaa aactagctgg gtgtggtggc gagcacctgt     3240
agtcccagct actcggcagg ctgaggcagg agaatggcgt gaaccgggga ggcggagctt    3300
gcagtgagcc gagatcacac cactgcactc cagcccggac gacagggcaa gactctatct    3360
caaattaaaa aaaaaaaaa aaaaaaaaa aagagagag agaatatgca tctatctcag       3420
tgagcagaag gatgactttg aatggaatgg gagcagttcc tagcttgaac ttccccttta    3480
gcttcagtga tttgggggct caaggtatgt tcctttcaca tacctcagcc tcccaagtag    3540
ctgggaccac aagtgcatgc caccacacgt ggctaatgtt ttattttttt tgtaggaata    3600
gggtctcact atgtgtccag gctggtctaa aaccccctgag ctcaaatggt cctcccgcct   3660
cagcctcccg aaatgctggg attacaggca tgagccagca tgcccggcct agtctacatt    3720
tttataaatt gctaattcaa agttccctct ccaaaacctc atggttttcc ctgttctcat    3780
cccctgcacc ctcccttccc ctggagtact cacctggcct tggaggtctg gtgtgagccc    3840
ggacttcgat tctaggcaca gcatgtgatg agcgccccca ggtcaaacac ctcccctctg    3900
cggcctgtgc ttcaccgcct tgacagtgag aaaggtctcc cttcggctca ttctcgaagt    3960
ctcaaacttc acttctcctg tgcgctgatt ctgaattcag cccccgtcca aggtcctggc    4020 cccttttctct tctgcttggc gtgttgttca tcaccactgt gcactgctga gggtaagtgc    4080
ggttctctgg acctctgctt tatcattaga acagactctt gcggtttccc acgacattcc    4140
tttcacttct cacttggaag atgagccgtg aggaaatcct gtgttgtgtg gtatgtgggc    4200
tgtgcttctg cttgacttga gggccaagca gcattgcaag ccatggttt aaataagaaa      4260 gaacatttct aaccttcatc ttctagtaag gaaacaagtg ggctttagag ttcttgctca    4320
ggaaagacct atgtcccagt ccaaccggac cttttactaa agagatcttc ctgatcctcc    4380
tccccaggcc aggggagggg tcctcccctg ggttggagcc tttagtaggg ggtcggagac    4440
acgacgtagc cttcatgaca ttcatagtct agttacacga tccctgtaag ggtcagttga    4500
agtaagtgct acaaaggaag ggaggtgctc agtggagagg gctctcttt atgtattata     4560 tttctttcat ggggagggat atggatcagg gatcagcaga ggtgtttcag tcccgaggga    4620
aagaaagtca gcgtggcttg ggagttggga gcagcaagac agtggctcaa gatatcttaa    4680
```

```
gactagtgga gtacaccttg catgttaaaa gccttgctca gggctgcctg gttcttgtag    4740
gacgacagag atggcctagc tctgcatact gcaccccag gggctcagaa cagtgcaaat     4800
gtcagtctat ctgtcagtgg cagagccagc cttggagcag gggtgcaagg aggtctctgc    4860
actggccagg catgcagaac attctgttca gtagcactgg acagaaggcc ccatctagat    4920
gagacagagc tggtggggca ggacaaagac tcctggcagc tcaaacggcc tggcagatgc    4980
ttggagagag ggggcttctt gagacagcac catttctggg aagagagtca cctgggaggg    5040
atgaggccac gctccggctt ggaggtgaag agaggggctg ctgcaagaaa gaattagaga    5100
catgccagcc tttgctgtgt tgcccaggct ggtcatgaac tcttggcctc aagcaatctt    5160
cccacctcag cctccccaag cgctgggatt atagacatga gcccccatgc tggccaataa    5220
aagatgattt tatggagggg atggtggtga aggttgtggg tggtatgaaa tagtaagaaa    5280
tatatattgg tctgcaccca gttcctgcca cagagctcct aaaatcctga gaacttcctg    5340
ggtgagcatc ttttgttcta atgaggtgac tcttggtggc tcctggatag gagtgaatca    5400
ccagaaagat caagccagag ttagaagcag aaagtgctgg ctataacaca ggaaagctgt    5460
aacacaaata ataaagtttt tttttttttt tttgagatgg agcctcactc tgttgcccag    5520
gctggagtgc aatggtgcaa tctcagctca ctacaagctc tgcctccag gttcaagtga    5580
ttctcctgcc tcagcctcct gagcagttgg gactacaggt gtgtgccacc acatctggct    5640
aattttgta ttttagcag agacggggtt tcaccatatt aaccaggctg gcctcaaact    5700
ccttaccttg tgatccgcct gcctcagcct cccaaagtgc tgggattaca ggcatgagcc    5760
accgtgcctg gccaaaagac attgttctta aagaatcaa ctaactaacc aaataaataa     5820
aaatctaacc taattaagaa actaaaaata cacaaaaatt aatttcaagg ggagaaaaat    5880
catgtaaaga gagaaagata atgaatactt tgcagaaatt tatgaacata aacataaaac    5940
ttggatgaaa tgcatttcta ggaaaacata atttatcaaa actaaccaca agtaaaatag    6000
aagcctaaat aggatatttt caagagaaga agtaaagttg tcaaagtgct acccttcaaa    6060
aaaacaccag gctcaaacaa tctgacatgg gaatgttagc acaccttaga gagcaaataa    6120
aactttgaat gggcttgaaa tattccagac tctagaaaaa caaaacttcc caattctttt    6180
tataaagcaa gtataaattg ataccaaaat cttataaaga ccttatacaa aacttcatac    6240
caatctcttt tatgaataca aaaccccttaa taaagtatta ccagacagaa cccaacaata    6300
cataaaaatg tcacatcata acatagtggg gtttatttca ataatgcatg gatggttcaa    6360
tacaaggaaa ttcagtaaca caatataata gatcatgtga atatacccaa agaaaaaata    6420
gattattttc atagatgctg taaaggcatt tgaccaaatt caacacctac tttttaggtg    6480
gtcaataaaa taaattagtt actccttctt tagcatgata aaatatattt atcagcccag    6540
aaggcatcat tttacccgat aagggcacac gctggaggga ataatgttaa aattaggaat    6600
aagaggatag ctagtttctt tcttcttttt ttttttgag acggagtctt gctctgttgc    6660
caggctggag tgcagtggtg caatgttggc tcactgcacg cccccgcct cccaggttca    6720
agcgattctc ctgcctcagc ctcccgagta gctgggacta caggcgcgca ccaccatgcc    6780
cggctaattt ttttttgtat tttagtagag atggggtttc accatgttgg tcaggctggt    6840
cttgaactcc caacctcacg tactgggatt accggtgtga gccaccacgc cagcccaact    6900
actttcaaca ttatccttaa tactgatgct tattgactta ctatgggtt acctctagat    6960
aaatccataa taagttgaaa atataagtaa aaaatgccct taatacacct aacctaccaa    7020
acatcatagc tgagcccagc ctgccttagc tatgctcaga cactgacgtc agcctacaat    7080
```

```
tggcaaaatc acacagcagc acagtctact gcagagcatc tgctgtttgc ccttgtgact    7140
gcgtggctgc ctgggagctt cccagcttca aagacagta ttacgtagca catcactagc    7200
ctggggaaag atcaaagttg aaaatttgaa gtgtggtttc cattgaatgt gtactgcttt    7260
tgcaccatca tcaagtcaaa aaattttagt tgaaccagcc taagtttggg accatcttta    7320
ttttcaggag gaacttccat gtacattgat gacggacgat agaatccgtt tctatcatcc    7380
taatgaacat aatgaataaa tccagacaaa cataaacatt aacagagtaa gcagctttcg    7440
gggctggaag ccagaagagg gtgggagcgc agagagagag gccaaacacc agggctgctt    7500
ctgctttgcg ggtatttgct gatctggaca aggtatctgg aaggctgagc taagcctcct    7560
ttttttttga ggtggcgtct cactctgttg ccaggctgga gtgcaatggt gcgatctcag    7620
ctcactgcaa cctccacctc cctggttcaa gcgattctcc tgcctcagcc tcccgagtag    7680
ctgggattac aggctcccgc cactacaccc agctgatttt tgtaatttta gtagagacgg    7740
ggtttcacca tgttggccag gatggtctcg atctcttgac gtcatgatct gtccacctcg    7800
gcctcccaaa gtgctgggat tataggcgtg acccaccgtg ccccgtctga gctaagcctc    7860
ttgagcatag gggactaaaa atgaaatcta gcgcatgcca agtttagggt cccaggcaat    7920 tccttttccac tttggggtcc actttgggt ccaccccacc caagaagaag gatgacttgg    7980
aagtaaacca gctctgaaat atggatggtc tctgggacc ataccaatcc cttcatatca    8040
accacatcca gttcctcaaa actggaactt ggattaagat ggcctaggac ttctagtgtc    8100
ccaggagcct ggcattgcaa acaaaaatcc tctccggaag aagataatac cttaagcttc    8160
aaatgactct ctaataaatt tcaaatacaa tgtccagcac acaaacacaa attaccagga    8220
acgtgatatg aggcctgatg gatgggaatt agcagaaact tcaggcatga gaaacatacc    8280
ctcagaggcc tagaatctat ctagtgtcta gataatggag atatgaaata cagacactta    8340
aacaactatg tttcccatgt tcaaagagga aatttgcaaa acttgaaagt gttggcagga    8400
aatcagaaac tataaaatgt gacaacagca tactttagag tcagtataaa ttacggtccc    8460
gaaaactgca gaattccaga acttaatggt aaagcaaggg tttaacagca gaatagaaat    8520
agccagagag aactaggaag taagtcagat gacactaccc agaataaggc actgagaggc    8580
caaggaatgg aaaatgcaga agaaaggata tggtgagagg atctaatata catttatttg    8640
gagtaccagg gagagagaga aggagaagaa cagaagccgt gtttcaagga cggtgactga    8700
gaggcttcga aactgatgaa agccatcagt tcacaaattc aaagcccagt gaattccaag    8760
gagaaaaaaa gaaatccata ctgtgaaagc aagtccagac aatgacaaac accatcaaca    8820
atacacagga caggcataag atgcatttaa tggggacact cagaggcaga gggttatcag    8880
aaggaggcac ttctctccca agttctcatc atcccagggc cagggacagc tggtcacacc    8940
ttagggagtt cactaggaga gggatctggc ttcttgtcat tctgggtatt tgtagggaaa    9000
ttggaaggga accgagagca cctagccaat cgcatagcaa tgggagattt caggctgtgg    9060
ggaatgtctt tgctggtgaa aagaacatcc tgaccttaga aatctttcac cgagggggat    9120
ctgcgttcca gaacttctgg agctggtata ggtaaggctt tgagctttcc tactgagcca    9180
gcctgttgct aggttaccaa aggggacctc gagggccatc tggccaacaa gcagacttgt    9240
ctctccttac accccagac gtatcactgc aaaactacag aaaaccaaag acagagaaaa    9300
tcttaaaagc agccagattt aaaaaatggc atattagttt caaagcagca gccatgaaat    9360
tgacagctga tgtctcaaca gcaagaatga aaagtggaag acaggccagg tgtggtggct    9420
```

-continued

| | |
|---|---|
| caggcctgta atcccagcac tttgggaggc cgaggcgggt ggatcacgag gtcaggagac | 9480 |
| caagaccatc ctggctaaca tggtgaaacc ccgtctctac taaaaataca aaaaattag | 9540 |
| tcgggcatgg tggtgggtgc ctgtagtccc agctactcgg gaggctgagg caggagaatg | 9600 |
| gcgtgaaccc gggaggcgga gcttgcagtg agccgagatt gtgccactgc actccagcct | 9660 |
| gggtgacaga gcaagactct gtctcaaaaa aaaaaaaaa aaaaaaaaa aaagggtgac | 9720 |
| gaagcttcaa tctcctgaaa ggaagcaact gccgcctttg attcgatacc caccaaaatc | 9780 |
| cgtgaagaag gaaggcaaaa taaaaacact tcctgattga actggaaaga tttccgcaat | 9840 |
| agaagaccca ctgtccaagg aattctaaag gatgctttcc aggcagaaga aaatgacccc | 9900 |
| agaggaagat cagagattca ggaaagaaat ggagagtgat aaaaatggaa aattcggggg | 9960 |
| ccaatttaaa caaagctga ctgctctaca actgttgtgt ctctatcttt tgtaacatat | 10020 |
| atgtgtgtgt agctttttt tttttttttg tcaagatgga ttctcactct gtcgcccagg | 10080 |
| ctacagtgaa atggcacggt ctcggctcac tgcaacctct gcccttggg ctcaaatgat | 10140 |
| tctcttgcct cagcctcctg agtagctgag attacaggtg cctggcacaa tgcctggcta | 10200 |
| attttgtat ttttactaga gatgggattt ctccatgttg gccaggctgg tcttgaacac | 10260 |
| ctgacctcag gtgatccacc tgcctggcc tcccaaagtg ctaggattac aggcgcgagc | 10320 |
| cactgcatct ggcctatgtg tgtgtttata tggaattaaa acacatgca ataatacct | 10380 |
| ccaaattggg agaaaccaaa aatagcattt aaatgttgta agctccctgc ataatcaaga | 10440 |
| agagaataga tttacgttag attttgatac ctggaggatg aatgttgtaa tttctagggt | 10500 |
| gaccatgaaa agaggagaca acggtgtatg tttttttttt tttgagatgg agtctcactt | 10560 |
| tgtcacccag gctggagtgt tgtggtgtga tcttggctca ctgcaacctc ctcctcttgg | 10620 |
| gttcaggcca tcctcccacc taggcctcca gagtaggtgg gatcacaggc acctgccacc | 10680 |
| acacctggct aatttttttt tttttttaaa tatttagtag agatgggggtt tcaccatgtt | 10740 |
| ggccaggctg gtcttgaact cctgacctca ggcgatctgc ctacctctgc ctctcaaagt | 10800 |
| gctgggatta caggtgtgag ccatcgcgcc cggccaacag tgatcacttt caaactaaca | 10860 |
| gaggttcaaa aataaaatca gacttaacca aaaaccaggt aacagagctg gtaggatata | 10920 |
| cagaaagact gacctcacgt atatcaacga ttacagttaa tattaatgaa ggaaatgctc | 10980 |
| tagtttaaaa acgagggttg tcaaagaccc cacataagaa gctccttacc agcggtgcac | 11040 |
| ctagaaccta aggaaacagg acagatgaag gaggacgcgc cccgccgct gtcctgcgcc | 11100 |
| tcagccatcc tatgagacgg gaaaggtttc tgtctgcagc tgggcccgtg ctctttacca | 11160 |
| gctcctggct ttcttctctg gaaggttcct gcctgttttg ccctcacacc tgctcctctc | 11220 |
| tcagccctct caggggtggg gctggaggcc accaaagagc ctcctctgct ctccagttgc | 11280 |
| tcgactgctc ctcatttccc cctggggtct gcgtcagggt ttccttcttt tccagcccca | 11340 |
| ccccgcgtgc atcccacctg gtctcgggtc ggggctgctc ccgcttactg ccccctgccc | 11400 |
| aggctggtgt gcacccctc tggctgcttt caaggcctct tctctcttct cggcaggaca | 11460 |
| ggcacaggca ggtggccagg tgtcatgctt agctccccgc ccagtgagat tctttcattt | 11520 |
| aacaatcttc ccctgaatag ttcatgttca ttgctgaaaa tttgaaaaat atggaaaagc | 11580 |
| acaaagatta agatataaac cgccctcaat tcccctgccc agagagagtc actgctatga | 11640 |
| cttggtgact aggaacccta tttctctctc gctctttttt tttttttga cacagagtct | 11700 |
| tgctctgtca cccaggctgg agtgcagtgg ctcgatctca gctcactgca acctccgcct | 11760 |
| cctgggttca agcgattctc ctgcctcagc ctcttgagta gctgggatta caggcacctg | 11820 |

```
ccaccatgcc cggctaattt ttgtattttt agttgagaga gggtttcatc ttgttggtca    11880
ggcggacttg aactcctgac ctcaggtgat cagcccacct cggcctccca aagtgctggg    11940
attacaggtg tgagccactg cgccttcatc tctcttctgt gtatgtgtac gctgtttttt    12000
ctttagaatg ggggacgtta tcaggctcta catggtgtgt agtcggctag catgttgtaa    12060
gcctttccct gtgtcacaag tgctcatctg aacaggatt ctaatgactg cctgtggcta     12120
tgttgggatt cctttaactc agctccttct gcccagcatc tatcttttt ccatcttttg     12180 tcctaagtgt tgctataata aatcattgat cacacatgcc tgactgtttg cataggataa    12240
attacgggaa atgttttgc tgttcaggga ctgtgcccat ttttaggcct cagagacacc     12300
atgccagact gcccagtatt gatcttact cttttagat gatgccaaac ttttctgtga      12360
actttaaaaa cctgtgtctt gacagtccat ttctgtaagt ctttcacatt agatttcctg    12420
tcaggatgat agtcaattct aggcagatga tgttttctca gccatggctg aagcagttgt    12480
gatttgttgt ggccatgtaa agtcccgatg atccattgcc tccctggatg ggttggaata    12540
atttggtttg ggagcatata acagaatgac ctggagtcac agcagctcag acggaagtgt    12600
atttctccct tacagatgaa agaattccag gccaggctgg aatgacaact gcacacagtc    12660
atctgggccc cctccttcca gctcccatca ccccaggatg tggcttttat gcagatgatc    12720
caaaatggct gctcaagtcc cagccaacac atcccattcc agggagcagg aaaaaggtgt    12780
gtctttccct tcattttatg tgattccttt ctagaagtac tactcattac ttctgcttgc    12840
atctccctgg ctagcactta cttagttata tggccatagc tagctgaagg aaggacaggg    12900
actgtcatac actagctaag aggcaaactg cttagataaa aaggtctcta aagaaggtca    12960
gagcggctgc tagggtgcaa ctctattact tattgttatg ggacgaactg tgtccctcat    13020
tcaggttgat gtcctaagcc ccagaacctc agaatgggat tgtatttgga gacaggttct    13080
ttaaggaggt aaggaggcta aaatgagatc attagggtgg gccataatcc gactgatgtc    13140
ttacaagaag agattaggac acggacatgc tcagagggac ggccacgtga ggacaccaag    13200
aaaggcagct gtctgcaagt caaggacagg gctcagggga aaccaacctt gccaacacct    13260
tcatctcgga cttctagcct ctaggaccat gagaagatac atttctgttg tttaagctgc    13320
ccggtctgtg gtactttgtt atggcagccc aagtaaacaa atacagtcat ctgctgctgg    13380
aacaaatcac cccagcactg tggcttggca gcacacatgt ctagtcatag agttatatgt    13440
agttacgtgt agagccatat gtatcgtcac acgttctgtg ggtcaggaat ttggacccag    13500
cttaaccagc tccacttctc gccagggttc agtcaaatac cagctgcctc ccacctgaga    13560
gctcagccgg ggaagggtcc ctttccaatc tcacgtggtg ttggcaggat ccagttcctc    13620
atggcctgct ggactgagaa cctcagttct cactgcctgt tggccagagg ccgcctttat    13680
gtcctcgcca tgtgggcctc tccaacatgg cagctgactt catcagagca tccatgccaa    13740
gaaggcaaca gagagggcca gggagactga agtcataccc ttttgcgacc tagtcatggg    13800
gtgacattcc atcacctttg cccattggtt agaagcaggc caccaggtac agcccaagct    13860
cacggggagg ggtcatacaa gggtgtcaat accaggaggt gaggggtgct ggggccatct    13920
tatgagtctg cccactgagg taactaacaa ccttgaggcc tgacacagtg acaaaggcc     13980 cttattaaca gcagagaact gggaacttta tttatttatt tatttttgag acagagtctc    14040
actcttgtca cccaggctgg agtgcaatgg catgatcttg gctcactgca acctccacct    14100
cccaggttca agcaattctg cctcagcctc cggaatagct gggactacag gcatgcacca    14160
```

```
ctacacccgg ctaattttg tatttttagt agagacaggg tttcgccatg ttggccaggc    14220
tggtctcgaa ctcctgacct ctggtgatct gcctgccttg gcctcccaaa gtgctgggat    14280
tacaggcgtg agccaccgca cctcgctgga acttaatttt tttagagaca gtgtcgctct    14340
atcacccaag ctggagtgca gtggtgcaat cctagctcac ttgcagcctc aaattcctgg    14400
gttcaggtga tcctcccaca tcagcctccc aagaactggg aactaacagc tgtttctctg    14460
ctgtccttct caagaaaagg gaggctactg ctaccccact ggggacaatg ctgggtttcc    14520
ctttaggaca ggctctgaga caaggcggag gtgctgtttg tggccacaga gcagggact     14580 ctgggttgca ggtgtggcct ggctaaagta ggctttactg ggctcctctc tgcctgcatc    14640
accccccggc tgggcggttg tctctgaggc caaccttact ccctgctggg caggctggac    14700
agctgccctc tccgttttgcc cctctaccac ccaaaaggca ggaggctctg gagaccagga    14760
ccctgcccgc cacggcctgt gtcccaggcg tgagggggtg cccacagac ctctgctgag     14820 ctgctgctga atgacgcccc ttgggggtcc tgccggaagg tcagagcagg ggtgcactcc    14880
cataaagaaa cgcccccagg tcgggactca ttcctgtggg cggcatcttg tggccatagc    14940
tgcttctcgc tgcactaatc acagtgcctc tgtgggcagc aggcgctgac cacccaggcc    15000
tgccccagac cctctcctcc cttccggggc gctgcgctgg gaccgatggg gggcgccagg    15060
cctgtggaca ccgccctgca ggggcctctc cagctcactg ggggtggggt gggggtcaca    15120
cttggggtcc tcaggtcgtg ccgaccacgc gcattctctg cgctctgcgc aggagctcgc    15180
ccaccctctc cccgtgcaga gagccccgca gctggctccc cgcagggctg tccgggtgag    15240
tatggctctg gccacgggcc agtgtggcgg gagggcaaac cccaaggcca cctcggctca    15300
gagtccacgg ccggctgtcg ccccgctcca ggcgtcggcg gggatccttt ccgcatggg     15360 cctgcgcccg cgctcggcgc cccctccacg gccccgcccc gtccatggcc ccgtccttca    15420
tgggcgagcc cctccatggc cctgcccctc gcgcccac cctccctcg ccccacctct       15480 caccttcctg ccccgccccc agcctcccca ccctcaccg gccagtcccc tccctatcc     15540 cgctccgccc ctcagccgcc ccgcccctca gccggcctgc ctaatgtccc cgtcccagc     15600 atcgccccgc cccgccccg tctcgcccg ccctcaggc ggcctccctg ctgtgccccg       15660
ccccggcctc gccacgcccc tacctcacca cgccccccgc atcgccacgc cccccgcatc    15720
gccacgcctc ccttaccatg cagtcccgcc ccgtcccttc ctcgtcccgc ctcgccgcga    15780
cacttcacac acagcttcgc ctcacccat tacagtctca ccacgccccg tccctctcc     15840 gttgagcccc gcgccttcgc ccgggtgggg cgctgcgctg tcagcggcct tgctgtgtga    15900
ggcagaacct gcgggggcag gggcgggctg gttccctggc cagccattgg cagagtccgc    15960
aggctagggg tgtcaatcat gctggccggc gtggccccgc ctccgccggc gcggccccgc    16020
ctccgccggc gcagcgtctg ggacgcaagg cgccgtgggg gctgccggga cgggtccaag    16080
atggacggcc gctcaggttc tgcttttacc tgcggcccag agcccattc attgccccgg     16140 tgctgagcgg cgccgcgagt cggcccgagg cctccgggga ctgccgtgcc gggcgggaga    16200
ccgccatggc gaccctggaa aagctgatga aggccttcga gtccctcaag tccttccagc    16260
agcagcagca gcagcagcag cagcagcagc agcagcagca gcagcagcag cagcaacagc    16320
cgccaccgcc gccgccgccg ccgccgcctc ctcagcttcc tcagccgccg ccgcaggcac    16380
agccgctgct gcctcagccg cagccgcccc gccgccgcc ccgccgcca ccgcccggcc       16440 ctgtggctga ggagccgctg caccgaccgt gagtttgggc ccgctgcagc tccctgtccc    16500
ggcgggtccc aggctacggc ggggatggcg gtaaccctgc agcctgcggg ccggcgacac    16560
```

```
gaaccccegg ccccgcagag acagagtgac ccagcaaccc agagcccatg agggacaccc    16620 gcccctcct  ggggcgaggc cttcccccac ttcagcccg  ctccctcact tgggtcttcc    16680
cttgtcctct cgcgagggga ggcagagcct tgttggggcc tgtcctgaat tcaccgaggg    16740
gagtcacggc ctcagccctc tcgcccttcg caggatgcga agagttgggg cgagaacttg    16800
tttcttttta tttgcgagaa accagggcgg gggttctttt aactgcgttg tgaagagaac    16860
ttggaggagc cgagatttgc tcagtgccac ttccctcttc tagtctgaga gggaagaggg    16920
ctgggggcgc gggacacttc gagaggaggc ggggtttgga gctggagaga tgtgggggca    16980
gtggatgaca taatgctttt aggacgcctc ggcggggagtg gcggggcagg ggggggggcgg   17040 ggagtgaggg cgcgtccaat gggagatttc ttttcctagt ggcacttaaa acagcctgag    17100
atttgaggct cttcctacat tgtcaggaca tttcatttag ttcatgatca cggtggtagt    17160
aacacgattt taagcaccac ctaagagatc tgctcatcta agcctaagtt ggtctgcagg    17220
cgtttgaatg agttgtggtt gccaagtaaa gtggtgaact tacgtggtga ttaatgaaat    17280
tatcttaaat attaggaaga gttgattgaa gttttttgcc tatgtgtgtt gggaataaaa    17340
ccaacacgtt gctgatgggg aggttaattg ccgaggatg aatgaggtgt acattttacc     17400
agtattccag tcaggcttgc cagaatacgg ggggtccgca gactccgtgg gcatctcaga    17460
tgtgccagtg aaagggtttc tgtttgcttc attgctgaca gcttgttact ttttggaagc    17520
taggggtttc tgttgcttgt tcttggggag aattttgaa  acaggaaaag agagaccatt    17580
aaaacatcta gcggaacccc aggactttcc ctggaagtct gtgtgtcgag tgtacagtag    17640
gagttaggaa gtactctggt gcagttcagg cctttctctt acctctcagt attctatttc    17700
cgatctggat gtgtcccaga tggcatttgg taagaatatc tctgttaaga ctgattaatt    17760
tttagtaata tttcttgttc tttgtttctg ttatgatcct tgtctcgtct tcaaagttta    17820
attagaaaat gattcggaga gcagtgttag cttatttgtt ggaataaaat ttaggaataa    17880
attattctaa aggatggaaa aacttttttgg atatttggag aaattttaaa acaatttggc    17940
ttatctcttc agtaagtaat ttctcatcca gaaattact  gtagtgcttt tctaggaggt    18000
aggtgtcata aaagttcaca cattgcatgt atcttgtgta aacactaaac agggctcctg    18060
atgggaagga agacctttct gctgggctgc ttcagacact tgatcattct aaaaatatgc    18120
cttctctttc ttatgctgat ttgacagaac ctgcatttgc ttatcttcaa aatatggta    18180 tcaagaaatt tccttttgctg ccttgacaaa ggagatagat tttgtttcat tactttaagg    18240
taatatatga ttacctttatt taaaaaattt aatcaggact ggcaaggtgg cttacacctt    18300
taatccgagc actttgggag gcctaggtgg acgaatcacc tgaggtcagg agtttgagac    18360
cagcctggct aacatggtga aaccctgtct ctactaaaaa tacaaaaatt agctggtcat    18420
ggtggcacgt gcctgtaatc caagctacct gggaggctga ggcaggaaaa tcgcttgaac    18480
ccgggaggca gagtctgcag tgagttgaga tcacgccact gcactccagc ctgggtgaca    18540
gagcgagact ctatctcaaa aaaattttt  tttaatgtat tattttttgca taagtaatac    18600 attgacatga tacaaattct gtaattacaa aagggcaata attaaaatat cttccttcca    18660
cccctttcct ctgagtacct aactttgtcc ccaagaacaa gcactatttc agttcctcat    18720
gtatcctgcc agatataacc tgttcatatt gtaagataga tttaaaatgc tctaaaaaca    18780
aaagtagttt agaataatat atatctatat atttttttgag atgtagtctc acattgtcac    18840
ccaggctgga gtgcagtgat acaatctcgg ctcactgcag tctctgcctc ccaggttcaa    18900
```

```
atgcttctcc tgcctcagcc ttctgagtag ctgggattac aggcgcccac caccatgtcc   18960
agctaatttt tgtattttta gtagagatgg ggtttcacca tgttggccag gctggtcttg   19020
aactcctgac cttgtgatct gtccacctcg gcctcccaaa gtgctgggat tacaggtgtg   19080
agccaccatg cctggctaga ataataactt ttaaaggttc ttagcatgct ctgaaatcaa   19140
ctgcattagg tttatttata gttttatagt tattttaaat aaaatgcata tttgtcatat   19200
ttctctgtat tttgctgttg agaaaggagg tattcactaa ttttgagtaa caaacactgc   19260
tcacaaagtt tggattttgg cagttctgtt cacgtgcttc agccaaaaaa tcctcttctc   19320
aaagtaagat tgatgaaagc aatttagaaa gtatctgttc tgttttatg gctcttgctc    19380 tttggtgtgg aactgtggtg tcacgccatg catgggcctc agtttatgag tgtttgtgct   19440
ctgctcagca tacaggatgc aggagttcct tatgggctg gctgcaggct cagcaaatct    19500
agcatgcttg ggagggtcct cacagtaatt aggaggcaat taatacttgc ttctggcagt   19560
ttcttattct ccttcagatt cctatctggt gtttccctga ctttattcat tcatcagtaa   19620
atatttacta aacatgtact atgtgcctgg cactgttata ggtgcaggc tcagcagtga    19680 gcagacaaag ctctgccctc gtgaagcttt cattctaatg aaggacatag acagtaagca   19740
agatagataa gtaaaatata cagtacgtta atacgtggag gaacttcaaa gcagggaagg   19800
ggatagggaa atgtcagggt taatcgagtg ttaacttatt tttatttta aaaaaattgt    19860 taagggcttt ccagcaaaac ccagaaagcc tgctagacaa attccaaaag agctgtagca   19920
ctaagtgttg acattttat tttatttgt tttgttttgt ttttttgag acagttcttg      19980 ctctatcagc caggctggag tgcactagtg tgatcttggc tcactgcaac ctctgcctct   20040
tgggttcaag tgattctcat gcctcagcct cctgtttagc tgggattata gacatgcact   20100
gccatgcctg gtaatttttt ttttttccc ccgagacgga gtcttgctct gtcgcccagg    20160
ctggagtgca gtggcgcgat ctcagctcac tgcaagctcc gcttcccgag ttcacgccat   20220
tctcctgcct cagtctccca gtagctggg actacaggcg cctgccacca cgtccagcta    20280
atttttttgt attttaata gagacggggt ttcaccgtgt tagccaggat gatcttgatc    20340
tcctgacctc gtcatccgcc gaccttgtga tccgcccacc tcggcctccc aaagtgctgg   20400
gattacaggc atgagccact gtgcccggcc acgcctgggt aattttttgta tttttagtag  20460 agatggggtt ttgccatgat gagcaggctg gtctcgaact cccggcctca tgtgatctgc   20520
ctgccttggc ctcccaaagt gctaggatta caggcatgag ccaccatacc tggccagtgt   20580
tgatatttta aatacggtgt tcagggaagg tccactgaga agacagcttt ttttttttt    20640 ttttttgggg ttgggggca aggtcttgct ctttaaccca ggctggaatg cagtatcact    20700
atcgtagctc acttcagcct tgaactcctg ggctcaagtg atcctcccac ctcaacctca   20760
caatgtgttg ggactatagg tgtgagccat cacacctggc cagatgatgg cttttgagta   20820
aagacctcaa gcgagttaag agtctagtgt aagggtgtat gaagtagtgg tattccagat   20880 gggggggaaca ggtccaaaat cttcctgttt caggaatagc aaggatgtca ttttagttgg  20940
gtgaattgag tgaggggac atttgtagta agaagtaagg tccaagaggt caagggagtg    21000
ccatatcaga ccaatactac ttgccttgta gatggaataa agatattggc atttatgtga   21060
gtgagatggg atgtcactgg aggattagag cagaggagta gcatgatctg aatttcaatc   21120
ttaagtgaac tctggctgac aacagagtga aggggaacac cggcaaaagc agaaaccagt   21180
taggaagcca ctgcagtgct cagataagca tggtgggttc tgtcagggta ccggctgtcg   21240
gctgtgggca gtgtgaggaa tgactgactg gattttgaat gcggaaccaa ctgcacttgt   21300
```

```
tgaactctgc taagtataac aatttagcag tagcttgcgt tatcaggttt gtattcagct    21360
gcaagtaaca gaaaatcctg ctgcaatagc ttaaactggt aacaagcaag agcttatcag    21420
aagacaaaaa taagtctggg gaaattcaac aataagttaa ggaacccagg ctctttcttt    21480
tttttttttt tgaaacggag tttcgctctt gtcacccggg ctggagtgca atgatgtgat    21540
ctcagctcac taaaacctct acctcctggg ttcaagtgat tcttctgcct cagcctccca    21600
agtaactggg attacaggcg tataccacca tgcccagcta atttttgtgt ttttagtaga    21660
gatggggttt caccatgttg gccaggctgg tctcgaactt ctgacctcag gtgatccact    21720
cgcctcagcc tgccaaagtg ctgggattac aggtttgggc cactgcaccc ggtcagaacc    21780
caggctcttt cttatactta ccttgcaaac ccttgttctc attttttccc tttgtatttt    21840
tattgttgaa ttgtaatagt tctttatata ttctggatac tggattctta tcagatagat    21900
gatttgtaaa aactctccct tcctttggat tgtcttttta cttcttgat agtgtcttt     21960
gaagtgtaaa agtttttaat tttgatgaag tcgagtttat ctattttgtc tttggttgct    22020
gtgcttcaag tgtcatatct aagaaatcat tgtctaatcc aaagtcaaaa aggtttactc    22080
ctatgttttc ttctaagaat tttagagttt tacatttaag tctgatccat tttgagttaa    22140
tttttatata tggttcaggt agaagtccaa cttattctt ttccatgtgg ttattcagtt     22200
gtcccagcac tgtttgttga agagactatt cttccccat ggaattatct tagtacccctt    22260
gttgaaaatt aatcgtcctt aattgtataa atttattct agactgtcag ttctacctgt     22320
tggtctttat gtcgatcctg tgccagtacc atacagtctt gattactgaa gtttgtgtca    22380
cagtttaaat tcatgaaatg tgagttctcc aactttgttc cttttcaaga ttgatttggc    22440
catgctgggt cccttgcatt tccgtacgaa ttgtaggatc agcttgtcag tttcaacaaa    22500
gaagccaagt aggattctga gagggattgt gttgaatctg tagatcaact tggggagtat    22560
tcgcatctta acaatattgt cttccaccta tgaacatggg caaactttgt gtaaatggtc    22620
agattgtaag tatttcgggc tgtgtgggca cagtgtctct gtcacagcta cgcggctctg    22680
ccattgtagc atgaaagtag ccataagcaa tatgtatgag tgtctgtgtt ccaatagaat    22740
tttattaatg acaaggaagt ttgaatttca tataattttc acctgtcatg agatagtatt    22800
tgattatttt ggtcaaccat ttaaaaatgt aaaaacattt cttagcttgt gaactagcca    22860
aaaatatgca ggttatagtt ttcccactcc taggttaaaa tatgatagga ccacatttgg    22920
aaagcatttc tttttttttt tttttttttt tttttgagac ggagtttcac tcttgttgcc    22980
caggctggag tgcagtggcg cgatctcggc tcactgcaac ctctgcctcc caggttcaag    23040
acattctcct gcacggcctc cctagtagct gggattacag gcatgcgcca ccacacccag    23100
ctaattttgt atttttagta gagacggggt ttctccatgt tggtcaggct ggtcttgaac    23160
tcctgacctc aggtgatcca cccgcctcag cctcccaaag tgctgggatt acagggtgtg    23220
agccaccaca ccctgctgga aagcatttct ttttggctg ttttttgtttt tttttaaac    23280
tagttttgaa aattataaaa gttacacata tacattataa aaatatcttc aagcagcaca    23340
gatgaaaaac aaagcccttc ttgcaagtct gtcatctttg tctaacttcc taagaacaaa    23400
agtgtttctt gtgtcttctt cccagatttt aatatgcata tacaagcatt taaatgtgtc    23460
attttttgtt tgcttgactg agatcacatt acatatgtat ttttttactt aacaatgtgt    23520
catagatatt gttccatagc agtacctgta attcttatta attgctatgt aatattttag    23580
aatttctttt taaagaggga cttttggaga tgtaaaggca aaggtctcac attttttgtgg   23640
```

```
ctgtagaatg tgctggtgac atattctctc taccttgaga agtccccatc ccatcacct   23700 ccatttcctg taaataagtc aaccacttga taaactacct ttgaatggat ccacactcaa   23760
aacatttagt cttattcaga caacaaggag gaaaaataaa ataccttata aagcactgtt   23820
taatattgta ttaaattgga tcaatttggg ggctagaatg tatgttagag acatgatatg   23880
tccataggtc cttgctatca cagtgaggtc tcagggacag tcgtttggta tcatttggga   23940
tctcataagc agactctctc tgcttgacct gacaaatcag agtctgtgtt ttaacaggtt   24000
cagtgagtga cttacatgca cattggagtt tgggaagctc cactgtaggt gcttagacct   24060
tacctttgtt gttgctaata acaatgcaag catttgggag gaagacctgt gttgctcata   24120
tgtgtccagg tgtagctgag gtggccttgc ttatctgctg tagggccgtt gagcatttct   24180
gtagctgtga tgagtgagct gaggtgagcc tgcggagagc tcccagccat tggtagtggg   24240
actcgcttag atgaactgga aggacccttt catctgagca gccactatgg agaaaaacaa   24300
ccgaatgagg ggagagacaa tgtgcaattt tatttagggc acaaaggaga gctgtggtta   24360
gaaggtgaca tttgagtgga aagggggcaa gccatgtgta tagcgggaga agagaggtcc   24420
aggcagagtt aacagaaggc agaaatgctt tccatgtttg agaaccagta aggaggccag   24480
tggctgaagt aaggtgaagg gcagaaataa ggatgaggct gcgagagatg agaggttaga   24540
gacgagcgtc ttgtgcacca agataagctt gtgtggtcaa aacaagtagt ttaatttatg   24600 ttttttaaaag atcattttgg ctgggcacaa tggttcatgc ctgtaatacc agtagtttga   24660
gacggtgtgg tgggaggatt gcctgaggcc agacgaccag catagccaac atagcagcac   24720
ctataaggtc tctacaaaaa actttaaaaa attagctggg catagtggtg tgtgcctgta   24780
gtcccagcta ctcaggaggc tgaggaggct ggaggattgc ttgagtccag gagtttgagg   24840
ctgcagtgag ctatgattat gccactacac tacaacctgg gcaagagagt gagccctgt    24900 ctctaaatat acacacacac acacacacac acacacacac acacacacac acacacacac   24960
acacacatat atatgtatat atatgcattt agatgaaaag atcactttga caataccaca   25020
tgctggtgag gatttagaaa aactaggtca cttattgctg gtgggaatat aatatagtac   25080
ggccactctg gaaaacagtt tggcagtttg tcataaaact gaacataccg ttagtataca   25140
gcccagcagc aactacaatc ctgggcatta atcctagaga aatgaaacct taatgttcac   25200
ataaaaacct atactcaagt atgcatagca gctttacca taatatctaa gaactggaat    25260
cagctcagat gtccttcaac aggtgaatgg ttaaactact cagtaataaa aaggaatgag   25320
ctactgatag catgcaacag tttaggtgaa gttatgctaa tgaaaaaagc caatcccaaa   25380
aggttataca tactgtatga ttctatgttt ttttgcaatg gcacagtttt agggatggag   25440
aatagattag tggttgcctg gggttagaga tggggtagta gagtaggtta gtggtggcag   25500
aggagagaaa agagagggag gtgaatgtgg ttataaaagg acaacacagg ggaatacttg   25560
taatggaaat gctttgtctt ttttttttt tttttttttt tggcgacaga gtcttgctct     25620
gttgcccagg ctggagtgca gtggcatgat cttttctcac tgcaacctct gcctcctggg   25680
ttcaagtgat acttgtgtct cagtctccca tgttcagagt gaaacaaacc agaggtaatg   25740
ttcatccaaa taatccaaca cacatgacat taaaacatca agatcaggtc ggacgtggtg   25800
gctcatgcct gtaatcccag cacttttggg aggccaaggt gggcagatca cttgaggtca   25860
ggagttcgag accagccggg ccaacatgat gaaaccccat cttgactaaa aatacaaaaa   25920
ttagccgggc atggtggtgt gcacctgtag tcccagctac ttgggaggct gaggcaagag   25980
aactgcttga acccgagggg cagaggttgc agtgagctga gagtgcgcca ttgcacttca   26040
```

```
gcctgtgtga cagagtaaga ctccatctcc aaaaaaaaaa aaccaagatc aattaaaata   26100
cagcattact gggccgggtg tggtggctca cacctgtaat cccagcactt tgggaggccg   26160
agatgggcag atcacgaggt caggagatcc agaccatccc ggctaacacg gtgaaacccc   26220
gtctctacta aaaatacaa aaaattagcc gggtatagtg gtgggtgcct gtagtcccag   26280
ctacttggga ggctgaagca ggagaatggt gtgaacccgg gaggcagagc tggcagtgag   26340
ctgagatcgc gccactgcac tccagcctgg gcgacagagc aagactccgt ctcggggaa    26400 aaaaaaaat aaataaatag aatgctgtag tgtccttgag tttacatgcc cctccttacg    26460
cttgtgtgcc cgtgcagatt gcttgattac acaattagag gaggctggcg gaggattgtt   26520 ttaattttt  tttttttgag acagtctggc tctgttcccc aggctagagt gcaatggcgc   26580
aatcttggtg cactgcaacc tctgcctcct gggttcaagc agttcttctg ccgcagcctc   26640
ccgagtagct gggattatag gcgcccgcca ccacgcccaa ctatttttg tattttagt     26700 agagcagcgt ttcaccatgc tggccaggct ggtctcgaac tcctgacctc agatgatctg   26760
ctgccccagc ctcccaaagt gctgggatta caggcgtgag ccacacctgg ccgtttgttt   26820
taattttgaa ggtgaagtga aagtgactac atttaccaaa agtgattgaa aagccaggac   26880
tgttcttacc ctgttttcc agttcttgct cagagcaagg tggtttcttt ttcacttaat    26940
caccatactt acttttcatg tagaacaagt cagtttgagt tatcagttca tcatcttaac   27000
taaattccat gggggaagga attagtttta gtttcttaaa cttccaggtt tgcttattgg   27060
acaaaatgag atagcaaggc agtgttttta agttagattt tttatttctt tggtaataca   27120
attttctcag aaacttagta gtcttttagt ttagttgttt ttagttggtc ctatgttttg   27180
gatcacccct ctctacttta ttttgatagt gccaactgtg aagacatctg aagccatagg   27240
tttggatggg aaggaggcat ctttagcctg atcatcttcg ccaggctgtt tatctccttt   27300
tgcttggctg agaagtctta ataggaggct tattcccagc tatttgggga catagaagca   27360
gttagccatt gcttatattt tactgaggtc tgtgtggtat gttgattgta gtcagttaac   27420
gattttgaga actgaaggca gcctggtata tatagagtag gtattagact gtgtttcttc   27480
taattgaatt tcccatctct tgtaatctat gccatcatct tctgtactgc tgagaaagaa   27540
agaaagtttc taatcaaact ataccactgg ttgtaagatg cagtttggct ttagtgatgt   27600
taacacatga ttcaaacgtg aaattgattg agtattggtg aaatacagag gagatttaaa   27660
gccagaagac ctgggtttaa atgctggctg tatgacttca tatctgtgtg atcttgggca   27720
tgtcatggtt ggcacttcaa tttcttctct ctataatggg ggaagtgagg ccagtcatgg   27780
tggctcatac ctataatccc agtgctttgg gaggccaaga tgggaagatc gcttgaggcc   27840
aggagtttga gcaattgggc aacatcgtga ggccccgtct ctacaaaata ttttgaaaaa   27900
attagccagg cccagtggtg cgtgcctgtg gtccgcgcca ctcaggaggc tgagacggga   27960
ggatcctttc agcctaggag tttaaggcta aagtgagcca tgattgtgct atcgtactcc   28020
agcctgggca gcagagcaag atcctgactc taaaaaaaag taaaataaag taaaatgggg   28080
gaaatgaact gctttagtaa catcatctgt tttttctgtg agcagcgtag cttgacagcc   28140
attggtgaac tcgtgccctg tgcttccctg tccagatccc cattctgccc gcaacatgga   28200
gtataacggt ttattcatag tagtcgagaa acactcactg aatgaatgaa tgaggtgtag   28260
aactaagtgg agtgggtaat tcaacacata ttaatttcct tcttttttt  attttagaa    28320 agaaagaact ttcagctacc aagaaagacc gtgtgaatca ttgtctgaca atatgtgaaa   28380
```

```
acatagtggc acagtctgtc aggtaattgc actttgaact gtctagagaa aataagaact   28440
ttgtatattt tcagtcttaa tgggctagaa tattctttgt gtcccagcta ttttaaatgg   28500
attcagaaat ccatttaaga tgaagaagga ccctttttcccc atatttctgg ctatatacaa   28560
ggatatccag acactgaaat gaataatgtt ccctttttgt aatcttttat gcaaaaatta   28620
aaaccattat ggtaattgaa caacatgttt atgtttagtt aacacccctta gcaactatag   28680
ttatttttaaa accatctatg gtttgatatt tttgcatttg ttgcaatagt aggaacagca   28740
caagacagtt cagtttgtct ctcttatttg cttttttcttg gcagtttgct gtcctattgt   28800
acctctgctc ctagcagtgg ctggagccca ctcctctgtg cttcgggatt agtggggatc   28860
gtggggcatt gactgtaggt cagcttttcct tgcttgatct ttctcactgg gatgaactag   28920
cagcaccttc ttttgtagct gctttgcttt tgactatctt tctgaccgtt gttcctagta   28980
gctgtagatg gtaaatatat ttaggcctgt ttccaatggc tcagtaggag acatattcac   29040
ctatgatatc tgaattctgt tacccacatg ggcatgcgtg aaatagttgc cttgccttac   29100
tttcccttgg aataaataat tcatgttatt ctcctggtag aagctagaaa aagcctttat   29160
agtcagtcag aaaaaaattt ttagacaaat aatcttgatt ttagtactga caaaaacgtg   29220
tggtgattct tttttttaatt ttttttttgag acggagtttc actcttgttg cccaggctgg   29280
agtgcaatgg cgtgatctcg gctcactgca acctctgcct cctgggttca agtgattctc   29340
ctgcctcagc ctcccaagta gctggagtta caggcatgtg ctactgtgcc cagctaattt   29400
tgtatttttta gtagagatgt tggtcaggct gatctcgaac tcccaacctt aggtgatctg   29460
cccgcctcag cctcccaaag tgctgggatt acaggcgtga gccagggcgc ccggtgattc   29520
atttgttttt tcaaaaaatt tcctcttggc cattgctttt cacttttgtt ttttttttt   29580
ttttgagacg gagtcacgat ctgtcaccca ggctggagtg cagtggcatg atcttggctt   29640
actgcaagct ctgcctccca ggttcacgcc attctcctgc ttcagcctgg cgagtagctg   29700
ggactacagg tgctcgccac cacacccggc taatttttttg tattttttagt agagatgggg   29760
tttcaccgtg gtcttgatct cctgacctca tgacccgctc aactcagcct cccaaagtgc   29820
tgggattaca ggcgtgagcc accgcgcccg gccctctctt gtctttttat tgtggtaaaa   29880
tgcacataaa attgactgtc ttaaccattt ttaggggtac agttcagtat atatattcgt   29940
aatgttgtac agccatcact gccatctact tcataagttt ttcttctgtc aaaactgaac   30000
atctgtcttc attaaactcc ctatcatcca ttctttcctg tagtcccttt ctactttctg   30060
tctgtatgag tgtaactgct ctggagacct catgtaagtg gattcctaca ggatttgtgt   30120
tttttttttg gtgatctgct tattttaaat gcctctgtgc atttgtatta tatactttca   30180
aagtgatttc acaaaaccgt ttcattttag gttaactcat ttctgttgtt tgtgaaatac   30240
tgtgtatgat tctgttctgt ttctgtctaa tttgtggaaa tgttgtggga agaaaatgaa   30300
ataacaaatg agcatatgtc ctgaaaataa aatataaaa attctaagtt agcatgctat   30360
tgtagaatac aacgctatga taaaagtagg aaaaaaaaag gtttgaattc tatctctgct   30420
acctgtgtaa gctgggtgac tttagataag ctgtaacgtg tttgagcctt actggctcat   30480
ttttgaaatg taatccctag ttacacagtt cttgtgggat cagatggtac atgtgaaaca   30540
ctgtgaaaaa gcaactgcat agatatgttc attagccacc tgagcgggaa gcgtatccca   30600
ttgcgatgcc catcatccaa agctatatgt tatctttact ttttttttt tgagacagag   30660
tcttgctctg ttgcccaggc tagagtgcag tggtgcaatc tcagctcact gcaagctcca   30720
cctcccgggt tcacgctatt ctcctgcccc agcctcccaa gtagctggga ctacaggcac   30780
```

```
ccgccaccat gcctggctaa attttttgtat ttttagtaga gatggggttt caccgtgtta   30840
gccaggatgg tcttgatctc ctgacctcgt gatccgcccg cctcggcctc ccaaagtgct   30900
gggattacag gcgtgagcca ctgcccctgg ccatctttac ttttttttgtg aaatgacttt   30960
aaatacttgg caaacatttg gtcattgttc atctgatctc caccatccag gtctcagaga   31020
acataaattc tctctgaaag cttattgacc caggaaataa gatctctttc aatctgagtg   31080
cgtcaggctt tattcttgtc attttgtctt ttgataattt tcaaatggaa ttcatggaat   31140
gttggcttat attcatatat tagtaaagta tgttgagaca tcttaagatt gatttgtggt   31200
tctatatgcc atattaaatc aaaataatag ctgttaatgg ttttcacatt agtctgtctc   31260
ttgttttttat ggagtaatgc tgagagttca ttatgcttgt tctacagaag agcatgttaa   31320
aaggagtttt tggagtcaga gaggttattc ttggtttcat aggatacact ctatactttt   31380
tagggatttc agagtatata gctgaaggtg atattttatg taaatatgtt ttatggaaac   31440
ttattgctca tcgctgtttc ctgttaactc tcctaaaata taattaaact tttggaactt   31500
ttttatagct tttgtgctag actaattttt gtctctaatg aggttatata aatggcagct   31560
tctgacgttt tcaatgtagg aagtcattta aaacttcatg tatattgtga aaatgtagtc   31620
tgctttaagc tctctaaagt ggtctaagtt actggttcct aagtatggat gagcatcaaa   31680
atcatctgga aaatttgtta aaaatacagt aatgaaggca cctcactgtc ctttttccca   31740
aacatacttc tgcattctgt ttgagtaggt agggactaca cattttttcac aagtatcctc   31800
ttgggaatac ccaggaatgc ttacttgagc aacctcttac taatatgtac cttgataagg   31860
tggctaggta aacataaata tacaaaaatc catagatctc ccatatatta gcataaatca   31920
gctagaaaat ataacgttta aagatctagt tcacagtagc accaatatat cgaactctaa   31980
ggaatcgata aatatgcaaa aactttataa aaacttctgt taatgtttct gaaagatata   32040
ggtgaccact ttctagatag gaagatttta tattactaag ttgaattttc tctaaattaa   32100
cacagaaatt taaaataatc ttgatcaaaa ttctagtaga ggtattttg aacttgttca   32160
ctgcaagaat aaaatacataa ttgcaaagaa tatctcaaaa tcatccagg gcctggtgtg   32220
gtggcccatg cctgtaatcc cagcactttg ggaggctgag gcaggcagat cacctgaggt   32280
caagagtttg agaccagctg gaccagtgcg gtgaaacact gcctctacta aaaatacaaa   32340
aattagctgg gtgtggtggt gcatgcctgt agtcccagct acttgggagg ctgaggcagg   32400
agaattgctt gaacccagga ggtacaggtt gcggtgagcc tagatcgcac cactgcattc   32460
cagcctgggc gacaagagca aaattctgtc tcaagaaaaa agagaaaaaa gaaaagaaa   32520
tcaacactaa tatggtgaga cttaatgtat gtgacattaa aatagtgatt ggatgttaaa   32580
acaggtatag aacagaaaga agagtgtatg tgtgtatctg tatgaattta tgatgggtgt   32640
aacatatatg tattagggaa atgagggaaa tgatacattt ctctgacttt gggagaacat   32700
tatatctcta cctcatattg caaacaaaca taaagttcag attaattacc taaatgtgaa   32760
aaaatgaaat aatttctta aaaatgtaa tcttagtttg aggaaggtta acattataaa   32820
ggaaaaaact gttttgagtg gaatatagtt caatatgtca aaatccacct tcaacaaaat   32880
tgaaagtaaa ttgaacttgg ggaaagtatt gacagcatat agatcaaagg ttactagcct   32940
gtgtaaagag cagttataaa tatcgttaag aaaaacactg tcgacctgtc ggcaccttgt   33000
tctccgactc ccagcctcca gaactgtgac gagtaagtgc ttattgttta aaccacccag   33060
tctgtatgtg gtattttgtt atagaaactc aagctgatta ggacactagt aatcagtaga   33120
```

```
ctgaaactga acaaaaata agaaccttt  ttacctgtca aattggcaaa cattaagaat    33180
attcagattt tgtcagagg  tgatacaacc  ttctaagaag  gcaatttggg aaaatataaa  33240
gctttagatt attatatgtc tgacctagca gttttacctc tagggtgctt accectagga   33300 aagtgtgtaa tgatattggt gcagtgccct tcatcccatt agaaaattaa aaataacctt   33360
aatggcctac cactaaaagg ggattgaaaa tttaagatat atttatttat gtgtttattg   33420
agatggagtc ttgcactgtc cgcctgggcc agagtgcaat ggtgcgatct cggctcactg   33480
caacctctgc ttcccgggtt catgtgattc tcctgcctca gcctcctgag tagctgggat   33540
tacaggctca caccaccgca cccggctaat tttttgtatt tttagtagag atggggtttc   33600
actgtgttgg ccagactggt ctcgaactcc tgacctcatg atccgcgccc tcggcctcc   33660 cagtgttggg attacaggtg tgagccactg cgcctggcca gatacattta tacaagagaa   33720
tgttagttaa cattcataga tatttatatt ttgtttactt tttattaaaa aattttttt    33780 tagagacagg atcttactct gtcacccagg caggatgcag ttgcacaatc atagcccact   33840
gcagcctgaa ctcctgggct taagtgatcc ttctgcctca gccttttgag tacctggggg   33900
actttaggca gtgctactat acctggctaa ttttaaatg ttttatagat gagatcttgc    33960
tgtattgccc aggctggtct agaattcctg ggcccaagtg atcctccac  cttggcctcc   34020 caaagcgctg agattacagg catgagccac cacttctgac caatagatat ttatatttgt   34080
gactggaaaa tatattaaca atgtgttaaa aaattcagtt aaaaaataat gaaagatttt   34140
tgcttctggc taagatagaa taacaaggac agcatttatc ttcttgcctt gaaatagttg   34200
aaaacggaag aaatatatgt aacagtggtt ttcaagttat tgggcatcag gcaaagaaga   34260
atagttatcc caggaaaatg aatgtggaga gccctacaat ttccttacat tactgcctgg   34320
tcatggcaag aggaaaaact gagagggagac tgaggctgag ccagtggttt gctgggttga   34380
ggaggcagag ctgggagtgc agagatgcaa ggtggtgaga gcccatatgg aagaatacca   34440
gggaagagag ctgcagaggg agctccggag acctgcaccc tgccctctca gtaccctgtc   34500
atgtgtgtag ctgagtactg acgagcactt gcttgtgcgg aaatgaccca gggctggagg   34560
tagagccacc tgaaaggatt agaaggaaca gttgctgaaa gtcacacagg gccaggaaga   34620
atttctaatc acaccagttg gagtggaaaa cctcagctct catagagcag gtagggtact   34680
cagaagggtt tgcccaccta gccccagact aagtttcgtt actctgaccc tacctaatat   34740 taaaagaga  ttaattaaat tgttcgcaac aaaaataata tatttcagtg tttgtaacac   34800
gtagaagtga attgtatgac aatagcataa aggctggaag agcagaaatt gacatgtatt   34860
tgcgctgggc agaataatgc tcccctcttt ccccaaaaga tatcaagtcc taatccctgg   34920
agcctgtaaa tattactta  tatggaaaat tgttttatga tgtgattaaa ttcaggatct   34980
tgagatgagg gggctatctt ggatgatctg ggtaggcact aaatgcaatc acatatatat   35040
aaaaaggagg cagagggaga ttttacacac agagagaagg ccctgtgaag atggaacaga   35100
aagatttgaa ggtgctggcc ttgaaaattg gagtgatgaa gctataagcc aaggaatgca   35160
gcagccacca aagctggaag aggcacggag cagttctcat ttagagccta ctccagaggg   35220
aatgtggtgc tgccaattcc tttttttttt tttttttaa gatatcattt acccctttaa    35280
gttggttttt tttttttttt tttttttta gtatttattg atcattcttg ggtgtttctt   35340 ggagagggggg atttggcagg gtcataggac aatagtggag ggaaggtcag cagataaaca   35400
tgtaaacaaa ggtctctggt tttcctaggc agagggccct gccacgttct gcagtgtttg   35460
tgtccctggg tacttgagat tagggagtgg tgatgactct taacgagtat gctgccttca   35520
```

```
agcatctgtt taacaaagca catcttgcac cgcccttaat ccatttaacc cttagtggac   35580
acagcacatg tttcagagag cacggggttg ggggtaaggt tatagattaa cagcatccca   35640
aggcagaaga attttcttta gtacagaaca aaatggagtg tcctatgtct acttctttct   35700
acgcagacac agtaacaatc tgatctctct ttcttttccc acatttcctc cttttctatt   35760
cgacaaaact gccaccgtca tcatggactg ttctcaatga gctattgggt acacctccca   35820
gatggggtgg cggccgggca gaggggctcc tcacttccca gatggggcgg ccgggcagag   35880 gcgccccca acctcccaga cggggcggcg gctgggcggg ggctgccccc cacctcccgg   35940
acggggcggg tggccgggcg ggggctgccc accacctccc ggacggggcg gctggccggg   36000
cgggggctgc cccccacctc ccggacgggg cgggtggccg ggcggggggct gcccccacc   36060 tcccggacgg ggcggctggc cgggcggggg ctgcccccca cctcccggac ggagcggctg   36120
ccgggcggag gggctcctca cttcccggac ggggcggctg ctgggcggag gggctcctca   36180
cttctcagac ggggcggctg gtcagagacg ctcctcacct cccagacggg gtggcagtgg   36240
ggcagagaca ttcttaagtt cccagacgga gtcacggccg gcagaggtg ctcttcacat    36300 ctcagacggg gcggcgggc agaggtgctc cccacttccc agacgatggg cggccgggca   36360
gagatgctcc tcacttccta gatgggatga cagccgggaa gaggcgctcc tcacttccca   36420
gactgggcag ccaggcagag gggctcctca catcccagac gatgggcggc caggcagaaa   36480
cgctcctcac ttcctagacg gggtggcggc tgggcagagg ccgcaatctt ggcactttgg   36540
gaggccaagg caggcggctg ggaggtgaag gttgtagtga cccgagatca cgccactgca   36600
ctccagcctg ggcaacactg agcactgagt gagcgagact ccgtctgcaa tcccggcacc   36660
tcgggaggcc gaggctggca gatcacttgc agtcaggagc tggagaccag cccggccaac   36720
acggcgaaac cccgtctcca ccaaaaaaca cgaaaaccag tcagacatgg cggtgcgtgc   36780
ctgcaatccc aggcacttgg caggctgagg caggagaatc aggtagggag gttgcagtga   36840
gtagagatgg tggcagtaca gtccagcctt ggctcggcat cagagggaga ctgtgcgagg   36900
gcgagggcga gggcgaggga attccttaat ttcagtttag tgatactaat tttggactct   36960
ggcctctaaa actgtgaaag aaaaaatttt ttgtttgttt gtttcttta agccacatag    37020 tttgtggtaa tttgttacag cagctgcagg aaactaattt atgctgcatg tgaaatggtg   37080
taataaggta gattgtgatg aagatacata gtataaacaa ttaagcaaca actaaaagca   37140
caacaaggaa ttatagctaa tgaaccaaaa aaggagatta gaataataaa aatggtgaat   37200
cccaaagaag ccagaaatag gggaagaggc aaataaagga aagaaagagc ttgatggtag   37260 atttcaaccct aactatgtca aaaggacat tacatgtaaa aggcagcgat ttttcagatt    37320
gaatggaaaa gtaagactcg gtatatgctg ctgcctgcaa gaaacacatt ctaaatataa   37380
aggcaaaaat aacctacagg taacagaacg gaaagaagtt cactgtgctt acaagaatta   37440
gatgcaagct agactggttc tgttaatatc agacaaagtg gatttcaaag caaggctct     37500 tgcccaggat gagatggtca tttcataatg atgaagggga ttcgttcatc agcctggcat   37560
agcaagctga aatgtttatg caccggacta cagagctaaa atacatgaag caaagcctga   37620
cagaactaca agtagaaaca gacaaatcca cagtgataga gatttcagta gccgctctca   37680
atgatttgta gaacacgtag ccataatatc tggatctaga acacttgacc aacactgtcc   37740
cctgtgcaac ctcattggca tttacaggac actccaccca gcaccagcag aagagacact   37800
ctctcaagtg ctcacagaat gtttgccaag atagagcaga tgctgggcca taaacaagt    37860
```

```
ctctaaatta aaagcattca aattattcag agtatgtttt ctgacctcag tatcattaag    37920
ttggaatata ttataggaag ataacctgga aaagcctcag atatgtggaa aaacccattt    37980
ccacatggcc catgggtcag aagtgaagtc aaaagggaaa tttgaaagtc ttttggattg    38040
actgatataa aaacaataga tttctaaact tgtggggtgc tgttacagca tagtaaatgg    38100
aaatttctag cattaaatgc ctgttttagg aaagaaagat ttcaaatcaa tgacctcagc    38160
ttctaccttt ggaaacttga aaatgacaag caaatggaat ccagagttac agaagggcc     38220 aggtacggtg gcttatgcct gcagttctgc cactttggga ggccgaggca ggtggattgt    38280
ttgagactgg cagttgaaga ccagcctggg cagcctaggg agaccccata tctacaaaaa    38340
acaaaaaaat tagccaggtg tggtggcatg tgcctgtagt cccagctaac caggagtcta    38400
aggtgggagg attgcttgag tctgggaggt tgaggctgca gtgaactgtg attgtgccac    38460
tgtgttccat cctgggcaac agaatgagac cctgtctcaa aaacaaaaac agttactaga    38520
agaatggaca tcataaagat aggagcagaa gtcagtaaaa tagaaaacaa aaatacatag    38580
gaaatcaata aaaccaaaag ctggttcatc aagaacatca ataaattggt aaagctgata    38640
ggaaaaacag tgaagtcaca aattagcaat atcaggaatg agggagatga cagtagtata    38700
gattatatag atattaaaag gactgtatga ggcaggtgtg gtggttcacg cctgtaatcc    38760
cagcaccttg ggaggccgag gtggacagat cacctgaggt caggagtttg gaccagcct     38820 ggccaacatg gtgaaactct gtctctacta aaaatacaaa aattagttgg tcgtggtgct    38880
gtgtgcctgt aatcccagct acttgggagg ctgaggcagg agaattgctt gaacctggga    38940
ggcggaggtt gcagtgagct gagattgtgc cgttgcactc cagcctgggt gacagagcaa    39000
gactccatct caaaacaaat aaataaataa aaggactat atggtaatat tatgaacaac    39060
tttatgccaa taaatttgac aacttataga tgaaatggat gagttccttg aaagacacag    39120
aaactattaa agctctctca agaagatata gataagctga ttagccctat atctattta     39180 ttgaattaa atgtaaaaat caatatttag ttactggaaa acttttaagt gtggttggaa    39240
atggtatacg aacttttca actgaatttt atgaagtcta atcacaggta aaggttttct     39300
gatgaaaatt tagtgtctga attgagatat actgtaaaaa atgttatata tcttaattat    39360
ttcttcacat taattacatg ttgaaataat actttgggtg tattgggtta aattaaatat    39420
tatgaaaatc ttgcctgttt ctttttact tttgatgcgt cagctaggaa atataaaagt     39480
gtagctcaca ttctgtttct gttgacagta ctgctttgga gcacagtgtt tgaatgatct    39540
atcatttcaa agacctttcc tcagttcgtt attcatggct gtctgtattc cacatagata    39600
aggtctgaaa tactgctaag tggcatgttt tgttttatgc ttttataagt tgttgatca     39660 ttactgatgt ggacttttgg tgcctcttag gctcattgct atcttccaac cattgtttgc    39720 aattttacc tagagataaa gagaaagaga catttggttt cagagtagtt agattgggat     39780
catgaaagag caacctcatt tgatgcttc aaaaatagca catccccgt attactggga      39840 tttgctattc ttgggattac ttcaagaaca tccttgtgtt actggtttgg atgcttctga    39900
atgctgtgaa gtcagtttca tgtacatggc tcatcagttt agctctctct tggctttgtt    39960
tagacagttg gagcatgatg gcctaaacag cttctttcaa ttaaacattt taaaatagtt    40020
tacaaatagt aaacaaactc cagttttgt gactctttgt ctcgcacaac aaaaacacaa     40080
tctgaccatg atcatctggc atcttagggt gaaatatggt tatactttgg cccataccga    40140
aagcaagatt aaaaagggc aggagagata gactgctgaa ctgattttca aggttccaag     40200
aatattgtag gttaagagta aaagtaaaact tttggtagaa agcagtgggt tgtctaggat    40260
```

```
tgaagtatct gaagttttta aacgaaaatt taaaaagaaa aatgagaatt gccttacaag   40320
tacaatctct tcttttttaa aaaataaact ttattttgaa atagttttag atttatagaa   40380
aaaaattaga tagggtagga agttttcata taccctacat ccagttaccc cagttattat   40440
catcctaatt tagtgtgaga cattttcatg tttaatgaat caatattgat atgctattaa   40500
cttaagtcca gactttattc agattttctt aatttctatg taatgtccct tttctgttcc   40560
agaattccat gcaggacacc ggatacctca ttacatttca ttgtcatgtc accttaggct   40620
cctcttgaca gtttctcttc tttttttgct tagaaattct ccagaatttc agaaacttct   40680
gggcatcgct atggaacttt ttctgctgtg cagtgatgac gcagagtcag atgtcaggat   40740
ggtggctgac gaatgcctca acaaagttat caaagtaaga accgtgtgga tgatgttctc   40800
ctcagagcta tcattgttgt aggctgagag aagaagcgat cattgagtgt tcttctgttt   40860
tgagtccctg aggatgtctg cacttttttc ctttctgatg tatggtttgg aggtgctctg   40920
ttgtatggtt tggaggtgct ctgttgtatg gtttggaggt gctctattgt atggtttgga   40980
ggtgctctgt tgtatggttt ggaggtgctc ttgtatggtt tggaggtgct cttgtatggt   41040
ttggaggtgc tctgttgtat ggtttggagg tggtcttgta tggtttgcag gtgctctatt   41100
gcatggtttg caggtgctct attgtatggt ttggaagtgc tcttgtatgg tttggaggtg   41160
ctcttgtatg gtttggagat gctctattgt atggtttgca ggtgctctat tgtatggttt   41220
ggaagtgctc ttgtatggtt tggaggtgct cttgtatggt ttggaggtgc tctgttgtat   41280
ggtttggagg tgctctgttg tatggtttgg aggtgctctt gtatggtttg gaggtgctct   41340
attgtatggt ttggagatgc tctggtatct gcctgcattg cttgccacac ctgcccggtc   41400
agaaggcgct atgttgacaa ttgtgcctgc acggtgccta ggtcaatgaa gggaaccgat   41460
ggtagccact ggatgctcct gggaaaatgt cactacaggc accagagaag ccagagctat   41520
gcccaaattt ctatgagtct cagttttctt aaccataaaa tgggatcaat gttttttgtgg  41580 catgtgtatg agtgtgtgtc tgtgtatgtg tgaggattaa attgtgtatg tgtgaggact   41640
aattgccact actggatcct caaagtggta agaagtgttc ttattaataa tgacatcctt   41700
acactcttac ccagcaagat tgatgggtgt ggcactgctt ctcttttcc atcacatggt    41760 ttccatggta tccttttgcc cagggaatct ttgctttgtg gctagcactt tgttgtttgg   41820
ctaatcacgc tttctgtggt caggacgctg gcttctctgg agccatggga ttctagctcc   41880
ctgtcttgtc cctagagtgg tcactgtctt ctctctccgc ttgcaattcc tgctttgctc   41940
gcatctcact tatgcagtga cgtatatcag tttcaccttg ttctccgtgc ctgctgatca   42000
ttggcaccac ttgcatggtg ccatttaggg cctgcttcca gttaagcttg cttctccaca   42060
ggcctaaata tccttgcttg cttcttttat tctcactggc aggaccaggg cggtctgtct   42120
ttgcatgaga cagggtctcg ctcagtcacc caggctggag tgcagtggct gatcacggct   42180
cattgcagcc ttgagctacc gggctcaagc tatcctcctg gcttggcccc ttgagtagct   42240
gggactacag gcgtgcacca ccatgcccag ctaattttta aaattatttg tagagatggg   42300
atctcgccag gttgcccagg ctggtcttga acgcctgggc tcaagtgatc ctccctcctt   42360
ggtttcccaa agtgctggga tcacaggtgt gagccactgt gcctggccct tgatgtttca   42420
gttcttgata tttgatcctc agagtcagaa aatctaaaaa gagggctatc ccaggttgcc   42480
ttggttcatg gcaaatggga cgttaagagg gcagagagaa tatgaacaga aactgttcta   42540
atattggtca tttaatgtgt aagtattgtt cttttttaaa cctccttcat ttttttttcca   42600
```

```
ggaattgctg acacagtggg cttggtgtgt gtctgaggac tgtaggccat ggccctaggt  42660
tgtggtttta ggtctcaggt gctcttcctg gctgtctcct tgcttctttc ccatgtcctc  42720
ttctttgttt ccagccattt ctcccttatg cttaagtttg gtgcagcagg gtttggctgc  42780
tctcagattc ctgcttcctc agatgctgta gttgtcaggc ccagcgggct ggcagcggga  42840
tcaggatctg gctaggtttg ctctcactgt ggcagagtag ggggaggcgt gggagagcac  42900
gtgtgacccc aggccagctg tagggagcat aggcatggtc acgtagcctt caggtcctag  42960
actttgtctt ctcatgagta tggctgtgtg tgtatggtga aaactaggtt ctacttagcc  43020
caagaaaatg ggcacatttt gcatgtggtt tctgtagaga aatgcactgg gtatctgaca  43080
tagcctggca gcatgcctcc ctcaggtagg ttagtctcag gcggtgaagc acgtgtgtcc  43140
agcaagaact tcatatgtgg cataaagtct ccgttctgtg aggtgctggc aaatcaccac  43200
caccgtcaag aggctgaagt gattttttgtc tagggaggca ggaaaggctt cctggagtca  43260
gcagccagta ggtgaaagag tagattggag accttcttaa tcatcaccgc ctcttgtctc  43320
aagggggtgcc aggaagctgt ggaggctgaa cccatcttat gctgccagag agtgggacac  43380
catgagggtc aggtcaaggg gttgtacctt gtttggtaga gaattagggg ctcttgaaga  43440
cttttggatgt ggtcagggga gtgtatcatt taggaagagt gacccggtga ggacgtgggg  43500
tagaggagga caggtgggag ggagtccagg tgggagtgag tagacccagc aggagtgcag  43560
ggcctcgagc caggatggtg gcagggctgt gaggagaggc agccacctgt gtgtctgcgg  43620
aagcagggggc aagagggaag aggccagcag cgtgctgcca tcacccagcg actggcgtag  43680
attgtgagag accattccct gctcttagga ggggctgagt tttagttttc tcttgttata  43740
caataagctt ggtatttgtt tacaaaacat ttgtaaagct aaatcaaggt ttgataaggc  43800
ttctagttttt atttaagaag taatgttgaa ataaatgttt gtccaattcg ctttgctcat  43860
ttaaggactt tcagtacaaa ctgcaacaac aggattagga tttaaacgtt tctgagatgt  43920
ttttactcct cagaatttcc cagaatgtga tctggttttg attttcaagc ttgctgaccc  43980
aataggttaa cccacaagtt ttacgaagac catctcagtc cacttacatc aactgcccat  44040
gccacggtta aagagatcat cgactgatgt ttggcacagc ttcctccctc ttgggtgggc  44100
aagcatttgg aagagaaggc tcctatgggt gagagtgggg caccaaagtc ttccctgtcc  44160
catcccctag cttgagaagc ccttctctaa tgtggacttt tgtgccgttag catcgttact  44220
agcttgaagt tgaccatctg gacgtacttt ctggtttagc ctcacaagtg agcaaggagg  44280
gttgagagat gtgctgtgag gaatgtgggg ccccagctgg cagcaggctc tgggtcaggg  44340
gggcagggac cacgggcata cctgacagtg aggaggggcc acacctgcag aaaaggatgc  44400
aggactccgc cttgggaagt gttctaggcc agagcgaggg tctgtggttt ataagtacac  44460
ccacagtgct cgggaccctg cagatgtcca gggtgccgtc tgagcccgta tcatccaaca  44520
gaatgttctg ctagtgaaga ttaaagattt actccagggg ctttaggatt tattatatat  44580
atataaatcc tatatatata attttttttt tttttttttt tgagatggag tttcgctctt  44640
gttgcccagg ctggagtgca atggcgtgat cttggctcac tgcaacctcc gcctcccggg  44700
ttcaaactat tctcctgcct cagcctctcg agtagctggg attacaggcg cccaccacca  44760
cacccggcta atttttgtat ttttagtag agacggagtt tctccatgtt ggtcaggctg  44820
gtcttgaact cctgacctca ggtgatctgc ccgccttggc ctcccaaagt gctgggatta  44880
caggcatgag ccacccccacc tggccaggat ttattgtatt tgaaccatct accatttaa  44940
ttttgatgtt atgtagtatt tgatgataat gaaagttaaa ttgttttttct ttccattttt  45000
```

```
ctgtttaagt gaatgacctg tatctagttt attcagtaac ttcctgcata tatttgtttc   45060
tttcattctt aatgaatata ttcttaattt agttgctatt atgttttgct ttgccccaaa   45120
attgaaatct tagtttcctt ttagctcgtt ttagaactag tgatgggatg tgtcttccat   45180
aaatctcttg tgatttgttg taggcttttga tggattctaa tcttccaagg ttacagctcg   45240
agctctataa ggaaattaaa aaggtgggcc ttgctttttct tttttaaaaa tgttttaaat   45300
tttaaatttt tataggtaca cgtatttgt aggtacatgt aaatgtatat atttatgggg   45360
tacatgagat attttgatac aggtatacaa tacataataa tcacaccatg gaaagttgga   45420
tatccatgcc ctcaagcatt tatcctttgt gttacaaaca atccagttac atgctttact   45480
tatttatttt tattttgag acagagtctt gctttcaccc atgctagagt acagtggcat   45540
gaccttggct cactgcaacc tccgcctccc gggttcaacc gaactttggg ctggtctcaa   45600
actcctgacc tcaggtgatc cgcccgcctc ggcctcccaa agtgttggga ttacaggcgt   45660
gagccactgt gccgggcctg attgtacatt ttaaaataac taaaacagtc agggcacagt   45720
ggctcatgcc tgtaatccca gcattttggg aggctgaggc aggtgatcac ctgagatcag   45780
gagttcgaga ccagcctggc caacatggag aaaccctgtc tctactaaaa atacaaaaat   45840
tagccaagtg tggtggcggg cgcctgtaat cctggctact cgggaggctg aggtagggga   45900
atcgcttgaa cctgggggtg gaggttgcag tgagccgaga tcacgccact gcattccagc   45960
ctgagcgaca gagtgagact ttgtctcaaa aaataaaaat gaaataaaat tgggccgggt   46020
gtggtggctc acaccttagt cccagcactt tgggaacctg aggcaggtgg atgcttgaga   46080
ccaggagttt gagaccagca tgggcaacat ggcaaaacgc tgtctgtaca gaaattagct   46140
gggtgtggtg gtgcacaact atagtctcag ctacttggga gattgaggtg ggaggattaa   46200
ttgagcctgg aaggttgaat ctataggtag ctgagattgt gccactgccc ttcagcctgg   46260
gcgaccaagt gagaccctgt ctcaaaagaa aaacaaaaaa acaaaaaaca aaccactatt   46320
atcgactata tattattgtc tatgatccct ctgctgtgct gtcgaatacc aggtcttggg   46380
cccttatttc catcactgag caaacttcac tctgttaagc agcaggtgtg ggatttcatc   46440
gttattcagt aattcacaat gttagaagga atgctgtttt ggtagacgat tgctttactt   46500
ttcttcaaaa ggttactctt tattagatga gatgagaatt aaaaatggta acttacttta   46560
tatctttata attgaagccc actagacctt aaagtagtta ccagatgttt tatgcattta   46620
aatggccttt tctctaaaat tagaaagtaa caaggaaaga aatgcttcg tttctatgca    46680 accctcttgg tgactagtat gtgactctta atgcaaccct cattgcaccc cctcagaatg   46740
gtgcccctcg gagtttgcgt gctgccctgt ggaggtttgc tgagctggct cacctggttc   46800
ggcctcagaa atgcaggtaa gttgtacact ctggatgttg gttttttgtcg ggggccagct   46860 gctactgatc ctttatgtct cagctcagat gtcatttcaa aagtctgctc tgccctctcc    46920
aaattgcagt cgaccttgcc ctgtttatgt ttccctcata gcactaatcc atgtcagaaa   46980
ttgtcacgta cagtctatct gtgtgcttgt ttattttcta tcccaccctt ccgcaagaga   47040
cttatgggat gtgtgcccca ggacagcagg ggtcttactg tcttatgctc tgttgcagcc   47100
cagcagcgat aacagtgtct gcacatagta cttgcttaaa agatacttgc caaattgttg   47160
aaggttgagg taccaatttc attattgctg actataggag ttatagcaaa atatccattt   47220
gtctgttaca tgagttaaaa atatggttgt tgcactgtga atagtttggt ttagtcaaaa   47280
cagttgtatc ttaacggatt gagaaacaaa agcaggacca cttttcatca gctccctcct   47340
```

```
tctccttaac cagcaataca tgctgatgct gatatcccat agaccctcag ctccatcctg    47400
agtcactggg aatgtggtct aaaccctcac tattaatatg aactgagttt caataagaat    47460
cttatatggg tcgggcatag tggctcatac ctttgatccc agcacttcag gaggccaagg    47520
caggtggatt gcttgaccca gactaggcaa catggtgaaa cgccgcctct acaaaaaata    47580
caaaacttag ccaggcatgg tggtgcgtgc ctgtggtcac agccactcga gaggctgagg    47640
tgggaggatc acttgagcct gggaggtgga ggtcgtgttg agccaagatc gcaccactgc    47700
actccagcct gggcaacaga gtgagacctg tctcaaaaaa accaaaatcc agaaagaac     47760 ttatatggct gcagaggtat aatcactaag gaaatttcct tttgtataat cttttttctt    47820
ttactatcat ttaaaaaaat gtgttatatt tctgaagcaa cacatccagg ttctgcacat    47880
agcagccaaa gtgaccttaa agaatataac tgggtcttgt cattcccta tttaaactct     47940 tgtacccatt tcccagtgcc gtttagatag agattccaga ctcgtcaatg gctctgtcac    48000
ctcagacacc ctgcattgac tcattagtct gattagagtc aggttttct tcctcctgat     48060 ggttttttt tcccccttag ttctcagcgg aacagtcact tccttaggga ggtttcccca    48120
gccaccctct gaggccgtgc ttgttgccag actctgccac tagagggcag ggctgcacca    48180
ctcctggcac ctcgcacccg gcctgccctg tcactctgtg tgttgggtga attcctgtga    48240
tctgtgactc actgctctgt gtcctacaca ttcggctttt cttctctccc cacaacccca    48300
ttttataatt ctccttttc aggaaagctt tattcccatt taaaaatttt tgttttaaa     48360 atggtatttt cttacactta ttttctaatt aaaaatgagt gttttaagaa gtattatgat    48420
ttactgcaaa taatttttaa acccagcctt ttagatcctc tgtgatcata agagaaatga    48480
aggatgtctc ccaacacttg agcttcatcc acatttcatc ctcctgttct ttcagctgag    48540
ttttccccat cccattaggg actgttggaa tataaaactg gcttttccct aacagggaat    48600
gaattgcttc tgtttctcct gaaggagagc tggaagaatg acttgcgttc ttttgcatac    48660
acaggcctta cctggtgaac cttctgccgt gcctgactcg aacaagcaag agacccgaag    48720
aatcagtcca ggagaccttg gctgcagctg ttcccaaaat tatggcttct tttggcaatt    48780
ttgcaaatga caatgaaatt aaggtatgat tgttgcctca ggtcacaaac atgcgagtga    48840
tgctgtgagt gagtctgtgg agggtgaggg cttctgaaca gggagtcctg tgggagtgct    48900 tcttgggta tgttgtatgt cgtaatttag actaccatca tttgtgttat ttttgaggca    48960
cctaaggact tcttttccact tctcatttct tactgtgggg tgaagagttg aattgggaga    49020
tggtttctag atgcaaattg aaaaggcatt tttccagagc agatttgttt tcggcgtact    49080
agagtgactc tttaacctag ctgcgggaag atgactgtgc caagactgca ggtaggagaa    49140
agctcactga cgaggccttg tgggtctgaa cgtcctgcag ctatcagagc ctgttggctt    49200
cctgttgtgc attccaacaa atcatcttca aacccacttt agtgttttgt ttataatgtc    49260
cagaaatagt gaccctgtca catgctctac agattacagg attcttagcc tcttcctttt    49320
tggtaggtca gtcctgggtt tgagcccaag tgaccctcct gggaggtgat gatacacact    49380
gggtagagtg gaatcagatg gacttggatt agaattctgt cctctttact agttattttc    49440
ctctaggcaa actgcccaac agctctaagc tatttccttc gtattctgaa aaataagcct    49500
taatgggacc catatagggc aactctgaga gtaaaataaa ggaatatgtg ttagagtgta    49560
gcatagtcac ccacgggaag ggcttagatg ttagctgcta ctgctcttat tagctgaatg    49620
atttggaata aactgttagc ctctctcatg tttttttctct tgagcttcga agttttcttg    49680
ttaatactaa ggagatattc aaactagtca tgggggttttg gaatgacgaa gggagatgat    49740
```

```
gaatctaaag aatttagtgt aatatttctt catgctcagt aaatggtagt ttctgctgct    49800 gttatttta ttaccatctc tttggaatgg gagtaggtgc tcctttgtgg tcagaggctg    49860
tgagagctcc acagcgccag tttgcccatc tgtacactgg ggtctgttga aggcagtccc    49920
ctctgtgata tctctggctg tcagagctca gatgatagat ggtattttg tactcttagt    49980 tctcatcatt ttcatgattt cgatcaccat ttgagtatga tgatgctaac actttgttga    50040
acgtagaatc cgttaattac ttccttcctg aacctttggc attaaaaaaa atctattctg    50100
ctacctctct gctcatttat ggttattcaa atttattatc aagagcctgg tacagtggct    50160
tgtgcctata attgtagcta cttgggaggc tgaggtagga ggattgcttg aggccaggag    50220
tttgagacca gcctgggcaa gatagtgaga ccctatctct aaaaaaactg aaaaaaaatt    50280
agctggacat gatggcatgt gcctgtggtc ctagctactc aggaggctga acaggaggc    50340 tcggttgagc ccaggagttg gagttcgagg ctacactgag ctgtgattgt gccaccacac    50400
tccagcatgg gtggtaaaac aagatgccat ttcttaaaaa aaaaaaatat atatatatat    50460
attatcaatg aaattcagta gtaccaacag gattataaac aaagatagta gttcccttcc    50520
tacttttcct cttaatcctt gtgtctcaca ggcaaacata actcttagta tttcttccaa    50580
tatttacttt catgtttctt tctttctttc tttttttttc tttgagatgg agttttgctc    50640
ttgttgccaa ggctggagtg caatgacgca atcttggctc accacaacct ctgtctcccg    50700
ggttcaagcg attctcctgc ctcagcctcc tagtagctgg gattacaggc atgcatcacc    50760
acgctcggct aattttgtac ttttagtaga gatggggttt ctccggggtg gtcaggctgg    50820
tctcgaactc ctgacctcag gtgatcctcc cacctcagcc tcccaaagtg ctgggattac    50880
aggcgtgagc cactgcgccc agcaacttcc acatttctaa ataacatgct tctactgcta    50940 ttttttttt caatttaga catttttta ctttcactat agttctatca gaattcagtg    51000
tgtacgttat tatgcctaag taaatagtca tggttgctta cgtattatat ttctttgatt    51060
gtgtttctta tttgatgaga aagctgtgtt ttttgctctg ggttgaaact ggagagagga    51120
cctggggagg aggaggagga cagatgaagt tggtgactgt accttcatgg ccatagctgg    51180
gttctcagca cccggggatc tgctgatcac ctactcatag gccaggcccc tatcgaagtt    51240
ctaggtgacc cagtgctggg gacgggggg ccacctgcaa ggtctaatca tggaggtggg    51300
ggctacagtg ttggcttgtg ctggggccag catccttagg aaggcatctt ggaggtggag    51360
gagacagccg cccacttctt gattgggcc ttcagcagca ccagcttctt gggcaggctg    51420
gtgctggctt tcatcaccat gtcgtgttca atcttcttcc agatcctgac ttctaggttc    51480
agctttcctc agaccctggt tccttttcaga ggccattgct gctgccttgc tctttgctgg    51540
cttgtgcctt gattatatgt ctttgtacaa cttttttgttt tcctggagtt aatcttcaca    51600 tctgtttct tggagttaat cgttacctct atatcgcttg cttattattc tttggccttt    51660
ttgtcttctc acaccttcca acttctttgt aaatatgtgtt tagtacaatt tttcatgaca    51720
ggtagtttac tgaatcagtt tttccccagt gtggtcatcc aacttgagtt atccagctct    51780
ctgccccagt ctgggcaggt tgatcttcag gtctgtagta cacttgtatc ctaggacttc    51840
tctttgccat tagcctggaa tttcctttgc agttctcccg ttggatgccc agttcctaga    51900
tgccatatgt ttttctatcg tctagtagct tcctgagaga agatgaatgg gagggaaatt    51960
gtatgaggtt ttgcattcat aaaaatgcca ttttttttcc tgtacacttg gctgggtatg    52020
gtgttctggg gtagaaatca ttttccctca gaaatgcaaa gtctttgccc tgttgtctta    52080
```

```
aaatctccaa cgtgacccga ttccttaacc tatgaatgta cttttctttg gaagctttcc    52140
attttggggg aggtgaagtg ctaggtactt agtaggcctt ttaatttgga aacttacatc    52200
ccttcagttc tgggaaaatt ttcttaacat ttctctgaga agttcttgcc ttttattttc    52260
tgtgttctct cctgaaattg gttagttgga tgttggtcct cctagattga ctcacatctt    52320
acctttttct tttctttttc tggtactttt tagatatcca tctcaaactc ttctattcat    52380
tgttatgttt ttaacttctt tcttttcttt gtctcttgat ggggtcttgc cctgttgccc    52440
aggttgtggt gcagtggtgc gatcatagct cactgcagcc tcaaattcct gggctcaagc    52500
agctgttctg cctcaccctc ccaagtagtt gggactacag gtatgcacca ccacgtccag    52560 ctatttctt tacttttttt tttttttttt tgagatggag tcctactctg tcgcccaggc    52620
tagagtgcgg tggtgggatt ttggctcact taagcctctg cctcccaggt tcaagcagtt    52680
ctcctgcctc agcctctcaa gtagctggga ttacaggtgt gcaccaccat gcccggctaa    52740
tttttgtatt tttagtagag ccagagtttc accatgttgg ccaggctggt ctcgaacgcc    52800
tgacctcagg tgatccgcct gccttggcct ccgaaagtgc cgggattaca ggcgtgagcc    52860
catcattaga tctttaaata ccagtatcta taagtctttt cctcttgagt cagctagtat    52920
ccctggaagg aaattactca ttttcctgct tggaggctat aagcttggct atgtttatcc    52980
tgcaaccggg gactgaagg agggggactg acagtgttgc tggtcagggt gccctcttac    53040
tttttgtttt ctgtgtgcat ctcacgtctg tcctcagcct atgtaaacac ctcttgagat    53100
tatccctctc aatctttgcc ggaggtgggg gaggggctgc ttcctgggct gccttggatt    53160
ggagggaaga cctcaggtga gtgggtggga atttgcccaa ggagccatga gaccagccac    53220
tatttcaccc tctccatccc tccacttttca gatgtatgtg gcgcctccaa agcccgagct    53280
cttcttggcg tctgtggctt caataagctt gcttttttgct ggtatccctc ctaccctccc    53340
ctgtccccag caaagcttgc atttgaactt cttcctacgg gctaacaaat cagtcagtta    53400
tgtagctctt gttactttt agcttccgaa gttttgttga cacccgtagt ctgctaatgt    53460
ccctgttctg ttctttctgt tcgtgtaaat atatgcttta tacaacttct ttacatgatt    53520 tttgtgggt ttctgggtag cagagcttca caagttcaat ccagcgtgtt ggattagaaa    53580
tctcccaccc tctggtttat tcttattctc aaaattacct gccaaacact gatactccct    53640
tgtttttcct tttcctgaca ggaaatgtac ataccataca ggacagaaat cattagtgta    53700
tcccttggtg aataaccaca aagtgaactt aacccttgta accgccaccc aggtcaagac    53760
agaatattac caagcactca gaagcctctc ccctattccc ccgtcactgc tcctgccttc    53820
ctccccaagg tcatgactgc tggcttctaa ttccagagtc tgttttttaaa ttctgtgtac    53880 atagaccatg gattaagtgt tctttttgtc tggtttattt tggtcgacat taagttcatg    53940
agagtcttct atattatcgt gtgtattagt attcctgtag ttttaggagc ttcatagcat    54000
tccattgtag ggatataccca cagtttattc attgtattat cactgggttg tttctagttc    54060
ttggctattg cgagcagtgc tactgtgacc actcttaggt gtgtcttttg gagtacatgt    54120
gcaggtttcc atcttgcaca gctagaggtg gagttgttgg gtgataggggt gtgtgcatct    54180 cagctgcagt agaaactgcc aaatagcttt ccttgagtgc ttgtaccagc tcacccttt    54240 gccactgtgt atggggattc caggagctct ggtcctcgct agcacttgga attgctgatg    54300
cttttactct tagccttcct gatgggtgtt ttctggaatc acattatgat tttaatttcc    54360
attccttaaa gtacccttgg ctctgaagtt taatgattca tgcatctctt ccctttgaa    54420 gtactcttac aggtatgttg tgcatgtgtt gaaaagtggc actatctatt ctaaaataca    54480
```

```
gtatgcctcc tctgtgtttg aacagttgta gcgtggcctt ggggcctcct gttagctggc    54540
ttggagaagg gattcttggg attgtagaga ttagacctga ggaggcccct tggagctctc    54600
tgactaaatt ttattcttta ttattccaaa ctatttaagc tcaccgtgtg ctgactcatc    54660
ataataatga gtagctctca ttgtgcttgt ctatttggac tcatacaatg attttttttt    54720
tttctttgag acagagtctt gctctgttgc ctaggctgga gtgcagtggc acaatctcgg    54780
ctcactgcag cctccacctc ccaggttcaa gtgattcttg tgcctcagct tctcaagtag    54840
ctgagactgc aggtgcgtac caccatgcct ggctaatgtt tgtattttta gtagagacgg    54900
ggtttcacca tgttggccag gttggtctca aactcctgac ctcaagtgat ctgccttctt    54960
cagcctccca aagtgctggg attacaggtg tgagccactg agcttggcca aagtagtttt    55020
ttaagatgtt agtatctttt cttgcagcta aaaaagtttg tcagagatga ttctactttg    55080
ttctccaggt gttttctcag ggagaaattg gaggcagtaa gccactgggg gagtcctgtg    55140 gctgggggt ggggtagtcc tgtggctcct tgtcagggag tcctgtggct ggcaaggaga    55200
gaagtcctgt ggctgggttg ggagggagtc ctgtggctgg ggtctcatcc tgtgcctaac    55260
agtgtccaga ggtgccgaga ccagctcagt cgggagacc ctaacccagc agcgctagag    55320
gaattaaaga cacacacaca gaaatataga ggtgtgaagt gggaaatcag gggtctcaca    55380
gcctttagag ctgagagccc tgaacagaga tttacccaca tatttattaa tagcaaacca    55440
gtcattagca ttgtttctat agatgttaaa ttaactaaaa gtatccctta tgggaaacga    55500
ggggatgggc cgaattaaaa gaagaggttg ggctagttaa ccgcagcagg agcatgtcct    55560
taaggcacag atcgctcatg ctattgtttg tggcttaaga atgcctttaa gcggttttcc    55620
accctgggtg ggccaggtgt tccttgccct cattcctgtc aacccacaac cttccagtgt    55680
gggcattagg gccattatga acatgttaca gtgcttcaga gattttgttt atggccagtt    55740
ttggggccag tttatggcca gattttgggg ggcctgctcc caatacagag gtctcgtgta    55800
aattccctgg gaggcgataa gcctctgaga aacagactat gctaaccacg ccatgaaaga    55860
gaaacttatt tataaatcag atgccagtta ctagtttact gcttatttgc ccaggcgtag    55920
ctctgacaga gtccccgact catagtgctt gctcagtgca tgctgaacaa tgattggaat    55980
caagtcatgg ctcagagcat agtttttgaat aatgggaaat ggatgttctt aagtaacata    56040
gtcaccaaga taatgcgact agctgggtca ccccttttca attttaggat attttttatca    56100 agatttaaat ggccatcatt agagttatag cactttctcc tttggattgt cctagaggcc    56160
catgagaaag tattccctaa tttcttagga gaacagtttg tgggtagtat gcggtcatgt    56220
ccagttaaat tgcagatatt tccgatcgaa gatgttccag tcctgagaac ttcgtgacat    56280
tagcaggact tctacaagcc atctcttagg gtggggcatt tactgcagtt ggctagtact    56340
cttttctcct taactttgtc atttgttgat tttttttttaa ctgtccccaa atactgtggg    56400
cagagtgtat ctagaattga ggcctccacc attgcggaga ggacatggat gctgagcagt    56460
cccctgagtg aaggttataa agaagcaaat agactacaca tgtctgtaaa ctgctcttga    56520
gtgtcccaaa tttggggtac ttcagttcag ctgtaggaaa agcctcaaac tgtttatact    56580
ttgcaagaat tggaaacttc taattcacgt taagttttat gtaatacatg ataagcttca    56640
taggagcttc atctttaatc tacttggact tttgcttccg taggttttgt taaaggcctt    56700
catagcgaac ctgaagtcaa gctcccccac cattcggcgg acagcggctg gatcagcagt    56760
gagcatctgc cagcactcaa gaaggacaca atatttctat agttggctac taaatgtgct    56820
```

```
cttaggtaag gtggaggcat atgagtggaa gagtctccag catgtactca agatagacct   56880
ttgaaataaa taaaaccaga tgatccctca gcttctagac caggctattt ggcactggtt   56940
gattgaatgt gaactgcact ggggctgctg tgagcccgca tgggtctctg tgaccctgca   57000
gatgcagccg tgcccaggga ctgggcagtg ggtgtgggct ggtgtgagcc ctgtctgcca   57060
cccagggcct ggccctctgt ctgtgtcggc catgactatg gtgagtcttg taggcttgag   57120
actgtgcctc gggttcctgc gggttctctg taggtcagtt gacagtttct cctgttgttt   57180
gggtaactgt ggaaacgaac actggcaagt gctgaagcga gcatgtggac gtgcgatatg   57240
aaataacgac ctggctttca aaggcagtga ggctctctgg aaaggacctt gctgagctag   57300
ggatgtgggt gtgtagccat tcccagtggg cctcatggcg tactcgttca tgatcatgtt   57360
tgtgccatct tgatctctca ggatctcttc tttttaaca gattaagccg ggaatctcca    57420
aacagtgagt cagatgttaa gatgtcttgc ttccacccc acaggcttac tcgttcctgt    57480
cgaggatgaa cactccactc tgctgattct tggcgtgctg ctcaccctga ggtatttggt   57540
gcccttgctg cagcagcagg tcaaggacac aagcctgaaa ggcagcttcg gagtgacaag   57600
gaaagaaatg gaagtctctc cttctgcaga gcagcttgtc caggtaggag cacagggttt   57660
actctaggcc ctgcatgtga atgactgaca ttcaaagaac cgattaattt ggaagagaag   57720
cggcagaacc gagagttaga ggtgtggact ctggagctgc gctgctcgtt ccaaccccta   57780
ggtgctgacc tctagctgtc ttccctctgt atgtccctgt caccgtgagt caaatgcggg   57840
tgatgcctcc tcaggtgccg tgttacctaa gcctctcaga gaccactgct accctgtttc   57900
taaaaccaga ggtcacgata tgtgttcatc cacccagtaa atactgattg agcacccact   57960
gtgtgctagg ctctgggata ggggctgggt atacaatggt gagtatttca gctgcagctt   58020
ctgccccgtg gaggctgtgg cctagcacac tggtctaggc acggtggtat atgctcactc   58080
aaggagatag ggacgtggtc gtttggggtg tcggaacaaa atgtcggaac ttctctttcc   58140
aatgcagaga aaccttgcag taattctaat gtactgtgat tggcagttga cttcagttct   58200
ttgtagcacg cttactcagg ttatttcact aactatgtaa ccatgcagcc tcattttaag   58260
caattggatt ttttgaactt tacttaaaat gttatgtcag ggtttttatt gtgcttaatg   58320
tgtgccattt agctaagttt tgtaggatac gaaattgtaa gtggcttaaa atgattctta   58380
atagaatcat gaattgaaga taatgctaat aatttaagca ctgagttagg tagtgtttgt   58440
aaaatgctta gaatgcttcc tggcacatgt taaggccatg taagtgctgc gtgttgataa   58500
acagctgagc aaaagtggac tcttaagaaa gtattgggc tgagagttct gttccaacca    58560
gctgcccttt ggttattttt cagaataaaa gcagagtctc atgggatatg acatttatat   58620
ttccttcaca aaaaacactg ctgagtgttt tgttgagtaa aaagggtgta gccatggtaa   58680
taatacattt aaaatatagt ttatttcatc tttaccttgc cttgtttttt ttttaagcta   58740 gcttttatt gagaattcca cacatacaaa agtatcaact catgaccagt tatatttcat    58800
ttataatcct acttctccct ttttttatta tttgaaagca acccccaatt atcctcttat   58860
ttcatctata agtatttcag tatctctata gatgaggact cttctttatt tttaaaactt   58920 tattttaaa atgatggtca gatgcagtgt tcatgcctgt aatcccagaa ctttgggagg    58980
ccaagctggg cggatcactt gaacctggga gtttgagacc agcccgggaa acatggcgaa   59040
accccatgtc ttaaagaaaa aaatcagcca agtgtggtga tgcatgcctg tagtcccagc   59100
tacttgggag gctgagatgg gagggtcaca tgagcctgga agatcaaggc tgcagtgatc   59160
catgattgta ccactgcact ccatcctggg tgatggagca agattctgtc tcaaaaaaac   59220
```

```
aaaactgcaa acaacgtca caaaacagtg ccattgttag acctgaaaat attaaacatt   59280
tcctacatca aatacccacc aactcattat caattttct ctctactctt ttggaatcag    59340
catctaaata aaattggtcg ataaggattg taaatctctt tgatgaactg gttccctcc    59400 atcccagttt ttttccctta gagttcattt attgagaaac cagattgttt gtcttctaag   59460
ttttcctgtg gtctgatata ctgcttccat ctccactgtg taaattaaca ccttttctc    59520 ttctctgtat ttcctgtaaa tcaataattg gaggaaaagc cttgtcagat ttagtgtata   59580
ttttatatct gagtccagta tttcttatat aatattttaa gataagtgta ctcttttaaa   59640
aagtattgaa actatatgct caatttttt taactgatgc ttttaagaag gctgcttgat    59700
cataaaagtt tagagatcat tggtctgatg ggaaaagcaa ataattacta aaccgtttag    59760
caaggttgag gtgcacatgg tgggggcctgg agaagttcag tcatgagccg tcacttatgg  59820
gcacgtggaa tctgacccgg cacagagttg ggagaagaca ggagctttat agacagaaaa   59880
tgtggtcttt gctaagtccc aggagtgaaa gggtgagaca gtgctcacag cacacgagtg   59940
tgggtgcgta gacagagcaa gggtgggtcc tgaaaaggcc tgcaggcttt ctcatagatt   60000
agcaagagtg ctggttacgg aggtttctaa catttgtgaa cagatcgaaa ctgtgttaaa   60060
ttgggattgc agtaatcctg gaaggacagg gatagagggt gaaggggaaa aagggtatg    60120 gatgtgagac ttaattgctg attttcttaa gacctttctc caaagtaaat aaatgatgtg   60180
gcacattttt gaactggcaa attctaaact ctagatatga ttatctctat aacatatctt   60240
actccatctt cttttgacta aaaactgttc ttaattaaat taccatgaga cgttcaattc   60300
agcaaatgta gtttggctaa ccatatttaa ttagaattta atataatcct aggcctggcc   60360
aaactattaa gcaagtgtgg gcaaaatatt gataatttta gatatgcagg aacttagttt    60420
gctttccatg tgtgcttttc gaaaaaggaa taaattgaaa aatagaggaa gccctgaaat   60480
ccaagaagca aactctctca cctaggcatg cagtaaaagc aattctagga tgattgctgt   60540
ttggcgcgta gttcgtatta gaaaccattc ttcttgaata aatagtatgt ttaagaagct   60600
gggcagaggg aaggcatatg catatattat caacaaggag ggagaaaaag gcaattagta   60660
accatccata ggagggtcag caagatttat aaaggaaatt tgtgatccaa gtatgaagca   60720
aaataaggtg cagaataaat tttaagcaag taatagatta gagtaagaga acccatttga   60780
ccattaacct tgggacattc tctttcaaat gacatggagt agtactgaaa tctttctttc   60840
tttctgagtc taggttattg tgactggact cagaagaaa tatttcatta ttgcagtgaa    60900
taacatttgt gaacattatt gttcataaat tatgcagtga ataacattta tgaacacgtg   60960
atgtgtaaga tacatactgt ttattttag ttaagttttt tggctcaact tctaggcaga    61020
gaacattaaa tgtaaatagt gttacctagg agcatgtaaa tggaaatctc catagtatga   61080
aagcagtgct gttgctaaca gaatttagga gggggcagat gaggtgaagg aaatgtgggt   61140
gctgatttcc ttattacatt gagaggagcc aggagattct tgttcaaaa tggatggctt    61200 aagaagtcaa agtataagct gattacgtag agcaggtacc caaaaatgtt ttgtgtaagg   61260
ggccagatag taaatatttt cagtcttgca ggccatccca agtctgtggc agctactcaa   61320
cactaccttt gtagcatgaa agcagccaca ggcagcccat aaatgtggct ctgttccggt   61380
gaaactttag gtacaaaagc aggtgcaggc cagacctgac ctgtgcactg tggtttgctg   61440
acctgggatt caggggtata gaagttacca tcagaagagc taaagtgag acttttact    61500 ttatactctt ctacactgtc tgattttgaa aaaagaaac atgtatttta taatattaaa    61560
```

```
gatagggttg gcaaatagca aataaaaata cagaatacca gtgaaatttg aacttcagat    61620
acattatgag taattttatg gtgtaagtat attccaaatc atgtgggaca tacttacact    61680
acaaaattat tgttgtttg tttacagttt aaatttgagt gccttgtatt ttatctggca    61740
actgtaatta aagggaaaaa gaataaaattc attatgttca tataatgtga tatagcaggg    61800
gtccccaacc cccaggctgc agagtggtac tggtccatgg gtccccaacc cccaggctgc    61860
agagcggtat tggtccatgg cctgttagga accaggctgc ccagcaggaa gtgagcagca    61920
ggtgagctgg cattcccacc tgagcaccgc ctcctgtcag atcagtggca gcattagatt    61980
cccataggag tgcaaaccct attgtgaact gcacatgtga ggggtctagg ttgtgcgctc    62040
cttatgagaa tctaatgcct gatgatctga ggtggaacag tctcgtcttg aaaccatccc    62100
ctggccctgt ggaaaaattg tctcccatga aaccagtctc tggtgccaga aaggttgggt    62160
agcactgtga tatagtatta aaagtgctaa taaatatggc atactgcctt taaaatgtct    62220
ggtagctctt tctcagtggc actcataata gtgttttttg attttaaat gtgtgtcaag    62280 ctgactctcc cctccgtgta tgctgggctt tatttccct ttcctagtca ccagttttgg    62340
gaaatagaga tcttcattct catgctgctc ctctagtgca agtgctccat ttattttaa    62400 ggaattaata taacaaaaaa tcatgggaat ttagaaaaca acatggaagc taatgatcac    62460
attggtggaa gtgataggga aatatttagg gggagaagtt aaggtataaa ctttgtcaat    62520
gaagtcctat taaaaacaac aaaaaagtga agcttaggat gcattttata aactctgacc    62580
agaacacctg tgtttctctg tttctaggtt tatgaactga cgttacatca tacacagcac    62640
caagaccaca atgttgtgac cggagccctg gagctgttgc agcagctctt cagaacgcct    62700
ccacccgagc ttctgcaaac cctgaccgca gtcggggca ttgggcagct caccgctgct    62760
aaggaggagt ctggtggccg aagccgtagt gggagtattg tggaacttat aggcaagtta    62820
ttagcaaggt ctactcttac aattaacttt gcagtaatac tagttacact ctattgatta    62880
tgggcctgcc ctgtgctaag cagtctgcat tccatcttcc ttgccaaaac ttataataca    62940
aatttcatct ttattttata aatagggag ttgggctggg tgtggtggct cacgcctgta    63000
atttcagcac tttggaagga tcgcttcagc ccaggagttt gagacaacct ggccaagtga    63060
gaccctgtct ctacaaaaaa aaaaaaaaa aaaaaattag ctgggcatgg tggcacatgc    63120
ctgtagtccc agctgctttg gaggctgagg tggtaggatt gcttaagccc aagaggttga    63180
ggctgcagtg aatcttgatg gcagctgcac tgagcctggt gacagagcaa gatgctgtct    63240
caaaataaat ttaaaaataa aataagagaa ttaaagttta gcaggttggg tggcaaaatg    63300
aggccacaca tttaaagccc ctcctcctga ttcttttctc tgccttggct gcctcctgtg    63360
gcattttagg tgctgagaaa tgaaaacagt agggaaaata gttccaggat cctcatgtta    63420
atttgccaga aatggcatct tcaagtcgtc agagggatct gagagttcct tcctggcctg    63480
acttgagaaa atccgtctgt ccccagctct gcgtctgcct ccactgccca gtcacctcct    63540
ctccatgctc ttggggctgg gccctacccc accatgcagt gctgcccttgg agcagtgagc    63600 ttggtgggtc ctgtctggca tgagagctgc cttttgggagc tggatcccag cctctaccac    63660
tgggtctggt gcctagcagg ctatggataa acttctgctg actccggcct ctcctaagcc    63720
actgcaacgt ggtcggtgta gtgcacagtg tgtgtgcagc gtggccttac tcacagcctc    63780
cacattagag agaatctgac tgaagtctta ctgctgcctc gtgtgaacat aaatgttgc    63840 cagaaccatg agcaggaaat gttaatctgc cttgtttcct gtcctttaca cggaagaatt    63900 ttttctgta tggaatgcgt gccttacaaa taatgagtgg aaatacccat cgctaatgaa    63960
```

```
aagttatact tgactgttag tcagctaaat aatctgagat ttctaatact tttaatttgg   64020
cttttacaat gcaatttatc ttagctttt tgatttctta ggtcatatct ttagaactat   64080
atatttgaat gttaatgtaa ttttcatatt gaaattaaaa tgttgaactg cgatgttaag   64140
tgtttcctgt ggaaaaacgt tcacattttc tctagtttta aagttgaatc aagctgtttg   64200
aagattttca catttcttct agattttatc agcttgttac tttatctgtc actttctgtg   64260
atttgcagct ggagggggtt cctcatgcag ccctgtcctt tcaagaaaac aaaaaggtga   64320
ttatttcaga aatcagagtc ttgtgttgaa tcttactgat tttcttgtat ttctgtaatg   64380
taatgtatct tgtatttctt gtaatactgt attggactct gtgtatatct cttctcagat   64440
gagtgattat atgtgtgaat gttgctggaa tctgataacc aggcctgaat agttttgtag   64500
ggtggctttt aaaaattact ttcatatcag aattgctttg tcataaattt tgaacgcatc   64560
ataaatttct aatgttcggg gtcagcagac ttttttgta aagggacaga gtgtaaacat   64620
cttagcttta tgggccatat ggtctctttt gcaacattca gctctgccct gtgacaggaa   64680
tgcagttgta aagacatgag ctactggcca gctatgttcc agtagaactt tacttacaga   64740
aacagacagg ctgtagtttg ccaataccctg ccttagggaa tgtgttgtta tattttgtga   64800
gttaccttct cagtaaattt tatttagtat tagtcaggaa tattattaag tagcttcttt   64860
tccagcctgg tcaacatagt gagacccggt ctctaccaaa acaaaacaaa acaaaaaaac   64920
agccacgcat gtggcatgtg cctgtagcct cagctgctgc tcaggggct gaggcaagag   64980 gattgtttga gcccaggagt ttgaggtcac agtgagctgt agtcatgcca ctgcactcca   65040
gcctaggcaa cagaatgaga ccttgtgtct taaaaaaaaa aagtttcctt tgttgggtta   65100
ttttaatttg gacctggtta tcatttttca gccatattta actttgtaca tatcagaatg   65160
ttctgataaa acttaacttt tattaaagtg tttgtgatat aatctgctag ttttggtaca   65220
cattatcttt tgcaatgcca gttattttct tttccagtgt gggttgcat aggaaaagaa   65280 ttgctgtcac tttctattt gaaatcttaa aagactgatc ctttttgtg tcatgatttg   65340 agtatttaat tgagagccta atgcctaata ttatttgcag tattaaatgg gatcttaaca   65400
ggaatagcat tctagccttc attgaattaa gtaaacattt cttaagagaa cttggaatct   65460
ataatatttg cgtcatcata gtatgagata cttaatcaag tttgagattt tagtgaaaca   65520
ttgtttagaa gccaaaagga ttctaggaaa aattaatgtc tatattcttg aattaggaga   65580
gattttggga cgtgtgacta agttacgctg acacttgttt gtttcttagt cgcttttttcc   65640 agtggcggtg agaacgaaga tgactgattc acattgctca gatgagttta tcctcttctg   65700
gctgggacat gggatatatc ctgtctcttt taagccttt tggtatttt ccccattga   65760 gagctgtgtc ttcaaactct tctgttatag ctggaaaatc ctttttaagt gaaatctgcc   65820
caaattataa gacagatgaa ggtagagttg tgttggatat aggattaggg tgaaagtagt   65880
gggggtgtcc tggagcctct cttctggtgg cagcctagct cttgtgcctt tgaggaaatt   65940
accctgggga cggctctgtg gaacatattt gcaaaccact gatttggaag atagagatgg   66000
cttttgttaa gatctgaatt cacctttttg gcattttatt tgattctca aggtaaagaa   66060 cttatttgt aataaagttt cctattattt agtagataag ccaagttgct gtgttaattc   66120
catgtagatt ttgggttcc tttgctcatt ttttcactct taatctcaca tcattgtaag   66180
tttatggaag ttatcatact tctgactttt tctttgaaga gcagaaatta gaattccca   66240 ataattattt tgatagtgtc atttaatgac actcacatgt gatgtagcca caagagattta   66300
```

```
atgagttcag ttttaaatca tattaagact gttggtttca tttgttctca ttaatgtaat    66360
tctgaagatg aacaataaaa tgtattttta gaactttcaa atgaaatatt atttcatcct    66420
tccagatcat ataatgctta agttctgatt gttaatcata aagtctagaa aattaaaaga    66480
taataaaatg aaagtgactt ttaggtatta gagttttatt ataaattctg gtgtgtcatt    66540
ggagctatga catgaatatt tcaaaggcca atagcattgg atctttacag ttataactta    66600
ccattttaa gtttaagtag taatatagat tatttaataa tcaaaatcaa taaatattaa     66660
ttattaaaat gttttgtggt atagtttgag aatcattgct tttaactttt tccatatagg    66720
tttattgact ttaatagcat tctaaacata acatctctac attctttgtg tttaatactg    66780
tggaggtata aaaatactta tatgatga taaactatat tagagtaaat taaatattct      66840
tatgagtttc attttagagt gcatttactt aattttgaag tccttatttt tagcaaacta    66900
aaaggaatgt tggtacatta tttactaggc aaagtgctct taggagaaga agaagccttg    66960
gaggatgact ctgaatcgag atcggatgtc agcagctctg ccttaacagg tagttctcac    67020
tagttagccg ctggtgtgga ccttcactgt ctgccttcca cccttgccc ttcctgctcg      67080
tcccctgca cctggtggac agcacgactg ggggcagcag tggagccagg ttgcttaaat     67140
ggggcatatt cgggcttctt ttataatact tactctgaag cttgtgtgtc tgtggtgttt    67200
gcatcatata tttgttgttt tccatggttt aggctgtttt aaaattaggt ttatggcttg    67260
agcatagggc tttgtgagta ggggatggca ggtcgaaaca tctcatgagt tggatgggtt    67320
atgctggggg ttgggaaatg ggatgaaaaa ttatgggatg aaaaattgcc tatggatagt    67380
ttaacttgaa agaatctgcc tttgtttaca gatagttatc ttttttcttt tttgagatag    67440
agtctcacac tgtcacccag tgcagatacc cagtgtcact ggagtgcagt ggtgtgctct    67500
tggtgcactg cagcctccgc cttctgggtt ccagcgattc tcctgcctca gcctcccaag    67560
tagctgggac tacaggtgcc cgccaccacg cttggctaat ttttgtattt ttttgtggag    67620
acgggttttt gccatgttgg tcaggctggt cttgaactcc tgacctcaag tgatctgcct    67680
gcctcagcct cccacagtgc cgggattaca ggagtgagcc actgtgcccg gccagttaca    67740
gatacttatc taatgaaatt ctctgtgtac tttataaaag atgaggatta actgaaggta    67800
ctaataactg gattatatga gggtggtttt ggttgtataa tcctatctaa aagaatattt    67860
tagctataac tgaaagtaag acttaaatat ttagagagga aaatctgaat aattctagta    67920
gtaattattt atttacaaaa taaaaataga ttttttttg attacacaaa ttaaacaaca     67980
ataaacatc acagcaatcc ggatactata aagctcacat gcttaccgac ccaactgccc     68040
caggagtgac cactgccaac agcttcatgt cgaccttttt gccataattt ttatatagcc    68100
ttttttgttt ttaaatggta atttagaaag tcaactagga aaatgtgtta caggtttatc    68160
ttccaggaga ataggactgg agtcgagatc ttgaatgtgg cttggaagaa ggcaagccca    68220
ccccagagag atgagttgac agttgtttct gaccactgct tgcttagagg gcctgcgtgt    68280
ctgtgaccgc ctagctttgc gcccctgact aggctgcccc ttaattacaa atgtctttat    68340
atattgctcc agctaaggct tggagtagtc ggttaagaac ttgaacttcg gttttttgcag   68400
tgaaacagca tttgagaata tcaccttctg ataagcctta ttttataagg tgggtactgt    68460
agtgggaggc agtgtgagag atgcttgaag gatgcactgc tgtcctgcat ttcagcatct    68520
tcaggatgct gtgcagctga aacatttgat aacggtggaa ctgttcgtta ttttgcaagc    68580
ctgtgattcc ctattgaatg ttttctctcg ccatttgaca aatgagtgtt tctctgtctt    68640
cagcctcagt gaaggatgag atcagtggag agctggctgc ttcttcaggg gtttccactc    68700
```

```
cagggtcagc aggtcatgac atcatcacag aacagccacg gtcacagcac acactgcagg    68760
cggactcagt ggatctggcc agctgtgact tgacaagctc tgccactgat ggggatgagg    68820
aggatatctt gagccacagc tccagccagg tcagcgccgt cccatctgac cctgccatgg    68880
acctgaatga tgggacccag gcctcgtcgc ccatcagcga cagctcccag accaccaccg    68940
aagggcctga ttcagctgtt accccttcag acagttctga aattgtaagt gggcagaggg    69000
gcctgacatc ttttttttta tttttttatt gagacagagt ctcactccat agtgcagtgg    69060
aggccgggca caggggctca tgcctgtaat cccagcactt gggagactg aggcaggcgg     69120 atcacttgag gtcaggagtt cgagaccagc ctggccaaca tggtgaaacc ctgtctctac    69180
taaaaataca aaaattagtt gggcgtggtg gcacatgtct gtagtcccag ctgttaggga    69240
ggctgaggca ggagaattgc ttgagcctgg gaggcagagg ttgcaatgag ccagatcgt     69300 gacactgcac tccagcccgg gcaacagagc aagactccat ttcaaaaaaa ataaaaaaat    69360
aaagtgcagt ggctcgttct cagcccactg caacttctgc ctcccaggct cgagcgattc    69420
tcccgcctca gcctcctgag taggtgggat tacaggtggg caccaccaca ctcagctaat    69480
gtttgtattt tcagtagaga cagggtttca ccatgttggc caggctggtc tcaaactcct    69540
gaccttagat gatccaccca ccttggcctc ctaaagtatt gggattatag ttgtgagcca    69600
ccatgcccgg ccctgccacc tgccatcttt gagttcttc cctggagacc tagacctgaa     69660
ccctcctgct tgttctcttg ttatctaata cccctattga cagcgcagct tagatcatta    69720
atggagagct tgacctcatc tgataccttc actgaaggaa acaacttagt gtcttttgtg    69780
ttgaacactg aggtaaaaaa ttggaatagt tgattatatg aactctgcta aaattgagtg    69840 catttttacat ttttttaaggc cttgttgggc cctggttaaa taattatttt taaaaatcct   69900
taaggagcct attataaaca gatctgtggt cttaatgaaa tgtgattaat actgtgcatt    69960
attttaagaa cttttgactt ttcaaaaaac tttacaaca tttcccattt gatagcggca     70020
taggtttaag cacttctcat ctctaagtta gtggacaaaa aaccctcatg gatagtctaa    70080
taatgtttgc tacaagtcca tgttgagttt tatactccat tttatttca gttttaaaaa     70140 ctgtggttaa atatgtgtaa cataaaattt atgttcttaa ccattttttg cgtatacagt    70200
tcgctggtat taaatacatt taaataatgt catggaatca ttgctaccac ccatctctgt    70260 aacctttttga tcatgtaaca ctgaagctct gttcccattg aactctattc ctcctttccc    70320
gccaagtccc tggcaaccac gattcttctt tctgtcttct gaatttgact actttgggtt    70380
ctcatatact ttaggagtca cacagtattt gttttactta gcataatgtc cccaaagctc    70440
atgcatgttg tagcctatgt tagaacttcc taatgtttca ggccaaatac tattccattg    70500 tatgatagg ccacattttg cttttccatt cctctgtcca tggacacttg tattgcttca     70560
tgttttagcc attgtgaatc atgctgttat gaacgtgggt gtacagatag ctcctggaga    70620
ctctgctttc cattttttg gctaaatacc cagaaatgga gttgctttta cattccaatt     70680
ttaatttaaa acattcatat cattgagtgt tttacttaat agtatagtag ttaacaaact    70740
taataaaata gtattttggt aataatttgc tggtagtcca ttgttcagtt tttttaggta    70800
aattacacag acatttcaa gtggacatga aacatcttgt gatgtggaat catgccccaa     70860
gctgatggct aaacatatga aataccatac cctaaattta gtagatttag tctttgcaat    70920
ttaggagata acctgttata ttgttaggtt tttgtcgaaa agctttgtcc tcatatttcc    70980
aacttgctgt aaaatttgtt tgtgaagaca aatattttg tatgggtttt ttcttttttca    71040
```

```
tattaaaaag aaatgtccac attggaatttt ttttggagtt tttagagcta atagagcttt    71100
tcataatgta gtgggaatga gtgatcagta agctcttagc agtttccatg cgtgcatttc    71160
tgtgccttga aataaatgac agatgagtac atttgtgttc tgtgtgtaaa atgtgctctt    71220
tcctcattgc acttccatgt tggagggctt gtctcttggt gatcacactt caaaattctc    71280
acagccccc ttgaaccgtt taggtgttag acggtaccga caaccagtat ttgggcctgc     71340
agattggaca gccccaggat gaagatgagg aagccacagg tattcttcct gatgaagcct    71400
cggaggcctt caggaactct tccatgggta tgtggactac aggtgatgcg ctacaaagtg    71460
gtttgtattc agacctggac atcttaatta tatctttgct tccaagaaga agtcctttga    71520
tactgttttc tgagttctga atagctgatg aaaatgacca attgaggaat aatcatactt    71580
tttcttgatc taaatcttat acttttgagt tatcttagca taaatgtata attgtattt     71640
aagtggaaat ttgtcactta atcttgattt ctctgttttt aaagcccttc aacaggcaca    71700
tttattgaaa aacatgagtc actgcaggca gccttctgac agcagtgttg ataaatttgt    71760
gttgagagat gaagctactg aaccgggtga tcaagaaaac aaggtgaggg acataggctt    71820
gagacgactt ggtgtttctg agcttgtgtg aggatttaaa atcgccctgg ctactgtcta    71880
ctttattgct ttcccatccc tgggccttta aatttcccct ttaaatacca gctcttccca    71940
ggcctgttgt tttctgcctt tccaggtact acccacagcc ttgagaattg cctgagttct    72000
gcctcctttg agagtgtgcc ccagacaaat ctattctgta ctgaatgttt ccttgtctga    72060
tttcttggat cattcatttg atggttgcgt atggcctgca acgtttcttg ttttggttct    72120
actgaactgt tctaaaagtc tctcttcata ttatctttt acatgtaaat gtaactgtct     72180
tcacttttaa ttcctcaagg acaaggaata gcgtttcaca gttcgtccca tcaatcagaa    72240
ttatagcctt tggcatctcc ctatctacca ggcccacttc ctcttagatt tgggcttccc    72300
caggctgttg cctttcccca agtagcttct gcttgtcctg tagaagacct ttcatgcttt    72360
gcttctgcag cagccgttcc tgaatgccta gtgtcaactg ccttcttacc acgcccaccc    72420
tccctgcatg ctgcatttat cccctgccac agccctgtga ccctgtgtcc tgctgcctct    72480
gacttgtctg tttctgcttg gccatggtct ctgtgaggtc aggtgtgcat atgggcacaa    72540
accagggcat ctctttatcc ccagcacctg gcttaagtgc tgctctggaa ctatctgttg    72600
aatgaactaa tgcatgaatg tattgttgag tatgagacaa acaagtgtca ttgtctcctt    72660
tctagccttg ccgcatcaaa ggtgacattg acagtccac tgatgatgac tctgcacctc     72720
ttgtccattg tgtccgcctt ttatctgctt cgttttgct aacagggga aaaaatggtg      72780
agtacaaaag gggatgtgca cagttgaagg aaataactag gtttcagagg tcagcttggt    72840
ggcctgtttt tgccttgcgt gcagcagagg aagtagaatc tgaggatgag tttggttttc    72900
actagccgag gggagggagg aaatgatggg agcaggtagg ttattgggtc tggttttgtt    72960
catttgaaaa caatctgttg tttgaggctg aaggtggctt gggtgatttc ttggcagtgc    73020
tggttccgga cagggatgtg agggtcagcg tgaaggccct ggccctcagc tgtgtgggag    73080
cagctgtggc cctccacccg gaatctttct tcagcaaact ctataaagtt cctcttgaca    73140
ccacggaata ccctggtatg ttaaaagttc acatcttatt ttctcagatt taatcattat    73200
tgtaaaaact atttcagtat tgactatttt agttttagag cagtaagtgt tttgagttca    73260
tttgggatat ttgacctgcg ttgtagctct tcagaaaaca catgaatagt gaagttcttt    73320
gtttcatggg ttccctttag atgaaaccca tagaggagaa aagtagaaac ctcagcacgt    73380
aagagccaac atatatacac atcggattta aacctaaagc acaaattgtg cctggtcgca    73440
```

```
gtggcgctga gtcgcactca gccaggccag gcattcacac tcagggtgag tgggaaccag    73500
gactggctga ggcagcagtg gacccaagtc tccatcgcgc ccatgcttac tatggagcct    73560
tctcgttctc tcttttcctt tgggtgagag ggtacacttg tgtttttgaa tttatatgag    73620
gtaagtgtgt aatagggttt tttctaatct tttttaagtg gaatctggaa ttttaatcag    73680
atttattatc tgacaaccta gaattataat ccagaaagtc tgtggtattg aggacatatt    73740
ggcaatatga tgaatctcta attcttaaat cctgaaactt ttttttttt aatcacttag     73800 ggttattata gtgaagtcat ttctgaattt ggatcttctc ttcacacctc ttttctctt     73860 tcctgagaat taagcttttg tttcgagtta gaaagttgat agtagggaat tgttccatgg    73920
ctgagcaatt tatctccaca gaggaacagt atgtctcaga catcttgaac tacatcgatc    73980
atggagaccc acaggttcga ggagccactg ccattctctg tgggaccctc atctgctcca    74040
tcctcagcag gtcccgcttc acgtgggag attggatggg caccattaga accctcacag      74100
gtaacggcca gtttttcagc tgtgtttttt ctagttatgc ttactaaggt ttaagtttag    74160
atgatgatgt ttgttgcttg ttcttctggt taggaaatac attttctttg gcggattgca    74220
ttcctttgct gcggaaaaca ctgaaggatg agtcttctgt tacttgcaag ttagcttgta    74280
cagctgtgag ggtgagcata atcttctgtg gaaccatttc ttcacttagt ggacatttta    74340
tcattgctac aattaaaatt ggagcttaat aggaaatatt tccatgcact ctaaagctgt    74400
aaccagtaat acccaccatg tatccatctc tcagctttag aaagaaaacg ttgccagtaa    74460
agttaatgct tcataaactt cagtttaagt tctaattctc agaatatttg tttgaaatag    74520
acctcttcct aaaggatata tttagaaata acctatcatt aagtgtaaag tctgttgaat    74580
atgctgggca cggtgactca cacctgtaat ctgaccactt tgggaggcca aggtggaagg    74640
attgcttgag cccaggagtt caagactatg gcaacatag ttgaccctgt ccctacagaa      74700
aattaaaaaa aaaaaaaaa aaagtagctg ggtatggtgg tgcatacctg tagtctcagc     74760
tactcgggaa gctgaggtgg agggggatt gcttgagccc cagagatcaa ggctgcagta     74820
aggcgtggtt acaccactgc cctctagcct gggcaacaga gtgagactgt ctcaaaaata    74880
atagtaataa taatcagttg aattaaaaaa aaaaaaaaa aaaccactgt gctaggccca     74940
tagtatggta agagttaaag tgagccttag ggattatta ctcaacctct gtttctgtat      75000
aaagtggaat aggctcaatt cttaagtga tagcatgttg aacctttcca taccaactgg      75060
ctcataagtc acaactggcc agtcaacaag agtaaaaatt aactggtaaa aatcaaagca    75120 aaaacctac aattgtcaaa tttgtgggat aactcccct tttaaaatgt catgcctgac       75180
agtaatttct ctctagtttc caggttttca gtcagttgtg tcttttttga gcagaaggaa    75240
gcatgctaag agctcaatct tgtggctagc tgggggtctt tgtgtcagcc atgcatgtga    75300
tggtgcccct gggtgcttgg ggctgcaggg gagggtaca gcagtagggg cctgttctgt     75360
tctctcgtgc tgtggagtac atagtgacat agtggggtgg tccttggtgt aggtcccttg    75420
ttcctacccc tgggtctgag atttatttag aagtggtgtt ggggctgtgc ggcaggcccc    75480
tctgtaactg atcaatgttt gtgaagttgc tgtttgagag ttgaaaccat gacataagca    75540
gaaatggaag gaagaaagaa ccagttatgt gaaagggaca catttacttt taagcttgta    75600
tttactgaga taaagtattc ttaatcaatg ttcttgagag gtgtgggaaa aatgcaacat    75660
cctggttgca gttaaaccca gaacattgtg tgttgaagag tgacggttct caaaccgtca    75720
agacgcgggt actgagtggg actaacctgc tgtcctcttg ccttggacct tgtgttccag    75780
```

-continued

```
aactgtgtca tgagtctctg cagcagcagc tacagtgagt taggactgca gctgatcatc   75840
gatgtgctga ctctgaggaa cagttcctat tggctggtga ggacagagct tctggaaacc   75900
cttgcagaga ttgacttcag gtaagtgagt cacatccatt agatttcatg aactaagctc   75960
aattgaaagt tctgggatca cttgatgcaa ggaatgatgt tatcaagtac cctgtccatc   76020
agaaatccga gtggtttagg tagatgacag tgattttctc ctcccagtgg cttttttgctg  76080
aactttgccc tatgcttgga atttttatttt atttttattat ttatttagag acaagatctt  76140
gctctgtcgc ccaggcttga atgcagtagc acaatcatag ctcactgaag ctttgaactc    76200
taggactcaa gtggtcctcc tgcctcagcc tcccgattag ctaggagaat aggtgtgtgc    76260
cgtcacactg gctaatattt tttgtagaaa tggggtcttg ctatgttgcc caggctggtc    76320
tcaaactcct gggcttgatt gatcctccat cttggcctcc caaagtgctg ggattacagg    76380
catgagccac tgtgcctggc ctagaatttt aaaatataag tagaagagta datttttttt    76440
tttggtagtc ctcgtcattt aagtattctg gatagtggga ataaaagagc ttagaatttt    76500
tcatctttgt cttaaacttt taaaaaaatg tagcttatat taattctgct tgtttaaaaa    76560
gaatatactc ttcattatac tgaacctagg taagacagct ggtttatatt ttgttgcaat    76620
taaaaaacgt gagctgtggt tgcagtgagc caagattgtg gccattgcac ttcagcctgg    76680
caacagagtg agacttggcc tcaaaaaaaa aaaaataaca tgagctgtgt tggcactttc    76740
attttctaag agtagttttg gctggagaag ttttctttca gtactttctt ttagaaggga    76800
aattttcctt tataatttag ggtttgtttt tttttttttcc aagccacctt ttatagagcc    76860
cttgtgggtt atttcattta atccttagaa tgtttataaa tctgggcttg ttctcggctc    76920
cacccacaga tagggacgct gagcgtgcat gagtgggcag caagatagca ggttatggag    76980
ggcccagctc accccttctg tggcttgagc caatttttata gggcacttac agagtctttt    77040
gaaatagtat ttatttttgaa gaaaagaaa aacagtttac tgagtactgt cttattgagt    77100
ctggaattgt gagaggaatg ccacctctat ttatttaaag ccattggcct ttttttgttgt    77160
tttgagtaag tgctgcccaa ggtccttcca gggcacctgg atgagcctgc tctggagcaa    77220
gctggcggta agtgtttact gagtaactaa atgatttcat tgttaaatgt gctcttttgt    77280
taggctggtg agcttttttgg aggcaaaagc agaaaactta cacagagggg ctcatcatta    77340
tacagggta agcggtttat ttttgtgaga tgctgtttta ccttcaagaa ggtgaaagtg     77400
aggctttcct tgtggaattt ctctaaatgc attcgtcatg ttttagatgt ttatttcaca    77460
gtttatatca tgaaagttat aatcttgtca tatggattta agtctagtaa tgttgagttc    77520
tttctcacta gctttccaaa atatcttacc taaaatttag tcaaatacaa gattatgttt    77580
atttttatta tccttctctc taaagctttt aaaactgcaa gaacgagtgc tcaataatgt    77640
tgtcatccat ttgcttggag atgaagaccc cagggtgcga catgttgccg cagcatcact    77700
aattaggtat ttaccaatat tttatctctt ttccttttttt ggttgaagta ctaaaagata   77760
cgagaatgga aagagaggga agaattcaaa ggatgtagag cagtattcct gaatctgagc    77820
tcatttcagc cattctattc ttaaactata atgaaaaaaa aatccaaaaa agtctaaaat    77880
tataattaaa aaacaacaa aatactaact gtccattgta aaaagtaatg cactttcatt     77940
gtaaaaattt tggactatag agaatagtac taagaagaaa aaaaaaatca ccttcaattc    78000
tgctgccacc tggaggtaat cactgttaat attttgctat atactctatg agtttcttgt    78060
tcaaaatcag gtcaaaatta catgcaattt tgtaatctga caatttccac ttaatatttt    78120
attagcattt tcctgttatg aaacagtaat tttagttatg ggtcgttgtt ttgctatgcg    78180
```

```
gttgggataa aatttttatat acttttttttg gcaattactt attatacata aatgtttgtg    78240
tatagttttc ttttttctgag aattcctgga agttgagtta ccaggcccgg ctttgaattt    78300
tttttttat ttttttttttg agacagagtc ctgctctatt gtccaggtgc tatctcggct    78360
cactgcaacc tctgtctccc tggttcaagc gattctcctg cctcagcctc ccgagtagct    78420
gggattacag gggcacacca ccacgcccaa ttaattttttg tattttttagt agagacaggg    78480
tttcacgata ttggccaggc tggtctcgaa cttctgaccc cgtgatccac ctgcattggc    78540
ctcccaaagt gctgggatta caggcgtgag ccatggcgcc tggccaggct ttaaatttaa    78600
aacaaatctt ctaatagctt tatggaggtt ataatttaca tttcttgaaa tgtactcact    78660
ttgagtgtat agtaaactcc aattttatca catttctgtc accccaaatg tatccttgtg    78720
cccatttgct gtaacctccg gttcctgccc caactcctag gcagccactc atctattttc    78780
tgtcccttaa gatttgtgtt ttcgccaggc gctcatgcct gtaatcccag cactttggga    78840
ggccgaggtt ggtggatcac ttgaggtcag gagttcgaga ccagcctggc caacatggtg    78900
aaaccttgtc tctactaaaa atacaaaaat tagtcggatg tggtggcaca cgcctgtaat    78960
cccagctact cgggaggctg aggcaggaga atcacttgaa cctgggaggc ggaggttgca    79020
gtgagcagag atcgcgccac tgccttccaa cctgggcaac agagagagac tgtctcaaaa    79080
caaacaaaga tttgtatttt ctggacattt tatagtactg gggtcatagt atagatggac    79140
ttttgcattt ggcttctttt acttaattgt gagattggtt cttgttgtag catgtatcag    79200
tagtttgttc attttttattg gcgaaagtat tctattatat gaataatacc atattttatc    79260
tatccatcag atggatatta tagagttcat gttttggcta atttatgaat tatggtactg    79320
tgaacatttg cctgcaagat tttgtgtaga catgtcttca tttctcttga gtagatcacc    79380
tagaagtgga ttttttaaata attttggtac ttactgtgaa actgctcttc aaaaacatac    79440
cattgttcct tccttccttc cttccttcct tccttccttc tttccttcct cccttcctcc    79500
ctcccttccc tacttccctc tccctttccc tttccttcc ccttttccct tccccttccc    79560
gcctgcctgc ctgcctgcct tccttccttc cttccttcgt ttctttctac atatacacat    79620
ttttttaaat ttcaatggtt tttggggtac aagtggtttt tggttacatg gctgaatttt    79680
ggttacatgg tgaagtctga gattttagta cacctgtcac ccgagtagtg taccttgtac    79740
ccaatatgta gttttttgtc cctcaccttc cagccttccg ccttgtgagt ctccaatgtc    79800
cattatacca cactgtatgc ccttgcgtac ccacagctca gctcccactt ctgagaacat    79860
atagcagaaa catgccaaag tatactccca ctaccagaat gtgattgtgc ctgattcttc    79920
tcaccagtac aaatatttca aaaaagtta aatatgtatc agtttttggg gcagaagttg    79980
atacttctct ttatttattt atttttttttg agataggggtc tcattctatg atgcccagc    80040
tggagtgtgg tggtgcgatc tcggctcact gcagtctctg cctcccaggt tcaagtgatt    80100
cccacgtcag cctcccagga agctggaatt acaggcgagg ccaccactg ccagctaatt    80160
tttgtatttt ttggtagaga tggggtttca ccatgttggc cagactggtc tcaagctcct    80220
gacctcaagt gatccacctg ccttggcctt ccaaagtgct gggattacag gcgtgagcta    80280
ccacacccgg ctgatatttc tttttaaaat aacttacctt cttttgaaag taatacatgt    80340
ttaatgaaca gaatttaagg aaaatataaa aaaacgaaat aatctttgta atcaaactac    80400
tgaaaagaaa accaaagtta catttggtg catattcttt ttcatttttca tcattgtaat    80460
ttgcatttct ttgattactt gtgagacact cctttcattt acttaatagg tttatatgac    80520
```

```
ttgcctattc agagattttg cagctttacc attttctgca aatgatagca acttcttttt   80580
gtttgtttgt ttgtggagac agagtctcgc tctgtcactc aggcaggaat gcagtggtgg   80640
aatcttggct cattgcaact attgcctcct gggttcaagc gattttcctg cctcagcctc   80700
ccaagtagct gggattacag gagtgtgcca ccatgcccgg ctaattttg tatctttagt    80760
agagatgggg ttttgccatg ttggccgggc tgatcttgaa ctcctggcct caagcggtcc   80820
ccctgtctcg gcctcccaaa gtgctgggat tacaggcgtg agccaccgta cccagccagt   80880
agttacttct tatattctag aaaaaattct actcatgatc aagtctccat gaggaaagag   80940
actttaattg aagatcatgg ggcttgcaga ccaatatgat aaaatagttc attgtttcta   81000
aaagtattac tgagtgttga tggcagatat gaacccttt gttttttgtag aaaatgtta    81060
cccgtattct ccatttgaat tcagtttaga tttgttagga atcgcagctt aagctttgcc   81120
atctgggagt gtttgggaca gttttgcaga caaaattgca aaagtgccta aggaatgcag   81180
ctggcattca gacctgctct gtgctcagta ctctgtggac agacactgtt cagcacttgt   81240
tgatcagaag gtttagaaag agaactttca aagttggttt ttaattaaag catttaatag   81300
tgtaaataga aagggattaa attttatgac agacaaaaga aagtacagca cccagctggg   81360
cgtgggggct cacgcctgta atccagcact atgggggct gaggtgggtg gatcacgagg    81420
tcaggagttc aagagttcaa gaacagcctg gccaaggtga tgaaaccctg tctctactaa   81480
aactacaaaa attagccggg cgcggtggca ggcgcctgta atcccagcta ctcaggaggc   81540
tgaggcagga gaatcacttg aacctggacg gcagaggttg cagtgagcca agattgcacc   81600
attgtactcc ggcctgggcc acagagtgac attctgtctc aaaaaaaaaa aaaaagaaa    81660
aaagaaagt acagcaccca gttatgtccg agtgggtgca tgagagtgac cctgagattg    81720
gagacaacgc tgtcacgtgc ttgaagaacg ccacctgaga aagggggcga gaagtggtgt   81780
ccgctggtaa ccagaggtgt tggcttagcc atctgcaggg aggagggtgg tctatcacag   81840
gtgagtttca tctactttct taagcaaatt aaccttactt ttgtgttagg cttgtcccaa   81900
agctgtttta taaatgtgac caaggacaag ctgatccagt agtggccgtg caagagatc    81960
aaagcagtgt ttacctgaaa cttctcatgc atgagacgca gcctccatct catttctccg   82020
tcagcacaat aaccaggtat gctgacccag tggcatcttc acattgtcgg gaaaatgccc   82080
tttcctgatg ccttctttta ggctttaatt gaaaacattt tatttctag aaaaaagctt    82140
cagctcagga tgtttgagtg taggtcagtc ctttgatagg atattatcat tttgaggatt   82200
gaccacacca cctctgtatt taagctctgc cacaatcact cagctgtgac actgtaaatc   82260
tcttaatagt ttattacatt ccatgtgctg acagttgtat ttttgtttgt gacacttacg   82320
tattatctgt taaacatttt tcactttagt tgtgttacct ttaaagagga ttgtattcta   82380
tcatgcctgt tgattttttg gtgagcgggc tattaaagtc agtgttattt agggttatcc   82440
actagttcag tgatttgcga gattatcatt cacattatt gtggagcttt tgaatatcgt    82500
gtcaaatggc cacatatatc ccattcttat ctgcttctta ggtgagtggg acacagtgct   82560
ttaatgaagc tataatcttc agaattctag cttgcagaga agattgcaga agtgataaga   82620
cttgtgctt ttaattttgt cttttaaatg ttattttaaa aattggcttt atatgatact    82680
ctttttttct gctgagtaac agtgttttac aaaacttgga ctaaatgact tctaagctta   82740
aatgatcact tgatgctttt tttctgaatt aggaactcag cttatcaaat atcaaagtca   82800
taattcctga ataaataacg tctttttttca tgtaaagact gctttaaaaa acacatgaa   82860
ggctgggtgc ggtggctcac gcctgtaatc ctaacacttt gggaggccca ggtgggcagg   82920
```

```
tcgcttgagc tcaggggttc aagaccaccc agggcaacat ggcaaaaccc acctctactc   82980
aaatacaaaa aattagccag gcgtggtggc gggcccctgt aatcccagct actcgggagg   83040
ctgagggatg agaatcactt gagccccgga ggcagaggtt gcagtgagcc aagattgtgc   83100
cattgcactc ccagcttggg ctacagagtg agactctgtc tcaaaaaaag acacacacac   83160
aaacaaaaaa aacatggaga cattttttg gccaccttaa tatttcccct cagataattt   83220
cctttgttta aactcagaac tggcattttc tctcttggag aagattcagg acaaatactc   83280
ctttaagata agtagaagca gtgaaagagg atttgattat caggaatttg ataagcttag   83340
aataaattgt tgcttcttaa tgtcatttca gaagatgaat atttattaat agatgccaac   83400
tgagatatca ttaaaattga ttactaacta ctacttggaa aagtctccca gttccaaact   83460
tcagcaggcc tcttgacaat tcagctgtgg tcaattggg cttgcgtgat agatacaatg   83520
accaattgtg cagcagagtg tgctgcttag ctgcctattc tgttagcatt catgtgttaa   83580
cttaaaatca taatctcctt agttttgttg agtgtctccg tggacaagac actgtgaggg   83640
atacaaaatc agattggctt tattcaaacc actggggtat tataattcat ttataattta   83700
ttttattttt tgccttttt ccatgtgttc taaaggaatt agagtttgta tataactata   83760 atggggata gaaattgaca tgtgccatga agggaatgca aaaagtgcc gtgggagatg   83820 agaagtggag aaaggaattt cttttttctt ggaagcagga ataacttcat gaagcatgta   83880
tttcaactta aacagatagt aggcaacgct gtaagggag tatggctgca gcaaaagtgt   83940
tcggggcaga ctgggaggaa gggagggaat aaattcagcc attgttatgg aataatgatc   84000
aaaatttatt ttcagcccgt ttcacttaaa agttgagact gcttaacttt ttttaatctt   84060
taatcttaaa cttttaaatg ccatttgatc tttaaaaata tatgttttaa tagtgtattt   84120
taagtctcta tattttgtt attagaatat atagaggcta taacctacta ccaagcataa   84180
cagacgtcac tatggaaaat aacctttcaa gagttattgc agcagtttct catgaactaa   84240
tcacatcaac caccagagca ctcacagtaa gtctctttct tgatcggtct tactgacatt   84300
gtaatagttt ttggtagctt gtatggccag ttagttgtat ggtcatctta cggtgaggtg   84360
cttgtcttac agctcttact tatccatgag gcttgctaag aaattgtgct tctgtgaaaa   84420
gaatctcagc ttactccagg aatgtaaatg actatgtttt ttctgattat taaagtaata   84480
cacgcccaaa ataaaaaaat tcagccaatt taggaagaca caacaattaa aataagccag   84540
gcatggtggc tcatgcctgt aatcccagca ctttgggagg ccaaggttgg gggctcactt   84600
gaggtcagga gtcggatacc agcctggcca acgtggtgaa accccatctc tactaaaaat   84660
acaaaaatta gctgggcgtg gtggcgggcg cctgtaatcc cagctactca ggaggctgag   84720
gcaggagaat cgcttgaacc tgggaggtag aggttgcagt gagctgaggt caagccactg   84780
cactccagcc tgtgcaatag agcgagactc tgtctcaaaa aaaaaaaaa aaaagaaaa   84840 gaaaaaagta aactactgtc acctgcattg gtaatgtatc agaagtttaa aatgtctaga   84900
ttataattaa ctcagtgacc tggtaatata tactaaggga aaaatattta aatttacat   84960 ttttacattt ttattttttt aattttatta tttttttttt gagacagagt tttgctcttg   85020
ttgcccaggc tggagtgcaa tggcatgatc tcagctcacc acaacctcca cctcccgggt   85080
tcaagcaatt ctcctgcctc agcctcctga gtagctggga ttacaggcat gcaccaccat   85140
gcccggctaa ttttgtattt ttagtagaga cagggtttct ccatgttggt caggctggtc   85200
tcaaactccc aacctcaggt gatccgccct cctcgacccc ccaaagtgct gggattacag   85260
```

```
gtgtgagcca ccatgcctgg ccttacattt ttataataag aatttatgtt gctgacatta    85320
gaaaagaacc ataatatcca agaatccaag aataattaaa ttatgtacat atgctagtat    85380
atagtgtgat gctttggaga attttttaaca atatggagat gtataatctg gattgtaata    85440
ttgagtgaaa aaaggcagaa tacaaacctg gtggggtat agtcggattt cagttaagaa      85500
aaataatatt tacatatata catttctcac actggcagat aatcaccaag ataaattttg    85560
ggattgtgga tgattttttt cttctttata tttttcagat attctcaaat tttctaaaat    85620
gagcaagtat aacttttgtt atcagaaaaa aataatatac aaaagtaatg ttaatttgct    85680
ggtgaccagg ttaaaccttt ttattttat tttttgagat ggaatctcac tctgttgccc      85740
aggctagagc acagtggcat gatcttggct cactgcagcc tccgcttcct gggttcaaat    85800
gattctctgg ccccagcctc ctgagtggct ggaattacag gcgtgtggca ccacacctgg    85860 ctaattttg tattttagt agaggtaggg tttcaccagg ttggtcaggc tggtctcgaa      85920
ctcctgacct cgtgatccac ccacctcggc ctcccaaagt gctgggatta caggcgtgag    85980
ctactgcgcc cagccagacc tttttatttt atttgacaaa agaaatactt ccatgttata    86040
gaagactaaa tattgtttgg gctgtctgca gtatggtctt cccttgattt gttcaaaata    86100
tcgtaaactt tgcttattta ttttattgt ggccgactgt gtcgggcact gttgtaggct      86160
tgggatggaa aaacaggatt cctgcccttta ggtttctgc aggctggtca gggagacgat    86220
gtggtaagct ggagctcagc tcctaaggat gtgcaggggc agttgagagg cggaagggtg    86280
ggagatcatt ccagggtgtg ggcagcacag gaacctctct tcattgggat ataattgcca    86340
ttctgataac acgtgtttga ggtgtctaaa gtaggaagtt gtaccatggt gggacagata    86400
tcctgtggtt atcatacaca gatctcagtt ttcttctcat tgtttgtact ttttataaag    86460
ggtaacagga gatataattc aataaacctt tgtggtgttt gggtgtgatt ttattgtttc    86520
tttcttctca gtttggatgc tgtgaagctt tgtgtcttct ttccactgcc ttcccagttt    86580
gcatttggag tttaggttgg cactgtgggt atgtattttc ctcagtatat attaatagtt    86640
gtctacaaca gtatgacata aacatagtta ttaggatgcc ctttttcttt cttttttaagt    86700 cttttatcaa tttggctttt tggaaaaata tctgatggaa tacttgtttc tgctatatta    86760
gctgtgtgag actagtgaca ggagctgtgg gaaatgaatg ccaaatgttc ttaggcattg    86820
atgggaattt cagggtgtgg tcttcaagtt catttaaggg aattttcata tgctggcaaa    86880
aggcttttct cattagcttg actctttcca aaattatttg ctgtgaatta aagtttagg    86940 aacctttttt cacttaattg tgacctagca tacgaaatgg tgatgattta ggaactactg    87000
ttcttgtatt aacagctttt atttaaaaat gattttcctc cagtagatgg ccctactagc    87060
atctgggaaa taatttcaag tcttctccag cattcaggaa taggctttca ttttgtgtat    87120
caattactga gaatgatttt ggtgactcac atcacatttg agaagtaaac ctgcagattt    87180
cttgtgtgtg tcagcaaatg accaactgat atttgcttga agtggattac attatctgct    87240
ctagaatgat tgctttccca ccttcctcac atacagactg agcagctacg gtttctaatc    87300
ataggtctgg cactagactt cacttctggg caactttggc attggagtaa aatgtattaa    87360
tttaaagaaa gttaaaaatc cgttcaagta aacatacagt tctaatactt tttacaattt    87420
aaaatataga tttaaatgat aaaataaaaa agaaaatatg ggtagacacc ataatcctcg    87480
tttctgcatc tgttcacaag gggttgatat ttatgagttc tattctccat atccattcta    87540
tgttctctta atgctcagtc agcacctcag gtggttggaa ttcaatgctt ggtagtttga    87600
cttacactgt cttttctagg ggattgagcc ctgggtagtc ctgcttattt gaggttgcaa    87660
```

```
tttgtctttc aataactttt actacaagat atggcgtgtt aaaggatacc attggggaac   87720
caacataata atatcaggaa aactaaccac gtcagacctg ccccattgtg tatcaagtac   87780
actattttc catagtaata aagagttcac cccagccaat tctcttttat tttgtgcctg    87840
tttactcaat ggcattaaca tgcccaaatg tctgggtagc tgtctcatct ccagttcagc   87900
agaaccattg tcatatgccc tagtaaaagc attccttcat tggacactta ggccccaata   87960
cttcattca gatctactac ctgatttcat ttctcaaatg attttatgg agctctgatt     88020
tataggaaag atgttagttg attaaaaata aaacaatttc tgagctggta taaaatgtat   88080
tgtgacatgc cttcctcttg gaattgcaag agaaaggaag actgttgttt gcttaaaaat   88140
tgtctataat ttgactttgc aaatgtctgc ttccagagtg cctccactga gtgcctcaga   88200
tgagtctagg aagagctgta ccgttgggat ggccacaatg attctgaccc tgctctcgtc   88260
agcttggttc ccattggatc tctcagccca tcaagatgct ttgattttgg ccggaaactt   88320
gcttgcaggt actggtactg agttgaaaca gggactccag gacttggatt ttgatttcct   88380
taggggaat gggggtggtg agcatatgag gggaaaatac tataaggtca ttgccagtga    88440
tggcttgtcc ctttagtcaa atttcagatg ttacctatat gcataaacac atgcagttgg   88500
cagctgttct gtgctgagta ttttaaagta gcctcttccc aatatagccc ctcagttaac   88560
tacaagtaaa ctcattttga atttcatttt aatgggcacc atatgccagt actccctcgg   88620
gcactgggat gttaagaaag tataatgtat ggacttcatt ctcaagttag ttttagatta   88680
gaggggata cacgtaaaca aaagtgcagt ggtcacacag agtggcccta atcactctcc    88740
ttgggcagat ttatgggctg gtaggaaaga gcacaacacg gagagggtgt agcaccttgg   88800
cgatgataat ggaggatgtg gccagcaagg aagacggagt ccattgaaat tgattttggg   88860
agaagttgcc aatctccatg aaagaattgg ggcctgtgct atttgcttca ggggctata    88920
ggagagtttc gtgaaaggga ctaaaagatg agtattttaa taagatcatt catccaactt   88980
gaacatgggc tggaggagaa ggtagggaga ctcaggagat taatgttgat gctaaggcaa   89040
gataatggct ttgggactgt agggaagaca ctgattgtaa gagaatgaag gaggcagaat   89100
tgccaggcct ggttcaccaa ctgaacttcg gttgtgaaga caaagaaacc tgggatgact   89160
tcacatcctg ggcaggtgtg tggtggtgac agtcatggaa attgggaaca cagatttgtg   89220
cgggaaacat cagtttcagt ttgagttttgg cttatcagtt gaatatcagg cacagatgtc   89280
tggccaactc tcaacatagg gtcttaaatg acttcagttc cccaagcaat ttgtccttcc   89340
catgctattg gggtggagag gtaatgtctg tgcccatatc acagccagtg ctcccaaatc   89400
tctgagaagt tcatgggcct ctgaagaaga agccaaccca gcagccacca agcaagagga   89460
ggtctggcca gccctggggg accgggccct ggtgccatg gtggagcagc tcttctctca    89520
cctgctgaag gtgattaaca tttgtgccca cgtcctggat gacgtggctc ctggacccgc   89580
aataaaggta atgtcccact ggggtgctgg attcatacag ccttaatgac tatgggtttc   89640
cagactacct ttgtttagta atctgtccct tctttattct cttttttgctt taaatgaaca   89700
aaattgctca gattgtgaca ctaaatttaa catcaaaatg tgaccatgtg gatgggtgca   89760
gtggctcgtg cctgttattc cagcactttg ggagactgag gcaagtggat cacttgaggc   89820
caagagttcg agaccagcct gggcaacatc acgaaacccc ctctctacta aaaatacaaa   89880
aaattagatg ggttgggccg ggcgtggtgg ctcaagcctg taatcccagc actttgggag   89940
gccgaggtgg gcggatcacg aggtcaagag atcaagacca tcctggctaa cacagtgaaa   90000
```

```
ccccgtctct actaaaaata caaaaaatt atctgagcat ggtggcgggc gcctgtagtc    90060
ccagctgctc gggaggctga ggcaggagaa tggcgtgaat ccgggaggcg gagcttgcag    90120
tgagccgaga tcgtgccact gcactccagc ctgggtgaca gagcgagact ccgtctcaaa    90180
aaaaaaatta gatgggcatg gtggtgcgtg cctgtaatcc cagctacttg ggaggctgag    90240
gcaagagagt tgcttgaacc tgggaggcgg agtttgcagt aagccttgat tgtgccgctg    90300
cactccagcc tgggtgacag agtcagactc tttccaaaag aagaaaaaaa tgtgaccatg    90360
tgttttatag ctctttagt atcatcagtc actgttatcc ctaagaggga aatacctagc    90420
tttagtttta ggtttccagc attagccaag aaagctcaga attgatgttc ctggccaagt    90480
acctcattgc tgtctcctta aatcttggtt aatggctact gtcctggcta gcatagttat    90540
ggagcatttc catggttgta gaatgttctg ccaatctcag ggacagtttt gcttttctgt    90600
gaagcaataa aatcaacttc aaaacaaatg ttaactattt gtacaatgga tttaagatag    90660
accagttcac atactttttt tttttttttt ttttgagatg gagtttcatt cttgttgcct    90720
gggctggagt gcaatggtgt gatctcagct cactgcaact tctgcctcct gggttcaaac    90780
gattcttctg cctcagcctc tcgaggcaga ttacagctgg gattacaggc atgccacc     90840
acacccagct aattttttg tagttttagt agagacgggg tttcaccatg ttggtcaggt    90900
tggtctcaaa ctcctgacct gaagtgatct atccgcttcg gcctcccaaa gtgttgggat    90960
tacgggcatg agccaccacg cccagcctaa gatagaccag ttcacttact gtttatatct    91020
gattactctc tctttgcctt gtcttctacc tttaaaaatc tccctactaa cttcccattc    91080
tcctttagct gccatcagtc ttctcccttc tctgcaaaca tctctggaga gtcccagcct    91140
cagcccacag agcttcccac tgctctgagg tggaccttgt ttgcaaggct tctttggctc    91200
tcttggcctg gaccctgtct actacttcag ccatccttcc ttaaccctg ctggtggttt     91260
ctgttgccac actccatagc agcgtttccc gcccagatca tgtctttaca tctctgggca    91320
ctgctctggt cctgcctgcc tttccctctt tgtatcctgc aggctgctac ccccatcttg    91380
agtgtcctct tcagttggct ttcagagggc ctcctgggtg ttcccttacc cacttgccac    91440
tccccagtca ctgggttcag tccttcctgc ccaccagcac atgctttcta ggctctgtcc    91500
taggccgtct tctctctttg tagtctctgg gccagtgctg ttctagagag tggcagaatt    91560
ttctataacc atggcagtgc tccatagcta tgccaggcaa gacagtagcc actaaacaca    91620
tatagctgtt gagcccttga aatgcagcta gtgtgactga agaactgaac cccgattcgg    91680
tttaattttc attaaattta aatttaaata accttatgtg ggtagtggct ccagtattgg    91740
gcagggcagc ctgagagtcg gggctgttct cctgtcttca gtgtctagat gagggacctc    91800
agaggacctg tctctggagc tgcagttcaa tgtagccagc tgccccgtga cacttacata    91860
tagctgattt gtggatatgt cagacacggt gtgatgagct cagctttctg tcctcctccc    91920
cacatctgcc cctgccccat ttaccccact ttgtgtctta tcaagctaga aacaggtcac    91980
cacaagtctt catttccact caccaagtct tttgtttccc ctactaaata ttttgcgaga    92040
agaaagtgtg tacctttgta ttcacataca tgtacatgca catatacatg cacatatgca    92100
ggggtcccca acctctgtta aaaaccggac tgcaggccgt gcgtggtggc tcacgcctgt    92160
aattccagaa ctttgggagg ccgagaccag tgcatcacaa ggtcaggaga tcgagaccat    92220
tccggctcac acggtgaaac cccgtctcta ctaaaaatac aaaaaaaaat tagccgggtg    92280
tggtggcggg cgcccatagt cccagctacc tgggaggctg atgcaggaga acggcgtgaa    92340
cctgggaggc ggagcttgca gtgagccgag attgtgccat tgcactccag cctgggcgac    92400
```

```
agagcgagac tctgtctcaa aaacaaaaca aaacaaaaaa aaaaaaaacc aggctgcaca   92460
ggaagaagtg agcaagcatt accatctgag ctctatctcc tctcaggcca gtggtggcat   92520
tagattctca taggagcgtg tatgagttcg ttctcacact tctgtaaaga catacctgag   92580
acatataaag aaaagaggtt taattggctc acagttctgc aggctgtaca ggcttctgtt   92640
tctgggaagg cctcaggaaa cttgcagtca tggcagaagg tgaaggggaa gtaggcacat   92700
cttcacatgg cccacaggaa aaagagagaa ggagagagag agagagacag agagagagag   92760
agaaaaagaa agattgagag ggagagagga gggagaaagg agagtgcctg taggggagt    92820 tgctacacaa aggagcacca gggggatggt gctcaaccat tagaaactac ccccatgatc   92880
caatcacctc ccaccaggcc ccacctccga cactggagat tacaattcag catgagattt   92940
gggtggggac acagagccaa accatatcag agcatgaacc ctattgtgaa ctgcacattt   93000
gagggatcta ggttgcatgc tccttatgag aatctaatgc ctgatgatga tttgaggtgg   93060
aacagtttca tcccgaaacc atcccccgcc aaccctggtt tgtggaaaaa ttgtcttcca   93120
cagaaccggt ccctggtgcc aaaaagtttg gggacctctg cacatatgca tgcacctgta   93180
catggacaca taatacatgt acatatgcat actttatatt ctctgccact tctggtccag   93240
actgatatac tatctcattt ggattactgc actagccttt tgttttggaa acagcatttt   93300
ttaaaaaatt taatttaatt tttttgagat agggtgtcat tctgttgccc agcttggagt   93360
gcagtgtcat gatcatagct cactgcggcc tcgatctccc aggctcaagt gatccttctg   93420
cctcagcctt ctcagtagtt gggactacag gcatacccac catgcccagc taatttttg    93480 atttttttt tttttgaga cagagtctca gcctgtcgcc caggctggag tgggttggcg     93540
cgatctcagc tcactgcaac ttctgcctcc caggttcaag tgattctcct gcctcagcct   93600
cccgagtagt tgggattaca ggcgcctgcc accacaccca gctaacttt tgtattttta    93660 gtagagacgg ggtttcacca tgttggccag gctggtctcg aacttgtgac ctcgtgatta   93720
gcccgcctcg gcctcccaaa gtgctgggat tacaggcgtg agctaccgct cccagccagg   93780
aaacagcatt cttgagataa ttcatataat tcacccattt aaagtatata attcattctc   93840
tttagtatgc ccacagagtt gtacagccat caccagaatc agttttagaa cccataaagg   93900
aactctgtac tctttacccca aaacctccat gcctccagct gcaggcagcc actaacctgc   93960
cttctgtctc tgtgactcta cgtcttctgg acattactgt ggatgggctc atacagtcag   94020
tgagcttgtg actggtgcct ctaccaagc agggttttca gtgtagcagc ctctctgttt    94080
ttcttttttt tttaaattgt gacggaactt ctgcctcccg ggttcaagcg attctcctgc   94140
ctcagcctcc cgagtggctg ggactacagg cccatgtcac catgcctggc taattttttt   94200 ttttttttt tttagtagag atgggttca acatgttagc cagggtggtc tcgatctcct    94260
gacttcatga tccgcctgcc tcggcctccc aaagtgctgg gattacaggc gtgagccacc   94320
atgcccggct aacctttcat ttactgtctg catttcttcc ctgatgcctt ccagtccatg   94380
cacccgattg tagccattca tcctattatg gtttaaggtg actgtcttag tcagcatggg   94440
ttgccataac aaaataccat agcctgggtg gcttcaacaa cagaatttac ttctcacact   94500
tctggaggtt gggaagtcca agatccagga cttcgccctt gccctcatgt ggtgaggggg   94560
tgaggaagct ctgtggggcc tcttatatat ggatgctaat ctcattcatg aggggtctgc   94620
cctcatgacc cagtcacctc ccaaaggccc cacctcctaa taccatcacc ctggtaatta   94680
agtttcagtg tataaatttg ggggactata gacattgaaa ccataacaag cacttttcta   94740
```

```
agatcaggga gtgagtaagt agcagagcta ggacctcaat tccacatgtc agtcatcttg   94800
ccttcactct gctccatgat ggctgcctcc tagagcattg ggagtctcga tgttctatat   94860
gctctcatgt gttgtgtatt ggagatagtt gaggctttat gaatacatct ggatttgttg   94920
acttctagct ttgctggtaa ccagctgtga ccttgaataa gttacttcat ctctgagcct   94980
gtttcctctt ttagaaacag gagtttaaaa tgctgctttg ggttgggcac ggtggctcat   95040
gcctgtaatt ccagcacttt gggaggctga gatgggagga tcactggagc ttggagttcg   95100
agaccagcct gggcatcata gtgtgagatc ctgtctcctc aagaaattaa aaaattagct   95160
gggtgatgtg cgtgtgcct gtggtcccat ctactctgga ggctgaggtg ggaggattgc    95220
ttgagcccag gaggttgagg ctacaatgaa atatgattgc accccatcct gggtgacgag   95280
tgagaccctg tctcaaaaaa gaaaaaaaaa atgctgcttt gtaccccttt catgtcatgg   95340
cgtcatggcc aacatagaat gccctggttg tttgctgttg gagggcatgg gcctggggc    95400 tccctgaggg ctccttccat cttcaactca ttctctgtgc acctgttagg aagttgtggg   95460
ccagtcccta ccatgtatca ttgtgtgggt aaaagtaaat aaaatgtgta cagtgtctga   95520
actgtacata tcagggtcca agaacaaat gagtgacatg ggttagctct ttttaataaa    95580
tggtaaaacc aaatattcta attttcagtt ttgttatact tccatcacat gttttgtttt   95640
ttttgttttt tgtttttgtt tttctatttt aggcagcctt gccttctcta acaaaccccc   95700
cttctctaag tcccatccga cgaaggggga aggagaaaga accaggagaa caagcatctg   95760
taccgttgag tcccaagaaa ggcagtgagg ccagtgcagg taggaaacag cgtggggaag   95820
ggagggacat gagtgcagca tctgtcatgt agaaacatag gatttaagta acttggtgtt   95880
ttagagaaat aaatataata cacatcagta aagtgagaga aagtttctcc aggtgcggtt   95940
caagatatta gaaactaatg actgatgtac acagaccacc ttttggtctg aagcatttct   96000
aagtgccact ggctgacatg cagcccctac agcctccagg cttccagccc tagcatggag   96060
catcactctc ctatgcttcc ctggttgcag gtgatggctg gagaggcctc ctgattttca   96120
gtaagggaag tggtgtagat gcttaggaat agatgtagtg agtgaaaaaa ctgattctga   96180
tatgtcaaaa attctgattg gaaatggaat atttacattt ggaagagcta aaggcgagag   96240
aaagtgggga taaagtcatc tgagttggag gagcttaaac cattcacaag tttggaggac   96300 cttttttttac ccatgaaaag gtcagaacag aaggggctag gatttaggtg tgactgcagt  96360
ttattgaatt cccatccata ctgctctcgg tgggcagtgg caggggcagg agaggagcct   96420
ggcaaagcat gaagtgactg ctgctgcctc tgctatctgg gacgcctggc cacctgtctg   96480
tacagtctcc ctccagaccc attctcacgc tgtctcttgg cacccagggg ccagtgatgg   96540
ttctcccatt tgttttgtgt atatagcatt tatatcaagg ctatttattt atttatttat   96600
tttatttatt tattttttg agacagagtc tcactctgtc acccaggctg gagtgcagtg    96660
gtgcaatctc ggctcagtgc aagctctgcc tcctgggttc aagcaattct cctgcctcag   96720
cctcctgagt agctgggact acaggtgtgc accaccacac ctggctaatt ttttgtattt   96780
tttattagtg gagacggggt ttcaccttgt tggccaggat ggtcttgatc tcctgacctc   96840
gtgatccgtc cacctcagcc tctcaaagtg ctgggattac aggcatgagt cactgtaccc   96900
ggcctattta tttattttta attgacaaaa ttgtatatat ctgtaatata caacatgatg   96960
tttgaaatat gtgtacattg gccaggcgtg gtggctcaca cctgtaatcc cagcactttg   97020
ggaggctgag gtgggcggat cacgaggtcg ggagttcaag accaaactgg ccagcatggt   97080
gaaatcctgt ctctactaaa aataccacaa aaaaaaaaaa aaaaaaaaa agccgggcat   97140
```

```
ggtggctcgc gccagtcgtc ccagctactt gggaggctga ggcaggagaa ttgcttgaat   97200
ctggcaggtg gaggttgcag tgagctgagt tcatgccact gcactctagc ctgggcgata   97260
gagcgagact ccgtctcaaa aaaaaaaaaa aaagaagaaa tacatatgca ttgtggaatg   97320
gctaattaac ctgtgcatca cctcacgtat cattgttttg tggtgagaac acttaaaatc   97380
tactctttca gtgattttct tgcatatggt acattgctat taactgcagt caccatgcta   97440
tacagtagat ctcttgaact cattcctcct gtctataaat gaaattttgt atccttgacc   97500
aacacattca aggtttttt tgagatggag tcttcttcac ccaggctgga gtaccatggc   97560
acgatctcat ctcactgcaa cctccgcctc ccaggttcaa gcaattctcc tgcctcagcc   97620
tcctgagtag ctgggattac aggcacatgc tactgcacct ggctaatttt tgtattttta   97680
gtagaagtgg agtttcacca tgttggccag gctggtctcg aactcctgac ctcaagtgat   97740
ccgcctgcct tggcctgcca aagtgctggg attacaggtg tgagccactg cacccggcct   97800
caagcgtttt aaaagatgct cttttctaag gattgactgt agtacaggag gaagattgac   97860
ctgttgaaaa gcctcagcct ttacaagtgt aaaattatca gtatattact atcatctttc   97920
tgatgaatta ataaaactaa ggactccaag tcaaaagtct tcaaactgaa gtagaatagt   97980
tgtatatagt gcttggcact ttaatattta gtatcggttt aatgataatg tttgtgcctt   98040
tgccgtcttt aaaacatttt tacatcatcc ctgtttgatt acttggtgtg ctcatgaagt   98100
tgttggccac taaggaatct taggctcaga gaggttctgg aattggccag tggtccttga   98160
atcagctgct cctatgattc tctaactgat ttctcacaaa gcaaacaagc aatcataaca   98220
aaacaactgt gcacactgct cttcttattt tgttatttaa aaagtactta ggctctactt   98280
atgtttgtta gtcaatttct cattacttct agttaatcaa aaggtcagag gaaatacttg   98340
aatattttca tactagaata ctttaaaaaa tcatgatttc cagtaatctc tttaaaactt   98400
ggcaagttat tttgatctaa aagtttatct tttgtgtgca tattttttaaa gcttctagac   98460 aatctgatac ctcaggtcct gttacaacaa gtaaatcctc atcactgggg agtttctatc   98520
atcttccttc atacctcaaa ctgcatgatg tcctgaaagc tacacacgct aactacaagg   98580
tatgggcctc tgcatctttt aaaaatatat atgcacacat acttacgtct aatggatagt   98640
tgatgttttt cttatgattt gtaggatgta taagccctt gagatatgag ttacatttag   98700 tttttttcaag tttgtttgtc tttcagcttt gtttatgata gcttctatca tacaggtgtt   98760
ttggattttc atattgtttg tactcacagc taagattgat tacagtgaca gagctaggat   98820
gtgcagccag gttataggg gaagtggccc tggtggagtc tggagggatc cgtgtacagg   98880
cttccttccc tcccgtgagg ctcacacaaa aatacagcaa catgctggtc ctgcaggtac   98940
cctctgccta acatgagcca caattccaga ctcacagaag aaaagcaggt gttcggcata   99000
aaccatgtgt ttcaaatagt ctgggcatgg tgagccactt gttatcagct agggaaagtt   99060
tatgtcagcg taagaaactg ttcaccagat accccaaga gccagccttt ctgtctaggg   99120
atgttttagt ttttttagttc atttttttttt ttaactttaa aattttctgt tcatctgcaa   99180
tttgttagat atgaagtatg tgtctaattt aattttttgtt tttggttgtc cccaataatg   99240
tttacagaag aatttttctg cactaattgg cttgagttac ttacattctc atagttctct   99300
agtttcagta gtttcatttta ttattttgtt atatcaatct atctgtctgc tcatctatta   99360
gaagcatcct tgtttttttt ttttcttttt tagacagagt cttgctctgt ccccaggttg   99420
gagtgcagtg gtgcaaccat gcctccctgc agtctcaggg ctcaagtgat cctcccacct   99480
```

```
cagctcctga gtacctggga ctaccggcat gtgccaccac acccagctaa ttttacatt    99540 ttttgtagag acagggtctc cctaagttgc ctgggctggt ctcaagctcc tggcttaagt    99600
aatcctccct ccttggcctc ccaaagtgct gggattacag gtgtgagcaa ctgcacccgg    99660
ctacaagtat acttcttaat tattgtagct taatggtatt tatgagggga tcagttcccc    99720
tgttgttctt tagaattttc tggatattct tctttattga ttttgggatg tgaacaatag    99780
aatcaacttc tacttgtaga ttgatttagg gagaacttat acctcagatg ttaagtcacc    99840
ctgtccagaa tgtgggatgc tttcctattt gttcagaact ttttaaatta cctcagaagc    99900
acatgaaatt taaaggattt taaaaaaaac ttaaagatta tttcacatag ctcttgcaca    99960
tttcttgata aatgaatcct caggtattcc tctgttttg ttactaatag ttacttctta   100020 tgggttttt ttcccctgaa aatcatttat caaacgtatg tggcttattt tctgaaggat   100080
gtttgataat tttggaagat atgaaagtct tcatatttta caaggtttga ggtctcttta   100140
agctgcatgg ttctcatgtc agctcccaaa gcagaagacg gcatgttgaa aaatgccgta   100200
gagaagatac ttcttttcca cctgttttca actcatatca tcttgaattt cagggcacct   100260
ttccatgctc ctagtgcttg ctatctgttt attattttcc ttcctgaata ccctgaactc   100320
cagcatgttc tgctgtaatt ctggcctccc tggcatcttg gactcctgtt tcctttgctc   100380
tgtcatcccc gcggtcagct cctgctgcgc agcttctcag ctgaagtgcg tttggagtgc   100440
ctggcgtgtc ttgctggatc tttgagtatt gcctctggtt tccttggttc cttctgctga   100500
gttgctcagc gtctccactc cccatttctt gtgtggccct tcctgcactc ctctgattcc   100560
ttttgtcttc cctggtttct tgctttggtt tcgagtctcc acagaacttt tgcagctctt   100620
ctgaagacct ggaagctttt tcatcttaat tctcatctca tgacctcttt tcccttcttt   100680
gagagctaga acttcccatg gtgaacttct cttttccagaa ttccatgcct tcttttccct   100740
cccacttacc tgttgtccag gagaggtcag attgctgtgc atattggagg agaacccttt   100800
cttccctggg ctcttcatct cacatgacat caccacatca cctcgttcct tggaccctca   100860
gtggtgtcac tgctggattt ttctttcctt tggctggcct tagggcacac ccaggttgac   100920
tagcgtagtc atggtattta gatccactca catttcagt ttctgtgtct gtctcttgcc    100980
tgcttctgac ttcgcccaga gaaagcttct cttttcacaag ggttcttaga tttatgttca   101040
ctgagcacct tcttttctga ggcagtgttt taccaatatt tattttccta gtcagtctcg   101100
ccttaccttt cttgttatgc atgtctttgg tcctgaccca ttctctgagt ctgtaaaata   101160
gaattgctgt ataatttaat tacatgaaat cctttagaat cttaacacat cttacacctg   101220
atttaatatt ttattgtatc caaattgaac caaccctatg tgaatttgac agtgattcct   101280
cccagggatc ctagtgtata aggaatagga cttagtattt tctatttttt gatataccac   101340
ataccagata ctgattatga tggacattta accctttttt ctcattatga aagaaagtta   101400
ggaattattt cttccagtag cgccagtgta acctgaaagc ctttgaaaga gtagtttttg   101460
tatagctatc tgaaaggaat ttcttttccaa aatatttttc cagtgctgac aacaaacacg   101520
cagacacacc ctgcaaggtg agtgtacggc gccgcacagt ggaggcatct gctgcagccg   101580
tcgatgtttg tgtctttggt tgtacattat gagatcgtga cagggccagt aaccgtgtgt   101640
tctctccttc accttcccaa ggtcacgctg gatcttcaga acagcacgga aaagtttgga   101700
gggtttctcc gctcagcctt ggatgttctt tctcagatac tagagctggc cacactgcag   101760
gacattggga aggtttgtgt cttgtttttt ctccttgggt tgtggctggc acacttgatg   101820
tgcgtcttct gggctgagtt catctaggat ggagcctggt tctccagggt gcctccggga   101880
```

```
gactcctccc tgccccacgt gcttgcgtca caggacccaa gtctgactct gccttagcca    101940
tgaagtttag ggggaagttt ctatttgtat tctattttg tctgttatca tgtattagct     102000
tagacccagt ttagtttgga aaatcagtgg gtttcaaaat gtgtttgtag agtcctttat    102060
ttcttaactt gaccttttca agtggaaagg ggcaaaacag acgggtaagg gggcggggcg    102120
ggaggtgtga cttgctcttt tgtgcctgag gaagtaacag agctggggtt gacagtcata    102180
ttctctgaca cagatagtct ctgacttatc tcacagaaag tcagcggcag agcctgagtt    102240
aaaagtctcg tagatttct ttttcttttt tttggtggct aatttcagtt ttatttatat     102300
ttgtttattt atttattata ctttaagttc tgggttacat gtgcagaatg tgcagttttg    102360
ttacataggt atacacgtgc catgatggtt tgctgcaccc atcaacccat cacctacatt    102420
aggtatttct cctaatgtta tccctccccc agtcccctca ctcccatgg gccccggtgt     102480 gtgatgttct cctccctgtg cccatgtgtt ctcattgttc aatttccact tgtgagtgag    102540
aacatgcggt gtttggtttt ctgatcttgt gatagtttgc tgagaatgat ggtttccagc    102600
atcatccatg tgcctgcaaa ggacatgaac tcatccttt ttatggctgt atagtattcc     102660
atggtgtata tgtgccacat tttcttaatc cagtctatca ttgatggaca ttcgggttgg    102720
ttccaagtct ttgctattgt gactagtgcc acaataaaca tacatgtgca tgtgtcttta    102780
tcgtagaatg atttataatc ctttgggtat atgcccagta atgggattgc tgggtcaaat    102840
ggtatttcta gttctagacc tttgaggaat cgccagactg tcttccacaa tagttgaact    102900
aatttacact cccaccaaca gtgtaaaagt gttcctattt ttccacaacc tctccagcat    102960
ctgttgtttc gtgactttt aacgatcgcc atcctaactg gcgtgagatg gtatctcatt    103020
gtgattttga tctgcatttc tctaatgacc agtggtgatg agcattttt cgtatgtctg    103080 ttggctgcat aaatgtcttc ttttgcgaag tgtctgttca tatcctttgt ccatttttg    103140 atggggttgt ttgcttttt ttcgtaaatt tgtttaagtt cttttgtagat tctggatgtt   103200 aatcttttgt cagatgggta gattgcaaaa attttatccc attctgtagg ttgcctgttc    103260
actctgatga tagtttcttt tgctatgcag aagctcttta gtttaattag atcccgtttg    103320 tcaatttttgg cttttgttgc cattgctttt ggtgttttag acatgaagtc tttgcctatg    103380
cctatgtcct gaatgttatg gcccaggttt tcttctagga ttttttatggt cctaggtctt   103440 atgtttaagt ctttgatcca tcttgagttg attttttgtgt aaggtataag gaaggggtcc   103500
agtttcagtt ttctgcatgt ggctagccag tttttcccaac accattttatt aaataggggaa 103560 tctttttcccc attgcttatg tgtgtcaggt ttgtcaaaga tcagatgatt gtagatgtgt   103620
ggtggtattt ctgaggcctc tgttctgttc cattggtcta tatatctgtt ttggtaccag    103680
taccatgcag ttttggttac tgtagtgttg tagtatagtt tgaagtcagg tagtgtgatg    103740
cctccagctt tgttcttcta gcccaggatt gtcttggcta tgcaggctct tttttggttc    103800
catatgaagt ttaaaatagt ttttttccaat tctgtgaaga aagtcagtga tagcttgatg    103860
gggggatagc attgaatcta taaattactt tgggcagcaa ggccatttttc acgatattga   103920 ttcgtcctat ccatgaacat ggaatgtttt tctattttgtt tgtgtcctct cttatttcct   103980
tgagcagtgg tttgtagttc tccttgaaga ggtccttcac atcccttgta agttgtcttc    104040
ctaggtgttt cattccctta gtagcatttg tgaatgggag ttcactcatg atttggctct    104100
ctgtttgtct gttattggtg tataggaatg cttgtgattt ttgcacattg attttgtatc    104160
ctgagacttt gctgaagttg ctaatcagct taaggagatt ttgagctgaa ccaatagggt    104220
```

```
tttctaaata tacaatcatg tcatctgcaa acagggacag ttttacttcc tctcttccta    104280
tttgaatacc ctttattgct ttctcttgcc tgattgcgct ggccagaact tccaatacta    104340
tgttgaatag gagtggtgag agagggcatc cttgtcttgt gccggttttc gaagggaatg    104400
cttccagttt ttgcccattc agtatgatat tagctgtggg tttgtcataa atagctctta    104460
ctatgttgag atacgttcca tcgataccta gtttattgag agttttttagc atgaaaggct    104520 gttgaatttt gtcaaaggcc ttttctgcat ctgttgagat aatcatatgg ttttttgttgt    104580 tggttctgtt tatgtgatgg attacgtttta ttgatttgcg tatgttgaac cagccttgca    104640
ttccagggat gaagctgact tgattgtggt ggataagctt tttgatgtgc tgctggattc    104700
agtttgccag tattttattg aggattttca catcgatgtt catcagggat attggcctaa    104760
aattctcttt ttttgttgtg tctctgccag gctttggtat caggatgatg ctggcctcat    104820
aaaatgagtt agggaggatt ctctcttttt ctattgattg gaatagtttc agaaggaatg    104880
gtaccatctc ctctttgtac ctctggtaga attcggctgt gaatccatcc tggactttt    104940 ttggttagta ggctattaac tattgcctca agtttagaac ctgttatcag tctattcaga    105000
gattcagctt ttttctggtt tagtcttggg agggtgtatg tgtccaggaa tttatccatt    105060
tcttctagat tttctagttt atttgggtag agatgtttat agtattctct gatggtagtt    105120
tgtatttctg tgggatcggt ggtgatatcc cctttatcgt ttttattgag tctatttgat    105180
tcttctctct tttcttcttt attagtcttg ctagcggtct acctatttta ttgatctttt    105240
caaaaaacca gcacctggat tcattgattt tttttggagg gttttttttc gtgtctctat    105300
ctccttcagt tctgctctga tcttagttat tttttgtctt ctgctagctt ttgaatttgt    105360
ttgctcttgc ttttctagtt cttttaattg tgatgttagg gtgttaattt tagatctttt    105420
ctgctttctc ttgtgggcat ttagtgctat aaatttccct ctacacactg ctttaaatgt    105480
gtcccagaga ttctggtatg ttgtgtcttc gttctcattg gtttccaaga aaatttttat    105540
ttctgccttc atttcgttat ttacccagta gtcattcaag agcaggttgt tcagtttcca    105600
tgtagttgtg tggttttgag tgagattctc aatcctgagt tctaatttga ttgcactgtg    105660
gtctgacaga cagtttgttg tgatttctgt tcttttacat ttgctgagga gtgttttact    105720
tccaactatg tggtcagttt tagaataagt gcaatgtggt gctgagaaga atgtatgttc    105780
tgttgatttg gggtgcagag ttctgtagat gtctattagg tccgcttggt ccagtgctga    105840
gttcaagtcc tggatatcct tgttaatttt ctggctcatt gatctgccta atattgacag    105900
tggggtgtta aagtctccca ctattaccgg gtggagtct ctttgtaggt ctctaagaac    105960
ttgcttcatg aatctgggtg ctcctgtatt gggggcgtgt atatttagga tagttagctc    106020
ttcttgttga attgatccct ttaccattat gtaatggcct tctttgtctc ctttgaactt    106080
tgttgattta aagtctgttt tatcagagac taggattgca atccctgctt tttttttgct    106140
ttccatttgc ttgttagatc ttcctccatc cctttatttt gagccaatga gtgtctttgc    106200
atgtgagatg ggtctcctga atacagcaca ccaatgggtc ttgactcttt atccaatttg    106260
ccagtctgtg tcttttaatt ggggcattta gcccatttac atttaaggtt aatattgcta    106320
tgtgtgaatt tgatcctgtc attatgatcc tagttggtta ttttgcccgt taactgatgc    106380
agtttcttca tagcgtcagt agtctttaca atttggcatg ttttttgcagt ggctggtact    106440 ggttgttcct ttccatgttt agtgcttcct tcaggagctc ttgtaaggca ggcctggtgg    106500
tgacaaaatc tctgcatttg cttgtctgta aaggatttta tttctcgttc acttatgaag    106560
cttagtttgg ctggatatga aattctgggt tgaaaatact tttttttaaag aatgttgaat    106620
```

```
attggctccc actctttcct ggcttgtagg atttctgcag agagatctgc tgttagtctg  106680
atgggcttcc ctttgtgggt aacccgacct ttctctctgg ctgcccttc cttcatttca  106740
atcttggtgg atctgatgat tatgtgtctt ggggttgctc ttctcgagga gtatctttgt  106800
ggtgttctct gtatttcctg aatttgaatg ttggtctgcc ttgctaggtt ggggaagttc  106860
tcctggataa tatcctgaag agtgttttct aacttggttc tattctcccc atcactttca  106920
ggtacaccaa tcaaacgtag atttggtctt ttcacatagt cccatatttc ttggaggctt  106980
ggttcatttc ttttcactct tttttctcta atcttgtctt ctcgctttat ttcattaatt  107040
tgatcttcaa tcactgatat cctttcttct gcttgattga atcggctgtc gaagcttgtg  107100
tatacttcac aaaattctcg ttctgtggtt tttagctcca tcaggtcatt taagctcttc  107160
tctacactgg ttattctagc cattagtcta acatttttt caaggttttt agcttccttg  107220
tgatgggtta aacatgctc ctttagctcg gagaagtttg ttattaccga ccttctgaag  107280
cctacttctg tcaattcatc aaactcattc tccatccagt tttgttccct tgctggtgag  107340
gagttgtgat cctttggagg agaagaggtg ttctggtttt tggaattttc agcctttctg  107400
ctatggtttc tccccatcat tgtggtttta tctacctttg gtctttgatg ttggtgacct  107460
acggatgggg ttttggtgtg ggtgtccttt ttgttgatgt tgatgctatt cctttctgtt  107520
tgttagtttt ccttctaaca gacaggcccc tcagctgcag gtctgttgga gtttgctgga  107580
ggtccactcc aggccctgtt tgcctgggca tcaccagcag aggctgcaga acagcaaata  107640
ttgctgcctg atccttcctc tggaaacatc gtcccagagc acgaaggtgt ctgcctgtat  107700
gaggtgtttg ttggcccta ctgggaggtg tctcccagtc aggctacatg ggggtcaggg  107760
acccacttga ggcagtctgt tcattatcgg agcttgaatg ccgtaccggg agaaccactg  107820
ctctcttcag agctgtcagg cacgtatgtt taaatctgga gaagctgtct gctgcctttt  107880
gttcagatgt gcccttcccc cagaggtgga atctagagag gcagtaggcc ttgctgagct  107940
gcagtgggct ctgcccagtt cgagcttccc tgctgctttg tttacactgt gagcatagaa  108000
ccacctactc tagcctcagc agtggtggac acccctcccc cagccaagct cctgcatccc  108060
aggtcgattt cagagtgctg cgctagcagt gagcaaggcc ccatgggcgt gggacccgct  108120
gagccaggca caggagagaa tctcctggtc tgctggttgt gaagactgtg ggaaaagtgc  108180
agtatttggg caggagtgta ctgctccttc aggtacagtc actcatggct tcctttggct  108240
tggaaaggga agtcccccga cccttgtgc ttcccaggtg aggcaacacc ccgccctgct  108300
tcggcttgcc ctccgtgggc tgcacccact gtccagcaag tcccagtgag atgaactagg  108360
tacctcagtt ggaaatgcag aaatcacctg tcttctgtgt cgatctcact gggagctgta  108420
gactggagct gttcctattc ggccattttg gaagcatccc ttgttttttg aggtggagtc  108480
ttgctctgtc gcccaggctg acgtgcatcg gcacaatctc ggcccactgc aacctttgcc  108540
tcctggtttc aagcgattct cctacctcag cctccggagt agctgggatt acaggcacct  108600
gccaccatgc ctggctaatt ttttgtattt ttagtggaga tggggtttca ccacattggc  108660
caggctagtc tcgaactcct gaccttgtga tccaccacc tcagcctcct agagtgctgg  108720
gatcacaggt gtcagccacc acgcccagcc atatttcag atctccctct ctttgcccta  108780
aaccactgtg cttaataagt agttttagt ggccagcagt ctccatgtat aacacatttt  108840
agcaaaatgg aaaatactat atgttttaaa tttgaacgtg agattatact gaaataaaaa  108900
tcatctaact gggattcttt aaatagtaag attttctttt ttgtatgtgg gttttttttt  108960
```

```
aaccttatta ttatgactgt catatataga aatggctgtt tttcagttac agtcagtgaa 109020
tgtatcaaat gctgccttat ccaaataata aaagtaaatt attaataagt cacaatttaa 109080
tgaagattga tgttagttga tctttatatt cttgaaatca gccatatggt tgtgtgtgta 109140
tgtatatatt tttaaaggta cataaagata ataagctcat ctctgaaaat ttttacattt 109200
ggcataagaa taactggata attaagcatc ttattctctg gcctgtgtct ttacagttaa 109260
aggtagattt actcacctct cctttttttgt ttttctaagt tcatcttttt tgctgtttca 109320
agacagaggc ccattttagc tttctcgcat atccttttgt ttgtactttg gaagcctcac 109380
ctgcttaatt gttgagtttt tatccgtggt cttttagagg gggatatgta gggtagaagc 109440
tttcacaggt tcttgtttgc acttggcccc tgactgtttt gaggaatctc cctcactgac 109500
tcacagcatg gcaaggtttc agatctcttt ctgccacaca gcagttctga ggcagctgga 109560
aagatatcca gatgcttaga ttgtcaggcc aggcttgaga tatacaaact attgagcctt 109620
atctgtgacc ttgcttaggt gaaggcatca gagcccctgc accaacatgc ataggcctct 109680
gcatgtgtgc ggggctgggt gttgaggtct gagcacaagt gtagctggag aggtgagctt 109740
gatgtggcga cgggtatgag caggttttct tcagacttct gtgagtttac ctagttccag 109800
gatttaaagg cacagagact ttagaattaa aatagaatca ttttctttttt ctaaatagca 109860 acactaggaa taaaaaataa taattccaca ttcttgacag gtaatgtttt ttcttgtctt 109920
ctaatcctta tttattccat actcattttt atacataatt gaaatgtatt atgcattgga 109980 ttttttctttt gcattatatt atagacgatt tttcatgtaa ctccttactg ttccattta 110040 tatgttttgt ctggtttaag actttatctg caaaccggga aactgtctct acaaaaagaa 110100
aaacaaaaat agttggccgc agtggcatgc gtctgtggtc ccagctactc ggggctgagg 110160
tgggaggatt gcttgagcct tgggaggttg aggctgcaaa gagccatgat catgccattg 110220
cactccagca tgggtgacag actttatact gtctgttttg ggtgatttga taatgatatg 110280
ccctgatgta gttttttttat atcttgtgtt tcttgtgcct gggtttattg aggttgggtc 110340
tgtggcttca tagtattttt aaagtttgga aaattttagg ccattctttc tttctttctt 110400 tcttttttttt tttttttgaga cagtgtctcg ctctgtcgcc tgcgttggag tgcagtgaca 110460
ctatcttggc tcactgcaag ctctgcctcc tgggttcacg ccattctcct gcctcagcct 110520
cctgagtagc tgggactaca ggcgcctgcc accacgcctg gctaattttt tgtatttta 110580 gtagagacga ggtttcactg tgttagccag gatggtctca atctcctgac ctcgtgatct 110640
gcccgcctgg gcctcccaaa gtgctgggat tacaggcgtg agccactgca cccagctagg 110700
ccattatttc ttcaaagatt tttttttctgc cctgcctccc tcctttttttc cctctcttaa 110760 aggggctgtg atttcctgaa tgattgctta gtgttgtccc atagcttact gatgctcttt 110820
tcagtgtttg attgttttat gtgttttctg ttttgtatag tttctattat tgtgttttca 110880
agttctctga tcttttcttc tacagtgtct actctgttgt taatctgtta atctgttgtt 110940
aatcctgtcc agcgtatttt tttttttgtt tttgaaacag tctcactctg ttgcccaggc 111000
tggagtttag tggtgcgata tcagctcact gcaacctcca cctcccaggc tcaagcaatt 111060
cttctgcctc agcctcccga gtagctggga ctataggcac gtgccaccac acctggctaa 111120
tttgtgtatt tttattagag atggggtttc accatgttgg ccaaactggc cttgaactcc 111180
tgacctcagg tgattcatcc gcctcggtct cccaaagtgt tgggattata ggcatgagcc 111240
accgtgtctg gcccctgttc agtgtatatc actaattttg ttttatctc tagaagtttg 111300 atttaggtct tttaaaaatg tctccctgtg tttctgttta gctttgtgaa cacaattgta 111360
```

```
ataactgttt taatatcctt ctctgctagt tctaagatct tctaataact tcccagttct  111420
tggtgtttct cattggttga ttgatactcc tcgttttggg ttgtattttc ctgcctcttt  111480
gtatggctgc caattttta ttggatgccc aaccttgtga attttacttt gttggatgct  111540 atatatttt gtgttcccat agatcttctt gagctttgtt ctgaggttag ttgagttaca  111600
tatagatggt ttactctttt gggtcttgct ttataatttg tcagatgggt tggagcagtg  111660
cttagtttag gactaatttt tttttttggac taattattcc tctttaggaa taattaggta  111720
ccatgcttag gaggcaagac catcctgagt actctaccta atgaaccaga aagtttgggt  111780
tttccagtcc gcctgctgag aacagtgact ttctagccct gtgtgagcgc tgagctctgc  111840
tccttctaat cctttccaat gcttctttcc ctggcctcag ggagttttct cacacacata  111900
tctctgctga gtactcgaga gggaccttcc ccagatctcc agagctctct ctgtcttgtt  111960
ttctcttctc tggtgctctg tcttatgaac tgtggctgtc ttggtctcct tagattctca  112020
gcacctcttc aattcagagg gttgcctgtc cctcctcctt gtgccacagc ctaggaactc  112080
tctcaaagca gcgagttggg gcagccatag ggctgactta gtctctcgtc tcccagggat  112140
cactgtcctt cattgctcat gtccagtgtc ttgaggactc tgggttttgt ctgttttgtt  112200
ttttggtttg ctttggttgt ctcaggcagg agggtaaacc cagtccctca ccctcattgt  112260
gctcagtagt ggaagtctca ctctattaca ttagatatta gtatttgtag cagagccctg  112320
gttccctggt acttggggag ctcttgaaag gccagaaaca gcatgctttc tcacctttc  112380 cagggcttca gtttctggtg cacatcaagc attccataca catttgttaa agtcctttgt  112440
tagacaagta gtgattcaca ggttctattt gtaattttt cagttaacat gtattgggta  112500
tctgctggga gctagtaaaa acaaaaagtg gtgtgtgaca aattcaattc tgacaagaac  112560
aaccttaaac acttagaata tactttgagc atatcagaat tttaaaaatg tgtggcccttt  112620 gagtatttga aaccaacaag aatctattgc ttattagtag aggatatttt gttaaacaag  112680
tggagagaga ggcattttca gtctaattgg tgttggcttt tagcagctga tggaaaccag  112740
ttcgtgatta gccaggcagt ggtgaaacag gctgtgcatt ctgaatgcct aggtatctag  112800
gcattcagaa tggtggcgct cttgagtta gcatcttctt cttcttgat tcttttttt  112860 ttttttga gatggacttt cgctcttgtt gcccaggtaa caactccagt gcaatggcgc  112920
catctcggct cactgtaacc tctgcctccc tggttcaagc gattctcctg cctcagcctc  112980
tcaagtagct gggattacag gtgtgcgcca ccacgcctgg ctaatttgt attttggta  113040 gagatggggt ttcactatat tggtcaggct ggtcttgaac tcctgacctc aagtgatgca  113100
cctgcctcga tctcccaaaa tgctgggatt acaggcgtga gccaccactc ccagcccctt  113160
cttgattctt gaaaaggaca ttgggtgctg tacatctcgt tatagatgtt gataaaaatg  113220
cttgtgagaa gagtaacatt aaggtagtta tttggtcatt tttgcagatt attttaagac  113280
aattctagga ctgatttgtg gtaaatcaca cattgctgta tcatagttgt gttcactgaa  113340
catattcagg ggctctacag atgcagggct cttagctgct ttgcacactt ctgaattcct  113400
gccctgcgaa caggactgga tacctaatag acaacaggta cttgataaca gtttattgaa  113460
ttaatgagtg aatgaacaga tacataaatg catgaaagaa tggttgtaat gtatataact  113520
tggatttcaa gacttttttac tgactgttca aaataagaaa ttgaaaactt tcctctgatt  113580
ttcctctact atttacacaa tttaaatgga agttatcttg taccttcaat ttctgtctag  113640
gattcgtaca ataacgggtc atctctgagt cgcttaatgt ctcacttgtc tttctacagt  113700
```

-continued

```
gtgttgaaga gatcctagga tacctgaaat cctgctttag tcgagaacca atgatggcaa   113760
ctgtttgtgt tcaacaagta agagcttcat tcttttcctc ttctgttaag acgttcgggt   113820
atgacagcaa aacgctgcta ctccttaaga ggcaggcgct gttggcataa tcagctggga   113880
ggattgtggg gtccagcgca gcacttttg gctcagtcca tgattgagcc aagaggccat    113940
ccttcccttc actccccagg aggacgaggt ctgtcactgt ggagggcaga ggacaccaga   114000
agctcctctg caacctcgct agttaacttc cagtccctcg gagtttctgt ttagaatgct   114060
caatctcatt tagaattgca aggaaaccca aaacgcctat ttaaggtaca aacagcactt   114120
catacaatat ctcatgaggt attaatagtg attcacagga agaatttcac gctgtgagtc   114180
tttgctaaca tatccagtta tttacagatg gatttgatat ttgtgtggga gattcttaaa   114240
agtgttgttc acgccacatt gttgatgcct catttttttc actgtagttg ttgaagactc   114300
tctttggcac aaacttggcc tcccagtttg atggcttatc ttccaacccc agcaagtcac   114360
aaggccgagc acagcgcctt ggctcctcca gtgtgaggcc aggcttgtac cactactgct   114420
tcatggcccc gtacacccac ttcacccagg ccctcgctga cgccagcctg aggaacatgg   114480
tgcaggcgga gcaggagaac gacacctcgg ggtaacagtt gtggcaagaa tgctgtcgtt   114540
ggtggaagca cgaaagagca agcaggaaat actttgtaaa agaataaaaa cgaaaaatgt   114600
tagcgaacat cttctaatag tctgctgtat tcagagaact ctaggagata tatatggttg   114660
atgcaaagat gatttaaggc atagcccggc cttccaagaa gtgtgtggcc agtgagtgag   114720
atgggcttgg gacttacaca tctcagaggt gggggtagag gaggaggaac actgagtggg   114780
ctgagaagca gccagctctc attgccaaag tgtgtcagca aaccagaatg cagttcataa   114840
tgtccccacc cattcaaagc acaggacctg tagagtggtg tggcatgtgt tggtggcact   114900
tttcaggcct gtaacaagga tgaaagaaca gcttcatagc agcacagtag tgctggtgtt   114960
cagaggtgtg tgaaggccat agaagcatct tggatatatt accttgtgtt ttgtcagctt   115020
tatgactaga agtctctttt cacttaaatt tgttttttt ttttttgaga cggagtcttg   115080
ctctgtcgcc caggctggag tgcagtggtg caatctcagc tcactgcaag ctctgcatcc   115140
tgggttcatg ccattctcct gcctcagcct cccgagtagc tgggactaca ggcgcctgcc   115200
atcacgcctg gctaactttt ttttgtattt ttagtagaga cggggtttca ccatgttagc   115260
caggatggtc tcgatctcct gacctcgtga tctgcccgtc ccggcctccc aaagtgctgg   115320
gattacaggc gtgagccacc gcgcccggcc tcttttcact taaatttatg tttgtgtttt   115380
taatgcctag tatacaggac ttcttaaatt gccttaagta tgaacaggta tttgagttgc   115440
taatctgtat agtagcaata atagaatccc ttgttttttcc ttttataaat ttagcgatta   115500
aatagctaca attaaaacac tagagtcagg agtcaaggaa atacccatg ttccaggctg    115560
tatgttagtg atgtacttac tatatattgg agtttcagga gtaagtctgt ttcaatgctt   115620
tctgtaacca tttggggtat taataagcat gtgagtgtgt gcatgtttgg gttaatttca   115680
tatatgtttc ttagaaggga tatcattgat gtaaatattt taaaggcttg tcctccaaaa   115740
aaatcatgta atttcttcta aattactgat cttttaaatg accttcacct ttctctcaaa   115800
tctcacttaa gactgggctg agtagtcagt ttcctgtagc agaaaaaagc tcagacttga   115860
gtagccttct gcgagtgagg agacttgatg gctgtcaggc agctgtaaac tctaaataga   115920
gtgtcattat ctgaagaggg cgatgctgcc acactgagtg gcctttcaag ttgtttctca   115980
atctgacacg ttctgatcgt gtgaatgtga aattggtttg agcaggagta tatctgagtg   116040
cagaggagat tatttaaaga tattctcatt ctctgcttcc cttttattcc catttggcag   116100
```

```
atggtttgat gtcctccaga aagtgtctac ccagttgaag acaaacctca cgagtgtcac   116160
aaagaaccgt gcagataagg taaatggtgc cgtttgtggc atgtgaactc aggcgtgtca   116220
gtgctagaga ggaaactgga gctgagactt tccaggtatt ttgcttgaag cttttagttg   116280
aaggcttact tatggattct ttctttcttt ttttctttt tatagaatgc tattcataat   116340
cacattcgtt tgtttgaacc tcttgttata aaagctttaa aacagtacac gactacaaca   116400
tgtgtgcagt tacagaagca ggttttagat ttgctggcgc agctggttca gttacgggtt   116460
aattactgtc ttctggattc agatcaggtt tgtcactttt atctttcatc catcatacct   116520
gttcctaatt tagtacaaat taccctaaaa gacactgaaa tctactttaa agaaatgtgg   116580
tctgcatgtt tccctcatca gttgctgctg cttatctttt tcatgcacct agctggtgca   116640
gaaggcctgg ggcatagcca gcctcagcaa gtcagcatcc ttgccccagc tccctggact   116700
caaggctaac ctggggttgg ctgttaggga tttccaaagg tttgtcccat ccacttgcct   116760
cccctccaaa ataagtttga atttaaattg tgagatacaa ttaagattta ttgtttgggg   116820 aacattttg caaaatctag agttagttta aacagattat caattattac cataattgat   116880
catctgcagt ttcaagctat ctaacaggtt cacttacctc tttaaaaagg aatggaattt   116940
agcaggacag taactgagac ccgtgctcct ggagtccatg tgggagctgt gtggctctgc   117000
acaagcattt gcacgcttcc cctcttgact gcattacctt cctcctatag ttgctgtggg   117060
caccagattc tggctagtcc tgtcccttca tgatgcacat tttcctcaag attcgtccca   117120
gttaaatcac tgcagatgaa actgcctttt catcgtcaaa atttaactgt catttttgag   117180
ccgtgatctt gggctacttt cttatgtggg gtaggaatat ttgtgagtta gaaatattac   117240
acttctctat ttccttctag acgtaaatct gttaatcctg tcagcactgt tactcacctg   117300
aaagggtctg tttccctagg agaactgagg gcactcggtc aacactgatt ttccacagtg   117360
ggtattgggg tggtatctgc ttgttttttt tgttgttgtt gtttgttttt ttttgttttt   117420
tttttgagat ggagtctcgc tctgtcaccc aggctggagt gcaggggtgc gatctcggct   117480
cactgccagc tccgcctcag aggttcacgc cattctcctg cctcagcctc ccgagtagct   117540
gggactacag gcacccacca ctacgccagg ctaattttt gtatttttag tagagacgag   117600
gtttcactgt gttagccagg atggtctcca tctcctgacc tcgtgatctg cccgcctcgg   117660
cctcccaaag tgctgggatg acaggcgtga gccaccgcgc ccggcctggg gtctgctttt   117720
aatgaaggag gcatcaaggg gtgggctttg cgttggcctg atgctttcat ctttctttca   117780
caaaacctgt ccgaagaaaa tccgtctaaa tgggccattg ctctcctcag gaaatagtca   117840
ttgggaactt ctttcctt cctttgacac taggaggctg actggggaga gccctggtc   117900 tatggctgtg ggcagcaggg gctgagagga gcaggctctc aggggggcac gggtacccca   117960
agggaagcca gagccctgat tgttccatt ctagtaagaa caaagactgc tctggtttca   118020
tgtttgttct gattgccttt catcaaccgg tcccctttct cccagttctt aagattcagt   118080
acagtgacag ttttatgaac aagaatagaa cactagaaca gacaaaccat tgaactctat   118140
gctgataaag atttattgag ctcctgctgt atgtttgcat tctgcccaga ggctctgaga   118200
aaaccaggcc atatgctcca tgctttatcc atggaagctc cccgtcaggt tgggaaagct   118260
gacagctgca gggaatacag tgtgacacaa aactggctcc catgcagccc ttacgtgtcg   118320
cctctcagat ggttgggga cgaaggtcga ctccctttggg tatcttatta ctaaaccagt   118380
ttcagggaat ctgtgccacc ctatctgcca ttaacgtgaa cagatgagtc cccaaggtgt   118440
```

```
aattttgggt attgtctgat gtctcttgga atttattatt tgttttttcca atgagatttc  118500 acctcagggt atagtaaagt tgttgagggg attcctggat gtgttctgca attatctagg  118560
ctgatttcag aatagagtta tgcttatagt caaatttatc agctgtcaag aatttttattt  118620 aaaatttatg cagataagca ggaggaaaag aagcctggtt tttacatttt aatcctatta  118680
ttgatgtgaa atttttatttt ccttcctgta ggtgtttatt ggctttgtat tgaaacagtt  118740
tgaatacatt gaagtgggcc agttcaggta atagcatttt attatttag attttttcct  118800 tcttcttgtg tacttacatg taatttaggt tattaagtga atgtttaaac tactgttagg  118860 cattttttgct gttttctttta aatggaaatc tgactaacat actgtgcatt tttgcttctc  118920
ttaaaaatta atgtatatct caagacttgt ttggaagtag ttatgtatct gaaaattcca  118980
tatgttgtca gtattcattg cacatttcaa agcatttaat tgtgttgaca gatggtggaa  119040
tgaaatcttg tggtggagca ctagttttta aatcttctta gagaaagcag ttttatataa  119100
tgttgtcttt agtaattatt atgcatttgt attctctgca gcttttttctt gctagatgtt  119160 gaggttttaa tacttcttgc tagtccatta caggtttata attattaaaa gttaaaattc  119220
ttttagtacc taaaatgctt aataaacatt gtaattagga aaatttagtg cagaaggaaa  119280
gtgttcccag attccctggg gtctggaaac atagtgttta ttctaattac atgacacctc  119340
cactgtgttt tggggcaagt tactgttttct cttttgagtt tcaatttctt caagagcaaa  119400 gaggcagagag agagctagga agatcgtagc tgctgtgccc ctgtgccgtc gggtgccttc  119460
tacctgctgc ctccgaacct ttacacatgt ccctgctctg cgcgagggca cagatgggat  119520
gcactgtggc aggggtgggg ttagagtaga tcacggacac ctgttagctt gatgtgtgct  119580
tgctgtcaag gttgaatcat gaattatttt atgttgctta tattgatatg tatcttaatt  119640
ttaaaagaaa ggtctaaatg gatgtttttg ttttaggga atcagaggca atcattccaa  119700
acatcttttt cttcttggta ttactatctt atgaacgcta tcattcaaaa cagatcattg  119760
gaattcctaa aatcattcag ctctgtgatg gcatcatggc cagtggaagg aaggctgtga  119820
cacatggtaa cgggacacac cttttcactgt cgtcttcggt gtcgtgatgt gcttggcagt  119880
gttcgttttc atatacccac tttgaacgtt gtcagtggca gccatgtgct tctcaggctc  119940
tgcatgtgtg tctgtgtatg tgaaggtact ggttagagac gtttcaaaag agaagagagc  120000
atattcttta ctctcagcaa tttgtaatct tctcagggaa aaaaattcaa gaaacagtaa  120060
gataacctaa ggtacagata gattctgaat ataaagttcc tgttcattca catgaaacgc  120120
taaaagttct tcacttgatc ttagccaaaa ggccaagaag cgatgcaaca ctaaaaattc  120180
ttaaatcgaa cttgccgtga attaaatttt gatctctcat ccagtggtat tggagatata  120240
gtttgacttg ggtcagggc tttctgttttt gcctgatgat tttgctggag cttaaataag  120300
gaacccagga gatggccagc tgtgcaagcc cccagcctgt ggaaggagct agtgtggttt  120360
tatgaatgag ttgcaaatct ttctttgagc tttttgaact gatcttccag cattgcccta  120420 ttgaccccctc cctgactcct ttgctggaat ctgtaggctt tgaactttg acagggacac  120480 atcctaagac ccttgcaaac tcccagatgt gagaatggca ctactactta gagtcttttc  120540
gactcagcgt gtgtgcagaa gagcatcaac cgggctgtgt tgcgaggcag ggccttggct  120600
gacctctcag tgtttacata gctaagccag ttagtgtttg ccacggcctc acaagggctt  120660
cagattcaca cagccaaagt atagattatt aaaggcatag gtgtttggtt tcctggactt  120720
ggagggtctt tggacagaaa atcagtaggc aaccacaccc agtactttgt gctgggaagc  120780
ttggtcatct gtgagagggt cagagagtat acccatgcgt gcatgccacc gaagggtcag  120840
```

```
tgagtattcc tgtgtgtgca tgtctcaggg ccggagagag tatgtgtcac tgagaggtca    120900
gagtgtttgt gtgtgtgtca aagagggttg cattgtgccc ttcactgagg ggtcagaggg    120960
tgcctcgcgt gtgtgtgtgt gtacgtgtgt gtgtgtcact gaggggtcag agtgtgcctg    121020
tgtgtgtgct tgtgtgtgcg tacatgtcac tgaggggtca gagtgtgcct ctgtgtgtgt    121080
gctcatgtgt gtgcatacgt gtcactgagg ggtcagagtg tgcctctgtg tgtgctcatt    121140
tgtgagcgta tgtgtcactg aggggtcag agtgtgcctc tgtgtgtgtg ctcatgtgtg     121200
agcgtatgtg tcactgaggg ggtcagagtg tgcctctgtg tgtgtgctca tgtgtgagcg    121260
tatgtgtcac tgaggggtca gtgttcctat gtgctcatga cattgagggt cagagtgtgc    121320
ctgtgtgcca atgaaaggca tttcttatat tttttttatat gtggtcatag tagaccagtt   121380
aatttatttt gactcctgtg ttagaccaaa ataagacttg ggggaaaagtc ccttatctat   121440 ctaatgacag agtgagttta cttaaaaaag cataataatc cagtggcttt gactaaatgt    121500
attatgtgga agtctttatt gtcttttcag atgaatcaag tagattattc ttgagaccag    121560
gaatgttgct gttttggtta tttggaaagt tttatcattt tcaaattgac ttttgaattt    121620
gagtcacctt ttttcagaag tggtgttaaa ttataggagc cctaggtttt ttttcttttt    121680
ttagaagtca tcacaaaatg atcagtgttc agaggaagag ctttgacctt ccacatggta    121740
taatgattga taaccttaat tcatctctta ccataaacca agtatgtgta agggttttct    121800
ttatttcttg aaagcattttt gtagatgttg agagcagttt tccaaatgta atttccatga   121860
aatgcctgat aagggtaccc ttttgtcccc acagccatac cggctctgca gcccatagtc    121920
cacgacctct ttgtattaag aggaacaaat aaagctgatg caggaaaaga gcttgaaacc    121980
caaaaagagg tggtggtgtc aatgttactg agactcatcc agtaccatca ggtaaggaga    122040
atgtatgttg gaactgtcgt ggatacttta ttgacccgtg cagatggaag gaagtgccat    122100
gtggtaacgc tcactgttaa ctgtgttact ttgaaccagg tttgggcttt ctggggcctg    122160
ggtagatgcc ggtgcagggg gatggggagg gaggcggggg gtgggggggt gtggtggagt    122220
tggggaggtg cagtggcagg aagtgttgtt ggtgtgtatc ctttttttttt ttttgagatg    122280 gagtctctct ccgtcgccca ggctggagtg tggtggcacg atcttggctc attgcaagct    122340
ccacctcccg ggtttaagca attctcctgc ctccacctcc cgagtagctg ggattacagg    122400
catgcaccac catgcccagc aaattttttt ttttgtattt ttagtagaga tggggtttca    122460
ccatgatggc caagctgttt cgaactcctg acctcaagtg atcctcctgc cttggcctcc    122520
caaagtgcta ggattacagg cgtgagccac catgcccagc ctggtgttta tctttaaagt    122580
gggcacagcc acaggagttc acctgactcc tggtctgaga gtcacgagat cgttcaagat    122640
agtgaggccc tcttttccaa aacgaggacc aaaaatcaat tgacagtgtt ggtcaagatg    122700
gtagaaacct taaaatgata gaaatctcaa ctctgaaata aaaactttat ttgtatattt    122760
atttaccact atttttgacat agggctaagg tcttttttctt tgagctgatt tctggttttg    122820
ttttcttaaa gtggcataag aattcaaaga cattttgagg aaggctgagt gcagaaatct    122880
ctctttttaa atgacttctc ctttcttttta acttgcactg ttgtctagcc ctcacttatt    122940
ttgtcaattc ttttttagctg tttgtctttg aatcttcata aagccatagc ttttctcata   123000
agaagcagca ctttctttgt tcattcatat tttaatgaac ccctgtagta tttaattaaa    123060
tacttaatgc ctaattaaat cacataattg caatgcaaaa gtacatgtat cataaagagg    123120
tctgaaaatg agcaactggc aagcaggtgg tggcaggcag agctgcttgg gtgggtgggt    123180
```

```
gtcatggaga ggagttcatc agccacatgt tcagtgagct ctggatatgt ctgtttagaa 123240
atgatcacta ataaacttgt gctcaaccat gtatacctct gggaagcagg tgctcttcag 123300
tagattgcct ctgcagagaa cacagaattg aagtgaatgt ccacaaaggc aatgagccac 123360
ctgcagaata gtttagtcaa ggctgtgttt gaagtttgcc aaagattaat atacatttga 123420 tttcatgtt gtgccttttc tctgattgtg aaatattaca aattctatac aaataacaat 123480
gatggcaaat cctcctgagc aaagtgtgca ccttgtatgt gccctagagg aacttgtgtt 123540
tcgttctgat tcccctacat ttctcatgtc atagagtggg ggttgcatta gtgtcccct 123600 gtcctcgctg ggatcacatc tgtttggatc ctagagtctt ccagctgaac tgggacaagt 123660
ataacagacg gacacgtagg ggtggaaagg cgtctcttgg cagcagactt tctaattgtg 123720
cacgctctta taggtgttgg agatgttcat tcttgtcctg cagcagtgcc acaaggagaa 123780
tgaagacaag tggaagcgac tgtctcgaca gatagctgac atcatcctcc caatgttagc 123840
caaacagcag gtttgtcccc gcagccttgg cttgttgttg catagtgatg gtagcttaag 123900
gtccttgtga aagtgggtg gctggaatca gctcttcctt cagtcctaat ctgtgccttg 123960
atagcagttc tccgtgctag tcatgggaca gctgacttca tttcttctca caatgccatc 124020
tcaggttggt attgcccacc tactttacag gggggatccc acagctccga gaggttatgg 124080
aggtgatcag gcagcacaca gctttagagt gctggggtga gggcgggcca aggctaactc 124140
taaagcccga acccttacct cctacactgc ctcctgcatt ctggtcaacc cagtgtttta 124200
tttggtggtt agattttgt ttttgttacc ttactgcttg taatttagca gttttccttt 124260
ccttcccttt cctttccttt ccgacagggt ctcactctgt cacccaggct agagtgcagt 124320
cgtgtaatct cactgcaaca acctctgcct cccaggttca accaattctc ccacctcagc 124380
ctcctgagta gcaaggacca caggtgtgca ccactacgcc tggctagttt tttgtatttt 124440
tagtagagat gaggtctcgc tgtgttgccc aggctggttt taaactcctg ggcgcaagtg 124500
atccaccaac cttggcctgc caaagtgctg gcattacagg tgtgagccac ctcgcctggc 124560
ctattcatca ctaatcagaa tttctatgat caaatgacat gaatcattgt ttccacaact 124620
gcagtggaag gaaatggcct ggcagtgcca gtttcagaag cagcctgccc ccagtcaggc 124680
acaggccact gtgcccccag tgtagcagca cctctgtagc tcacagagaa gggtggtggg 124740
gacctccttg aggcagctct gccagaaaat ctcatgagct gcctggcaca gcttgaggtt 124800
gccttttaag tggactcagc aaatacatgt ttgttcatct tgattataca caataaacaa 124860
ctactctgta tagtacgagt agtccgtggt ttttggcatt tgatttaaac ttagaggcat 124920
gtgatattga tgttactgcc ttcatgactg caccccccatt ctgatttcat aatggaatgt 124980
tatcttgaga ccagttagac aacaggacag ggatcttggc ttctggtgag attgacagca 125040 gtttagtgt ggtcagggtc tccctgccta cagatggttt tagaatggtg ccctggaagc 125100
tttatcccat tcttttctgt gcgtaatctg agtagagtgg agatcgaagg cctgaataca 125160
tagtaaatac ctgacttaat atctgccgca atggaaattg tgtgatacaa catttatgaa 125220
acgcttagtg cagcacctgc caggtagctc accacaggtg catgttgcat tcagaagtag 125280
tgctagatac tatcctgtta ctggcagtgc atacatcagt gatcaaagca gattaaagaa 125340
agaccccctg ccttcttgga gtgaagattt tgttgggatg cgggtaaggg gacagacaat 125400
agaaaagcaa gtgagtgaag tctataccat ggcggctgat caggaacacc gtacagaaga 125460
atccaggagg gaagagagtt aggtggtgtc tgcggtggga gtggcattgt tcagctggtg 125520
atgagaagaa gctttggtga tctggtgaca tttgagtgaa tttgcagaaa ggaaagatac 125580
```

```
aagcctagga gatacctggg gaaggaacat tccaggcaga gcaaatagca gtgcaaaggc   125640
cctggcgggg ggcggacatg ctgttagggt acaagcaatg agggtggagg agtggggcag   125700
ccatggggag ggaagggagt gaggcctggt ggggtgaggc cagtgtggag gagccttgag   125760
agggtttgcg ctgatgtggt gtaggtttta gcaggatcat tcttattcct gagttgagaa   125820
tagccttgag ggggaggtga gggcagagca gggccaccca tgtgagaccc ggcactggag   125880
tggaatggcc caagtcagca tcccttggca gcatgaaagc aaaaccagca aggtttgctg   125940
gtggcttaga tgtggcatgt gagagagagc agggctttgg gggtgatttc agggtgagga   126000
cagggtggct gtgacaagg tagggcagac attgggggca gcaggaggtc agagcctgtc   126060
tggatgtagc agttgagacc ccataggtgc ctaatgaggt gaggccagca tcaggtgtat   126120
gagcctggag ttgtcgagag actgtggggc aggggtcag catctgagat gtccactcac   126180
agtggaccca gactggctgg agaggaggag gagcttgaat accgagcctg ctgagtccca   126240
gctccaaggt caggtaggtg aggggagcca gtgctgggc aggggagta ggcaggtgtg   126300
gggttcctaa agccaagatt tttttaagg catttgtgc aggagggcga catctgctgt   126360
cagcaccttg ggaacttggc ccaggtttgg cagcaccgag ggcactgatg agtgcttttg   126420
gaggagcaaa gggagccaaa ccctaatggg aatgtgttcc tgaaaggaca ggagagagac   126480
ttgggaaaag gtttttacttg aagagggaac ggagaaatag gcagtagcc agaggaggag   126540
aggagtcggc aatgggttaa gttggcagaa atgaaggcct gtttacgcac tgagggcaga   126600
agcaacaggg aggatcagtt catgacacag gagacacaaa tcgccgttgt ggtgttcaca   126660
gacatgggtt aggattggct gcatggatga cagagcactg tgggttctcc cagagttgct   126720
ggggaggagg cagagttggt gagcacaggc gagggtccag gatgcaggaa tcctggagct   126780
caagtcagtt gttcccttgt tgtaagatgt ggccagtgtt gtgagcttca catctgtgcc   126840
ttgaaaaaca ccacatctgt ttgcagagtt gtttactatg tatacacact cagtagaaac   126900
aaaaattgga aacagtcagt gcccaccatc aataagtaat ggttgaacac actgtggtat   126960
aagcttagac tattttagct tgggctattt tgcatgatta aaaatgttct ggccaggtgt   127020
ggtggctcat gcctgtaatc ccagcacttt gggaggccaa ggcaggcaga ttgcttgagc   127080
tcaggagttt gagaccagcc tgggcaacat ggtgaaaccc tgtctctact agaaatacaa   127140
aaagtagctg ggtgtggtgg tgtgcgcctg tagtcctggc taactcagga ggctgaggtg   127200
ggaggatcac ttgagcccat tcgtgcgcca ctgcactcct ggggcacaga gtgagactct   127260
gttagaaaga gagagagaga aagaagagag agggagggag gaaggaagga aggaaataaa   127320
tggaagaaat ggaagggagg aaggggaggg aggaaggaag aaaggaagtt cagccagttg   127380
ccttgggagt tctccattgc actgggttaa gtgagaagag cagagacgtt tatgattttt   127440
caaaacaact aaaacaaaac ctctgtgggt gaggggcaa ggatatggct ataggaacat   127500
ggggcagatt aagaaaggga tatacacaca ccacttagca tttgttacaa ctgttgtggg   127560
agggatggag tgcagaaaaa gaaaaaaaaa agtgcacacc atcccatgta tgtgtataca   127620
aagggacgct tggaagactg gtccccaaaa tgttggtaat gattgtgtca gggtgctgca   127680
gtgctagttg atttttttc acactttgt atatttgagt cttttacaga aagcatttat   127740
tatttatgta ataaaaatct aaatgacaag atttctgtta tggaaaaat gtagctatac   127800
agtgttgttg taaaaatgtt tgcttggttc accactgaac ttaaaatgct tttaaatgag   127860
ggaaggtgac gatgagatga ttatgatgat ttgcccttga gttacatagc tggtgtacag   127920
```

```
gaagctgtcg tttcttttgg cttacgtaga aatgtttgtg gtgtctaatt ccacagatgc   127980
acattgactc tcatgaagcc cttggagtgt taaatacatt atttgagatt ttggcccctt   128040
cctccctccg tccggtagac atgcttttac ggagtatgtt cgtcactcca aacacaatgg   128100
tgagtctctc gcctggctca gcagatgaat ctggacggct tgttcaggct ctgattactg   128160
ggaccacccc cagaatgtct gagtcagtca gtttgggtag ggcttcttga gagtttgctt   128220
tttttttttt tttttttttt ggtgtggggg tggtgcggaa cagagtctca ctctgtcgcc   128280
caggctggag tacagtgtca tgatctcggc tcactgcaag ctctgccttc cagcttcaca   128340
ccattctcct gcctcagcct cccgagttgc tgggactaca agcgcccacc accacgcccg   128400
gctaattttt ttgtattttt agtagagatg gggtttcacc gtgttagcca ggatggtctt   128460
gatctcctga cctcgtgacc cgcccatctc agcctcccaa agtgctggga ttacaggcgt   128520
gagccaccgc acccggcctt tttatttttt ttggagatgg agccttgctc tgtcacccag   128580
gctggagtac agtggcgcta cctcgactca ctgcaacctc cgcctcccgg gttcaagcaa   128640
ttttcctgcc tcagcctccc gagtagctgg gactacaggt gcgtgccact gtgcccggct   128700
aattttttgt atttttagta gagacggggt ttcactgtgt tagccaggat ggtcgcgatc   128760
tcctgacctt gtgatccgcc cgcctcggcc tcccaaagtg ttgggattac aggtggctct   128820
cgcaccaagc caagagtttg cattttttagc aaattcccag gtgaaactaa tgcctgcttt   128880
tctgggagca cactttggga ctcagtgata gagaggttta ttggtaggat agtaaaatag   128940
gagttatttt ctttcacaaa attggcaatt gggggaaatt taatcttcct ttttcttca    129000
gctgtgactt atgtattatg tttatttag gcgtccgtga gcactgttca actgtggata    129060
tcgggaattc tggccatttt gagggttctg atttcccagt caactgaaga tattgttctt   129120
tctcgtattc aggagctctc cttctctccg tatttaatct cctgtacagt aattaatagg   129180
ttaagagatg gggacagtac ttcaacgcta gaagaacaca gtgaagggaa acaaataaag   129240
aatttgccag aagaaacatt ttcaaggtat gcttctctatc tgagcctata actaacccat   129300
gccttttggg aagtcacgtg atgtttcaca gtcagtaagt ctggaataat acctggtctt   129360
gcttcacttc tgagttgggt aaagaagtct gtatcagtgt aattttctaa tccgtcctgc   129420
attatctatg gctcttggtt catacctgtc ttgaagttct gtcatgttct gtctcttgtc   129480
ctcagtagag atgctacagc agtggctcgc ctcaggcagg gcagggcagt gggggtggctg  129540
tcctgggggc aggcagtagg ggcacgctga cgtcaggaa gttgaaaccc aagagaagcc    129600
agtaaaagtg agtctcagat tgtcaccatg tgctggcagt tttacacgct gtcagtaata   129660
aaagtcttct ccctgcaggg cagcctgcct ccaataaata cgtgtagtat caaatcctgt   129720
cttccctcat aaattgtttg gaagctcccc aaggacagtg atgaggcact cgtaagtgct   129780
tgctgcctag atgggtccct ctccacctt gctagattct gagcattcac tgagttagag    129840
ctgcttctgc aaatgctg cttctgctaa gtggctgtga cttcatgcag ccttcacttg     129900
gtttgtcatc agtggagatg ccctgtgttg tcgaaggaga taagcccagt aagcctgctg   129960
ggcaccttt ggtttgcagg ttcagcaggc agcccatggc tttccctgtg tcgcattgaa    130020
gcagctggct aaaattgatg atacattaaa ttcctgtgac agatgatcag cttgtatttg   130080
tgtaatggtg tacagttcac aaagcttaaa aaaatgctac ctgccatttc atcctcagtg   130140
aggaaggtga tacacagaga gaccaagtga ctgtgtccac ggcgacggcg ctctgcattt   130200
cactttagcg gttaatgtac tctacctata ttttttacttt atatttacca tatatctttt  130260
catgtatact tggcgtaagt gctttatagt agtcacctaa ttcactgtca tcttttttgt    130320
```

```
ttcttggaag gtttctatta caactggttg gtattctttt agaagacatt gttacaaaac   130380
agctgaaggt ggaaatgagt gagcagcaac atactttcta ttgccaggaa ctaggcacac   130440
tgctaatgtg tctgatccac atcttcaagt ctggtaggtg aatcacatta gtcttcctgg   130500
agtgtctcgt tccccattct gcactataca ctctcagagt gtaggagctg tgctgcccgt   130560
tagaaactct gccttgccca gtgtgccagt tgaaaatatt tgttgctgta agagtacacc   130620
tgataccatg tgacccagca gttccactct tgggtatata cccaaaagaa tggaaagcag   130680
ggtggtgaaa agatatttgc atgccagcat tcatagcagc attattcacg atagctaaaa   130740
tgtggaacca actgaagtgt ccctcgatgg atgaatggat aagcaaaatc tggtgtatat   130800
ttacagtgga atattattca gccttaaaaa aaggacattc tgacacatgc tacaacatgg   130860
gtgacccctta aggacattat gctaaatgaa ataagccagt cacaaaagga caaatactat   130920
gtgattccac ttacatgagg gacctggagt agttaattca tagatataga aagtagaatg   130980
gtggttgcca ggggctgcag gggagggag ttattttac aagatgaaga gagttattct   131040
agaaatgaat ggtggtgatg gttgtataac attatgaatg tacttaatgc tactgaactg   131100
tacagttaaa aatagttaag aggaccaggt gtcatggctc atgcctgaaa tccaagcact   131160
ttgagaggcc aaggcaggag gattgcttga gccaaggagt ttgagaccag cctcagcaac   131220
atggtaggac cccatctgta caaacaaact agccggggat agtggtgtgc atgtggtccc   131280
agctactcag gagactgagg ctggaggatc gcttgagccc aggaggttaa gtctctagtg   131340
agatgtgttc atgccactgc actccagcct cggctataga gtaagaccct gcctcaaaaa   131400
aacaaaacaa aacaagacaa gagccaaaaa tggttaagat gggccaatca cagtggctta   131460
tgcctgtaat cccaacactt tgggaggtca aggtaaaagg atcacttgaa gccaggagct   131520
tgggaccagc ctgagcaaca tatcgagacc cctatctcta caagaaaat caaaaactag   131580
ctagatatgg tgggcacatg cctgtagtcc cagctacttg ggaggctgag gtgggaggat   131640
ctcttgagct caggagttcg aggctgcagg gagctattat tgcactccag cctgggctac   131700
agaatgatac cctgcctctt attaaaaaaa aatccaaaaa aaaaaaaaag taaacctgag   131760
agcttcctcc tcctgtgtta aatttggagg ccaagatgtt tttgttactt ttacaaatga   131820
tcaaggacgg tgaaggttgg gcatggtagc tcacacctga aatcccagca ctttgggagg   131880
ctgaggcggg gtgatcgctt gagcttgaga ccagcctgga caacatagca agagacccca   131940
tctccacaaa aataaaaaaa taaaaaaaaa tagccaggag tagtggcatg agcctgagcc   132000
caggaggtca agctgtagtg agccatgatc atgccactgc actccagcct gggcgagatc   132060
gagaccatgt ctctagagaa agaaaatgac aaggacagtg aacccaagaa agtcataaga   132120
tgccagctgt gcagcaagca tggaaagcag ccagtccaaa ttaggacagt gtgttttcca   132180
agaagaacga tcgtttgtaa tgagaatgct ttgctttaaa taaatgacta aatagctaga   132240
agcctagttc taggggatag gcacgtcttt cttctctcaa gaaaatagaa aggcaattct   132300
aatttctagt aacagcaaac agcattaagt catggtccaa atatgaggca aaccaaaatg   132360
tggcttgatt gttcagcagt tgatctgttg gaagcccttg atattaaaaa ggttctcctt   132420
taagcggctt aggagtcacg atcaaagacc tatagaaaga gatgccatcc ttctaggatc   132480
cttggctctc ttgggaacta gattcagata gtcataatgt aaatactgct tgagctttct   132540
ttctttcttt cttttctttct ttttttttttt gagacagagt ttcactcttg ttgcccatcc   132600
tggagtgcaa tggtgccatc tcggctcacc gcaacctctg cctcccaggt tcaagcaatt   132660
```

```
ctcctgcctc agcctcccga gtagctggga ttacgggcat gcaccaccac gcctggctaa    132720
ttttttgtat ttttagtaga gacagggttt ctccatgttg aggctggtct cgaactcctg    132780
acctcaggtg atccacccgc ctcggcctcc caaagtgctg ggattacagg tgtgagccac    132840
cgcacccggc ccgagctttc attttttgaaa tcaatgtatg actgaaacac tgaagactta    132900
ctgacttaat tatggtttca gaacagaatg aaaatgtctt cggttctgat gaatataaaa    132960
ggaaaactaa ccaagttaat ttggcaagta gatggtagag atagaggtgg ggagtggaag    133020
gggaactaaa atcttcacct agcattgttg ggattatatg gttacatcat ctgaagttga    133080
cagaccaaaa tatagaggct tcagaggtct ccaaatagaa ctaaacatgt aattcagatt    133140
gttaggaggt agtataaatg agctaaatct catctttatt acggtagagt taatgggtga    133200
tgtctaaagt tgtctgaagt ctataaatca tgacaaatta tgatgtggtg attgtattca    133260
acagtctttc agttgcaggg ataaaacccc agtttaaact agagtaagag aaagaatgtg    133320
ttggtttaag ctcctggaaa gtgcaggcaa gggtagttgg taggactgca tctagtgttg    133380
taattctgtg gtctgcattg tatatttatg catctcagct ctgctttctt cttttcattt    133440
atataatttt taaattttat tttaaagata gggtctcact ttgtcgccta ggctgaagtg    133500
cagtggcatg aagtgcagtg cgaggctcac tctagcctcg aactcctggg ctctagagtt    133560
cttcctgcct cagccttcta agtagctgag acaataggca tgtaccaaca tgcctggata    133620
ggttttaaaa tttttttgta gaaatggaag tcttgctgtg ttgcccaggc gggtctttaa    133680
ctcttagctt caggcgatcc tcctgcctct gcctcccaaa atgctgaggt tataggtgtc    133740
acccaccacg cccagtctca tctctgcttc ctgtgttagt tttgttctct ggtgggctgt    133800
tttcacatga ccgaagatga cctctagcag gctgtgttct cagcccctca agtaggccta    133860
tgtgattggc cttgcatgag taatatgggt gaccataaac ccctgaatgc tctggtccac    133920
atgggccaaa tgggagactg acagcattc cattgatgag gaggtggggc tggtctccgg     133980
gagtaaggga gaggagcaca tgcagtaact gatggtctgc tgcaagggat agcagcacag    134040
cagttagaat tttggaggta actaccagaa ctgaaaacag aaatgataac aagtagttgc    134100
cttaaaaagg gatgggagca gggtgctttt gtgatcaaag ctcctttctc ttactggatt    134160
tttgtacaca ttttgcatac atatcttaga gtaaaagata gcattttcag ccttggtcca    134220
tttgaggata ctcttggcgt ggcccgcctc catgctagca ggctctggtt gtgccaagtt    134280
cagttgagca tcctggctct tgcctgcacg gaacttccag tcagtgcgtc agtatcacaa    134340
gtcttgatat ttcctatgaa gaagaacagt agtgcagtga cagacgaaat gggtgggcag    134400
gcagaggcag gatttctgag ggagagaagt agctagcttt ttgcagagaa gagttccggc    134460
acccaagaga gcagctgaga gtacaggcag gcaggcagga tgccggtagg gcccggccgc    134520
acggcgccac agaatcctgg agaaaggggc ctcttcatgg cctctgcatt cagctgctgt    134580
caccctccgc acaggccatg gccaaaattt aattttcata gtggactcta gttttgagc     134640 cttacttgct attattgaaa taattttctt gtttcttttt aaagatcttc ggattatgct    134700
tcactgacca ctgtaataag tttaaagttg agaaaatatg gcttgttaat gaatgatagg    134760
tcaattttag tatgttggtc attttaatat tttgccacca gttggtttgg atttgatgcc    134820
aggaggagac agcctcattt ctaaggacta gtcttgcctt tgtgggataa gggtggtgtg    134880
ttctgtgtcc ttctacatgt ccgagcgatc tctgtgcagc tcaaatgtgg tcactgtctt    134940
attgcgctga tttcctctcc ttccatctca caattgaggc aaaatattgt tactgttgaa    135000
gtgttgtcca ataggacttc cagcagagac aggatgtctg cactgtctaa tttagttgcc    135060
```

```
tttagccaca tgtggtgttc tgtacctgaa atgtggctgg tctgattgga tagcttaatt   135120
tataatttta tttaattta attaacttaa atttaaacag ctctgtgtgg atagtggctc    135180
ctgtatgaga cagtgcaggt ctgttgagaa gcagctttac tggtgggagt ggagggcttg   135240
gagagggcac gtgggtttcc tgctggtatc ttttgacctt atttaatctg cccaacattt   135300
gcaagtaagt tgtgtgtgtg tgtatatata aatgtgtgtt tctgtcttct tgtttccttt   135360
gactgcattt atttgaaaga cactaggtgg cagaattact gtatttgatt ggtttcaaga   135420
taagagttga aataattcat ctcgtgtttt tatataagta aggtgtgttt agcatgtaaa   135480
attggtaata tgtattcacg tactgcttaa acaaaggcta tgaattccac ccataaaccg   135540
aaaatgaaga cctttaaatt tgtccatttc aggcgtgggt acttcttaaa taatacctgg   135600
ttcaggaact agtcagaatg gcacccttga ctttttgttt cctgctttc ctcttgttgg    135660
gagaggaggg tattcatccc aaagtggttt gcctatttca cattccatct aggataagca   135720
gaatagccaa gaaagatagc tgtcctcctg tttacaacat tggggtaac cagcatccct    135780
ctcttttggt ccaagataga ctggtttaga aacagatgat ggcaccagag gcccaggagg   135840
tggaaacatc agctttgttt gttgtccatg tggctgaatt agagctgtct ggccttgtag   135900
cctcaacacg gccttccagc tttgctcacc gtgatttca aggacacatc ttgtgctctt    135960
ccctgcctgc catccagact atacccagtc agggtggcag gagctgctgc cccttcctcc   136020
ctgagtcctg gtcgtgggtg gtggagatgt gccatgacgc tcacggaggc atgctcaccc   136080
cttcctctgt ggcagagggg atggctgcac gacagctctt ccctgtcctt tccaaagcgt   136140
ctgtggttcc acttttgggg gcaaagcagg aatactggaa gagagagaaa gtggtccttt   136200
ctatagtaat aaagttgaca ttgattcaag ttcatgcttg gggaaaggac agggctacta   136260
acaattataa tgctgggagc aatggaattt tctcatgggt atgtggtagg tttaattta    136320
attatcccag ttaattctta gaactgctct gtgaagtatt tcccgctttg tgcttaagtt   136380
ctaaaagatc ctgtgccaaa accaagaatg aaaacccaag cattcttct tgcccatcga    136440
tctttctctc atcaggccac ttcttgggtt gatagtggtg agtgtagccg ctgccacttt   136500
cagaatacccc accatgggcc ccagtcactg tgtggcgtgg agaagagatg gttctctctg   136560
tgtcatagct gaacaagccc agcccagaga ggtttctgcc ctaggagctc tcgatggtgg   136620
aattgggatg cgatcccaca tcctgcctgt tttgaaaaca gcattcttta tttccaattc   136680
ctgcttccat tgttcctttt aatatttctt tgtttagctc acaaaaacac ggcttgcgga   136740
gctgctgcgt gcagctgtag ctgtttctct gggtgcagcc tgcatccgcc ttcctgcccg   136800
cctcctttcc tgcactgcca tcgtggtctc cgggcacttg gtcccttct cttcccctga    136860
gtcccttgg ctccctgtg ccaccttgt gatccacagg ctctgccttc tttctgtctc     136920
agactgctgc tcatcactac tcgggaccct aggaagggag gttccaccga gaagcatctt   136980
ctcatctcag ccacgttctc agtgccactg ttgtctttgt taggtaatgg tagctactgt   137040
aacaaataaa ccaacatttc catggcttca caccagagaa ggttgttct tggttttatg    137100
acaatgtatt gagggtgttc ttggttcacg gatggttttc ctccatgtgg gaattcgggg   137160
acccaggctc ctttccttct tttggttctg ttctccaggc cttacatcc tctgtgtctg    137220
gttggggaca aggagaggga aggtaaagaa ggctttgtgg ccttggataa gtgacaggca   137280
tgcctttgct ggtgttctct cgtggtgaca ggtcacagcc ccaccctgta aaagggggact 137340
gagagacgtc gtcctgctgc ttcccagcag cagcactgtg gtctctgatg tgttttctgt   137400
```

```
gaggataaaa acaggtgatt ccaggatgag gaaagtcagg gaaacccttg gaaggagggg    137460
accaggcggg tgtcaccatg ggattagtgg tggcttcaga atgagctgca gcgagtgcca    137520
tgccttctaa agcttttgct attctgatat gcccacacca tgcccagcag gtgtctgcct    137580
tgctctccgc agagagagtg atgaatcctt ctcatgagcc tctgtccagt tgttcctccc    137640
tccacctgga agggaccctg ggttcctcat aacatcccag cggaacaggg gaccttctat    137700
cctgtcccca agttcatcct catcctcctg ccggcttcct ggcccctctt atgtctgctt    137760
cctgacgcca catccttctg gattctctgg aattgaattt tgcctttgat gcttatttaa    137820
aaatatccat tgcaggccag gtgtggtggc tcacacctgt aatcctgtgc actttgggaa    137880
gccaaggtgg gcagattgct tgagcccagg agtttgagat tagcctgagc aacatgttga    137940
aatcctgttt ctatagaaaa tacaaaaatt agctgggcat ggtggcgcac acctatactc    138000
ccagctactc aggaacctga gacaggagga tcaattgagc cccggaggcc aaagctacag    138060
tgggctgtga tcgtgccact gtactccagt ctggtcaaac agagtgagac cctgtctgaa    138120
aaaaaaaaaa aaatccattg catacttcac cgtagcgaaa catgtatgtc ttacctttcc    138180
tttcctgcct gtagctgctc ttttacactt aacagccaca ctaagccagc cttaaatgaa    138240
aaacaaacca gcacttcctg tgccctcctg cttccttcat gaggggtccc tccctctgtg    138300
tacactccat tctcattgcc catggtggtt tgtttccctc ttgtttctca agccatggca    138360
gcctgcctct tgccctcttt actaaaaagg cctttgcaga ggctgcctgt gttctttctt    138420
tctaggtctc tctcatccta ggccctccag cttgattctg tggagctgcc ctcttgtcac    138480
tcagtagctt gtggggtctt ctctgtctag ccacttaatt gattgtgttc ctcgagttgc    138540
tgtccatggt ctctcgttac tgttttctct gtgtttctgc ctctctcctt ggccttggta    138600
ggtccatccc ctttgtgacc ttggctgttg ctctcatgga caactttctc ttgctggtcc    138660
ttgtagtcct ggcatccagc ttctcgacac gggacttgtc ctgccagtac ctcagacttg    138720
cacttaaaat tgaactagca ccactgtcac tctccagggc ctcttcttgt taattagatc    138780
attagggatg ttcagaatcc cagcatcata gtatgttcct cctcccgcta ccccaggaac    138840
cctaacctta cctcctcctc tctatctact aggaggtggc cctcagagtc cgtctcatct    138900
tccacctgaa cttccctaat aggctccagc agctgccacc ccgggggctg agtacttcct    138960
ccatgccttg tgcagtgctg agcccttttac ctggggttctc ctgtttgctc cttattacag    139020
ccctgcgaac agatactgct cttaattcca tcttacacct aaggaagctg aggccccagg    139080
taaggtgcat ccaaggtcac ccaggtagta gacagtagag ccacgatctg aaccaggcag    139140
tctgattcag agcctgtgtt gacactcagc cacctagaac acagcttgga ttgtgggttt    139200
ctattacctg ttcaaaaccc ctacatcccg ggtctgtccc tgcacgtgct ctgtggcctg    139260
gctgcatctt ccttgaaggc agtgcatgcc tcttcactca gggggcccat gcaggaacag    139320
agggccccac agaaggatga ggccagtgca gaatgggctg gaggggacaa tgctgaccag    139380
gaagcaagtg tagagaaatc ccaggaaacc tggaggagcc agagacaagg cattagaact    139440
cctcgtcgtg acctggtctg cattctctga gtgtgctgct tctgttagct cgcttccttg    139500
gtctcaggtt atagtttaag gcattgtgga gccctaaaaa gcctgtactc tgttttacc    139560
tgttttagga ccctttcact ttggggatgt gttgattttt tttttttttt tttttttttt    139620
tttgagatag agtctcgctc cattgcccag gctagagtgc agtggcacga tcttggccac    139680
tgctgccccct gcctcctggg ttcaagcaat tcttgtgctc ccgcctccca aatacctggg    139740
attacaggca cccgccacca cactcggcca atttttgtat ttttagtgga gacagggttt    139800
```

```
taccatgttg gtcaggctgg tctcgaactc ctgacctcaa gtgatctgcc caccttggcc  139860
tcccaaagtg ctgtgattat aggcgtgagc caccacaccc ggcctgaaat ttaaatcaga  139920
aataaaattt tgatcccaac agtgatgcca ggcagcccag atctggggga gagggtggcc  139980
ttggccagct gggcctttct ctgtttccca agtcttgctg cctctccctg ctgggctttg  140040
cagcctgtgc atgtctctgt gcctttgacc ttgtttatcc aaaggagagg atagaatgaa  140100
gtcatgattc ctggagccct gagaaggatg ctgtggagaa atttgccggt agaatctagc  140160
tgagtgtgtt gctgaggtgc cagcattgtg tgtgggagg ctgaccgctt ggcctgccta  140220
ggcccaggat gctccatggc cgggcacaga ggccacttgg ctgtcaggtg tcaggagcct  140280
gcagagggca cacagagcct ggaccgcagg ggggtcctgc tttctcacct ggcctccttc  140340
agcatttctg tccctcagtc cttagcaagc ccaggagctg ttgagtttgg caggtgccga  140400
gtgctgttcc tgcctgtgta gctgtggctc agtcctgtgg gggccccgct gtggcccgag  140460
tgcagtgatt cgaggcgctg agtgttccct gactccttct ccaggagctg tgttcagact  140520
ttcgcagctc ttggcttgga gctcctggag gcttggcat tgccgaccaa tgtggaggtc  140580
gacagtgaga gaggaggaat gctagctttc ttgaccagtc cattaaataa gtgggatatt  140640
ggccaggcac ggcggctcac gccttaatcc cagcactttg ggaggctgag gcgggtggat  140700
cacgagctca ggagttcaag accagcctgg ccaacatggt gaaaccccct ctatactaaa  140760
aatacaaata ttagctgggc gtggtggcag gcgcctgtaa tcctagctac ttgggaggct  140820
gaggcaggag aacagcttga aaccggaagg tggagtttgc agtgagccaa gattgcgcca  140880
ctgcactcca acctgggcaa caagagcaaa actctatctc aaaaaaaaaa aaaaagtag  140940 gatatctgtt tctgcttaga aaatcagaa ttttctaaat gccaggtgtt ctgaatacgt  141000
aagtatggga gacgactcag cctgtttcat ttttatgtaa aatcttcgcg tagccatgtg  141060
gcactggacc gagatgaaag caaagacatt tctccttaac tttgtttcta ggaatgttcc  141120
ggagaatcac agcagctgcc actaggctgt tccgcagtga tggctgtggc ggcagtttct  141180
acaccctgga cagcttgaac ttgcgggctc gttccatgat caccacccac ccggccctgg  141240
tgctgctctg gtgtcagata ctgctgcttg tcaaccacac cgactaccgc tggtgggcag  141300
aagtgcagca gaccccgaag taggttcata atgccccaca gcccagggcg ccagcccagc  141360
accctgtcct gagactccca gtaacctgag cttttggccac cgttaaagca tttttcatttt  141420 ccatttttg tgagggcttg tgaaatttct gctgcatatt aatattcctt tcatggacag  141480
catattattg ggacaaacat gcggtccagc taaaggcatt caaaatagca gttgctttct  141540
aaatgcgatt ttctttggca ggttctttga caccattgca tcttgtggga tatgcttgtc  141600
atgctctgtg gctcctacta agttctagtc cttaaattgg ttccatagcc agacatgttg  141660
caatgtctta acctcattat aaagtaaatg tggttctggt tatccttaga taatgaagta  141720
acagtgtagc aaatttcaaa acctcttgga aatgttattt taccattcaa aaaggcttac  141780
taaggttctc gttatgggtg gccctctttt tgcaaaaggt tttcaggctt aagctccatt  141840
tctaggtgct ccaacactcc attatttgta tatgtatgga aataaaagct gtgaccaccc  141900
ccaaccctgg ccccgcccca gctgaatcct cagcacagta tttctggaag ctcaagatc  141960 ccacgctggg gaaaagaagt tctggagaca aaagagggca ggtgctgccg tgcctctctg  142020
ctcagtatgg atactggacc ttgtgctgcc agggctccca gtagggccag ttcatggcac  142080
tcagctggaa agtccactgt tgggaggcat tcttaaccat ccactctgtg ccgtatgtag  142140
```

```
tggggtctgg tcattctgtt ggaggagaca gaccagtgac gacatttgaa atgcttggtg   142200
gatgtcttag gcctgttacg atgactgagc actgtggggg caggagacag aaagtcagtg   142260
tctcctagtt ctgtgctgct ttaacgtgca tagaaatcag ctgcggattc agcagatcac   142320
tccttttctg acagatgggc ctgcttactc tgatgttata tcagaaagct ctgaatctgg   142380
gaattgtgtc ccctgaattg gagtaacaga aatgcttaga tgatgagtgt ttaaaagaaa   142440
taaaccaaag gtaaatttag tttggaattc agcaagcgtc ttcattcagc cctctgaggg   142500
caaactacag cttttttgtaa atgtaggtaa attctgtgac tgtttcgtga cccctctga   142560 tccagttttc ctttataacc ttctgtattg ttccttctat tatcctgaaa taacattaat   142620
agattaggct gggcgtggtg gctcatgcct ataatcccag ccttggga agccaaggcg   142680 ggcagatcac ctgaggccag gacttcgaga ccagcctggc caacatgatg aaatgctgtc   142740
tctactgaaa ataacaaaaa ttagccgagc atggtgacag gtgcctgtag tccctgctac   142800
tcagaaggct gaggcgggag aatcgcttga acctaggagg aaaaggttgc agtgagctga   142860
gatcgcgcca ctgcactcta gcctgggtga cagagtgaga ctccatctca aaaaaaaaaa   142920
aaaaaaaaaa aaattaatgg atcaatggat ttttaaccta ataattaaat ttcaaaaaat   142980
atcgttcttt aatggtaatg taaaggtaaa attaagataa tatgtaacaa gcatgtgagt   143040
gtctaaggtg tccccgtggt ggaaggaaaa aataaatccc cataagtgtc caagatgccc   143100
atagagagca gagctgttct ggtttaaacc cctgctctta gcactgtgtt tttccagctg   143160
tgggtggtgg gggatgagta tctttttatt tccatgagat gagaaaaatg aattactaga   143220
agtgtgaaat acaaaacaca gctgctcttt ttttagccat agactcagca gccataaaat   143280
tgctgtatcc agttgcagaa attcctgctg cttactcttg accctctctc ggtttgtgtg   143340
catctcctct caggctggct cccagatggg agctggctcc aggcgacact gggtgctctg   143400
ctccaggagg tccttatgtg ggtcctgccc tagcctagcc cctctcttat ggactctgtc   143460
actgtgggtt tatgattcac tctcaatctg tcttacctct tggtgaactg ttagagtcct   143520
gcctatactt tggcgcttgt gggtgtgttg tggtacacat gatgtgttgg tcacttccca   143580
gctcatcttg ttctgagtca ccctagattt gggacattca ttcgccacca gtaccgggcg   143640
gtgtatggcc tgagatttgg gggggcttgt gctgctacaa attggggctg aatttgagtt   143700
gacagtggac cttctttatg tctactgctc atatttgaat tgcaaatact gcctcttctc   143760
tttcagaggc tcattaccct atagctgtat tattgcaaag tgcacaatta cagcttgagt   143820
gtaagtcaca ctgcgctggc aggacggccc actgagaaag ggcacgtttc ctgttcgtta   143880
gttttcacat tgacacataa tttacaatac agtaaaatgt acttttctat caactgtagt   143940
cagtaacagc ccccctcccc caaccacatc aagatataga ggagtgctgt cacttcaaac   144000
agttccctct tcctctgcca catcctgccc ctccccaggt ctaaccacca atccgtgctc   144060
tgtccctctg ttcagcccat tgcagaaggc catagaaata gaatctatag gctaggtgtg   144120
gtggctcatg cctgtaatcc cagtattttg agaggctgaa gtgggaggat gacttgaggc   144180
tgggagttca agactagcct gggctgccta gcaagacccc atctccagaa aaaaaaatt   144240 taaaaattac aatcacgtcc ctgtagttca gctgcttggg aggctgaggc aggaggatca   144300
cttgagctca ggagttagag gttacagtga gctatgatcg tgccactgtg ctccagccta   144360
ggtgacacag caagacgttg tctctgggga aaaagaaag aaacggaacc acgcggtgtg   144420
cagccttctg agtctggccc ctttcggtga gcagtgtcta aagttctgtc gcgtgttgcc   144480
cacgcgtcgg tggctcgctc cttgcaactg ctgagcattg tatggctagg ctgtagtttg   144540
```

```
ttttcacttc accagttggg aaacagagaa aaggcacttt ttaaaaagtt taaatctgta 144600
gaattttggt ttttaccagt tctcttctaa atcctgaggg attacaggaa aagttgttgt 144660
atttcagaat attcttagct tgatgtgacc tctgtccccg ttaaggccct ttgccgcaat 144720
gggaaggacg tcgctcggtc agaccctgaa ggtcagaggg gcagtttggg agtgtgtcaa 144780
cattttaact gtatggacta gagccaagag tctcaaggtt tataattccc acgtattcaa 144840
aaagaaaaaa acaataaagt gagaagtcag tgtagagtga aataacctgt gttagtgggg 144900
aagaagtgtt tttaaacagg atttccataa cgtataacat caacatgttt agagtggtga 144960
tgtttcattg ggaaacgaac agtaaaacat gaaagcaggg aggttttcat tctggcagtt 145020
ggcaactttc acggcagatg gagaatttca aaagcaattg ctcaattatc aaacatagcc 145080
agtgtgagtt ctgaaataaa ggtgctgatt gaatgtgcag cttatgtgtg gattttgcta 145140
ttcaggcaag cattttaatt ttctgcctgt taaattctgt tttctttagt ttttcatatg 145200
tggtttattg tagcttagga atagataact gagagtatat attacacata caacattctg 145260
atatggcaat atttaaaaca acttgtctgt tttagaacta gaattaaaca taatcatctt 145320
cagtattttg caaataagct cactgccatc cagaaacatt gtcaatgcat ctgttgctcc 145380
ttctagaaga cacagtctgt ccagcacaaa gttacttagt ccccagatgt ctggagaaga 145440
ggaggattct gacttggcag ccaaacttgg aatgtgcaat agagaaatag tacgaagagg 145500
ggctctcatt ctcttctgtg attatgtcgt aagtttgaaa tgcctgtaaa cggggttgag 145560
ggaggtgggg accaggagaa catcctgtgt agatgacact tgcatggacc ctctggaacc 145620
cagaccgccc ggtgtcctgc caagctccat cgaaactaaa tctagaatga atgtttactt 145680
ctgctgtgac atataattgg agaccaggcc tggccttcca gtcactggat tctaagttgg 145740
actgtgagag ttttttgcagc tgactcattt atcaaatgcc cggctattgg ctcacgccta 145800
catgatgctg ggtatgtttg ttaatttgag ggaagcaatg gaataataat aactaatgat 145860
ttaaaaaaca aagtaagtgc attgactgta gtggggttct gatttttaaat ttttttaaaa 145920 attaatacca ggagcagtgg cttatgccta aattccagca actcgagagg ctgaggtagg 145980
aagatcactt gagcccagga gtttgagaca agcctgggct atggtgtgag acacccatct 146040
ctaaaaaaat aaaaaataaa aaattatcca agtgtggtgg ctcgtgcctg taatcacagc 146100
tctttgagaa gctgagggcg gaggatggct tgagcctggg agttcgagac cagcctggca 146160
acacagagaa accctgcctc taccaaaaaa agaaagagag gaagaaagaa aaattagcct 146220
ggcgtggtgg tgcatgcctg tggtcccagc cacctgagag actgagaagg gaggattgct 146280
tgagcccaga gtttgaggc tgcagtgagc tgtgactgtg tcactgcact ccggcctggg 146340
tgacaaggcg agaccctgc tctaaaataa tttttttaag ttaatttgta gaaaggtgt 146400 tagatgttct ttgtcacatt ttatgatgga ttcctgttta aatgccgttc tctttaaaga 146460
aaaaaaaata acttgtggga gtttttaacc ataaaactag catcacatat ttaccatgga 146520
gaatttacaa aaaaacaaat aaacggagga aaataaaacc tcctgtaatc atactactca 146580
gagataactt gctgttagat tttggtctag atttaatact ttttctatat ttatattaaa 146640
aatatttaaa acatatgcat ttctttgtca caaacatggt atcttataga tactactgtc 146700
acatagcaaa acagtgttaa atattctgaa tcagaaaagg aagccgactc tccaactgaa 146760
agaggtgtta tcctagagac ttttttctggt gatgacaatt tattaatagt cacttttgc 146820 tttactttct ctattgaagt agttttttcta ttttgttcta cttttaagga taatataatt 146880
```

```
tataatgctg tttttcacag aaatataaga aaaaagatac taattttata agttaataaa    146940
gtttgatcat cccaaatcca aaaatctgaa atccaaaatg ctccaaattc tgaagctttt    147000
tgagtgctga cattatgttc aaaggaaatg ttcattggaa ggtttcagat tttcggattt    147060
agggagctca acaaataagt ataatgcaca tatttcaaaa cctgaaaaaa atcctaaatt    147120
cagaatactt ctgatcccaa acatttcaga taagggttat tcaacctgta ctgtcagatg    147180
atcccaaatg aaaatatta atcgttaacc aaatatcaag gaattgatca cattttacag    147240
tttctgccta ggattatgaa tcaagatgaa aaggctctgc atgtttaaaa atatatattt    147300
ttattttctt ataaatctta aatatctaca cttaagattt atttgatatg tgggatccat    147360
tcatattttg gattcaacag ttctgtcaaa actgtggcag tgatagggga ttcttttttt    147420
cccactgaac tatcacaaaa ttggaaaaag agtaattgga gaaccccact ggcttagccg    147480
gcccgaagcc cgggagaggg caggcagtgc tgtggatggg gtcatcccag cgcaacgctg    147540
cccctgctac ctgcggatct cgctgaggcc tgcctttgtc ctttgaccct tggccatttg    147600
ttagtgtctc tgagagctgg actgctgtac cctacttccc caggggggcct aacttcacac    147660
agcctctgcc gcagtgcgtg gttggaggtg acggccttgg taaatcgagt ttcctacctc    147720
ctcaattatt tgtgctcata cactgtatat ttttagtgag gttatatttt gggatgtgtt    147780
ttctccttct tacccttttct ggcctttcta tggcattaat acctggtctc ttcttgtgta    147840
cttgaaaatg aatctctcat catatttttc cttagtgtca gaacctccat gactccgagc    147900
acttaacgtg gctcattgta aatcacattc aagatctgat cagcctttcc cacgagcctc    147960
cagtacagga cttcatcagt gccgttcatc ggaactctgc tgccagcggc ctgttcatcc    148020
aggcaattca gtctcgttgt gaaaaccttt caactgtacg tcttcatcct gccgactatt    148080
gccagttgca gttttccctg ccttaaaaat ggagtattga aattttttaac tttaatttct    148140
gatttgcaaa atagtcatct tttgttcttt tccttcttgc tgttagccaa ccatgctgaa    148200
gaaaactctt cagtgcttgg aggggatcca tctcagccag tcgggagctg tgctcacgct    148260
gtatgtggac aggcttctgt gcaccccttt ccgtgtgctg gctcgcatgg tcgacatcct    148320
tgcttgtcgc cgggtagaaa tgcttctggc tgcaaattta caggtattgg gaagagaaac    148380
cctgatattg atttatattg aaaatttagc aggccaagca aaacaggtgg ctggcttttt    148440
cctccgtaag tatggtcttg acatggtcac cgatagaaac atggaaacat ctgcaaactt    148500
gccgttactc gtgtgtccga tctgactgtt tcttgtattt ttttctagtc tgcccttact    148560
aggatgaact gtacacatca gttcatcctt tttaatgag catgaggtta ttttgggttg    148620
ttaggtgtta caaacacact aatgtgtttt tgtctattag agcagcatgg cccagttgcc    148680
aatggaagaa ctcaacagaa tccaggaata ccttcagagc agcgggctcg ctcagaggta    148740
atgctggaaa cacaggtcgt ccttgtgtta ggacaaccca ggatataaag gatatagatt    148800
tgtacgggaa taaattcaca ggacaagaaa tcgatgtgcc ttataggtgg gtttactgca    148860
gaagtgccat aatagaacct tcctactttt aaaacaacca gatctcactt tctaaagagt    148920
aaaggatgac cggcaggatc acgtctgtga cgtgagtgga ggcagtttgc actcctggtg    148980
gctgtttgag aggtagcatt tagaatgcct gtattcactg tcctgtgatg agtgggaaaa    149040
taggttatca ggtttatctt agcaaaatca aagcatgtca tctaattgct aaacaagagt    149100
tggcaaatct gagagacatt actcaatcct tggcatgcag gacttacatc tgcatcctgt    149160
tgccatttta tgtcttcaaa gcatttaatc atttagttgt gtttgcaaag tctttgagaa    149220
gcctttgtca gaaatcccta catctcctat gtgagtgtat ttccatgact gcagaataag    149280
```

```
ttaaactttt accttttttcc ttcccttgcg gggcggggtg gggggcaggg attgtgtgtg   149340
tgagagggag agagagacag cagagaagga gaatataatt atcatgctgt gtactttgag   149400
ctgaaactgc aaaaaaggaa aaacacacaa aaattattat gcttttcagt ctttagagta   149460
ccttgtctat tatgcttttc agtctttaga gtaccttgtt gatggtgttt ttaaatggga   149520
ttgggcacaa ttaggtggac agtttgggat gattttttcag tctgtagggc caagctcttt   149580
tgtaatttgc attatgaagt tgtcactctc atagcagatg gcgggagata aactattatt   149640
acttttttgac cctagactta gtcttcagtc cagatgaggg agattaaaag attataaata   149700
tcttgtgcca gatgaggtga tttatttttg aaatgaccat gaattcctat cagttgtctt   149760
actgggatat ttgatagtgg aatttgtgca tttgagtctt agatgatctg ttttacattt   149820
attaagaaag ccttattag ctttttatact gtgtattgcc tgttgcagtg tttgagtata   149880
aatgaaattt ctggaaaata ttaatggagt acaaactgtg atacttaaaa gtaaactagg   149940
gcctgcattt gtatcatgac ctgttttgagt attgatgaga agatagctgt gaagaaaaag   150000
gtttaaacaa gtgtattttc ctttaagaag ccactaatag tgcatctcct tagagtgtat   150060
atttctagaa tcctagtgtg cagagtttag actaagacta aaaaaaaaaa aaaacaaatt   150120
atactgtaat ttcattttta tttgtatttt agacaccaaa ggctctattc cctgctggac   150180
aggtttcgtc tctccaccat gcaagactca cttagtccct ctcctccagt ctcttcccac   150240
ccgctggacg gggatgggca cgtgtcactg gaaacagtga gtccggacaa agtaagtgtc   150300
cagcgtgtct gcatgggagg cacagggcgc tgagtgcctc tgtcacctgt ggcagataca   150360
gagagtgcag aggaggtgcc gtggacccaa ggagttctgg cgctcggctc ggctcagtga   150420
agctgtggtt agagacgtgg ggggccatca aggtctgagg gagccaagca gtgctgatgt   150480
gggaccctt tggtaggagt gtggggtgag tagttagtgg gtgaatcaag gaatagtcgg   150540
ccgtggcctg caggcccctg actgcacagg ccttcaagca catgtcaatg ccgttagcct   150600
ccctccatct cctcatacct tctggccacc tgtgagttgc actgccactg ccagccattc   150660
tggtatgttg tcagcacctc cactgctcat acctcatggt tagggaccac ctggagcctt   150720
ggtagagcct tggtagagcc ttggtactct actttcctgg acaaagttca gcttatgaat   150780
atgaatttag atttcaaaaa ccagcagccc aagtataaga agcgaaggt tcagtcctgc   150840
cttcttaggc tctattcgct aagcacctgc cctgccctgg ttgctgggga gagatgagta   150900
aagcagacaa cccaggagag gatggcaaag gggccgctaa cccttagtgg tttagctata   150960
tttggaaggc ctattggaag ttcaccaggt gaagggggag gctgtgaggg tgcccaggca   151020
ggtaacagaa gtccaaaggg gaaaacctgt ggtgtggtga gccgtatagc cacagcctgc   151080
cggccggcag ccctctcagc ctagtgcggt gttccaagc actggcctag gcctgtagct   151140
ccagggatgt gaagtcccct tgaacgccgc ccatcatgtt ccccttatcc atttttttct   151200
tcccaggact ggtacgttca tcttgtcaaa tcccagtgtt ggaccaggtc agattctgca   151260
ctgctggaag gtgcagagct ggtgaatcgg attcctgctg aagatatgaa tgccttcatg   151320
atgaactcgg tacgggggga gcagtggagg caaggaatcc tcagctttc ttgtgacttc   151380
caagtgggat ttgtctcatc atcatgtgac ccacttgttg acaacacatg ttggggactc   151440
cagtctgggc agggacggga tgtcggagag actccactct gaatgggcc gggaagtggg   151500
gaggactcca tttcagatgg ggtcgggaca tgggggttat gctgatcgag acagaaaagc   151560
acattgtttc agccacatta gaatccacgg aggtgttgtt ttgaaatcca gctggcccca   151620
```

```
aggctgggtg tatggtttgg gatgagaact atctggcctc cactggagga acaaacacag 151680
gatgttatca tctaagctcc atggccaaga cagaatggaa gtcaaggttg cgtatttgcc 151740
gtagacttca acacagtgtc gtaatgcgtg acgtcaataa cttgtttcta gtgtcttgga 151800
agttgatctt tagtcgtaaa agagacccct ggatgcagcg agatttcctc tactcacacc 151860
tctgttagat gtagtgaggt tcttcacccc ccaacccag atgtcagagg gcaccctgcg 151920
cagagctagg aggccatgca aagccttggt gtccctgtcc ctcacccgtg ggcaggtcct 151980
gtgagcagtg ggggggccac ctcttgggta tggtgcagcc atggcccaag cagggcttct 152040
tctcagacct actaggacgg gagaaacctc ctggtgcttt agccctgcgt tgatatgcag 152100
caaatgggag ggaagtgggc acctggggagg acaaatgcct gtagaggccg ggagtgacgg 152160
caggtgttca tgaaaagaga ccttgtgggg agggcaacac aacagtgtgt tctgatgtac 152220
tgaagagctc aactgaaaac aacaggagaa ttagcccaaa atccatttac taaaattgtt 152280
tatctttttt ttttttttg agacaaagtc tcgctgttgt cccccaggct ggagtgcaat 152340
ggcgctatct tggctcactg caacctccgc ctcctgggtt catacgattc tcctgcctca 152400
gcctcccaaa tagctggtat taacaggcat gcaccaccac gcccggctaa ttttttgtatt 152460 tttagtagag acgggatttc accatgttgg ccaggctggt ctcaaactcc tgacctcagg 152520
tgatccgccc acctcggcct cccaaagtgc tgggattata ggcctgagcc accacgcccg 152580
gcctaaaatt gtttatctta agattcatgc agtgaaagct aacttactga gtgataaatt 152640
tgcttagtga tctgtttatt aggttttcca aatttgctaa ttgggctttg aacagctgta 152700
aaagttctga ctgtaaaaga aagcttcaac ttttggcatt catgatgctt ttctgagtat 152760
taaactaaga tagatgtttt acctgaagga tcggccacca atctttaaat ggctaaacaa 152820
aagggttgct aaaacataat ccaaattgac ataagaaata ccattttcc aaccaaaatt 152880 ttggcattca tatggctact tttacgtatt tcagctgcat ttgaacatct ttttcaaact 152940
ttagggtggt tggtgtatca ctgaggtctt ggatgacact ttagctttga ttttgttttt 153000
atgaattaaa attgtcatac caaaattttt atttcaagca aatccaagag cataaaaaat 153060
taaaatatta cttaaaatac taagagagaa cagatatata ttttactaag catatgttga 153120
atgaaattgt tcaaatattt ataacaggca tagagtagaa ttttcttaaa aatattttg 153180 atggtatacc aatttgtatt ttctcagaaa catttgcctt attctttttt ctgttgtgtt 153240
tttcttacct gattgaaagc tcataatctg ttgttattgt ttgttaacct ttaatgctct 153300
gatttcagga gttcaaccta agcctgctag ctccatgctt aagcctaggg atgagtgaaa 153360
tttctggtgg ccagaagagt gccctttttg aagcagcccg tgaggtgact ctggcccgtg 153420
tgagcggcac cgtgcagcag ctccctgctg tccatcatgt cttccagccc gagctgcctg 153480
cagagccggc ggcctactgg agcaagttga atgatctgtt tggtaattaa aattaaaatt 153540
tatcttattt ttaaaaagca ttccaggggcc agtatagtac tttgcaccaa gtaaatgtac 153600
aataaaggca gtggatctaa tacattgaaa gcgtttacag aggtagctaa agagcagcac 153660
gggtgtcctc ggctcagaat ttcttcctgt gtgtttgcca cttttgccatt cattgacatg 153720 gtcatggaca tagggctcta agcccttgag gaaggctggg ccagacctca ggggagatgc 153780
agccccaaac cacgtgcagt cctgtggacg gatgtgtaga tgtgccactg aggaacaatg 153840
tcttgagctt tcatcagatt ctcagagaat tgcttgactg cctttcgaag ttgatgcatc 153900
tgtgctcacg tttgcaccca cccacgaggt ccttctgttt caggggatgc tgcactgtat 153960
cagtccctgc ccactctggc ccgggccctg gcacagtacc tggtggtggt ctccaaactg 154020
```

```
cccagtcatt tgcaccttcc tcctgagaaa gagaaggaca ttgtgaaatt cgtggtggca 154080
acccttgagg taagaggcag ctcgggagct cagtgttgct gtggggaggg ggcatggggc 154140
tgacactgaa gagggtaaag cagttttatt tgaaaagcaa gatctctgac cagtccagtc 154200
acttttccat ctcagcctgg cagtaagtct tgtcaccgtc aagttattgt agccatcctt 154260
caccctcacc tcgccactcc tcatggtggc ctgtgaggtc agccaggtcc ccttctcatc 154320
tgcacctacc atgttaggtg gatcctaatt ttagagacat gaaaaataat catctggaag 154380
tactttatgt cttaagttgg cctggacatg tcagccaagg aatacttact tggtttgtgt 154440
tagtgcttgt aattcgcccc cagaatgtgt acacgttctg gatgcattaa agtctggcct 154500
gtatccttaa agggccatcg ctgtgctgcc tgccctcagc aaggacacac tttgcagacc 154560
cacagaggct ccgcctccac ctcacaccaa agaaagggag gagtccaaag ggcatcagtg 154620
ccattactca caaaatgata aatacaccct tattctgaac cacgtggagt catatggttt 154680
gtgatccctg tccttcaggt ttcagcttag tggggaagtg ggaaagtcag cgtgtgatca 154740
cagcacaggg tgattgctgc tgattatatt atgtgcctgc tgtatgcagg atgaaatact 154800
ttatatgcgt catcttattt gactctcaca acccccgtgt agataggctc tgttactccc 154860
atttgacagg tgaggaaagc aaggcttaga gaatttcagt gacttgccca ggtcctctga 154920
gctaggaagt agccattctg gcatttgaac ccaaggcctg ctatccctag aacccacgct 154980
ctcaaattca acctatgaca gaggcaagcc ctggtgctgt gggagcccca aggaagagcc 155040
tctggcctgg tggccacgta gcccaggaga gatttctaca ggagcccaca gcgctgaagg 155100
agagagaggc agcagagtaa gggggctttg tggcagagag gggactggca ctttggggaa 155160
taggtgggtc aggactgaat gtaatggagc catgtcagag ctgtccttct ggaagggcaa 155220
gggcacctgg acgcgctgcc cctcagtgct ttggacggtt ccacaactgt gattcacacg 155280
gcttccccaa acgaaggtac acgagtgggc attctgtgac tcggtacttc cctttaggcc 155340
ctgtcctggc atttgatcca tgagcagatc ccgctgagtc tggatctcca ggcagggctg 155400
gactgctgct gcctggccct gcagctgcct ggcctctgga gcgtggtctc ctccacagag 155460
tttgtgaccc acgcctgctc cctcatctac tgtgtgcact tcatcctgga ggccggtgag 155520
tccccgtcca tgaacggtgg gttcctatca tagttcctgt ctgcttcacc atgtttttat 155580
tttgtgctgc ctgtttgcca ggtactaagc taggaattgg ggatggagag gtagataaaa 155640
tatgcatcag gaagggctgg gccccatctc ttactctcca atatattgga gtctacactg 155700
gaatttaact ggaatttgct ttttttagtca ttttatttag attttgaagt ttcagctttc 155760
atcaaaaata cctctaaact ttatgtctct gtgatctttg gtcttagctg ttttatgtat 155820
ttagtcttat atgatcataa gattaataac attacattca gaagattatt tgttttctgt 155880
cagagttaaa atgtttgttt ttatactgca ttgtaatatt aacgtactgt aaaataaaag 155940
tggcttgttc ttttcaagga acagtatcct caacaagggt cattagccac aattttttaaa 156000 aaattggacg tcatagttta catgttagag ggcgttttga agctttgtat ttttaaatta 156060
aatgttatag agtgatgttt tcatgttttca taattgtttt catctgtgca tttgtagcca 156120
acttgaaaac aaagatccag ggattactac ttaaaagcca gacttcttgg aggttatagt 156180
gatgattttg atagtatctt gagccgtctc ataataacct cagggtgaga gatggccaac 156240
aggagacagt cgagggactt agaaatctga atgaaatctg aagttcaaat cttcagacat 156300
ataccactaa ccaagagatt ggtacctcag tctagtattg tctgtttgtc taaaattggt 156360
```

```
tctaaggaat ctaggctagt ctgtctatcc ctttcaactt tgtgaggct gcacaaatgt    156420 aaaatgttga ataaaaagca ctgatggaag tgtgtagaaa ttcttctctt tgttctgttg    156480
taattttagt tgcagtgcag cctggagagc agcttcttag tccagaaaga aggacaaata    156540
ccccaaaagc catcagcgag gaggaggagg aagtagatcc aaacacacag agtaagtctc    156600
aggacccatt tttttcttac atgttgttcc tccaggactt aaaaatcatt cacagagacg    156660
tgcaccgcgg tgagtgtgga ctcctggaag cgcaccgtag ctccgctgtg tcctgctgct    156720
cctccctagc tgtcagggag gctgtagtcc attgctttgc cagctctttt gtttccgagt    156780
gaacacctta tccgtacaca tgcggctgtc tctgacccta cagaccagct gggatgccac    156840
tgggggagcg ctcccttccc cccgcacttc ccacactctg cagttattct gagatccttg    156900
agggcaggga acaggtttgt cttctttgtg ttctcagaaa ttaatgctcg gcctctggtc    156960
agcaagcaac aaccttttgt tgagtgataa tgaataaata aatgtttccc acatgagtat    157020
tcagtaacct cagtgtcagg ttcagccatc tgttttggtg atatttaaa agaaaattcc    157080 gcttttccta cagaaaaaaa aaaaaatcca aatcccagtg atttaagcca gttatagact    157140
tagacatata ctacggcttt tcatgcactt tcctcccaat tctagagtag gtattttact    157200
aggaaaatgg tggcagtgcc tgttgggagg aagattcttt ggccaagtgt cttttgttct    157260
tgccagggcc cctaggctgc tggggtgctt cagcttcttt agcccagtgt ctggtgggga    157320
atggcccctg ttgcctgtcc cacagaggtg ggggtgcctc acctggagcc tgtccacaca    157380
ttttacacag cacgcttacc tggagcatca ggcatctttt ccatgctctg tggctcagga    157440
aacacgcctt tcaatcatg agtgcaccag tgcttttggg cttttctcc ccgctttgt    157500 gcaatcctgg ttgtggatgg agttttcctg tctttagtct tctgcatagt acttttctct    157560
tctggttccc ggttcaaggt tttgtaatta gagaatgacc cagaagcaat ggcattttaa    157620
tgcacagcca aggacttctc tgaatttgta tctcaaacct ctgtgggtcc ttcaggcttc    157680
agtttgtgat ttcatgattt cttgttgcta cctaaggaat atgaaaacac ccacctccct    157740
actctgcatc ttccagccga gtggcacctc aggctgtgga tcctgtgctt ctgtggtgag    157800
gataagaata gtgccaaccg tgtggattga aatcaatcag ttaatccctc catgtaaagc    157860
acctggaacg gatgacagtc ttgttatgaa tactcaacaa atgctatcat gattttagt    157920 tagatttcca ttgcttaaaa acagttgaga catcttggcg gtttgagtta gagcaacggg    157980
ccctgaagtg ggttctgttt gggtgaagat gattatgctt attccccatg gccctcttta    158040
ggcaagagtg ggaagctttc tttgttttt taatcacctc gataggacgt tacttcttaa    158100
aggtcatcca ataaatatta ataggccggg cgcggtggct cacgcctgta atcccagcac    158160
tttgggaggc cgaggcgggc ggatcacgag gtcaggagat cgagaccatc ccagctaaaa    158220
cggtgaaacc ccgtctctac taaaaataca aaaaattagc cgggcgtagt ggcgggcgcc    158280
tgtagtccca gctacttggg aggctgaggc aggagaatgg cgtgaacccg ggaggcggag    158340
cttgcagtga gccgagatcc cgccactgca ctccagcctg ggcgacagag caagactccg    158400
tctcaaaaaa aaaaaaaaat attaataaag ccaactcgtt agcgtggggc ttaattgctt    158460
aagtccaatg agaagtcctt ctctatccta ggaagttgcc caaactgtag aatctcgtgg    158520
cctgtgggta atagccacgt aatacacact cactgcctca acaaatcata ttttagtagg    158580
tatgatattc tagactcaag acaccattct gtggatcttc ccaagggtgt gaagtgtcca    158640
cagcgtctgc cttgggagtt tccatgccca ccagaaccat gccccaagcc cctcaagcac    158700
tctgacctag gaaagccagt gaagcaagga tgacaacatg gcccttgat actagctgag    158760
```

```
ggacagacac aggtcctggg agaccagaga aagacgaggg gcagaggagg tgtcctaaag   158820
gaagtctgag gctgaggagc cacaggatgg cttccagctg tcacaggctg ctgctggcct   158880
tatcacagag agtgggccag agggctggga accaaggcca gagctcaggt tcaggaccat   158940
tccagcaatc ccagcagaaa atggggagaa ttgtatggta taggcggata tgaaggtaga   159000
atctgcaggc cttcagtggc caactcagag tctaagtgga ttccacagtt acagcttgag   159060
cagctggttg taggtcatgc tttctacact gggcatatag gatgtgtttt ttaaaaagtc   159120
ctctcttaac cgttgcttgt ttagatccta agtatatcac tgcagcctgt gagatggtgg   159180
cagaaatggt ggagtctctg cagtcggtgt tggccttggg tcataaaagg aatagcggcg   159240
tgccggcgtt tctcacgcca ttgctaagga acatcatcat cagcctggcc cgcctgcccc   159300
ttgtcaacag ctacacacgt gtgccccccac tggtgagtct gctcgttcct tgcagaagac   159360
caagtacggt gaaaggcacc ggtaggccct gggctgggca cacgtgagag ggcgggacag   159420
aatccccgca gcccagaggc tgcctgctgt ggttctggtg cccactgtgg ttctggtgcc   159480
aggctgcttt cctcaggcac cacgtgtgga ggtcgctagt agaaatactg ggttttctaa   159540
aatgaactga ggccctacat ccctaagaga ttagtgttag acctgattct agagcaacta   159600
gaccactttg cttaatagca gaccagaaac cacaccccct cgagtgagtg agatttttcct  159660 ttggagataa ttcatgtttt tctacacagt tttgcagttg tcttcagaat tggtttaaag   159720
taggtgttat tgccaggcgc agtagctcat gcctgtaatc ccagcacttt gggaagccaa   159780
ggtgggcgga tcacttgagg tcaggatttc gagaccagcc tggccaacat ggtgaaaccc   159840
catctctact aaaaatataa aaattagcca ggtgtggtgg tgtacgcctg taatcccagc   159900
tactcaggag actgagacag gagaatcgct tgaacccagg aggcgaaggt tgcagtaagc   159960
cgagatcgcg ccactgcact ctagcctggg caacagagca agactccgtc tcaaaaaaaa   160020
aaaaggtagg tgttattgat cagaacccctt gtttcagata acatgaggag cttagcttga   160080
ggagagtgag ggttgatgga gggggactga cttctgccca gtgaaatggc atcatctccc   160140
accagcccgc tgaaataaga tgatgggcc tgttccttag ggcctgcagc atcctcaggc   160200
aggaaagaaa ggccgacctg gcagggtgtg agccagcagg tgtaggtcag ggagaatgga   160260
gccaggtccc agggaagagg cttgtggctg cctgagaagg gtgcgtgcct gcctgtgtgt   160320
gtgtgtgcac gtgtgtgtat gtatgctgga gagtctaggg aggcttgctc caaggacgca   160380
gtattgtttg atcctgagag ataaggattc tgccgcaggg aatgaaggta ttccagatgg   160440
cgggcttatt ccgaagaaga ggccagtgcc tggcggtgct ggaagcagtt gcagaacagg   160500
gagttgtagg cttctcctggg aagagagcag caggggtgct ggagaagcag gccacacttg   160560
ctgcatgggg ttgctctcgg ccccactctt ggtgcacagc gagtcactgt gggttcatta   160620
gcatctggtt atgagacagt aactgctcct ttggaggggc tcgtggagac catgcaggag   160680
ggcacggtct tgaggtcatg ccgtccagag cacacctgag gataggccag gacgggctgc   160740
acgctgtagg taaaattcct ccagcaagct cttcactggc attgaggagt tccctgagtg   160800
cggtcatctg gaaggcagct gtaacaggca ctgcagtctc tccctgggtg ggtaccagag   160860
aggagcatag gggagcataa ccgatttaaa gagagggctt tcctgtggtg aggtaagaga   160920
ttagctggtc attatcatag agccccctct gcctttgtgc agatgggctg tgggaatcct   160980
ggggttccgt tgggtccttt gtcacctcac tgaaggcatg taagctgagc tggccagacc   161040
gtgagctgat cctgccactt gaacagcatc aagcctgcct ctggattctt ctgtgcatgg   161100
```

```
cacttgtctg agcacctcac gcacagagaa ctggacttca gagtttacag aaataagctg 161160
tatggttcat tttcatgcct gcttgccaat aaacatatct gagctgaacc tcattgaacg 161220
cctgccttta ttctagcaca gcacctgctg tttgtgggcg aggggtgctg tctctaactc 161280
ctgcctgctt ctcccagcac tccctgagtg gggtgtgcca gcagcctcag gatgaggaca 161340
ggaagtggga gggcagagca gatttgggag ggccacttga tggggaagga agtcccagga 161400
agcagttgga gctgttttct gggggagaag gtgccagctc tggacagtg ttggggtagt 161460
gaggagggag cccagtggag agaagtcggg cttcctgctt cctcacagta tgtctgtcct 161520
gactcaactc ggatgatgtc acttcctttt catcttctca ggtgtggaag cttggatggt 161580
cacccaaacc gggaggggat tttggcacag cattccctga gatccccgtg gagttcctcc 161640
aggaaaagga agtctttaag gagttcatct accgcatcaa cacactaggt actcttgggg 161700
cctctccttc aggtcaccat gtcggacat ctaccgggag gaaatccaga gcccccagta 161760
ctgggatctt ctcatttgac tccagaaaag atttaagcat gataataata caaacctatg 161820
tgaatacatt ttgcagtgtt ggcaaaactc ctttatact gagaaaatag atcccagttc 161880
ctgtgttttg tggcttgaat cccagctttg tgtattccgg gcttgtttga agtcaggaaa 161940
ggttcatgtg tagtggacaa cgtgagacca aattctgcct tagattttgc atttaggcta 162000
aacagtggca gcacttgtct cagaatgttt tcttgtgttc accagtctga tcctgttgtg 162060
tctcagtggt ccatttctc atatgggaac aagcagacgg gagcagatgg agtcaggttt 162120
cttggcactc gccttcccca gagcctagag gcagcatggg gagaaagcag gcttggggct 162180
cagacagtcc tggtctgctt ccagccctcc tacctgagca gcgcagggca agtccgtcta 162240
acctctagag accctcagtt ttgtcatatg taaaatgggg gtcgtgtcta tttcatagaa 162300
ttgttgcaga tttagaaatt acatttctaa acaaatgtta ccccttattt ctaaataagt 162360
gtctaaatga ataagtcacc acttttgccc ctatttgatg gcaagaggtg tgatcttgtg 162420
gtgggactgt aatcagtcag ttctcagtga ctgtgccctg ctgtggtgtt tcctggaatg 162480
ttcctgtctt gtcctagaaa gtctggcagg ggcaccctga ctccactgtc cagtcctctc 162540
cccagtccct cgggcttctg cagatttgag gcttgtttgg atcccagaag gttgtggcag 162600
gagacacctt gcctctactt tccccttat aattcaatgt ccaaagagag ccctgagcag 162660
gtacctcacg ccagctgcct cacggagctc ctcctcttcc tggctgtgag gatcggtatc 162720
agtggcctcc tgctctctcc cccttgccta acacgagcac ctttgcttac ttgggtgccc 162780
ttgctcttga actgcccatc ggacgtgcgt gacccaagac tgtgccgcag tccttgcctt 162840
gtctgtgctc atttctttg ttcattttt tccctgtaac gtaaattgtt atatttgtct 162900
gtatctgtgt ctgaatcagt cctgcacgct tccttctct ctgtctcttg ttctttcttt 162960
accccgttta tcacggggac cccgatgtcc attgctctag ttctcctgtc ctaagcaccc 163020
catcccgtct ctctggcctt accacaagtg gcgtggctgc ctcagacatc atgatgggga 163080
catgaagcac agctgtcaga aacaactgtt cgttagatac actcgaatgc agctcatcaa 163140
tagggatgga gggtctgtcg gatgtatttt cactgaatcc ccgttcctac cttgatacac 163200
tcttttaat ctattcttct agacaggtca gaggaaccat tactttgact tttaaatttt 163260
tagcagcttt attgaggtag aattcacata ctacagattt cacccactct aagcggacag 163320
cttggtggcc attagtttta tccacagagt tgtgcagcca gctgcacagt ctcagggctg 163380
gactccaggg aagattttag cccatttagt gagtggggca gaagtggccc tggccctgca 163440
cgaggttgcc tgcatgggcg tccctgccct gtccctgtgt ctgctccact gggggttgac 163500
```

```
caggctgcca gggccgactt gggcctgtgc cacctgcctc tcatgtgtct cggacagtgc   163560
agccgatgtc tatacttcgg tttcctcaat gatgaaatgg aggggatagt gttccccgca   163620
tcatagaact gtgtgaggtt taagggactc actgcccttg gcgtggagcc ttctccaggg   163680
gccgtgctgt gtcggcgtag ctgtcagctc tccgttacag gcttgagaag ggttgacact   163740
ctctcatgta acatttatat ttctaggctg gaccagtcgt actcagtttg aagaaacttg   163800
ggccaccctc cttggtgtcc tggtgacgca gcccctcgtg atggagcagg aggagagccc   163860
accagaagta aggccacacc ctgtgctggt tggcacatgg gcagttatgg ccgcttgcag   163920
gcctttggtg gggaataaaa taaggcagca agctggtgtt cttttttttct cttaccttat   163980 ttttgaaaga gtagctgaat ggtgtcttga ctgatattcc agagcaggga caaagcctgc   164040
tgaggtctgg gggctgcgat taccaatggc tggaatgcat tttattacgg tgcattccat   164100
gttaaggatc aatacgattg tgcccttttct ggaaaatatc ttttagttta tcaatattca   164160
gaggagtgta ggttgaatta aaatgaaaag gcactttata aaggccatga gtagtacctg   164220
gtttcatttt tctaatgtct tgcagagatt ttatcaggct tcttgaagtg ttcacgtaca   164280
ttacgctaac acgatattaa taataactgt gctctggtac agcggagcca gcagaatggg   164340
aagttgtgga atgcaggccc ttgattctga tagaaggtgt ggtttgaact cacagaaatg   164400
acagtttgga gggtagacat atgtcacaag tcatcaagat tgtctttaaa ttcatgcata   164460
gaagctaaca gggtgtcata agcaaggcct gtaaaatgta tgagggaatt caaagataat   164520
ttattaaaaa gtaattcatg tttggagttt tgtgcccaaa ggagtccttg atttgaaaaa   164580
tgggcttttg cccatcagat tgtttcaggg cccgtgtgtg cggaggccct gccttgtgcc   164640
ccgtgagctc agcctgacag aaatcctttg gtagcactta aggctcctct tcctcccatt   164700
gaggcaggga agactctggg ttctgcaggc agaggtggtt gtgggtgtct tgctgctctt   164760
gttgacatgt gggctctcct tccaggaaga cacagagagg acccagatca acgtcctggc   164820
cgtgcaggcc atcacctcac tggtgctcag tgcaatgact gtgcctgtgg ccggcaaccc   164880
agctgtaagc tgcttggagc agcagccccg gaacaagcct ctgaaagctc tcgacaccag   164940
gtttgcttga gttcccacgt gtctctggga catagcaggt gctggggaca gtgggttccc   165000
cgctgaagcg tccagcagct tcaaccaggc cgttttcctt cattgctaga attgaaaaca   165060
ccgtccgtgt ggcctgtgca ggagatgcag acccaaaggt ggcctcctgg tcagtgagaa   165120
gctggaaacg tgacaggaac tgacgtgggg ttattgagca tttaggggaa gacgttagca   165180
gagcaggaat gagcaggcaa ctagtagaac acccacttaa gggctcacgg acaggtgctc   165240
acttaggaag tgagtttcat ttggtattac accaggttcc tttaggcaaa gcggagggaa   165300
agttctggtg ttttttcactt gtaagatttt gaaggaaaca aaacactctt tacctttttt   165360
ctaaaatgta ggtttgggag gaagctgagc attatcagag ggattgtgga gcaagagatt   165420
caagcaatgt tttcaaagag agagaatatt gccacccatc atttatatca ggcatggat    165480 cctgtcccttct ctgtctcc ggctactaca ggtacctgag ggaaagggtg cggggagcg    165540 gttgtacttg ggctagaatg agagaagact ggcatgctca ccacaccagt gatgcgggaa   165600
gacctgagtg tggtctgagt tggaggctgt ggtgctaaat acgctgcccc tttcataagc   165660
aggagtctta gtcaggccca gggaggaagt aaaatctgga aatgaatgag aagcattctc   165720
tcctgccagt caagaaatga gaagcgaaag aattctcacg ggctgtaaga ccagcaggat   165780
ttaaaagttg aattagttgc ttatgttaag aactcaacca agttcatcta cacaagctga   165840
```

```
atctccagct tttcctaaga aaccatgtgt ggcagtggct gcagggcagg gcacagctgg 165900
gcctgagcac cccgctccct gcacctctcc cctccctggg ccctgcctgt cactgcccac 165960
tctcccacca agccttccgg ttgtgtgcct gccctatcac aggcatcgga gcttgtcacc 166020
tggtttaaaa gaagagagtt gtgtggggat ttgggatgca cgttttttcac tcaaaagtat 166080
tttagcgtag agctctgtga ttccgtagct atttaggagt ttaagcacct tgaaggcttt 166140
aattgcagaa agttctatgt ggacgtgcaa tgtgttatac gcagtgtcta tgagactcaa 166200
atgtttatta gggcgttgaa gtaaactgag cacttggagg gccatggatc cagccttcaa 166260
ggagctcata agtcaggagg acccaggagc aatgacctgt catagaaggc agaaaagagg 166320
ggcacagagg tgggtgggag gcatacacag gcagctcctg gagctccaag gggagcaagt 166380
gcttccaggg aaggggggcgt ggaggcccct ttggaggagg caagttgatc tggggtctgg 166440
cagagggtta gctggggaca tttagcggga ggctggtgcc cgggaattgg ggggatgccc 166500
agcagaaaga catgaggagg ctggcctggg gcgtgggggg gtgtgaaagg ttaagtgggg 166560
gcattatcct gctcccgctc ctgccggctg tatctggtca gcctgggcac cgaggtgggg 166620
ttctggaagg cactgttcac caaaatgctt atctgggtcc cccagagagc ttgcctgcct 166680
ggactgtcgg ctcgcctgca actgctgact cctaagcttt tgcagctcag cccacaacca 166740
gttcctattc acagaggtgg gagctgaggg gtgacaagtg actgctgcag tcttatttgt 166800
catagagaaa aagtgacaga gtccagcttg cccactggcc ctgccagctt aactggttat 166860
aaagtgacaa atccccaaga cccacagggc tctgcacaac ctgggccctc ctgccagtgg 166920
cggcgagggc aggtggctca cggctgggtg cctgtctggg caggagctgg gctggtatgg 166980
ggtgggcctg cggccctgcc cccctgtgca gatcaagact cagggtgctg gtgttcacag 167040
gtgccctcat cagccacgag aagctgctgc tacagatcaa ccccgagcgg gagctgggga 167100
gcatgagcta caaactcggc caggtcagtc tcgcgccccc gccgcctggc ctctgtccgt 167160
ttctgtcctc agactttggc gcttgacaca cccaggagaa aagctcagtg cacttttttaa 167220
atgaaaggaa gttttccttt ttttttaaaaa aaaatttaat gttcattgtt tttatctgtt 167280
ttattcctag gtcccgcaag cagaggaagc attagttttg ttttttattta tgttctgtat 167340
tccagaaagt agttaagaga cctcacatgt agcgatagag atgtgtgtaa gagacagtga 167400
gagggcgtga cttggactta agcaaggacc gtgagacaca aaaagggggg tgaggacaga 167460
gtggagtcag ctgaaatgct caggaggaag tagacgccat gaagggccat ggtatggggg 167520
gccgcaggcg tggccgtgag tgtccctggg gccagctctt ggggggctcc ctgagtgtcc 167580
ctgtccctgt ggccagttct gggtgggagc cccgtgtgca ggcagacagc tcggccactt 167640
cctagcaggt cacattggtc tgtgcttctg tttcctcctc agataagtga agggattcaa 167700
gggtctgggt gtggtggcta acacctgtaa tctataacat tttaggaggc tgaggcagga 167760
ggcttacctg agctcaggag gttgaggctg cagtgagcca tgattgcacc actgcactcc 167820
agcctgggca acagaccagt actctgtccc ttaaaaaaaa atgtaaacag aaacgtaggg 167880
ccatttgcat atgatggcac atggcgtgga gccctacagg tgtatgctgg gcggggcccg 167940
gctgtgctgg ccgacttgca cctttccctc caccccggtg ctgtgtcttt cgctcaccgg 168000
gttcctgatt tagtgaaagc agttgtgcag gacagttctc tttgtagctt tgtttctgt 168060
ggaaatgggt cagaatatgg tgtttagaaa cacttatgag ctctgagagt ttcctcttct 168120
gagttcctgg cctgcagcct tcacagcaga aaccctgtga tgtcacaagc ctgtttctgt 168180
tccctgctct ctgcctgtac tgtcctgttt tgtgcctgcc ggtttcagtg acaggaagca 168240
```

```
gggagctact ggaccagcct gtattttct agacatagtt ggaaaaagaa gtcccactct  168300 tctgtcctt  caccttgac  agatgttcc  accccaagat aagtgaaaat gaccaatagg  168360
atgcactgta ttttcatga aagtgttct  gaagggcagg ctgagagtga gaggcctggg  168420
gctcactggg tgcctctggc cttgtcctgg gcccaggac  actggtctgt gcccgaggta  168480
ttccctatcc ccccaacccc gctgcatttg ccacatcct  tcaatgtttg cgttgtgtcc  168540
agcgtccgca aaccaactgt catgggatca tactggggct gaagtacggt cccacccctg  168600
ccctgtctgg ggctgaagta cagtgccacc cctgccctgt ctgggctga  aggacagtgc  168660 cacccctgcc ctgtctgggg ctgaagtaca gtgccacccc tgccctgtct ggggctgaag  168720
gacagtgcca ccccttccct gtctggggct gaaggacagt gccaccctg  ccctgtctgg  168780 ggctgaagga cagtgccacc cctgccctgt ctggggctga aggacagtgc cacccctgcc  168840
ctgtctgggg ctgaaggaca gtgccacccc tgccctgtct ggggctgaag acagtgccc  168900 cccctgccct gtctggggct gaaggacagt gccaccctg  ccctgtctgg ggctgaagga  168960
cagtgccacc cctgccctgt ctggggctga aggacagtgc caccctgcc  ctgtctgggg  169020 ctgaaggaca gtgccaccc  tgccctgtct ggggctgaag acagtgcca  ccctgccct  169080 gtctggggct gaaggacagt gccaccctg  ccctgtctgg ggctgaagga cagtgccacc  169140
cctgccctgt ctggggctga aggacagtgc cacccctgcc ctgtctgggg ctgaaggaca  169200
gtgccacccc tgccctgtct gggatgttta gccctagat  gccactggac tgagccgcta  169260
cttgcttttg ggaaagaggg gtgggggtta ggggtctggg cgaggggagt gcagggctc  169320 ctccttggcc tgagagctgt tcatacagac tcctcgccca ctccctgcag ggtgctgggt  169380
cccagggggg aaatggccct tggtgccaag aacgtgagtt ggggctagtg ccagtgatga  169440
tggagaacag cttttatgg  gcacacagcc cacagcactg tgccaagtgc tcgaggcttc  169500
ccgagaacca ggcagaaagg aggacagtcg aggtgtgctg actgcgtggt ggctgcgtga  169560
tctagagcgc gggtcacaaa ggcgcgaggg agctctggcc ttgggtttac cgcaatgact  169620
gccagtgcgg gagactggaa aaggaatctc acgtattggt tccgtgtttt ggggactcca  169680
ttcagatgtc acttaggagt gaaagcatcc cttcgtagag cctctttctg tgtcaccctc  169740
ctcagctgct cctggggttg actggcccct gattcatgcc tttagcatgt gctggagctt  169800
cccagcagct gtccagcccc tgccccaccc tctctgtggg ctcccttgcc cgtaacctgg  169860
ggtgtctgaa cgaccttgc  taagggcag  actgttagac ggtaggcatg tgctgagtcc  169920
cagtggccac acccacccac caggagcctg gcactgtggc cgcagcactg agcagtgccc  169980
cgtttctgtg gcaggtgtcc atacactccg tgtggctggg aacagcatc  acacccctga  170040 gggaggagga atgggacgag gaagaggagg aggaggccga cgcccctgca ccttcgtcac  170100
cacccacgtc tccagtcaac tccaggtttt ccaatggcct ttttcttttt aacagaaatt  170160
tgaaatttct tatcagtcat ttgattttgt tgaggtgctt cttgaaatga gcctctcatc  170220
tcatgtactt ggaaaatacc catctcgcat attccacagg aaacaccggg ctggagttga  170280
catccactcc tgttcgcagt ttttgcttga gttgtacagc cgctggatcc tgccgtccag  170340
ctcagccagg aggaccccgg ccatcctgat cagtgaggtg gtcagatccg taagtgagcc  170400
ttcccattcc cctcacacct gcacgtgcca cacgcaccac acacgccaca caccccacac  170460
acacacaccg cccacacaca tgccacttgc acacacaccc ctcatgcatg caacacacac  170520
acaggccaca cgcaccatag acaccacaca cacatgccac atgcacacac atacacggca  170580
```

```
tgcaccatac acacaacaca cacagcacac atgccacaca cacacgccac accacatgca   170640
ccacacacat gccacatgca cacacactcc acatgcatgc accacacaca cacacacaca   170700
ccacacacac cacatgcacc acaccacaca ggttacatgc acacaacaca cacatgccac   170760
gtgcacacac cccacacacc acatgtatgt gccacacaca gcacacaacc acacacatgc   170820
accacacaca tgccacatgt gcatgcacca gacacatggc acacactaca cacacgccac   170880
gtgcacacac cccacacaca tgtacgcacc acacacatgc cacacacaca tgcaccacac   170940
acatgccaca tgtacacaca tgtatataca caccccacac cacacacaca ccacttgcac   171000
accacgcaca cacaccacat gcgcacacac acaccacata cgccacatgt acacaccata   171060
cacacaccat acatgcacca cgtgtaccac gcacccacac agacacagca cacgcataca   171120
ccacacacac acgcacacat gcgtcccgca cagtaatgtc tcttgggtgt aagaacacga   171180
cttgccagta gtagcgttct ggatgcgttg cctggattct aacagcgcga ttctcccctt   171240
gccctcctgg ttttccacat ctccagcttc tagtggtctc agacttgttc accgagcgca   171300
accagtttga gctgatgtat gtgacgctga cagaactgcg aaggggtgcac ccttcagaag   171360 acgagatcct cgctcagtac ctggtgcctg ccacctgcaa ggcagctgcc gtccttggga   171420
tggtaagtga caggtggcac agaggtttct gtgctgaagc cacgggggcc catctgcctt   171480
gggacctggt gttggccaga ggtgccgggt gcggctgcct ccttccaaga gttgacccga   171540
accggactcc acgcccacg tgagctgcag tgcttctcag atggaggggg ttcagcgacg   171600
gtcagtgcca ttcacaggtc actgtgatgt ggggttgtggc ggccaagcca tggtttgggg   171660
tcccgtatcc ctgggcttat gacatcattg tagtagccca tccccacaga accacggtgt   171720
gtggtggcgc tgaggcatcg tagatggtgg aaatgctact ggcttcccca tgctctgccc   171780
tgaggcctga ctgcctcact ccccttctca gttatgttcc aggccccccg agcttcctgg   171840
ctggacagct tctctcctgg gggccgtttt gtcacagtga ccctgtgttt ctagtcccaa   171900
atctgggtgc tatagtctct ttttagcgtg gtggttgtct tagtcttttt tggctgctac   171960
cacaagttac cttagactgg gtaatttata aacagtggaa atttacttct caccgttctg   172020
ggggctggaa gttttcatgg tcaaggtgcc agcagatttg gtgtgtgatg agggctgctc   172080
tctgcttcat agatggcatc ttctggctgg gtcctcacgg tggaaggagt gaacaagctc   172140
cctcaggcct tttagaaggg ccccaatcca caagggctct cccatcatga cctcatcacc   172200
tcccaaggcc ccaccttctt gtactgtggc actgcaaatt aggtgtcagt gtaggagttt   172260
caggagggat agaaacattc agaccatccc agcggtcaag tgttcatcct cttgagttcc   172320
tccttattct gcttctggtt tatcaggatt cagccagtgc agcatggtac ctgtattctg   172380
tggcacatca ccacatggta tttgccaagt atccatcacc tgcacacgtg aaatcattgc   172440
ccgtgggtcc cgacatctgg cgaagcatat tcaaggatgg cagaactgtc agagctggca   172500
cctctggttc cttgtcatgt ggcattacct agtaatccat tttatgatag caatggaaac   172560
tcatttcttc aacaaacacc tgagtggctg ccgtgtgcca gccgtctggg gcccttggtg   172620
agaatggcat ggtggtgccc atcagggcct gcctagcccg tgctctggac gggctcctgt   172680
gtgtcaggaa cgacaatgct gtcatgacgg tgaatgattt ttttttttgc catcactcca   172740
gccgctaaca tttgcggagc tcttcctccc gcaccccac ctgacaaggc caagggtgac   172800
cttggcccca ccctaggcgg ccaaggtcag aggttagctg gcttgtctgg gtcacacaaa   172860
atgcagcaga ggttgaggtg agcacatgtc cgtgacctgg agcctgactc cctctctgcg   172920
agtcttgact gctcttgcct agactctgtc ctccccgagc ccaaacgcca gtcatcttcc   172980
```

```
cttgtgggtg tccttcagcc tggtgccatg ctggtgactc agcagccgtc cagggagtgg    173040
aaacaattga gtgtgtgggt tccctgtgtg ggcatctctc ttcacggcga acaccctctg    173100
ggtgttgccc acacgatgtc aaagcggctc ttggaagggg tccttctcct ttgtgggaag    173160
tttcagctgc tgggctaact tgaattgtaa ctgtggtttt gtgctcaggc ccagatcccc    173220
ctaggcaagt gttgtgccat cagtaatcaa atgagaaata atcattttga aaagcagatc    173280
ctaaggcagg atggtcatgg acactcactc ccagctcttt gtgcactcat gcttctgga     173340 agatggccat cctctgtgaa ggttttcagc gcgtcatgct tggtacccac gtatccagag    173400
catgtcgttt tgaggtattt gcccaccgtt gtgaaatccg tgccacccga gagcaggtcc    173460
tgatgtgggg ctttcagaag tgggacctgg ggccgtacgc agtccttagg gaggggccgt    173520
gtggcgttgt gcgtgtgagg ggatagcaca gggtgaggtg ggggcccaag aaggaagtga    173580
cccacaaaga acagcctcct cttttggtcc ttgttcctgg gatggctggg agtggcttct    173640
gtgtcgtccg gccatttccc ctgcggagag gctcctacca ctgccagaaa cctcatcatt    173700
ccacaaaaac aagaggccgc ctggccatcc agcgctccat gggaattctg tgtccccata    173760
gtcttgggct gaaggagggt gacattcctt gctgacttct gcagggttct cctcactgtt    173820
aaagagcaga ttgaaagtga agaacgtggg ctaagtgttt aggtcgatat ttaaccctgc    173880
taggttttgg atactaagtg aaattgaggc cattttggtt gaagttgaca gaaaccacta    173940
tcagggatcc ccaagactac cccaggcttt tctagaaaga ctctcagcta agatgtgtta    174000
tggtaaaagc acacaaaaca aaatcagcaa agaaaattag caagggcaga ggcccatggg    174060
gcgatgtccc gaggacacca ggcttgagct tccagaatcc tctcccagcg gggtcgtgca    174120
ggacgcactt aactccccgc acagtgagcc gtgacagcgc gtgtgcagtg tcgtcgccag    174180
gaaagcacac tagagactcg gtgccagggt ttttactggg ggctgggcac atgggcaccc    174240
tctgcctgcc tcgtcccag actctggact cccggaggga aggcaagttc tcagcaccaa    174300
ccctggtgcc cacacaagca gctgagcaca gggagcccct cctcagtgag gatggtgggc    174360
accgtcccaa caccagccag gggccagcct tgcacacagg cctctcagga tggtctccgg    174420
cctgctgtgt agtctcttct gcacacaagc gtgagggcag cgccccgcc tcggctgtgg     174480 ggaggagcca ctgggacgtg agctctggtg gcatgcagca gcttttgtct gtgtgtgcct    174540
aggacaaggc cgtggcggag cctgtcagcc gcctgctgga gagcacgctc aggagcagcc    174600
acctgcccag cagggttgga gccctgcacg gcgtcctcta tgtgctggag tgcgacctgc    174660 tggacgcacac tgccaagcag ctcatcccgg tcatcagcga ctatctcctc tccaacctga    174720
aagggatcgc ccagtgagtg ggagcctggc tggggctggg gcggggtct cagaatgagc     174780 tgtgaaggaa gcagcatcac cctctccaag tgcccaggct cctggccaga tggcaggcca    174840
ggtatcagtg ggaacccagg tgggtgccat ggctgaggtc agtgagacgc aagagcacag    174900
gtgcgtccta gaggcttcct cgggcacctc cagcgagctg gagctctcgc ctctgctgct    174960
gtctcatgtg gcgcttagca cactctccca cgtgcccatt cctgactctg ctctcgaggc    175020
catcggctct cattctctgc tcccagaacc ctgttattac ccaggctagc ctcctctctg    175080
caccttcccc gccctggccc agtacctccc tcttgtttcc actgtgattc cgacctcacc    175140
ttatcttaaa gctgctggac ggcaggttct gtacacacgt gtccttgaca aagcacggct    175200
ggtgccgcaa cccctcagcg agcaagtcaa gctcttcaca gcgatgtctt acaagcgcag    175260
agggctctgt gacaccctgg tctcaccgcc actcttccaa agtcgcagag gctttagcag    175320
```

```
agatgggccc agcctctctg agtcataggc ttctgcacac gggagctgtc tttagaggga   175380
gggtggaatt tcatcagcca cccacatggg ggagttgagg gcaagaatta ggagcaaaga   175440
tgggaagggg tctgggagga atggccagtg atcccctttg acaagtgggc aggaaacggg   175500
ggctaggtca aagttgagtg gaagacctgg agggagacgg gaaggtctct gtaggcacag   175560
ttcagacagg agggaggtgt gagccagggc acatgccggt ggccgtctgg caggatttgg   175620
gacatgctgg agcagggaca gcggctcatc aggggccatt gccctcatcc aggccagagt   175680
gtcacaagcc cgtggggagg cccttctcgc ctgtcatcct tgctgggcag tgggtgctgt   175740
gctagcagga caggcggacg gctggcaact gtctctgcat ccctggagcc tggcataggg   175800
ccaagtcaca cggggcacag gcctgcaaat caggcacata tgttggtgca gtgacgtgat   175860
tttgggggc agccccagaa caggcccag acacaggcca aagccctgcc tgtgctggtg     175920
tgtttgggctg ttctatggct cttgctgtgg gcatggagga ctcagggaag gagagttgag   175980
gtggtccagg agttgcgttt gggatgcaga gagcttgtgg catccaggta gaaatggtgc   176040
gtggggctga cctcagcacc atgggcagag gggccgtgtc acgtgcctcc gaggtggagg   176100
tgggaccacg tggtgacaga tatacgcatc actgggcacg tttttgtggg tgttgggggg   176160
catcgtattg gctcctctgt tcacagtggc cactcattca gtccctggct accaggtcct   176220
cactgtgcca tggggaaggc cggcgctgtc ggggatcac agaaggcagc acgtcatgat    176280
ggcatgtgcc atgaaggaaa agcacagggc actcaggaag tagaggggac tggcctgggg   176340
tgtgggaatc tagggcctcg ttagggaca gagagaggaa gtgtgtggtg gccagcatgg    176400
aggtggccac aggggaggct gagttaggcc gagagggcag ggcgttgggg aggtagacgg   176460
gctcagccac tcaggagtg gtcaagcaga ggctgaaggg tcaggccagg ttgcagggggc   176520
ctgggggagc cactcagggt aggcgctccc gggagcccgc ctggcccata gctctacact   176580
cccgcgtggg gccggacatg ctgtgaagcc ctctccacgt tggatggggg tggctgagcc   176640
tggatgctgt ctcccgtttt cagctgcgtg aacattcaca gccagcagca cgtactggtc   176700
atgtgtgcca ctgcgttta cctcattgag aactatcctc tggacgtagg gccggaattt   176760
tcagcatcaa taatacaggt gagtgggccc tggctgtctt cctctgcaca cggggagtgg   176820
gcttcccttc tcttttcctt gcaggatcat accagtgggc cagttttgac ttggtcggga   176880
ggaggcatga acacctgaga ctgtgcagcg attctttgac acagaggcct ttctccctgt   176940
gcagatgtgt ggggtgatgc tgtctggaag tgaggagtcc accccctcca tcatttacca   177000
ctgtgccctc agaggcctgg agcgcctcct gctctctgag cagctctccc gcctggatgc   177060
agaatcgctg gtcaagctga gtgtggacag agtgaacgtg cacagcccgc accgggccat   177120
ggcggctctg ggcctgatgc tcacctgcat gtacacaggt gagcatgtac acggtgccca   177180
taaggccagc ccaagtcctg ttcaagggag gcaggagcat gctcactcaa gggacctcga   177240
ctaggtgccc tctgatttca cacttctggt gttgccccaa gccggcccca tcaccttgca   177300
agaaaggctc tggagccccc agggctggag tacctggtca gggttgaccg tccctgtggt   177360
cactcatccc atgtggctga gctgggctgg gtcctgggca agcaagggc tgatatcacc    177420
tgctttcaga tctccaggga ctcactggac ccctgtgtac aaagcactgt ctacagagcc   177480
tattgggttg tatagaggta accttcgtac tgaacacttt tgttacagga aaggagaaag   177540
tcagtccggg tagaacttca gaccctaatc ctgcagcccc cgacagcgag tcagtgattg   177600
ttgctatgga gcgggtatct gttctttttg ataggtaaga agcgaagccc catccctcag   177660
ccgttagctt ccctagaact ttggcctgaa gctgtgcttt tgtgtgtgtc tgctgatccc   177720
```

```
ctggcgctgt tgctggagtc ctgccagtga ttccccacca cagcctgacc atgggctgcc   177780
ttggctcagg gttccactgg cgagctggtg gtccttggac cccagcactc aggtgtagcg   177840
ttgaccagtt ccaaggttgt cccagtgcct gcccatctct cctgagggct caggacagt    177900 acctggcagt tgggggtgtg gcaggggca ggaatgacca gcctctggga gggtggggca    177960
gaagcctgta cagtgaggag gagctggctc agcctggctg cctatcgtga gaggggagcc   178020
cacggggctg tgggaggggg gccgtggtgc ctgtgagcag ggtgaggagc agcggcagga   178080
ggatgaaggt ggaacccaca catgcatctt tgagacccgt gtggtcagtg cttctgccc    178140 cccaccaccc cccactgctg tgcgtgcata gaattggctt ccctcacctg ctctggaagt   178200
gggttaggag cttggtaggg cttttttctca aggacaaggg cccctgattt gctctcaggc   178260
ctcagtcctg gcgacatggt ggatctggag ccttgttgca ctgccttgcc tgtgctctcc   178320
aatcagggtg gccagtgggg agccatttgg cttttctcaa gagcatactc aggtggacct   178380
tgctccactg tttgaccaga tgaggcattc tgaacagcca agcctgtgct ggtctgtttt   178440
catgttgatt ttttttttttc ttttcttttt gagatggagt ttttcccttg tcacccaggc   178500
tggagtgcaa tggtgtgatc tcggctcact gcaacctccg cctcccgggt tcaagtgatt   178560
ctcctgcctc agcctcccta gtagctggga ttacaggcac acaccaccat gcccagctaa   178620
tttttgtgtt tttagtagag acggggtttc accgtgttgg ctgggctggt ctcgaactcc   178680
tgaactcaag tgatccaccc tccttggcct cccaaagtgc tgggattgca ggcgtgagcc   178740
actgcgcccg ccccccatgt cgatttttaa atgcacctct gcatcgttct tcagtcccca   178800
tatgctcact gagcaccact gcgactggca gacgggcaca gggaggcgcc acgaccagtc   178860
ctggccttca aggggcttgt ggtctagtgg gcccaatgct agtggcgag  tgctccaaag   178920 agtgtggtgc acgccttccg cttgaccgct ccagacgc cacagggagg cacctcgcag    178980
ctgaccacag atttctctct gtggagcagt gtcttcagag cggctgccat gccactgctg   179040
ggcgagggtc tgcgggcggg tagagccagg agcacctgtg aggaagtgca ctgccatttt   179100
cgtagctgct tcccgtgtgt ctcagttaca cacggctggc atgtgtgcac tgatgagacg   179160
ggaacgtgat ggttgctttt cagcactgaa agggatactg ctcaggggc gtgtttcagg    179220 atctggttag ggaagaagca gcgagagcac agatggggcc ctgtgtggta acaagaaaaa   179280
agtcctggtt gacaacagtg ccacgaagcg ttagaacaca tagggatgtt tgtggagcat   179340
ttgcatgtgg aaagcagcaa aaacataatg ggaacgggtt cttttgttat gattttttaaa   179400 aatctctttt gtaacatcct tcccgctgcg ccgtttctgc atattccttt atgtagcttt   179460
caaactcctc ttaggagttc tggtccctac agggcgtggg agcccaggct ttacgtagct   179520
ttcaaactcc tcttaggagt tctggtccct acagggtgtg ggagcccagg cctgtgccg    179580 agcagcctgc ctccacgagc tagacagagg aagggctggg gttttgcctt tttagtctca   179640
aaattcgtac tccagttgct taggctctga ctttccccac ttggaaagtc cctcacggcc   179700
gagggtccct cccagccctg atttcacatc ggcatttcc ccagtattag agccaaggcc   179760
ctccgcgggc aggtggggca gctgtgggag ctggtgccag tctctgacct gcgtccctcc   179820
tcccaggatc aggaaaggct ttccttgtga agccagagtg gtggcagga tcctgcccca    179880 gtttctagac gacttcttcc cacccagga catcatgaac aaagtcatcg gagagtttct     179940
gtccaaccag cagccatacc cccagttcat ggccaccgtg gtgtataagg tgaggttgca   180000
tgtgggatgg ggatggagtg ggaaagcctg gaggtggagt tgcctccgac ttcccagcag   180060
attcgccagc agagcccagc tcctccgctt taaagcagca atgcctctgg cccccacccc   180120
```

```
accccccgcca cccaggcgca gcaggtgctt cccgtccccc cagccctgac actcaggcac   180180
ctgcttgctc cttgcaggtg tttcagactc tgcacagcac cgggcagtcg tccatggtcc   180240
gggactgggt catgctgtcc ctctccaact tcacgcagag gccccggtc gccatggcca   180300 cgtggagcct ctcctgcttc tttgtcagcg cgtccaccag cccgtgggtc gcggcgatgt   180360
atcctctctg ggtccctggt gctggccccg tttcccttgt caacaccgag gctcatgttt   180420
catgataagg tttgaaacc taacctttgc aaaaacccca cagatgccag ggtgacaggc   180480
cctcagcccc aggaagtaa aatgctgaca ggggtacaga aaggagcacg tccagacatt   180540
tgctgaccag ggcctctcag aggggccggt gtatggcagg agggtcgcag ctgagggggcc   180600 tttctgtgga gggcctgggt gaggggagcg agggtgggcg gtggtctctg cagacgtccc   180660
gcccactcgc gggctctgtg tggctgggct tctcctgaca ctgcttctca ttagctttgg   180720
tcattgtgcc tcgatcgccc tctcggggaa aggcttaagt aaagatccag ttcccacccc   180780
cagatgctgg ctgccaggag tttcccttc cacagcccctt ccccaagaca gaccacaaga   180840
gcctccaagc agcacagttg tcctggtgct gacagcacag ccttgcccgg cgtgcctggc   180900
acggctctgc cctcactgca ttggagcagg gctagtggag gccagcggaa gcaccggcca   180960
ccagcgctgc acaggagcca ggccaggtga gtgctgccga gtgggtgccc tgcctgcagg   181020
gcatccagcc agcaagggt tgcaggaatg gaggtggagg cgctgatgca gctggaggca   181080
tccaggtggc ccttccgggg ctctgctcgc tctccaggct ccctggaccc ctttgtagac   181140
tgtttcagga gaggaactcc caggtgagga caggaggca gcattcccct catttgccgg   181200
cctttttcct taactcctgc accagcctcc cacatgtcat cagcaggatg ggcaagctgg   181260
agcaggtgga cgtgaaccttt ttctgcctgg tcgccacaga cttctacaga caccagatag   181320
aggaggagct cgaccgcagg gccttccagt ctgtgcttga ggtggttgca gccccaggaa   181380
gcccatatca ccggctgctg acttgtttac gaaatgtcca caaggtcacc acctgctgag   181440
cgccatggtg ggagagactg tgaggcggca gctggggccg gagcctttgg aagtctgcgc   181500
ccttgtgccc tgcctccacc gagccagctt ggtccctatg ggcttccgca catgccgcgg   181560
gcggccaggc aacgtgcgtg tctctgccat gtggcagaag tgctctttgt ggcagtggcc   181620
aggcagggag tgtctgcagt cctggtgggg ctgagcctga ggccttccag aaagcaggag   181680
cagctgtgct gcaccccatg tgggtgacca ggtcctttct cctgatagtc acctgctggt   181740
tgttgccagg ttgcagctgc tcttgcatct gggccagaag tcctccctcc tgcaggctgg   181800
ctgttggccc ctctgctgtc ctgcagtaga aggtgccgtg agcaggcttt gggaacactg   181860
gcctgggtct ccctggtggg gtgtgcatgc cacgccccgt gtctggatgc acagatgcca   181920
tggcctgtgc tgggccagtg gctggggtg ctagacaccc ggcaccattc tcccttctct   181980
cttttcttct caggatttaa aattaatta tatcagtaaa gagattaatt ttaacgtaac   182040
tctttctatg cccgtgtaaa gtatgtgaat cgcaaggcct gtgctgcatg cgacagcgtc   182100
cggggtggtg gacagggccc ccggccacgc tccctctcct gtagccactg gcatagccct   182160
cctgagcacc cgctgacatt tccgttgtac atgttcctgt ttatgcattc acaaggtgac   182220
tgggatgtag agaggcgtta gtgggcaggt ggccacagca ggactgagga caggccccca   182280
ttatcctagg ggtgcgctca cctgcagccc ctcctcctcg ggcacagacg actgtcgttc   182340
tccacccacc agtcagggac agcagcctcc ctgtcactca gctgagaagg ccagccctcc   182400
ctggctgtga gcagcctcca ctgtgtccag agacatgggc ctcccactcc tgttccttgc   182460
```

```
tagccctggg gtggcgtctg cctaggagct ggctggcagg tgttgggacc tgctgctcca   182520
tggatgcatg ccctaagagt gtcactgagc tgtgttttgt ctgagcctct ctcggtcaac   182580
agcaaagctt ggtgtcttgg cactgttagt gacagagccc agcatcccct ctgccccgt    182640
tccagctgac atcttgcacg gtgacccctt ttagtcagga gagtgcagat ctgtgctcat   182700
cggagactgc cccacggccc tgtcagagcc gccactccta tccccaggcc aggtccctgg   182760
accagcctcc tgtttgcagg cccagaggag ccaagtcatt aaaatggaag tggattctgg   182820
atggccgggc tgctgctgat gtaggagctg gatttgggag ctctgcttgc cgactggctg   182880
tgagacgagg caggggctct gcttcctcag ccctagaggc gagccaggca aggttggcga   182940
ctgtcatgtg gcttggtttg gtcatgcccg tcgatgtttt gggtattgaa tgtggtaagt   183000
ggaggaaatg ttggaactct gtgcaggtgc tgccttgaga cccccaagct tccacctgtc   183060
cctctcctat gtggcagctg gggagcagct gagatgtgga cttgtatgct gcccacatac   183120
gtgaggggga gctgaaaggg agcccctcct ctgagcagcc tctgccaggc ctgtatgagg   183180
cttttcccac cagctcccaa cagaggcctc ccccagccag gaccacctcg tcctcgtggc   183240
ggggcagcag gagcggtaga aaggggtccg atgtttgagg aggcccttaa gggaagctac   183300
tgaattataa cacgtaagaa aatcaccatt ccgtattggt tgggggctcc tgtttctcat   183360
cctagctttt tcctggaaag cccgctagaa ggtttgggaa cgaggggaaa gttctcagaa   183420
ctgttggctg ctccccaccc gcctcccgcc tcccccgcag gttatgtcag cagctctgag   183480
acagcagtat cacaggccag atgttgttcc tggctagatg tttacatttg taagaaataa   183540
cactgtgaat gtaaaacaga gccattccct tggaatgcat atcgctgggc tcaacataga   183600
gtttgtcttc ctcttgttta cgacgtgatc taaaccagtc cttagcaagg ggctcagaac   183660
accccgctct ggcagtaggt gtcccccacc cccaaagacc tgcctgtgtg ctccggagat   183720
gaatatgagc tcattagtaa aaatgacttc acccacgcat atacataaag tatccatgca   183780
tgtgcatata gacacatcta aattttaca cacacacctc tcaagacgga gatgcatggc   183840
ctctaagagt gcccgtgtcg gttcttcctg gaagttgact ttccttagac ccgccaggtc   183900
aagttagccg cgtgacggac atccaggcgt gggacgtggt cagggcaggg ctcattcatt   183960
gcccactagg atcccactgg cgaagatggt ctccatatca gctctctgca aagggagga    184020
agactttatc atgttcctaa aaatctgtgg caagcaccca tcgtattatc caaatttgt    184080
tgcaaatgtg attaatttgg ttgtcaagtt ttggggggtgg gctgtgggga gattgctttt   184140
gttttcctgc tggtaatatc gggaaagatt ttaatgaaac cagggtagaa ttgtttggca   184200
atgcactgaa gcgtgtttct ttcccaaaat gtgcctccct tccgctgcgg gcccagctga   184260
gtctatgtag gtgatgtttc cagctgccaa gtgctctttg ttactgtcca ccctcatttc   184320
tgccagcgca tgtgtccttt caaggggaaa atgtgaagct gaacccctc cagacaccca    184380
gaatgtagca tctgagaagg ccctgtgccc taaaggacac ccctcgcccc catcttcatg   184440
gagggggtca tttcagagcc ctcggagcca atgaacagct cctcctcttg gagctgagat   184500
gagccccacg tggagctcgg gacggatagt agacagcaat aactcggtgt gtggccgcct   184560
ggcaggtgga acttcctccc gttgcgggt ggagtgaggt tagttctgtg tgtcggtgg    184620
gtggagtcag gcttctcttg ctacctgtga gcatccttcc cagcagacat cctcatcggg   184680
cttgtccct cccccgcttc ctccctctgc ggggaggacc cgggaccaca gctgctggcc    184740
agggtagact tggagctgtc ctccagaggg gtcacgtgta ggagtgagaa gaaggaagat   184800
cttgagagct gctgagggac cttggagagc tcaggatggc tcagacgagg acactcgctt   184860
```

-continued

```
gccgggcctg ggcctcctgg gaaggaggga gctgctcaga atgccgcatg acaactgaag   184920
gcaacctgga aggttcaggg gccgctcttc ccccatgtgc ctgtcacgct ctggtgcagt   184980
caaaggaacg ccttcccctc agttgtttct aagagcagag tctcccgctg caatctgggt   185040
ggtaactgcc agccttggag gatcgtggcc aacgtggacc tgcctacgga gggtgggctc   185100
tgacccaagt ggggcctcct tgtccaggtc tcactgcttt gcaccgtggt cagagggact   185160
gtcagctgag cttgagctcc cctggagcca gcagggctgt gatgggcgag tcccggagcc   185220
ccacccagac ctgaatgctt ctgagagcaa agggaaggac tgacgagaga tgtatattta   185280
attttttaac tgctgcaaac attgtacatc caaattaaag gaaaaaaatg gaaaccatca   185340
gttgttgctg tgtgaggctt gctttgcttc atgagaacct agaccttgct gagctggagt   185400
cttaggaagc agtctcctaa gtgcttctcc agcaggggca gaaactgtcc caccagctaa   185460
catctggcat tatggagggt cccccaggca gctgccagca gggacaggcc ccgtgttttc   185520
tgtagccagg gatgaggaag tggccccagg gcatggccct ggctgggtgc ttctgcaagg   185580
gccttcccaa accacagtac aggtggtctt cctgccctgc agatgggagc tgtgggagct   185640
gctggagctg ctggagcctt catggtcaag tgacatcata agcttatatg acatacacaa   185700
gcctcaggac ttggcccatg gcactgaagc aggtcatcag gcccagcaca gagactagag   185760
ctgtgttctc acagggccca ccaccttcc acctccttgg ccattgacac ctgcgtccct   185820
ggcccagctg ctcccaggta accccaaag cagctggcac atcccacctc tggtgtggcc   185880
ggggctgctg tgtgtccgca gggcctgccc cgtctattct agcttgtttg tcctgtctga   185940
accagcgcct actccaagaa gcctctgctc agcccagcgg ggatgcttct aagctccgga   186000
cgagcctctc ggaagccttg gtgattggtg gtgtagtcat cttgggatgc agatgtctta   186060
ccaacctgca agaacaaaaa ccctgtggct tcctctggtg cagggtattt agtcaatgtt   186120
tgctgaggtc ccgtctggtt ctggctaatt ggcaggggtc gtccacccat tctttccctg   186180
ctctgctgtc tgtgccagga gagacggggg ccagtcggcc aaggggccag ctcctgctgc   186240
ctgctcctct tgggcacgtg cggggccccc ctttctctga gcaggatag ggatcagtct   186300 gccggaggga tgtggtggac aggcctaaag catttgggc ggggcatgcc acttgagctc   186360
cctaaatctg tctcctcata ggtgacaccg ctccagggcc ccccagtggc ctctcctttc   186420
agagctacct aaattctggt cacttcagag aaatggagca ccccccttctc cctggtccag   186480 gtgtggacag cctggcacac tgagcacacc tggcatggct ggtaatttca gaaagaagag   186540
gggccggggt ccagtgggaa gcagcggtga acccctcgtg agtgggcttt gcagtccctc   186600
cccatgccac ggcagagctg ccctcaacac agccttcctc ttcctcatcg gagagcacac   186660 cctgtccct tgccgagctg tgccctgtgc cttcggtggt atttgatttt ggctgctact   186720
ggctttgttg ggatctggaa gtcgcttccc ctgcgtggtg cgtggagcac tgtaagtcag   186780
atgagggaag tagccagggt gaggtgagta ccggtggag ccgccactga agggactggg   186840 tagggggcc ttgcctctac atgatgtgac acagccaacc gaggacagag gaagcccgt   186900 tcctgggggt gtggggtgca cccctcaggg aagcctgcag tggggcctga ggaaaggcat   186960
cctccgcgag cccacgagtc tggtccatga gcaccgtgac agtgtctgtg ggtagaggtg   187020
gacccggcct tgtgtcatca ccaggacctc ttttgggaaa ccatgtggac atcgcttgcg   187080
ggtcccccag gctctgcagc cccagcagcc tggctgcctt ttgggcaagt ggcttgagcc   187140
acagaggacc cagtcctgtt gcagccacat cctctggggg ggcccgccag tgtggccggc   187200
```

-continued

```
tttctccacc ctacaccagg cctccaggtg tcctggtcgg gggtgtctgg gccctgggtg   187260
ggccctgtgg acctgtgagg tcagggtcag ggcatcactg gaggcagagg gctgaagttg   187320
tgggtctggg ttccccttgt gtgcacaggc ccctgccctc catgcttggt caggcagcta   187380
cccccaaaac tgctaggaca ggctggtcct gaggtggatc ctggccctg tacctctgg    187440 acagcccacc cgcccaacct tctaccctgc cccagcggcg gcagtgttgg ccacatcctt   187500
cccctcctgg ccccaattgc tctggggaag tccaggctcc ggagcctgcc caggggcccc   187560
ccgtgatttg ggcccaggac tccacgtggt tctctgcctt cacccaagcc ctgaactcct   187620
cagctgccaa atccccaccc atctgcacag gctgtgctca ccactgctgc tcctggaagg   187680
tgcccctcag tgggacgccc acctcctctc tgggcttctg tgtttgggag ccctgctgcc   187740
cccacccttg gtcagtcccc atgtcctgct ggcctgtcag gcagggcaga aaatccaccc   187800
agaaatgctg agcaggatga gagtctagtt gggcccagcc tcattattta gaagggatgg   187860
aggcctaggg agcatgcttc tagcctgagc ccagcagggc cccgcccatg tcccaggtct   187920
gcaccaggga cagctcctgc cgaggcctga cctgccccct tccctcagg tgctgctggt    187980 tgaccagcct ctggccctag gagaccccgt agcgactgag ggtcccagca ggccatgcag   188040
cttgtccaag gtacgagccc ctccccagca ggggacagat gtggggaccc tcccaggcag   188100
gagcagctgg gtgcctggtg ctgccatctg ctgcctgcct ggttcttgtc ctcacattgg   188160
aggtcagtgt gagggctctg cctcgggaaa ggccatggag cttgccctgt ccagggcctc   188220
ccatgtgcac tgagcctggg aagagagggt tggagttgag ccttttaccc tgggaatgct   188280
gcctggagga tggtgcgggt gtggggtggc accctgccag gcagggccct gcctcccctgc  188340 gcccactgga actcgggcag gcaggggtgt aggtgcctcc tctagagccg tccggtgggg   188400
gcccccggca gtggtggtgg tgtccactgg ccagcagctg ccccttcagc caggacagta   188460
ggcctgacgc tgtccccagc agctccaagg tggatttgtg gaagggggta gagggcacgt   188520
agaggcccca tgacctcccc agggttctgg gagggctgtg ccccttagc cagcaccatg    188580 ctgggtgata tagtcagatc ctgttacccc tgttgtggag gtgaggaaac aggttagtgg   188640
ggaggacatg actaaggtcc atgctgagtc gctagagctg cacccagaac cactgctggg   188700
accccatgcc tttctgctta ccccttgtgc cgggagatgc caagagatgc tgggagccag   188760
ccccacctct gcccttggag tcatggctac ggaaagggca ttcggaccgg tccctgacct   188820
caccggggag ggccgaaccc tgttcctgag gagccagggc ttcctagagg aggtaggcct   188880
tctagtcact ccttcatctg caggcactcc acagagctct ctgtgccagc ccccagcacg   188940
gagggctgac cttagtcgag tggagatgcc ccagtgccag gcagtaggga tgatgtctcc   189000
tgaggcccag atggaaggga ctggactagt ctcatgggc tgatggtggg gccaggcctt    189060
gaccagggac ccagtgtagg gggtgcagag accctctga gttcctcaca catccctggg    189120
gccctcccca tacacttcct atcctgactc cgggcaagag ggagcccag ttcgccttcc    189180 ctatgctggg cacccacagt ggggctgggc accccgcca tgcccctgcc ctgtccttcc    189240
cctgagagcc tcggtcccac ctccaaggtg cctcagagga cagcaggggc agcgggcaga   189300
ggccgagatg cctcctcatt ccaggctcag ctgcccttct tggggcagcc cacacctgag   189360
agtctcctgc agttggtcag gcctgaggag ggcagggggg tgcctgctgt ccctctgctg   189420
accacagtgg catttagcct gggcaccgcg cccagcacag tccatgctgc acaggtgccg   189480
tgggctccac agagccctgc ctgacatgca tgtgttacgt ttcgggtgcc gatgcccttg   189540
ggcggcactt ctccgggcag aacccccagg ccaccgctcc ggttccggtt ccgctgcatc   189600
```

-continued

```
tggggctctc ggcaggctgt ggtcctccgg ccagcctggg ggcatctcag tccctcagcc   189660
ccacaggggc ctgccccgca gcctgggcct cgagccccgt ctccgcacgc tgtgccgaat   189720
ctggctgccc atcagctccc tgcgtaccca gactgtgccc tgccatgccc gtggctcttc   189780
ccaggagtgc cctgtggcct cccctggct tgctgggctg attccctcct gtgtctcaaa    189840
cagagctcac ctttgccatc actgctgtcc tcaccggccg gtgccagagg cccgtgtctg   189900
tgtaccctgt gtctgcacct ctgggcaggg cctggctctg accaacccgg gcttccagtg   189960
tccacagacc taaggcccag ggcgcctggg ggctggagca agagaagcaa aaggagccaa   190020
gggtgggggt ttggggttct tgtgagggcc cagccccagg accccaggac caggacaccc   190080
aggagcccca gggcccagcc ccagttcaga aggcaggggc cttctgaggg agcttaaggg   190140
tcccacagcc caggaccccc accagggcca gtggccagcg ttgggggact cagcctcctc   190200
gtcgctcgtc ctctctgttt ctcccacctt ttgccccctt tctccttgcc tgttcccacc   190260
cgaggccccc tcttggcctg cgtgagccgg ggcggcactg aactgggggc cgatccgcct   190320
gggcggcggt gagaggcagg gccggagcc gggccgctgg gtttgggcct ggcccgctcg    190380
ccgcaatatt tgatggcccgt cagtgcagcc ctgattcctg tgctttcagt taaaaggttt   190440
ctgttgttgt agcttatgca gttgctctgt tgctatggaa acgtgacatc aaaatgacgt   190500
ttcccgttta aaagcttta actaaattcc tgcctgtcag atgtaggccc cattttgagc    190560
gtggagctgc cttcgagcga gcgtgagcgg cgcctcccgc ccatggtgcg tggggccggg   190620
ccggggccct cgctgagcgc gctctctcac cccacaggcg cctccggcat ggcggcggcc   190680
gaggggcccg gctacctcgt gtctccccag gcggagaagc accggcgggc ccgcaactgg   190740
acggacgccg agatgcgcgg cctcatgctg gtctgggagg agttcttcga cgagctcaag   190800
cagaccaagc gcaacgccaa ggtgtacgag aagatggcca gcaagctctt cgagatgacc   190860
ggcgagcgca ggctgggcga ggagatcaag atcaagatca ccaacatgac cttccagtac   190920
aggtgggcga gcgggcagtg tgggccccac caggacgggc gggcccgggc gtggcggcc    190980 gctcctgact ttcttggagc tctgagtcgg gacgatgtgt gggtcgtggc ctgcctgtcg   191040
gtctcctctg gccgggtatg ggcagaaccc cacggggtga gacggggccc acggaaaccg   191100
tgtgtgcagc cttccattgg ggaagtgggg aaactgaggc ccagcaaggg caggaaacca   191160
gtctaagagc tgaggggtag caggggtggg gctggtgctg ggcagaggcc aggatggctc   191220
ccaggacgta tgggcggtct gggcactgtc cctcggaggc agcaacactc atggtggtgc   191280
ccactgacct cacaccctgc tcccccatag ggaggcggcg gctgccagtg ccctccccac   191340
caccaagctc ccaagctcag caggggtttc aggggcctac tgcgtcattg gggaaattga   191400
gactgcaagt gagaaggagg ctcagtgctc tgcgacttgg agcatccact gagcctctgc   191460
catgagccgg tgagccccac tggggctggc cctagggtca cggtggggta tttccagaaa   191520
tcaccaggtg aggtgcagga ccagccagcg catgggtggg gcttacggtg cgaagaagaa   191580
agaggtggag gcctgccctg gcccaggact cccagcgtgg gggctcccgg cctggcccca   191640
cctctgctcc tgctacatgg caggtgggcc cttcctgccc tggcaacctg cagggaaggc   191700 cggagggggac cacccagcca gggagatgtt ggcgtctagg aggggacagg tgtggtccca   191760
cacacccagc atcttaaagt gcgtgggtcc ccagcccatt aggacagggt cccgggtggg   191820
caggggtcat ggtggggtga aggtctcagg cacaggcaag gtcacaggtg cggtgagggt   191880
cttgcagggt gtgaaggtca taggtgtgcg gtgaaggtca caggtgtggg gtgatggttt   191940
tgggtgtggg gagggtcttg cacggagcga gggtggcagc aagagctgga agctgcaggg   192000
```

```
ggagaatggc agcagagagc acccggccct gtgggcggcc tggacagggc tgggcctggg   192060
gctgccggag agcctgtcag cttccaggat gggagtggcc tcactcagct gctccacctc   192120
cgggtcaggc aggtgagcct ggggcagaga ggctgagagc acctgagcca cttgtgggag   192180
aggccacccc cactgccccc ctcaggcgag agccggcct ccagcacagc agaagggaac    192240
ccccagtccc cagccctagt gggagtgggg aagaggccca gcaaggcccc ggacagaccg   192300
ccagcctgtg aggtctccgc tttcagttgc gttgatttga ttttttctga gccttgaagg   192360
aggggtccgg ggcctggccc tgcccaaagg cccctaggca ggccccaaag ccgggaccta   192420
gggtgctgag catgacggat gttgggtttg agcggctggc ttgcgacgtg agggctgagg   192480
tgtgagcctg ggtatcttca gaggttcggt ggacacaggc agctgcccgc ggccccactg   192540
ttcccgtggc ctcctagtcc tgctcaggca cctggtgagg aagggacgca gagggcagtg   192600
ggaggtggcc acgactgttc cagcaggctc ccctctgact caggaattca cgggcaccac   192660
ctccctggct ggctctggtt ggtgtctggc caggttattc attatttatg ctgaaagcct   192720
cttcagagtc ccaggggagg gtttctgtct ccattcctgg aggctgagag atgagggtgc   192780
agcagagtgg gggcctccac tccagaccct gcagtctggg ctggccaagg gctgcaccgg   192840
tgcactgcac gtcatggctg atgaagcact tccacaccgc agccctcag agctgccaca    192900 gtcagcctta gttcaccgag ggggaagctg aggcccagag catgagaggg acttgcccag   192960
ggccacatag tccttagcag aggaagctgt ggctgggtga ctcgatcttt gtccttttc    193020 tttatacccg cagtctcccc atagcagagg ctttctttt tttttctttt ttctttttt    193080 tttttttaca agaactcttt atatattaag gctgttgggc tgaagaagcc tgagagggtg   193140
gctggttctg tggagcatgg tttgttgaag tacagtttgg gggcctccta cactgagaat   193200
aggccttttc tcgtttctcc aaagagtggg ctggctcaag tagggcagag agagaagcct   193260
ggggcagagg ttagggatgg gcacccagcg cctgccctca cacgctctgt gctggtgtct   193320
tcacagccac gtgccaccct gggcagcatc ccctgctcac catctggctg tgcctgtttg   193380 ctggggcac ctcattcaga atccagctta ttgtttccaa cggccaatgg ccacaccctg    193440
gcaggtagca agagtaggag agaggagaca cccactccga gcacaggttg ggtttggagc   193500
ccggccttgg ggcactctgt cactcaaagg cagagtgggg agtgggcact gggccttagg   193560
aggtactggg tccagtgagg cagagatgcc cctgccccac ccccaccttg tggcttcttc   193620
cctggcctgg ccagagctgt ctggccgcca tggggccctg tgtctcctgc cttgacctcc   193680
cagagggcag ccgaggccca ggggaggcct ggggacttag cctctcaggg caggacctgt   193740
ctgcaggagt aggtgggtgc tgggggtccc agtggtaatg aggcatcagg cagtgtggga   193800
aggggcccat ccgcccacc ccagggcctc tgggcaggtt gcaggttgta gcgctggatc    193860
taggctcctg cccagactgt aggttcaacc aagaatggca tgggagccca gcctgctgtt   193920
tgctttatta aatctgccct gtagctgggg gagggctta cttttgatcat cactatgtca    193980 ttgatataaa aatagaggct cagagaggtg aatgaacctg cccaaagtca cacagcaaag   194040
tgtggagatg agatactgac tcagggctgt ggacactgaa gcctgtgctc taacgccagt   194100
ggctgtcgct ccctgaggca ttctctcccg aacaacacag ttattatatt acaaaatatt   194160
atcactatat ttatatatct tataataacct tattattaca ataaaacctt attactctac   194220 cttcaaaat gaattattta aaagcagta tttgctcatt gcagagagtc tagaaactat     194280
agaaaagcaa gggaaaagca ataggaccag ccccaaggtc ccagcatgca cagataacct   194340
```

-continued

```
tagtaatact gggacgtgtg cttcctttt aacatctgag cccgtgtagg tcctgaagcc   194400
cagcttcttt ctaagtccat tgtcatcttg accctggagc ctggccgatt ttgctgggga   194460
ggcccttgcc agccgagagc ggctcctgcc tgtgccggcg tggcgcgccc ctctgctgag   194520
gctgggcagg acaggggctg ggccagctct gtttctcacc cttggctctt gtgtctctcg   194580
tttcaggaaa ttaaaatgca tgacagatag cgagtccgcc ccgcccgact ggccctatta   194640
cctagccatt gatgggattc tggccaaggt ccccgagtcc tgtgatggca aactgccgga   194700
cagccagccg ccggggccct ccacgtccca gaccgaggcg tccctgtcgc cgcccgctaa   194760
gtccacccct ctgtacttcc cgtataacca gtgctcctac gaaggccgct tcgaggatga   194820
tcgctccgac agctcctcca gcttactgtc ccttaagttc aggtagtgtg tctgcttgtc   194880
cttcccctgc cctggggtat ctcagccccc accatttaga gaaagggact gggagtggca   194940
aggccggcgg cggcggccac agtggttgca gaggccgtgg ctgcgggcag cgcctccagg   195000
gacaggcggc ctcagaccag ggagggcttt agtgtccaca ggcagaccga gtttgtctcc   195060
cagctccatc acttttgagc tgcacggaaa gttccttgac ttctctggcc tcagtctccc   195120
tcctataaaa tgggggtaaa tcagtacctt tctcagaggg tggctgggag catcacagga   195180
gagaagacgc agcatgggc ccggcacacg gagggagacc aagccccaga ccccagaatg   195240
cgcccctgg cctcccttag cccacacaga ccccacccc acaggctagc tgccctctca   195300
gcactgggga gggtgtcggg ctgcacctca tcacgtgttg ccgtgggcat gacccgtccc   195360
ctctgccatc catcccacac ctcagacccg tcccgtgctg ccacgtgac tgtgcctgca   195420
agatgctcac agggcagccg ggagccaggc agcatgcagg acagacacct gcggggtggg   195480
cctggggagc ccagagaagg tgcttttgag gaggggacat ttggggtggg ctttcaaggt   195540
aaaatagaag ttggccattt ggaggcaaga acaggaagat tgtggatttg agtcacagct   195600
tctcccctgc cctggtcttc aagtcttct gacaggaggt gtcagaaaag tatctttagt   195660
agagaaggcg tctccgagga gggtccctct catgccgggg gccgctgctt gactcaggat   195720
ttctcattga agacctgaga caaaaacgct tttgctggca gctagaagga accagcagga   195780
ggcctgagat ttgtggctgt tgttcccgtg gactgagccc agttctcaga ctcagctgcc   195840
tggggccttg cacaggactg gggcgtgggg gctgccctcc ctgatcaggc ccaaagcgcg   195900
gatctcacgc ccctgaggtt ggctgtaccc tctcagctca gagcagagtg tgggccaggg   195960
atgagcaggc actggagcag ggccctgggg tctgtgggtt ttggcagctc cctgcccttc   196020
agggaggtct gctgagacca cgggtggccc ctaccccagc agcagagctc tcaggaggcg   196080
cccacagggc tggactgcct ttactcacca cctctaccag agctctgagg tcctggggag   196140
agagcccagg cctcttgtgg gccccacacc ctctaggtgc ctgtccttct gcctctctac   196200
caaggtgtgc cggcccatt tctaggccgc cgggagataa gggggctcac atctcaggcc   196260
cttccttctg ggacctcagt ttccccatct gcctaaggcc gggtgggct ggtggtcttg   196320
gcttccctac aggggtcctg agtactctgc actacccagc ccccccacc cctgccttca   196380
tctctccctg ggggtggtct ctccacccct ggcccccaac tggggctgag ccccacctg   196440
cccagtttgg tgggtgaagg gtgctccctg gcaggatatg cccctctgca gcccagaaca   196500
tcccacccctt tccagaccga aggggtgtgg attgtcctgg gaccctggtc attggggtca   196560
tccgctagtc gcaaaggacg gcaatgcctg tggcctctct ttctttcttt ttctttttt   196620
tttttttga cacggagtct cgctcttgtg cagagagcag tggcgcgatc ttggctcact   196680
gcaacctccg cctcgtgggt tcaagcgatt ctcctgcctc agcctcccga gtagctggga   196740
```

```
ttacaggcac ccgccacaac gcctggctaa ttttttgtatt tttagtagag atggggtttc 196800
accatgttgg ccaggctggt cttgaactcc tgacctcagg tgatccacct gcctctgcct 196860
cccaaagtgc tgggattaca ggcataagcc tccacacccg ccacccctg ttactttctg 196920
tcaaaggcgg tgggttctgg cccctccttt gcacatggaa tatgagaccc tgagtaagtg 196980
acctgactcc ctggggcctc agtttcccca tttgcccagt aggattgtcg ggagggtccg 197040
gtgaggcccc tggtgtgccc aggctctgtg ccagcacgt ccacagccgg cactgtcctt 197100
ccaggtcgga ggagcggccg gtgaagaagc gcaaggtgca gagctgccac ctgcagaaga 197160
agcagctgcg gctgctggag gccatggtgg aggagcagcg ccggctgagc cgcgccgtgg 197220
aggagacctg ccgcgaggtg cgccgcgtgc tggaccagca gcacatcctg caggtgcaga 197280
gcctgcagct gcaggagcgc atgatgagtc tgctggagag gatcatcacc aagtccagcg 197340
tctaggccag caggcggcgg cggcggcggg gccgggcggc tggtggtact gctcaggcca 197400
cccagggcag gccactcagg ccaggcgggc aaggggggccg ccccgcgagc ggagaccgcc 197460
ttccacctgg cctctggcag gatgtccctt ctgagggta ttttgaggaa ccccaggcc 197520
ctggggaccg tgaggctcca gtctccagca tgaatgccct tcctcggaca caggccaggg 197580
cctctggggt tcactccgag taagaacgtc ctagagccac tctccagtgt cgttactatc 197640
aatgatactt gacgtggctt tgatattaaa cgtatactt ttcattcttg cctgaacgc 197700
acagtttgct gttgctggct tggtgaggat gccctgattg atggatcccg aaaatgaaag 197760
cagatggaaa cgggttgggg caggctggag ctggggagc tctctcctga agggaaccct 197820
gtgtcctccc tcaccaggac ctctgcgtct ctccttaaat ggcctctgac gcctgatgaa 197880
aaccccagcg accttccagg aggcttttat tcagctctgt ttggagcatc aggtgtttcc 197940
actgcctcct tagcaatgac actaataaaa gtcgtaacac ctgttcacat gcacagccct 198000
gttgagtgtt ctgggtgctg gagatatcat ggtggatgac acaaaggccc tggcctcttg 198060
gagcttatgc tcccatgcgg ggaagacaca tgggtcagta gagaaatggt tgcaggttgt 198120
gataagtgct ggaagggagg ggttggcctg aggacacgga ggcagacata cgtggagctg 198180
ggaacagtgg ccacacaggg aacggccagt gcgaaggccc agaggcagag gacactggag 198240
caagcccagg agcagctagg aggctggtgg ccagcagcca ggccacggaa gcccgtgcag 198300
cccgtgggga ggagtgttca tgcttttcaa gcttagtggg agtcttttgg ccagtgcagc 198360
tctgggtctg acatcggtgg gggacagagg ggtggtggag cggccacagc tgcaagctca 198420
cctcactgcc ggcccttcca ccagtttcaa actctttcta gaagctccag ctttcccaaa 198480
gctgaattct ctatgagcct ccttggccgg gactcgggcg tctggttgcc ctggctgcaa 198540
aggaggctgg ggcaggtgt gtttgagtca cctcctggaa ttaggcaagt tgctgcccaa 198600
atagaaggtt gttggcaggt gggtcagcag gtgaacagca tggtttgact cagggttcag 198660
aaaaatctcc ctctggctgc caagcgagca ggccgtggag acaggtgcag aggcaggtgt 198720
ggcagcaggc atcctgccag gcagtgctgc agtcatcctg cgacaagcag cagcagctca 198780
tcctaccctc taggggtct tgaggtcagc caggcaagag agcagcttgg actccactgg 198840
gtgtgggacc agcctgtgga ccatggtggt gtggagggtg ccctcggcct gcctgtgtga 198900
aggagaggcc ggcgtgttct gtggagccca aggggagct gggcaagcag gattcacttc 198960
actctgaggg tcctggagct cccacccctcc tcagccatct ccccagagcc tgtgtgccga 199020
ggactcggcc catgttgctg tgggatgaga ggcagagtgt cgtgagggtg taaggagcgg 199080
```

```
cggcagtggt gggaggaggg agcagcagcc agcgctacgg tgccagtttc cagctgccag   199140
atgacgccgc tgaccctgtg gttgagaaga gatgcacaga gccagctctt gcaagccagt   199200
gtggctgcca tagcacctgc cgagaagcag aaggaagggt ggccccagga ggacagagga   199260
tgcgggcaca tctgatgcgg gcctgagttt tgggagcttt tgctctagcc agtttccagc   199320
tccgggaccc acccgcctcg taggcaagac accacccaag aaatcatttg cttaacaaac   199380
acactgggct ccaactggac acctgtgcca ccctagatgc tgggaaccca gccatgcacac  199440 aggcacctgc ccccagctgc tgaccactga ggctggctag cagctcccat ggggccagtg   199500
tggggttccc cagcctccta acagggagcc agtcacaagc cctcgagagg gaagggtgcc   199560
cgcggccctg gcaggaaggt taggctggac gctcccacaa gacataacag atggaggttc   199620
taaatgatgt agcaacttct tcaccctgaa actgctgtag agtcagccat gacgcaccgg   199680
tacttcagta actgccaggc atccgggaca gcacaccgcg agtcgctgct gtgcttgggt   199740
tagaagtggt ttggtctgtt ttcttctcgc cctctctaat cagagtcagt gattcatgcc   199800
cttccatcac cttagagaag gggcaggcgc tgcccgacct tctccaggct ggagcagcat   199860
cgcctcatgt cagcagaact cagctgtaga atatcgtggg gttggtgcct ttcatcagca   199920
gcatgtcctt aacaactttc tgatttcttc cttagttgtt ggtccattaa ggagaaaaaa   199980
aatgatctca gccattgcta aaatatttga taagattcag caaagcagca tgttaacatt   200040
gaaaactaga atcaggagcc aggcagatgt gcttgctttt cacctgtagt atttcatgtt   200100
gttttgacgt ttttagctaa tgcattaaga taaataaaca aaagccgggc acggtggttc   200160
acgcctgtaa tcccagcact ttgggaggct gaggcgggag gatcctctga ggtcaggagt   200220
tcaagaccag cctgaccaac atggagaaac ctcgtcatta ctaaaaatac aaaattagct   200280
gggcgtggtg gtgcatgcct gtaatcccag ctacttggga ggctgaggca ggagaatcgc   200340
ttgaacccgg gaggcggagg ttgcagtgag ctgagattgc accactgcac tccagcctgg   200400
gtgacagtga aactcggtct caaaaaaaaa aaaaattaa aaaagataa ataaaataag   200460 caggataaga aatgaagaaa gtagagttac ctttgttttc agatttcatt tttgtatacc   200520
cagaaagcca aatgtacaaa agactgggag ctcttaaaac cagcttaaac ttgttgaaaa   200580
tgaggatgaa gaaatatccc attcagagtt ggaatgaatt taacccagaa ggaacaggac   200640
ctctactgaa gagaactatg cagtcttact gaaaaatcta ataataacct gagcgctgga   200700
gaaacttcgc acactcctga aagctccaaa gtcaatgtca tcatttattt aatgtcattc   200760
caaacatagt ctcaataata tcacttcttg gttttgacat ggacgcgatg atgtttaaat   200820
tcatatgaaa aaagaacggg gccaaaagtc caaggccagt cagcgtgaga agaccgctcg   200880
gcctccctcg gagtcgggga gttggaaccg cagactgaga tcatgtggct gctgaggcc   200940 aggacgaacg tcgggaaatg gagactcctg cgttgctggt gggatgtggt gcagccgctt   201000
ccaggagcaa tttggtgtcc cgtcctaaag ctgaagaaac gcatttcctc tggtcagtgc   201060
cactcctaga caggccaccc tgcggcagcc gtcctcaaac tggtctgagg accctcaac   201120 gctcttaaaa atcattaaaa gtgggccagg tgcggtggct cacacctgta atcccagcac   201180
tttgggaggc caagacaggc ggatcacgag gtcaggacat tgagatcatc ctggctaaca   201240
cggtgaaacc ccgtctctac taaaaataca aaaaattagc cgggcgtggt ggcgggcgcc   201300
tgtagtccca gctacttggg aggctgagcc aggagaatgg cgtgaaccca ggaggtggag   201360
cttgcagtga gctgagatca ctccactgca ctccagcctg gcagcagag cgagactctg   201420 tctcaaaaaa aaataataaa taaataaata aaataaat aaaataaat tcattaaaag   201480
```

```
tgccaaagaa cttttgctta tgtgagttct aatgaccaat attaatacac attagaatat    201540
cttattagaa attaaacctg agacctttag aaaacatgta ttcatttcaa aatagcaata    201600
aacccatgac atattaacat aaataacaat tgtatgaaaa atatattttc caaaacaaaa    201660
agttttcggg agaagtgtgg catagtttta catggtcgta aatctctggc ttaagagaag    201720
cccactggcc tctcagcagg ctctgggtcc gtccactttg ggggtgtttt ggttgtgaag    201780
tataggagtg aatggagaag ctcattctta cccagatgtg tatttgaaaa gaaaggaac    201840 attttaataa cctttgcaaa taatcggtat attcttccgt gatcctattc caacactgga    201900
caggtggtgg tttgttttt tttttttggag acggagtccc gctctgtcac tcaggctgga    201960
gtgcagtggc gcgatttcag ctcactgcaa gctccgcctc c                       202001
```

<210> SEQ ID NO 6
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 6

```
taaattgtca tcacc                                                         15
```

<210> SEQ ID NO 7
<211> LENGTH: 30
<212> TYPE: RNA
<213> ORGANISM: Artificial sequence
<220> FEATURE:
<223> OTHER INFORMATION: Synthetic oligonucleotide

<400> SEQUENCE: 7

```
agacuuuuuc uggugaugac aauuauuaa                                         30
```

<210> SEQ ID NO 8
<211> LENGTH: 30
<212> TYPE: RNA
<213> ORGANISM: Artificial sequence
<220> FEATURE:
<223> OTHER INFORMATION: Synthetic oligonucleotide

<400> SEQUENCE: 8

```
agacuuuuuc uggugauggc aauuauuaa                                         30
```